US006835741B2

(12) United States Patent
Murugesan et al.

(10) Patent No.: US 6,835,741 B2
(45) Date of Patent: Dec. 28, 2004

(54) BIPHENYL SULFONAMIDES AS DUAL ANGIOTENSIN ENDOTHELIN RECEPTOR ANTAGONISTS

(75) Inventors: Natesan Murugesan, Princeton Junction, NJ (US); John E. Tellew, Pennington, NJ (US); John E. Macor, Flemington, NJ (US); Zhengxiang Gu, Princeton, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/673,100

(22) Filed: Sep. 26, 2003

(65) Prior Publication Data

US 2004/0106833 A1 Jun. 3, 2004

Related U.S. Application Data

(60) Division of application No. 09/737,201, filed on Dec. 14, 2000, now Pat. No. 6,638,937, which is a continuation-in-part of application No. 09/643,640, filed on Aug. 22, 2000, now abandoned, which is a continuation-in-part of application No. 09/604,322, filed on Jun. 26, 2000, now abandoned, which is a continuation-in-part of application No. 09/513,779, filed on Feb. 25, 2000, now abandoned, which is a continuation-in-part of application No. 09/481,197, filed on Jan. 11, 2000, now abandoned, which is a continuation-in-part of application No. 09/464,037, filed on Dec. 15, 1999, now abandoned, which is a continuation-in-part of application No. 09/345,392, filed on Jul. 1, 1999, now abandoned.
(60) Provisional application No. 60/091,847, filed on Jul. 6, 1998.

(51) Int. Cl.$^7$ .................. C07D 233/32; A61K 31/415
(52) U.S. Cl. .................. 514/336; 514/340; 546/268.4; 546/272.1
(58) Field of Search .................. 546/268.4, 272.1; 514/336, 340

(56) References Cited

U.S. PATENT DOCUMENTS

| 4,880,804 A | 11/1989 | Carini et al. |
| 5,102,880 A | 4/1992 | Chakravarty et al. |

(List continued on next page.)

FOREIGN PATENT DOCUMENTS

| DE | 19738578 A1 | 3/1999 |
| DE | 19742717 A1 | 4/1999 |
| EP | 0324377 B1 | 7/1989 |
| EP | 0400974 A | 5/1990 |
| EP | 0400974 A2 | 5/1990 |
| EP | 0400974 A3 | 12/1990 |
| EP | 0412848 B1 | 2/1991 |
| EP | 0443983 BI | 8/1991 |
| EP | 0453210 A2 | 10/1991 |
| EP | 0454511 BI | 10/1991 |
| EP | 0459136 B1 | 12/1991 |
| EP | 0475206 A2 | 3/1992 |
| EP | 0497150 B1 | 8/1992 |
| EP | 0532410 A1 | 3/1993 |
| EP | 0537937 | 4/1993 |
| EP | 0539086 B1 | 4/1993 |
| EP | 0634175 A1 | 1/1995 |
| EP | 0702012 A1 | 3/1996 |
| EP | 0768305 A1 | 4/1997 |
| GB | 2 264 710 | 8/1993 |
| GB | 2 264 710 A | 8/1993 |
| RU | 93004661 | 6/1995 |
| RU | 96104545 | 10/1998 |
| RU | 96115359 | 10/1998 |
| WO | WO91/15479 | 10/1991 |
| WO | WO/93/04045 | 3/1993 |
| WO | WO93/04046 | 3/1993 |
| WO | WO93/16049 | 8/1993 |
| WO | WO93/23399 | 11/1993 |
| WO | WO94/07872 | 4/1994 |
| WO | WO94/27979 | 12/1994 |
| WO | WO95/26957 | 10/1995 |
| WO | WO96/31492 | 10/1996 |
| WO | WO97/29748 | 8/1997 |
| WO | WO97/33886 | 9/1997 |
| WO | WO98/49162 | 11/1998 |

OTHER PUBLICATIONS

Murugesan et al., J. Med. Chem., (1998), 41, pp. 5198–5218.
Chan et al., Bioorganic & Medicinal Chemistry 6 (1998), pp. 2301–2316.
Dascal et al., FEBS Letters 423 (1998) pp. 15–18.
Morlock et al., Bioorganic & Medicinal Chemistry Letters, vol. 7., No. 11, pp. 1399–1402 (1997).
Chan et al., Bioorganic & Medicinal Chemistry Letters, vol. 6, No. 20, pp. 2393–2398 (1996).
Walsh et al. Bioorganic & Medicinal Chemistry Letters, vol. 5, No. 11, pp. 1155–1158 (1995).
Ashton et al., J. Med. Chem. (1994), 37, pp. 2808–2824.
Wexler et al., Journal of Medicinal Chemistry, vol. 39, 3, (1996) pp. 625–656.
Webb et al., Medicinal Research Reviews, vol. 17, No. 1, pp. 17–67 (1997).
Larsen et al., "Efficient Synthesis of Losartan,m a Nonpeptide Angiotensin II Receptor Antagonist," Jnl of Org Chem., vol. 59, No. 21, 1994, pp 6391–6394.
Rivero et al., L–162, 389; a potent orally active angiotnesin li receptor antagonist with blanace affinity to both AT1 and AT2 receptor subtypes:, Biorg & Med Chem Ltrs., vol. 6 No. 3, 1996, pp 307–310.

(List continued on next page.)

Primary Examiner—Deepak Rao
(74) Attorney, Agent, or Firm—Henry H. Gu; Stephen B. Davis

(57) ABSTRACT

Novel biphenyl sulfonamide compounds which are combined angiotensin and endothelin receptor antagonists are claimed along with methods of using such compounds in the treatment of conditions such as hypertension and other diseases, as well as pharmaceutical compositions containing such compounds.

35 Claims, No Drawings

U.S. PATENT DOCUMENTS

| | | |
|---|---|---|
| 5,126,342 A | 6/1992 | Chakravarty et al. |
| 5,128,355 A | 7/1992 | Carini et al. |
| 5,130,318 A | 7/1992 | Roberts et al. |
| 5,138,069 A | 8/1992 | Carini et al. |
| 5,149,699 A | 9/1992 | Ellingboe et al. |
| 5,153,197 A | 10/1992 | Carini et al. |
| 5,155,117 A | 10/1992 | Reitz |
| 5,155,118 A | 10/1992 | Carini et al. |
| 5,157,026 A | 10/1992 | Chakravarty et al. |
| 5,157,040 A | 10/1992 | Greenlee et al. |
| 5,196,444 A | 3/1993 | Naka et al. |
| 5,198,439 A | 3/1993 | Roberts et al. |
| 5,210,079 A | 5/1993 | Carini et al. |
| 5,210,206 A | 5/1993 | Morton et al. |
| 5,223,499 A | 6/1993 | Greenlee et al. |
| 5,240,928 A | 8/1993 | Allen et al. |
| 5,250,548 A | 10/1993 | Winn et al. |
| 5,256,654 A | 10/1993 | Ellingboe et al. |
| 5,260,328 A | 11/1993 | Doria et al. |
| 5,270,317 A | 12/1993 | Bernhart et al. |
| 5,284,954 A | 2/1994 | Wittenberger et al. |
| 5,290,780 A | 3/1994 | Venkatesan et al. |
| 5,328,919 A | 7/1994 | Naka et al. |
| 5,332,744 A | 7/1994 | Chakravarty et al. |
| 5,352,788 A | 10/1994 | Bernhart et al. |
| 5,354,867 A | 10/1994 | Carini et al. |
| 5,371,226 A | 12/1994 | Mederski |
| 5,378,715 A | 1/1995 | Stein et al. |
| 5,399,566 A | 3/1995 | Katano et al. |
| 5,399,578 A | 3/1995 | Buhlmayer et al. |
| 5,401,764 A | 3/1995 | Naka et al. |
| 5,405,849 A | 4/1995 | Venkatesan et al. |
| 5,409,947 A | 4/1995 | Tomiyama et al. |
| 5,411,980 A | 5/1995 | Aston et al. |
| 5,424,450 A | 6/1995 | Boswell et al. |
| 5,444,071 A | 8/1995 | Roberts et al. |
| 5,498,776 A | 3/1996 | Ellingboe et al. |
| 5,512,681 A | 4/1996 | Boswell et al. |
| 5,514,696 A | 5/1996 | Murugesan et al. |
| 5,554,625 A | 9/1996 | Rivero et al. |
| 5,559,233 A | 9/1996 | Bernhart et al. |
| 5,563,139 A | 10/1996 | Reitz |
| 5,571,821 A | 11/1996 | Chan et al. |
| 5,602,153 A | 2/1997 | Reitz |
| 5,612,359 A | 3/1997 | Murugesan |
| 5,668,137 A | 9/1997 | Philips et al. |
| 5,674,883 A | 10/1997 | Fortin et al. |
| 5,696,116 A | 12/1997 | Clozel et al. |
| 5,703,110 A | 12/1997 | Naka et al. |
| 5,705,517 A | 1/1998 | Naka et al. |
| 5,760,038 A | 6/1998 | Murugesan et al. |
| 5,780,473 A | 7/1998 | Murugesan et al. |
| 5,827,869 A | 10/1998 | Murugesan |
| 5,846,985 A | 12/1998 | Murugesan |
| 5,846,990 A | 12/1998 | Murugesan |
| 5,856,507 A | 1/1999 | Polniaszek et al. |
| 5,861,401 A | 1/1999 | Bradbury |
| 5,916,907 A | 6/1999 | Bird |
| 5,939,446 A | 8/1999 | Murugesan et al. |
| 5,962,491 A | 10/1999 | Naka et al. |
| 5,965,592 A | 10/1999 | Buhlmayer et al. |
| 5,965,732 A | 10/1999 | Hunt |
| 6,004,989 A | 12/1999 | Naka et al. |
| 6,043,265 A | 3/2000 | Murugesan et al. |
| 6,080,774 A | 6/2000 | Murugesan et al. |

OTHER PUBLICATIONS

Weidmann, et al., "2–'2–Pyridylmethyl) sulfinyl] –1H–thieno0[3,4–d]imidazoles. A Novel Class of gastric H+/K+ ATPase Inhibitors", J. Med. Chem., vol. 35, No. 3, 1992 pp 438–450.

Quan, et al., "Balanced AT1/AT2 Receptor Antagonists. 4.1,2 XR510 and Related 5–(3–Amidopropanoyl)imidazoles Possessing Equal Affinity for the AT12 and AT2 Receptors", J. Med. Chem., vol. 38, No. 15, 1995, pp 2938–2945.

BIPHENYL SULFONAMIDES AS DUAL ANGIOTENSIN ENDOTHELIN RECEPTOR ANTAGONISTS

This application is a divisional of Ser. No. 09/737,201, filed Dec. 14. 2000, now U.S. Pat. No. 6,638,937 which is a continuation-in-part of U.S. application Ser. No. 09/643,640 filed Aug. 22, 2000, now abandoned, which is a continuation-in-part of U.S. application Ser. No. 09/604,322 filed Jun. 26, 2000, now abandoned, which is a continuation-in-part of U.S. application Ser. No. 09/513,779 filed Feb. 25, 2000, now abandoned, which is a continuation-in-part of U.S. application Ser. No. 09/481,197 filed Jan. 11, 2000, now abandoned, which is a continuation-in-part of U.S. application Ser. No. 09/464,037 filed Dec. 15, 1999, now abandoned, which is a continuation-in-part of U.S. application Ser. No. 09/345,392 filed Jul. 1, 1999, now abandoned, which claims priority from provisional U.S. Application Ser. No. 60/091,847, filed Jul. 6, 1998. The entirety of each of these applications is incorporated herein by reference.

FIELD OF THE INVENTION

The present invention relates to biphenyl sulfonamide compounds which are combined angiotensin and endothelin receptor antagonists, to methods of using such compounds in the treatment of conditions such as hypertension and other diseases, and to pharmaceutical compositions containing such compounds.

SUMMARY OF THE INVENTION

The present invention provides biphenyl sulfonamide compounds of the following formula I, enantiomers (including atropisomers), diastereomers, salts and metabolites thereof:

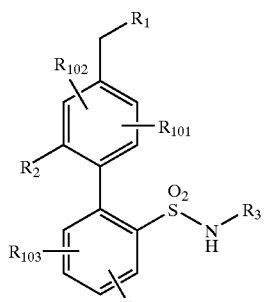

I wherein: $R_1$ is

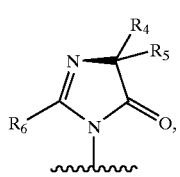

A

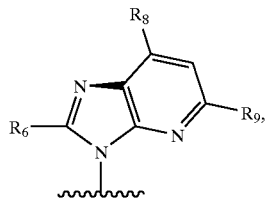

B

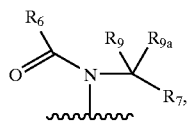

D

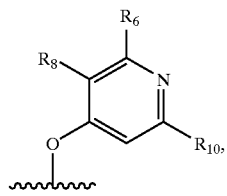

E

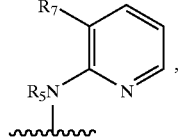

F

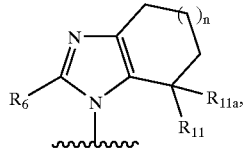

G

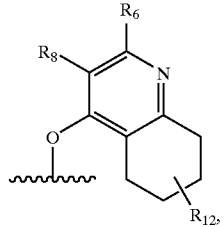

H

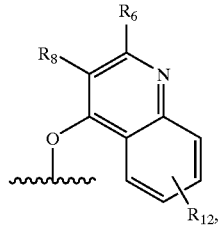

I

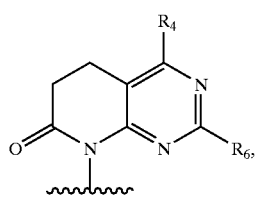

J

K
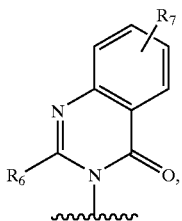

L
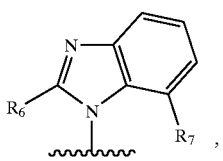

M
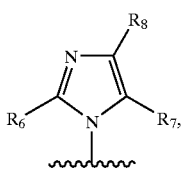

N
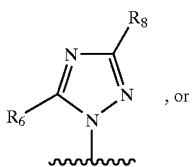, or

O
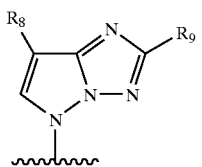;

R$_2$ is hydrogen, halogen, —CHO, alkyl, haloalkyl, (cycloalkyl)alkyl, alkenyl, alkynyl, alkoxyalkyl, haloalkoxyalkyl, alkoxy, aryloxy alkoxyalkoxy, cyano, hydroxy, hydroxyalkyl, nitro, —CH(OR$_{13}$)(OR$_{14}$), —(CH$_2$)$_w$Y; with the proviso that when R$_1$ is B, R$_2$ is not hydrogen, halogen, alkyl, haloalkyl, alkoxy, hydroxyalkyl, nitro, —(CH$_2$)$_w$NR$_{19}$R$_{20}$ or —NHSO$_2$R$_{22}$;

R$_3$ is heteroaryl;

R$_4$ and R$_5$ are each independently alkyl, hydroxyalkyl, cycloalkyl, hydroxy substituted cycloalkyl, alkoxyalkyl, or hydroxy substituted alkoxyalkyl, or R$_4$ and R$_5$ together form a cyclobutyl, cyclopentyl, cyclohexyl, tetrahydrofuranyl or tetrahydropyranyl ring which may be optionally substituted with one or more hydroxy group;

R$_6$ is alkyl, hydroxyalkyl, haloalkyl, hydroxy substituted haloalkyl, cycloalkyl, hydroxy substituted cycloalkyl, (cycloalkyl)alkyl, hydroxy substituted (cycloalkyl)alkyl, aralkyl, alkoxy, hydroxy substituted alkoxy, alkoxyalkyl, hydroxy substituted alkoxyalkyl, or —NR$_{16}$R$_{17}$;

R$_7$ is —(CH$_2$)$_w$—CO$_2$R$_{15}$, —(CH$_2$)$_w$—(C=O)NR$_{16}$R$_{17}$, —(CH$_2$)$_w$—NR$_{15}$(C=O)NR$_{16}$R$_{17}$, —(CH$_2$)$_w$—CH$_2$OH, —(CH$_2$)$_w$—(C=O)R$_{15}$, tetrazolyl, oxadiazolyl or triazolyl wherein said tetrazolyl, oxadiazolyl or triazolyl may optionally be substituted with hydrogen, alkyl, hydroxy or halogen;

R$_8$, R$_9$, R$_{9a}$, R$_{10}$ and R$_{12}$ are each independently hydrogen, halogen, alkyl, hydroxyalkyl, cycloalkyl, (cycloalkyl)alkyl, aryl, heteroaryl, arylalkyl, alkylthioalkyl, alkoxy or alkoxyalkyl, or R$_9$ and R$_{9a}$ together with the carbon atom to which they are bonded form a cycloalkyl ring;

R$_{11}$ and R$_{11a}$ are each independently hydrogen, alkoxy, or together form a carbonyl;

R$_{13}$ and R$_{14}$ are alkyl or together form a five to six-membered ring;

R$_{15}$, R$_{16}$ and R$_{17}$ are independently hydrogen, alkyl, hydroxyalkyl, cycloalkyl, (cycloalkyl)alkyl, alkoxyalkyl, aralkyl, heterocycloalkyl, aryl, heteroaryl or —(CH$_2$)$_w$Q, or R$_{16}$ and R$_{17}$ may together form a four to six-membered heterocyclic ring;

n is 1 or 2;

w is 0, 1, or 2;

Y is heteroaryl, —COOH, —COOR$_{18}$, —CONR$_{19}$R$_{20}$, —NR$_{19}$R$_{20}$, —NR$_{19}$—OR$_{20}$, —NR$_{21}$(C=O)R$_{22}$, —NR$_{21}$(C=O)NR$_{19}$R$_{20}$, —N(R$_{19}$)-(alk)-NR$_{21}$(C=O)R$_{22}$, —NR$_{21}$(C=O)OR$_{18}$, —NR$_{21}$SO$_2$R$_{22}$, —SO$_2$R$_{22}$, Q, R or S:

Q is 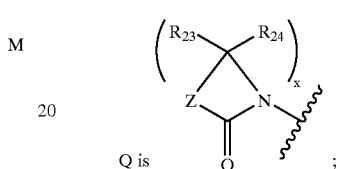;

R is 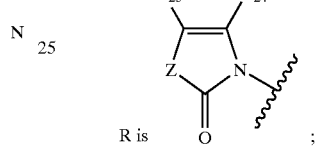;

S is 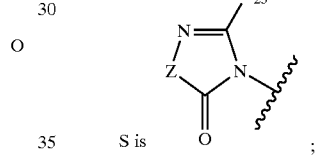;

R$_{18}$, R$_{19}$, R$_{20}$, R$_{21}$ and R$_{22}$ are each independently hydrogen, alkyl, haloalkyl, alkoxyalkyl, cycloalkyl, alkenyl, alkynyl, aryl, aralkyl, heteroaryl, or R$_{19}$ and R$_{20}$ may together form a four to seven-membered heterocyclic ring;

R$_{23}$ and R$_{24}$ are each independently hydrogen, alkyl or cycloalkyl, or may together form a three to seven membered cycloalkyl ring;

Z is oxygen,

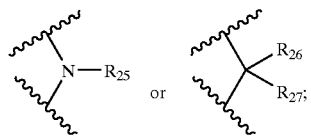

x is 2, 3 or 4;

R$_{25}$, R$_{26}$ and R$_{27}$ are each independently hydrogen, alkyl or cycloalkyl, or R$_{26}$ and R$_{27}$ may together form a three to seven-membered cycloalkyl ring;

R$_{101}$, R$_{102}$, R$_{103}$, and R$_{104}$ are each independently hydrogen, halogen, —CHO, alkyl, haloalkyl, (cycloalkyl)alkyl, alkenyl, alkynyl, alkoxyalkyl, haloalkoxyalkyl, alkoxy, alkoxyalkoxy, cyano, hydroxy, hydroxyalkyl, nitro, —CH(OR$_{13}$)(OR$_{14}$), or —(CH$_2$)$_w$Y; wherein said rings; aryl alone or as part of another group; or heteroaryl alone or as part of another group may each optionally be substituted by one or more hydrogen, halogen, cyano, alkyl, hydroxyalkyl, alkoxy, nitro or trifluoromethyl groups.

The compounds of the formula I and salts thereof may be used as combined endothelin and angiotensin receptor antagonists.

Preferred Compounds

Compounds of the formula I and salts thereof wherein one or more, and especially all, of $R_1$, $R_2$, $R_3$, $R_4$, $R_5$, $R_6$, $R_7$, $R_8$, $R_9$, $R_{10}$, $R_{11}$, $R_{11a}$, $R_{12}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{101}$, $R_{102}$, $R_{103}$, $R_{104}$, n, w, Y, Q, Z, and x are selected from the following definitions, are preferred compounds of the present invention:

$R_1$ is

A 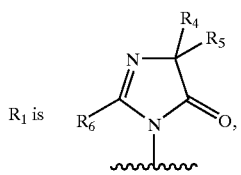

D 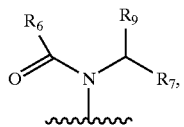

E 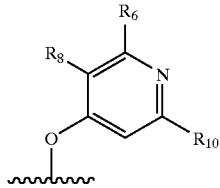

G 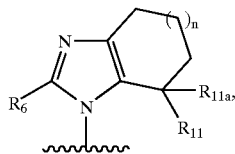

H 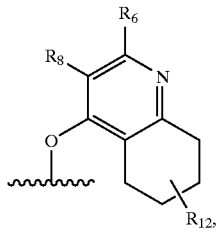

I 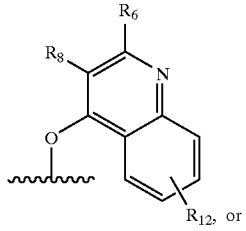

M 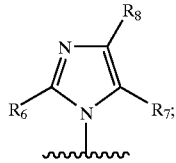

$R_2$ is alkyl, haloalkyl, (cycloalkyl)alkyl, alkoxyalkyl, haloalkoxyalkyl, alkoxy, alkoxyalkoxy, hydroxyalkyl, or —$(CH_2)_wY$, or when $R_1$ is D, $R_2$ is hydrogen, alkyl, haloalkyl, (cycloalkyl)alkyl, alkoxyalkyl, haloalkoxyalkyl, alkoxy, alkoxyalkoxy, hydroxyalkyl, or $(CH_2)_wY$;

$R_3$ is isoxazolyl, pyridizinyl, pyrazinyl or pyrimidinyl, each optionally substituted with one to three of the following substituents: hydrogen, halogen, cyano, alkyl, alkoxy, trifluoromethyl or nitro;

$R_4$ and $R_5$ are each independently alkyl, cycloalkyl, or $R_4$ and $R_5$ together form a cyclobutyl, cyclopentyl or cyclohexyl ring;

$R_6$ is alkyl, haloalkyl, cycloalkyl or alkoxy;

$R_7$ is —$CO_2R_{15}$, —$(C=O)NR_{16}R_{17}$ or —$CH_2OH$;

$R_8$, $R_9$, $R_{10}$ and $R_{12}$ are each independently hydrogen, halogen, alkyl, cycloalkyl, alkoxy or alkoxyalkyl;

$R_{11}$ and $R_{11a}$ are each independently hydrogen, alkoxy, or together form a carbonyl;

$R_{15}$, $R_{16}$ and $R_{17}$ are independently hydrogen, alkyl or cycloalkyl or $R_{16}$ and $R_{17}$ may together form a four to six-membered heterocyclic ring;

n is 1 or 2;

w is 0, 1, or 2;

Y is —$COOR_{18}$, —$NR_{21}(C=O)R_{22}$, —$NR_{21}(C=O)NR_{19}R_{20}$, —$NR_{21}(C=O)OR_{18}$, —$NR_{21}SO_2R_{22}$, —$SO_2R_{22}$ or Q;

Q is

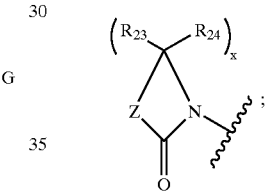

$R_{18}$, $R_{19}$, $R_{20}$, $R_{21}$ and $R_{22}$ are each independently hydrogen, alkyl, cycloalkyl, or $R_{19}$ and $R_{20}$ may together form a four to seven-membered heterocyclic ring;

$R_{23}$ and $R_{24}$ are each independently hydrogen, alkyl or cycloalkyl, or may together form a three to seven membered cycloalkyl ring;

Z is oxygen,

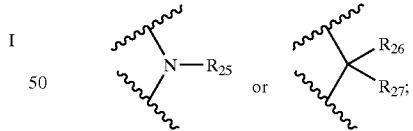

x is 2, 3 or 4;

$R_{25}$, $R_{26}$ and $R_{27}$ are each independently hydrogen, alkyl or cycloalkyl, or $R_{26}$ and $R_{27}$ may together form a three to seven-membered cycloalkyl ring;

$R_{101}$, $R_{102}$, $R_{103}$, and $R_{104}$ are each independently hydrogen, halogen, alkoxy or alkyl.

Compounds of the formula I and salts thereof wherein one or more, and especially all, of $R_1$, $R_2$, $R_3$, $R_4$, $R_5$, $R_6$, $R_7$, $R_8$, $R_9$, $R_{10}$, $R_{11}$, $R_{11a}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{101}$, $R_{102}$, $R_{103}$, $R_{104}$, n, w, Y, Q, Z, and x are selected from the following definitions, are more preferred compounds of the present invention:

R₁ is 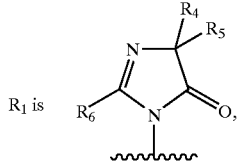

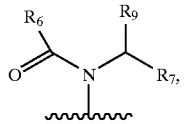

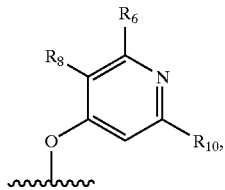

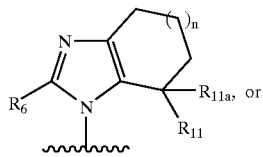

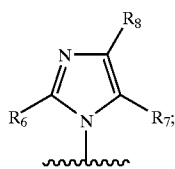

R₂ is alkyl, haloalkyl, (cycloalkyl)alkyl, alkoxyalkyl, haloalkoxyalkyl, alkoxy, hydroxyalkyl, or —(CH₂)$_w$Y; or when R₁ is D, R₂ is hydrogen, alkyl, haloalkyl, (cycloalkyl)alkyl, alkoxyalkyl, haloalkoxyalkyl, alkoxy, alkoxyalkoxy, hydroxyalkyl, or —(CH₂)$_w$Y;

R₃ is isoxazolyl, optionally substituted with one or two of the following substituents: hydrogen, halogen, cyano, alkyl, alkoxy, trifluoromethyl or nitro;

R₄ and R₅ are each independently alkyl, cycloalkyl, or R₄ and R₅ together form a cyclobutyl, cyclopentyl or cyclohexyl ring;

R₆ is alkyl, haloalkyl, cycloalkyl or alkoxy;

R₇ is —CO₂R₁₅ or —(C=O)NR₁₆R₁₇;

R₈, R₉ and R₁₀ are each independently hydrogen, halogen, alkyl, cycloalkyl alkoxy or alkoxyalkyl;

R₁₁ and R₁₁$_a$ together form a carbonyl;

R₁₅, R₁₆ and R₁₇ are independently hydrogen, alkyl, or cycloalkyl or R₁₆ and R₁₇ may together form a four to six-membered heterocyclic ring;

n is 2;

w is 0, 1, or 2;

Y is —NR₂₁(C=O)R₂₂, —NR₂₁(C=O)NR₁₉R₂₀, —NR₂₁(C=O)OR₁₈, —NR₂₁SO₂R₂₂, —SO₂R₂₂ or Q;

Q is

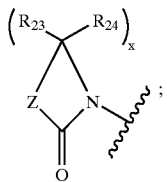

R₁₈, R₁₉, R₂₀, R₂₁ and R₂₂ are each independently hydrogen, alkyl, cycloalkyl, or R₁₉ and R₂₀ may together form a four to seven-membered heterocyclic ring;

R₂₃ and R₂₄ are each independently hydrogen, alkyl or cycloalkyl, or may together form a three to seven membered cycloalkyl ring;

Z is oxygen,

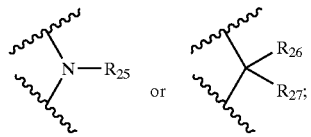

x is 2, 3 or 4;

R₂₅, R₂₆ and R₂₇ are each independently hydrogen, alkyl or cycloalkyl, or R₂₆ and R₂₇ may together form a three to seven-membered cycloalkyl ring;

R₁₀₁, R₁₀₂, R₁₀₃, and R₁₀₄ are each independently hydrogen, halogen, or alkyl.

Compounds of the formula I and salts thereof wherein one or more, and especially all, of R₁, R₂, R₃, R₄, R₅, R₆, R₈, R₁₀, R₁₁, R₁₁$_a$, R₁₈, R₁₉, R₂₀, R₂₁, R₂₂, R₂₃, R₂₄, R₂₅, R₂₆, R₂₇, R₁₀₁, R₁₀₂, R₁₀₃, R₁₀₄, w, Y, Q, Z, and x are selected from the following definitions, are most preferred compounds of the present invention:

R₁ is 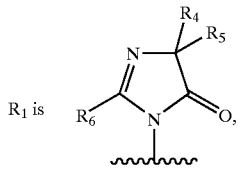

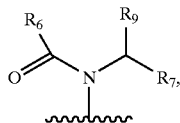

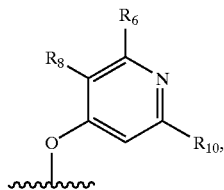

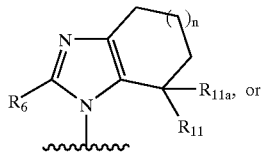

M

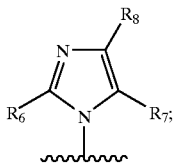

R$_2$ is alkyl, haloalkyl, (cycloalkyl)alkyl, alkoxyalkyl, haloalkoxyalkyl, alkoxy, alkoxyalkoxy, hydroxyalkyl, or —(CH$_2$)$_w$Y or when R$_1$ is D, R$_2$ is hydrogen, alkyl, haloalkyl, (cycloalkyl)alkyl, alkoxyalkyl, haloalkoxyalkyl, alkoxy, alkoxyalkoxy, hydroxyalkyl, or —(CH$_2$)$_w$Y;

R$_3$ is isoxazol-5-yl or isoxazol-3-yl independently substituted with two of following substituents: alkyl or halogen;

R$_4$ and R$_5$ are each independently alkyl, cycloalkyl, or R$_4$ and R$_5$ together form a cyclobutyl, cyclopentyl or cyclohexyl ring;

R$_6$ is alkyl, halo alkyl, cycloalkyl or alkoxy;

R$_7$ is —CO$_2$R$_{15}$ or —(C=O)NR$_{16}$R$_{17}$;

R$_8$, R$_9$, and R$_{10}$ are independently H, alkyl, cycloalkyl, alkoxy or alkoxyalkyl;

n is 2;

w is 0, 1, or 2;

Y is —NR$_{21}$(C=O)R$_{22}$, —NR$_{21}$(C=O)NR$_{19}$R$_{20}$, —NR$_{21}$(C=O)OR$_{18}$, —NR$_{21}$SO$_2$R$_{22}$ or Q;

Q is

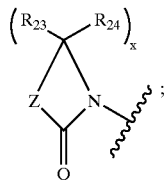

R$_{18}$, R$_{19}$, R$_{20}$, R$_{21}$ and R$_{22}$ are each independently hydrogen, alkyl, cycloalkyl, or R$_{19}$ and R$_{20}$ may together form a four to seven-membered heterocyclic ring;

R$_{23}$ and R$_{24}$ are each independently hydrogen, alkyl or cycloalkyl, or may together form a three to seven membered cycloalkyl ring;

Z is

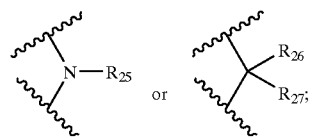

x is 2;

R$_{25}$, R$_{26}$ and R$_{27}$ are each independently hydrogen, alkyl or cycloalkyl, or R$_{26}$ and R$_{27}$ may together form a three to seven-membered cycloalkyl ring;

R$_{101}$, R$_{102}$, R$_{103}$, and R$_{104}$ are each independently hydrogen, halogen, or alkyl.

Especially preferred are compounds where

R$_1$ is selected from A, <u>D</u>, or E;

R$_2$ is selected from alkyl, alkoxyalkyl, and haloalkoxyalkyl, and further selected from hydrogen when R$_1$ is <u>D</u>;

R$_3$ is isoxazol-3-yl independently substituted with two of following substituents: alkyl or halogen;

R$_4$ and R$_5$ together form a cyclobutyl, cyclopentyl or cyclohexyl ring;

R$_6$ is alkyl;

R$_7$ is —(C=O)NR$_{16}$R$_{17}$;

R$_8$, R$_9$, and R$_{10}$ are independently alkyl or alkoxy; and

R$_{101}$, R$_{102}$, R$_{103}$, and R$_{104}$ are each independently hydrogen, halogen, or alkyl.

DETAILED DESCRIPTION OF THE INVENTION

The following are definitions of terms used in this specification. The initial definition provided for a group or term herein applies to that group or term throughout the present specification, individually or as part of another group, unless otherwise indicated.

The terms "alk" or "alkyl" refer to straight or branched chain hydrocarbon groups having 1 to 12 carbon atoms, preferably 1 to 8 carbon atoms. Lower alkyl groups, that is, alkyl groups of 1 to 4 carbon atoms, are most preferred.

The term "alkenyl" refers to straight or branched chain hydrocarbon groups having 2 to 12 carbon atoms, preferably 2 to 4 carbon atoms, and at least one double carbon to carbon bond, such as ethenyl.

The term "alkynyl" refers to straight or branched chain hydrocarbon groups having 2 to 12 carbon atoms, preferably 2 to 4 carbon atoms, and at least one triple carbon to carbon bond, such as ethynyl.

The term "alkoxy" refers to an alkyl group bonded through an oxygen (—O—).

The term "aryloxy" refers to an aryl group bonded through an oxygen (—O—).

The term "thioalkyl" refers to an alkyl group bonded through a sulfer (—S—).

The term "carbonyl" refers to the group —(C=O)—.

The terms "ar" or "aryl" refer to phenyl, naphthyl and biphenyl. Phenyl is a preferred aryl group. Aryl groups may be optionally substituted with one or more (such as one to three) of the following substituents: hydrogen, halogen, cyano, alkyl, alkoxy, nitro or trifluoromethyl groups.

The term "cycloalkyl" refers to fully saturated cyclic hydrocarbon groups having 3 to 8 ring carbon atoms.

The terms "halogen" and "halo" refer to fluorine, chlorine, bromine and iodine. Haloalkyl refers to an alkyl chain substituted with from one to three halogens.

The term "heteroaryl" refers to furyl, thienyl, pyrrolyl, pyridyl, pyrimidyl, pyrazinyl, pyridazinyl, triazinyl, oxazolyl, isoxazolyl, thiazolyl, isothiazolyl, oxadiazolyl, thiadiazolyl, imidazolyl, triazolyl, and tetrazolyl, each of which may optionally be substituted where appropriate by one or more (such as one to three) of the following: hydrogen, halogen, cyano, alkyl, hydroxyalkyl, alkoxy, nitro or trifluoromethyl.

The terms "heterocyclic" or "heterocyclo" refer to optionally substituted, non-aromatic cyclic groups, for example, 4 to 7 membered monocyclic, 7 to 11 membered bicyclic, or 10 to 15 membered tricyclic ring systems, which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system.

Exemplary monocyclic heterocyclic groups include azetidinyl, pyrrolidinyl, oxetanyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, and the like.

The term "ring" encompasses homocyclic (i.e., as used herein, all the ring atoms are carbon) or "heterocyclic" (i.e., as used herein, the ring atoms include carbon and one to four heteroatoms selected from N, O and/or S, also referred to as heterocyclo), where, as used herein, each of which (homocyclic or heterocyclic) may be saturated or partially or completely unsaturated (such as heteroaryl), and each of which (homocyclic or heterocyclic) may optionally be substituted by one or more (such as one to three) hydrogen, halogen, cyano, alkyl, alkoxy, nitro or trifluoromethyl groups.

Throughout the specification, groups and substituents thereof may be chosen to provide stable moieties and compounds.

The compounds of formula I form salts which are also within the scope of this invention. Reference to a compound of the formula I herein is understood to include reference to salts thereof, unless otherwise indicated. The term "salt(s)", as employed herein, denotes acidic and/or basic salts formed with inorganic and/or organic acids and bases. In addition, when a compound of formula I contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula I may be formed, for example, by reacting a compound I with an amount of acid or base, such as an equivalent amount, in a medium such as one in which the salt precipitates or in an aqueous medium followed by lyophilization.

The compounds of formula I which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula I which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl) ethylenediamine), N-methyl-D-glucamines, N-methyl-D-glucamides, t-butyl amines, and salts with amino acids such as arginine, lysine and the like. Basic nitrogen-containing groups may be quaternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Prodrugs and solvates of the compounds of the invention are also contemplated herein. The term "prodrug", as employed herein, denotes a compound which, upon administration to a subject, undergoes chemical conversion by metabolic or chemical processes to yield a compound of the formula I, or a salt and/or solvate thereof. Solvates of the compounds of formula I are preferably hydrates. Any tautomers which may exist are also contemplated herein as part of the present invention.

All stereoisomers of the present compounds, such as those which may exist due to asymmetric carbons on the R substituents, including enantiomeric forms (which may exist even in the absence of asymmetric carbons, e.g., atropisomers) and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations.

The present invention can be applied to the extensive prior art in the field of angiotensin antagonists to obtain additional novel compounds possessing potent antagonist activity at both endothelin and angiotensin receptors. In particular, a large number of groups (known to be useful within the field of angiotensin receptor antagonists) can be substituted at the $R_1$ position of Formula I without departing from the scope of the present invention. The table below outlines examples of additional suitable $R_1$ groups.

| Patent No. | Description of $R_1$ |
|---|---|
| JP 09291078 | Substituted imidazoles |
| JP 09301956 | Substituted imidazoles |
| JP 09323991 | carboxy methylidene cyclohepta imidazoles |
| WO 97/40040 | Pyrimidin-4-ones |
| U.S. Pat. No. 5,674,879 | tetrahydro-imidazopyridines |
| WO 97/30036 | N-acylaminoacid derivatives |
| JP 09110691 | Imidazotetrahydropyridines |
| JP 08208640 | Benzimidazoles |
| JP 08165292 | purine derivatives |
| JP 08143552 | Cyclohepta imidazoles |
| JP 08113572 | Imidazopyridines |
| WO 96/10559 | Ureas |
| EP 708103 | Imidazolones |
| WO 96/08476 | Pyrimidinones |
| JP 08041053 | Pyrimidines |
| JP 08034780 | Cyclohept:imidazoles |
| WO 96/05195 | naptho-fused lactams |
| WO 96/04273 | Pyrazoles |
| EP 696583 | Benzimidazoles |
| JP 07316055 | Pyrimidines |
| WO 95/34564 | Pyridylimidazoles |
| JP 07309871 | Hydrazotriazoles |
| WO 95/32198 | Pyridylimidazoles |
| AU 95/16257 | Imidazopyridines |
| WO 95/24902 | Imidazoles |
| DE 4407488 | Pyridones |
| WO 95/22543 | Imidazoles |
| WO 95/21838 | Pyridylimidazoles |
| JP 07157485 | fused pyrimidinones |
| U.S. Pat. No. 5,411,980 | N-arylsubstituted-1,2,4-triazolinones |
| WO 95/16677 | pyrimidine/pyrimidinones |

-continued

| Patent No. | Description of R₁ |
|---|---|
| WO 95/16675 | Benzazepin-3-yl-ureas |
| WO 95/16692 | Benzazepin-3-yl-ureas |
| U.S. Pat. No. 5,426,105 | Dihydroimidazopyridines |
| U.S. Pat. No. 5,424,450 | Imidazolinones |
| DE 4341453 | 4-oxo-imidazo-pyridines |
| JP 07112975 | Amino-azoles |
| DE 4339868 | 4-oxo-imidazo-pyridazines |
| WO 95/12598 | benzazepinyl urea macrocycles |
| EP 648763 | Imidazoles |
| WO 95/09632 | benzazepin-3-yl-ureas |
| EP 647627 | pyridinones |
| JP 07048357 | aminoacids |
| WO 95/03290 | benzofused lactams |
| DE 4342724 | 2-oxo-1,2-dihydro-pyridines |
| WO 93/17023 | pyrazolopyrimidines |
| U.S. Pat. No. 5,385,894 | 6-aminoquinazolines |
| JP 07002776 | N-arylmethlpyridines |
| JP 06340668 | pyrazolotriazoles |
| U.S. Pat. No. 5,380,719 | quinoxalines and its N-oxides |
| GB 2280438 | carboxymethylidene cycloheptimidazoles |
| WO/95/00517 | imidazoles |
| U.S. Pat. No. 5,378,704 | benzo- and pyrido-1,2,4-thiadiazines |
| JP 06287182 | alkylglycines |
| EP 623610 | pyridine and pyridones |
| U.S. Pat. No. 5,358,947 | pyrazolotriazinones |
| WO 94/22838 | pyrazoles |
| EP 621276 | 2,3,6-substituted quinazolinone derivatives |
| WO 94/21629 | 1-phenyl-imidazol-2-ones |
| JP 06211814 | thioureas |
| EP 618207 | 5,8-dihydro-6H-pyrido-pyrimidin-7-ones |
| DE 4305279 | triazolopyrimidines |
| WO 94/17069 | pyrazoles |
| WO 94/17067 | pyrimidones |
| U.S. Pat. No. 5,338,736 | 2,3,6-substituted quinazolinone derivatives |
| JP 06184086 | thioureas |
| DE 4300912 | 1-benzyl-1,2,3,4-tetrahydroquinazolin-2-ones or related analogs |
| U.S. Pat. No. 5,330,987 | pyridopyrimidinones |
| EP 607077 | 4-pyrimidinones |
| WO 94/13675 | pyrazolotriazoles |
| U.S. Pat. No. 5,326,776 | 5-membered heterocyclic rings comprising 1–4 N or 2 N and 1 O and comprising 0–2 double bonds |
| EP 602521 | imidazopyridines |
| WO 94/11379 | pyridooxazinones |
| WO 94/11012 | dipeptide analogs |
| EP 591891 | benzimidazoles |
| U.S. Pat. No. 5,315,013 | pyrazoles |
| JP 06100541 | pyrazolinones |
| WO 94/04516 | 5-membered ring heterocyles containing 1–4 heteroatoms |
| JP 06087833 | vinyl imidazoles |
| EP 594022 | 2-pyridones |
| EP 594019 | 2-pyridones |
| JP 06073008 | alkoxy-pyridines |
| JP 06072985 | ureas and thioureas |
| DE 4233590 | benzimidazoles |
| JP 06065236 | dihydrobenzimidazolones |
| JP 06056826 | quinoxalines |
| EP 589665 | 4,5,6,7-tetrahydro-1H-imidazo[4,5-c]pyridine-6-carboxamides |
| JP 06041122 | quinoxalines |
| DE 4230464 | imidazolylbenzimidazoles |
| U.S. Pat. No. 5,296,480 | 2-alkyl-5,6,7,8-tetrahydro-pyrido (4,3-d)-pyrimidine-4-ones |
| U.S. Pat. No. 5,294,617 | quinazolinones |
| U.S. Pat. No. 5,294,611 | quinazolinones |
| U.S. Pat. No. 5,292,734 | quinazolinones |
| JP 06032782 | pyrazoles |
| U.S. Pat. No. 5,290,780 | quinazolinones |
| JP 06025250 | thieno[3,4-d]imidazoles |
| JP 06025229 | imidazoles |
| WO 94/03453 | pyrazolyl[4,3-c]pyridines |
| WO 94/03449 | imidazoles |
| WO 94/03435 | imidazole-5-carboxylic acids |
| U.S. Pat. No. 5,288,720 | quinazolinones |
| JP 06016661 | imidazoles |
| U.S. Pat. No. 5,284,853 | quinazolinones |
| U.S. Pat. No. 5,284,852 | quinazolinones |
| JP 06009638 | pyrazolopyrimidines |
| WO 94/02467 | imidazoles |
| U.S. Pat. No. 5,281,604 | quinazolinones |
| U.S. Pat. No. 5,281,603 | quinazolinones |
| U.S. Pat. No. 5,281,602 | pyridopyrimidines |
| DE 4224133 | benzimidazoles |
| U.S. Pat. No. 5,276,048 | imidazoles |
| GB 2268743 | pyridines/pyrazines/pyrimidines |
| JP 05310696 | pyridines |
| EP 574846 | imidazopyridines |
| DE 4237656 | benzimidazoles |
| FR 2690442 | pyrazolopyrimidines |
| GB 2267089 | cycloheptimidazoles |
| EP 573218 | imidazoles |
| WO 93/23391 | indoles, 7-azaindoles |
| U.S. Pat. No. 5,260,325 | N-linked amides or thioamides |
| DE 4212748 | benzimidazoles |
| EP 566020 | benzimidazoles |
| DE 4212250 | benzimidazoles |
| U.S. Pat. No. 5,250,548 | aminopyridines |
| GB 2265900 | pyrazoles |
| EP 562936 | imidazolines |
| WO 93/18035 | aza-phthalimides |
| WO 93/17682 | bicyclic heterocycles |
| WO 93/17681 | 5-membered ring heterocycles |
| EP 561252 | 2-oxoquinolines |
| JP 05201994 | pyridazinones |
| GB 2264709 | imidazopyridines |
| JP 05194418 | 2-aminopyrimidines |
| WO 93/16049 | 4-oxo-dihydropyridines |
| JP 05178836 | pyridines |
| EP 556080 | pyrazolo[1,5-a]pyridines or imidazo[1.5-a]pyridines |
| U.S. Pat. No. 5,231,094 | triazolopyrimidines |
| EP 554107 | 1,2,4-triazole |
| EP 554098 | imidazo[4,5b]pyridines |
| WO 93/14086 | 1-isoquinolones |
| EP 552765 | benzimidazoles |
| JP 05155884 | benzopyrazines or pyridopyrazines |
| WO 93/13077 | hydantoins connected to imidazoles |
| U.S. Pat. No. 5,225,408 | oxadiazinone |
| JP 05140152 | quinazolindione |
| EP 550313 | pyrazolone and pyrimidinones |
| U.S. Pat. No. 5,219,856 | imidazoles |
| EP 547514 | imidazopyridines |
| U.S. Pat. No. 5,218,125 | imidazoles |
| GB 2262096 | 4-aminopyrimidines |
| U.S. Pat. No. 5,214,153 | imidazoles |
| U.S. Pat. No. 5,212,195 | indoles, azaindoles |
| EP 543263 | benzimidazoles |
| DE 4221583 | pyridones |
| U.S. Pat. No. 5,208,234 | imidazolephosphonic acids |
| WO 93/08193 | imidazo-tetrahydropyridazines |
| WO 93/08171 | pyrimidocycloalkanes |
| WO 93/08169 | aminopyrimidines |
| EP 539086 | pyrimidinolactams |
| EP 537937 | pyrazinopyrimidinones |
| DE 4132632 | imidazolylpropenoic acids |
| EP 535465 | imidazolylpropenoic acids |
| EP 535463 | imidazolylpropenoic acids |
| EP 535420 | imidazoles |
| EP 534706 | quinazolinone or pyridopyrimidinones |
| WO 93/05044 | pyrazolotriazines |
| W0 93/05025 | pyrazoles |
| WO 93/04059 | imidazoles |
| WO 93/04045 | imidazolinones |
| JP 05032661 | imidazolinones |
| EP 532410 | imidazolinones and larger ring analogs |
| EP 531876 | imidazoindolizines |
| EP 531874 | 4,5,6,7-tetrahydroimidazo[4,5-c]pyridine-4-carboxylic acids |
| EP 530702 | 1,2-dihydro-2-oxopyridines |
| WO 93/03040 | thienopyrimidin-4-ones |
| WO 93/03033 | imidazo[4,5-d]pyridazines |
| WO 93/03018 | pyrimidines |

-continued

| Patent No. | Description of R₁ |
|---|---|
| U.S. Pat. No. 5,187,168 | quinazoline derivatives |
| JP 05017480 | thienoimidazoles |
| U.S. Pat. No. 5,185,340 | oxypyrimidines |
| U.S. Pat. No. 5,182,288 | lactams |
| FR 2677016 | acyl amino acid derivatives |
| WO 93/00341 | imidazoles |
| WO 92/22533 | 4-aminoquinolines |
| U.S. Pat. No. 5,124,335 | fused pyrroles |
| EP 490820 | acylamino derivatives |
| EP 490587 | pyrazolo-pyrimidine and imidazopyridazines |
| EP 495626 | oxypyridines, oxyquinolines, and imidazoles |
| EP 497150 | 3-quinazolin-4-ones |
| EP 497121 | imidazoles |
| EP 498721 | 1,4-dihydroquinolin-4-ones |
| U.S. Pat. No. 5,132,216 | imidazopyridines |
| EP 499416 | oxypyridines |
| EP 499415 | aminopyridines |
| EP 499414 | Fused oxypyridines |
| EP 500409 | 4-pyrimidones |
| EP 500297 | 2-pyridones and 2-pyrimidones |
| EP 502725 | fused pyrimidones |
| EP 502575 | 1-(2H)-isoquinolinones |
| EP 502314 | benzimidazoles |
| EP 505098 | imidazoles |
| EP 503785 | imidazoles |
| JP 04230683 | 7-aza and 4- azabenzimidazoles (i.e., imidazopyridines) |
| EP 507594 | quinolines |
| JP 04235988 | imidazopyridazinediones |
| EP 505893 | imidazopyridines |
| FR 2672891 | pyrazolones |
| U.S. Pat. No. 5,145,699 | pyridopyrimidines |
| EP 515265 | pyrimidine derivatives |
| EP 511791 | pyrrolopyridines |
| JP 04257564 | benzimidazoles, imidazopyridines, imidazopyrazines |
| WO 92/16524 | benzo-fused lactams |
| EP 516392 | naphyridones and pyrido[c,b]pyrrolidones |
| WO 92/19211 | imidazobenzoquinones |
| JP 04295478 | imidazo [4,5-b]pridines |
| EP 5212768 | triazolo pyrimidines |
| WO 92/21666 | thiazole derivatives |
| EP 518033 | imidazo[4,5-c]pyridine-4-carboxylates and other heterocycles |
| U.S. Pat. No. 5,087,702 | 3H-imidazo-[4,5-b} pyridines |
| U.S. Pat. No. 5,087,634 | N-substituted imidazol-2-ones |
| WO 92/00977 | imidazoles |
| EP 475206 | various 6-membered heterocycles |
| WO 92/02508 | oxyquinolines |
| WO 92/04343 | tetrahydrobenzazoles |
| WO 92/04335 | 1H-1,2,4-triazoles |
| EP 475898 | Azacyclic compounds including imidazolinones |
| EP 481448 | dihydropyrimidines |
| QO 92/05161 | 1,3,5-trisubstituted 1,2,4-triazoles |
| WO 92/07852 | xanthine derivatives |
| JP 04120072 | pyrimidine derivatives |
| EP 487252 | quinolines and 1,5-naphthyridine derivatives |
| EP 483683 | thienoimidazoles |
| EP 470543 | fused imidazoles |
| EP 468470 | fused imidazoles |
| EP 467207 | purines |
| WO 91/19715 | imidazo[4,5-d]pyridazines |
| WO 91/19697 | pyridines |
| EP 465368 | imidazoles |
| EP 465323 | pyrimidines |
| WO 91/18888 | triazolones |
| EP 461039 | benzimidazoles |
| U.S. Pat. No. 5,066,586 | pyridoimidazoles |
| EP 459136 | benzimidazoles |
| WO 91/17148 | triazoles |
| EP 456510 | pyridoimidazoles |
| EP 456442 | quinolines |
| WO 91/15479 | imidazoles, oxazoles, thiazoles |
| WO 91/15209 | pyrimidines |
| EP 453210 | pyridines |
| WO 91/14679 | imidazolinones or pyrimidinones |
| U.S. Pat. No. 5,053,329 | imidazopyridines |
| U.S. Pat. No. 5,049,565 | conjugated imidazopyridines |
| EP 449699 | pyrazoles |
| EP 446062 | pyrazoles |
| EP 445811 | pyridin-4-ones and pyrimidin-4-ones |
| EP 443983 | amides, sulfonamides, carbamates |
| EP 443568 | thienopyridin-4-ones, thienopyrimidin-2,4-diones |
| EP 442473 | pyrimidin-2,4-diones |
| EP 435827 | pyrimidinones |
| EP 434038 | fused imidazoles |
| EP 432737 | cycloheptimidazolones |
| WO 91/07404 | azaquinolines |
| EP 430300 | xanthines |
| EP 426021 | fused imidazoles |
| EP 425921 | benzimidazoles |
| EP 424317 | pyrimidines |
| EP 420237 | fused imidazoles |
| EP 419048 | pyrimidinones |
| EP 415886 | fused imidazoles |
| EP 412848 | oxyquinolines |
| EP 412594 | triazolinones |
| EP 411766 | quinazolinones |
| EP 411507 | pyrazole-3-carboxylates |
| WO 91/00281 | imidazoles |
| WO 91/00277 | imidazoles |
| EP 409332 | triazoles |
| EP 407342 | pyrimidinones |
| EP 407102 | fused imidazoles |
| EP 401030 | fused imidazoles |
| EP 400974 | fused imidazoles |
| EP 400835 | benzimidazoles |
| EP 399732 | benzimidazoles |
| EP 399731 | fused imidazoles |
| EP 392317 | benzimidazoles |
| EP 890719 | imidazoles |
| EP 323841 | pyrroles, pyrazoles, and triazoles |
| EP 291969 | biphenyltetrazoles |
| EP 253310 | imidazoles |
| WO 95/28419 | indazoles |
| EP 638572 | fused imidazoles |
| DE 4320432 | aminopyridyl, imidazoles, fused imidazoles |
| JP 06279437 | imidazoles |
| EP 624583 | pyridones |
| EP 623611 | pyridines or 2-pyridones |
| U.S. Pat. No. 5,348,955 | diacyl piperazines |
| WO 94/07486 | benzo-fused lactams |
| JP 06128256 | imidazopyridines |
| U.S. Pat. No. 5,298,517 | imidazoles |
| U.S. Pat. No. 5,286,729 | quinazolinones |
| DE 4203872 | imidazo[1,2-a]pyridines |
| GB 2263637 | fused imidazoles |
| U.S. Pat. No. 5,177,097 | imidazolones |
| EP 519831 | imidazoles and pyrimidines |
| U.S. Pat. No. 5,153,347 | phosphonates or phosphinates |
| DE 4034728 | thienoimidazoles |
| DE 4032522 | thienoimidazoles |
| EP 461040 | fused imidazoles |
| DE 4006693 | benzimidazoles |
| U.S. Pat. No. 4,916,129 | imidazoles |
| U.S. Pat. No. 4,880,804 | benzimidazoles |
| WO 97/15556 | 3-spiroindolin-2-ones |
| U.S. Pat. No. 5,266,583 | imidazoles |
| EP 573218 | imidazoles |
| U.S. Pat. No. 5,264,447 | imidazoles |
| EP 569794 | benzopyridones or pyridopyridones |
| U.S. Pat. No. 5,091,390 | fused imidazoles |
| U.S. Pat. No. 5,256,658 | morpholines, piperidines, piperazines, thiomorpholines |
| EP 546358 | benzimidazoles |

Methods of Preparation

The compounds of the present invention may be prepared by methods such as those illustrated in the following Schemes I to XIII. Solvents, temperatures, pressures, and other reaction conditions may be selected by one of ordinary skill in the art. Starting materials are commercially available or readily prepared by one of ordinary skill in the art.

The following are the definitions of symbols used throughout Schemes I to XIII:

AA hydrogen, halogen (chloro, bromo, iodo) or —$OSO_2CF_3$;

BB suitable nitrogen protecting group, exemplified by methoxymethyl-[MOM], benzyloxymethyl-[BOM], 2-(trimethylsilyl)ethoxymethyl-[SEM], methoxyethoxymethyl-[MEM], or t-butyl groups;

DD $S_n2$ or $S_n1$ leaving group exemplified by halogen (Cl, Br, I) and sulfonates (—$OSO_2$-aryl (e.g., —$OSO_2Ph$ or —$OSO_2PhCH_3$), or —$OSO_2$-alkyl (e.g., —$OSO_2CH_3$ or —$OSO_2CF_3$));

EE halogen (chloro, bromo, iodo) or —$OSO_2CF_3$;

Exemplary conditions for forming and removing suitable nitrogen protecting groups may be found in T. W. Greene and P. G. M. Wuts, *Protecting Groups in Organic Synthesis*, John Wiley & Sons, Inc, New York, 1991, pp. 309–405. One skilled in the art can also recognize that the heteroaryl sulfonamide-NH in compounds of the invention will also have carboxylic acid character, and accordingly, methods used to protect carboxylic acids may be applicable to protecting the nitrogen NH of the sulfonamides in the invention, including intermediates to compounds of formula I. Exemplary conditions for forming and removing suitable carboxylic acid protecting groups may be found in T. W. Greene and P. G. M. Wuts, *Protecting Groups in Organic Synthesis*, John Wiley & Sons, Inc, New York, 1991, pp. 175–276.

SCHEME I

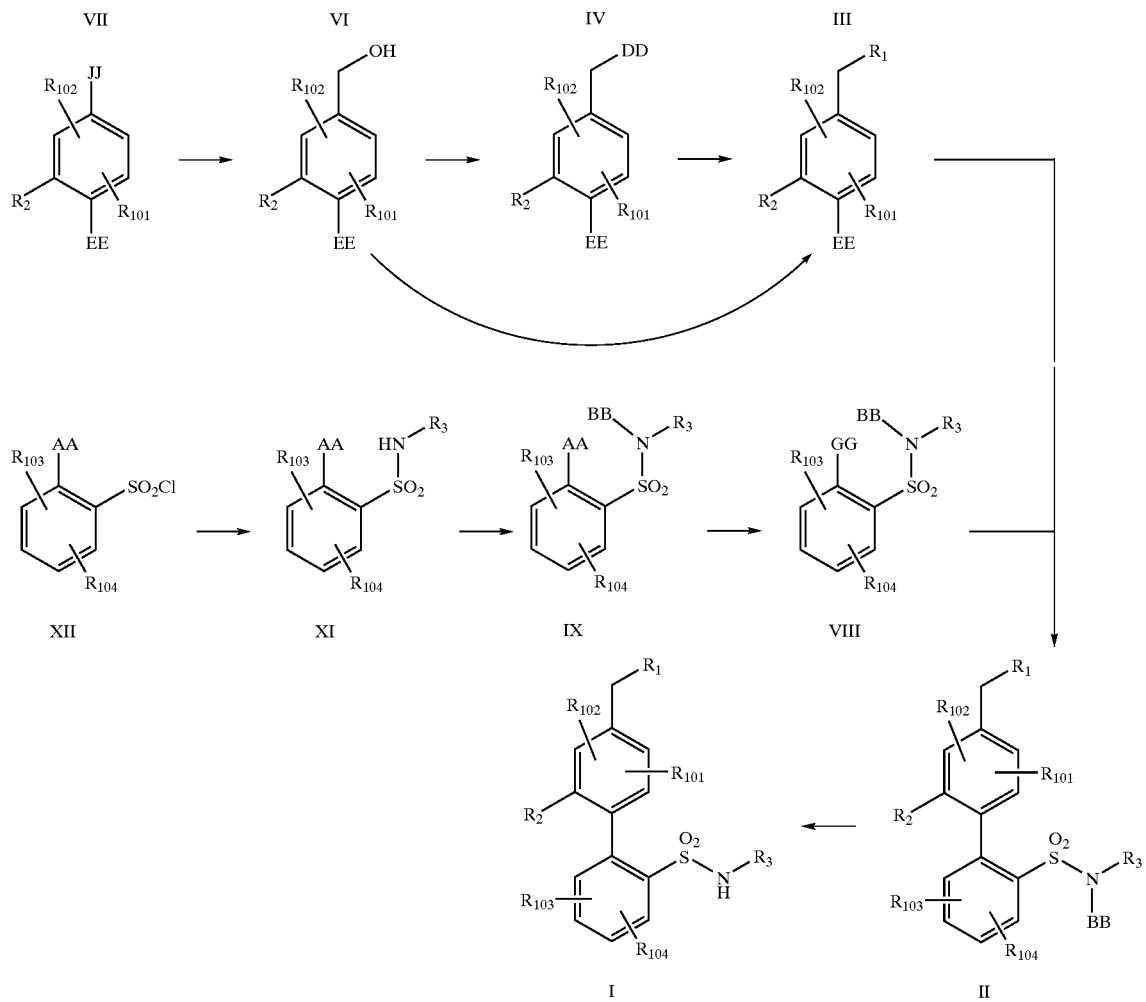

GG boronate ester or boronic acid, or trialkylstannane;

HH metal atom such as tin, zinc, magnesium or lithium as part of an organometallic compound used as an intermediate for transition metal mediated aryl-aryl coupling reactions;

JJ —CN, —CHO, or —$CO_2R_{20}$ wherein $R_{20}$ is hydrogen or $C_1$ to $C_3$ alkyl.

Compounds of formula I may be prepared from the deprotection of a compound of formula II wherein BB is a suitable nitrogen protecting group. Exemplary conditions for deprotection, and nitrogen protecting groups, may be found in T. W. Greene and P. G. M. Wuts, *Protecting Groups in Organic Synthesis*, John Wiley & Sons, Inc, New York, 1991, pp. 309–405. Preferred nitrogen protecting groups are the methoxymethyl (MOM), methoxyethoxymethyl (MEM), and 2-(trimethylsilyl)ethoxymethyl (SEM) groups.

Compounds of formula II may be prepared from a palladium catalyzed coupling of a compound of formula III with a compound of formula VIII, in the presence of a suitable base in an inert solvent. Exemplary palladium catalysts include tetrakis(triphenylphosphine) palladium(0), palladium(II) chloride or palladium(II) acetate. The preferred palladium catalyst is tetrakis(triphenylphosphine) palladium(0). Exemplary bases include tertiary amines, such as, but not limited to, triethylamine, or aqueous potassium, sodium, or cesium carbonate. The preferred base is aqueous sodium carbonate. Exemplary solvents include tetrahydrofuran, 1,4-dioxane, acetonitrile, toluene, benzene, or straight chain alcohols, or a combination thereof The preferred solvent is a mixture of toluene and ethanol. Exemplary reaction temperatures are between about 25° C. to 125° C., preferably between about 65° C. and 110° C.

Compounds of formula III may be prepared from a compound of formula IV via displacement of the leaving group (DD) by the conjugate base of a compound $R_1$—H, wherein $R_1$ is as previously defined, using a base in an inert solvent. Exemplary bases include sodium carbonate, potassium carbonate, cesium carbonate, sodium hydride, potassium hydride, or alkyl lithiums. The preferred base is sodium hydride. Exemplary inert solvents include ethers (tetrahydrofuran, 1,4-dioxane, diethyl ether), or N,N-dimethylformamide. The preferred solvent is N,N-dimethylformamide. Exemplary reaction temperatures are between about 0° C. to 154° C., preferably between about 65° C. and 110° C.

Compounds of formula III may also be prepared via a Mitsunobu reaction between a compound of formula VI and the conjugate acid $R_1$—H, preferably using a phosphine and oxidizing agent, in an inert solvent. Exemplary phosphines include trialkylphosphines, triarylphosphines and polymer supported triarylphosphines. The preferred phosphine is triphenylphosphine. Exemplary oxidizing reagents include diethyl azodicarboxylate, diisopropyl azodicarboxylate, or carbon tetrabromide. The preferred oxidizing reagent is diethyl azodicarboxylate. Exemplary inert solvents include ethers (tetrahydrofuran, 1,4-dioxane, diethyl ether), acetonitrile or N,N-dimethylformamide. The preferred solvent is N,N-dimethylformamide. Exemplary reaction temperatures are between about 0° C. to 154° C., preferably between about 20° C. and 65° C.

Compounds of formula IV (especially, where DD is $—OSO_2Ph$, $—OSO_2PhCH_3$, $—OSO_2CH_3$, $—OSO_2CF_3$) may be prepared from the reaction of a compound of formula VI with $ClSO_2Ph$, $ClSO_2PhCH_3$, $ClSO_2CH_3$ or $(CF_3SO_2)_2O$ in the presence of a base in an inert solvent.

Compounds of formula VI may be prepared from reduction of a compound of formula VII using a suitable reducing agent in an inert solvent.

Compounds of formula VII are either commercially available or available by means known to one skilled in the art.

Compounds of formula VIII may be prepared via lithiation of a compound of formula IX wherein AA is hydrogen or a halogen (chloro, bromo, iodo), and reacting the resulting aryl lithium with an appropriate borate derivative.

Compounds of formula IX may be prepared via the protection of the nitrogen in a compound of formula XI. Exemplary nitrogen protecting groups and methods of protecting the nitrogen are similar to those for protecting amines, such as those described in T. W. Greene and P. G. M. Wuts, *Protecting Groups in Organic Synthesis*, John Wiley & Sons, Inc, New York, 1991.

Compounds of formula XI may be prepared from the reaction of a compound of formula XII with a compound $R_3$—$NH_2$.

Compounds of the formula XII are either commercially available or available by means known to one skilled in the art.

SCHEME II

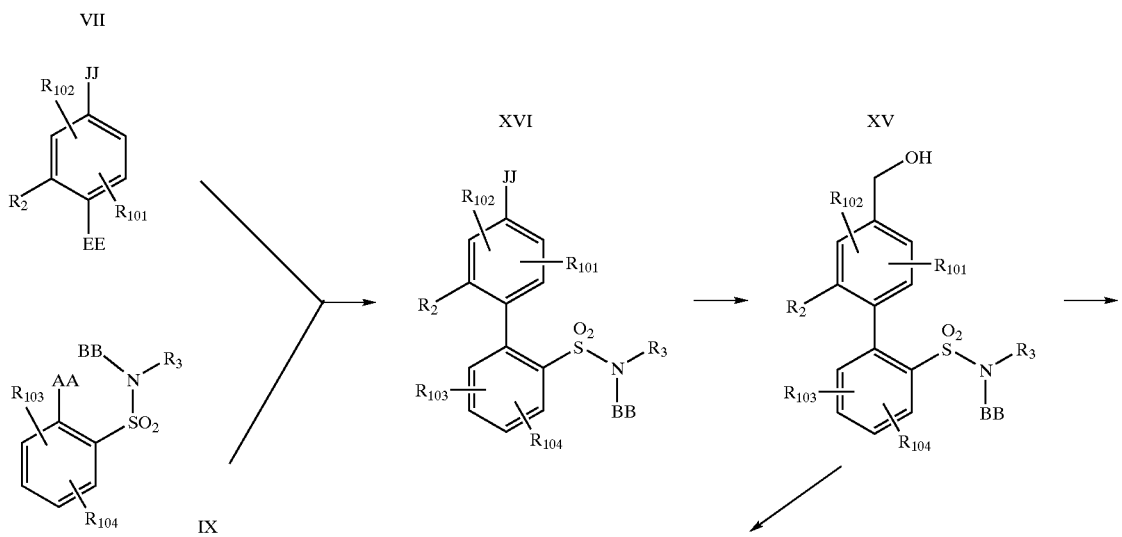

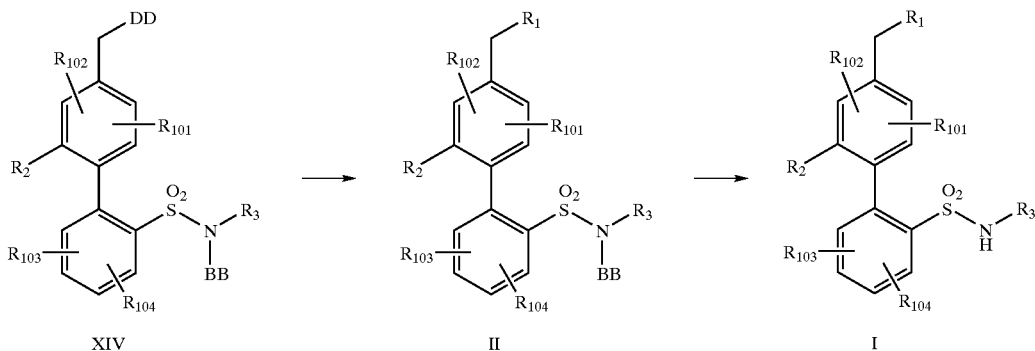

Compounds of formula I may be prepared from the deprotection of a compound of formula II as described in Scheme I.

Compounds of formula II may be prepared from a compound of formula XIV via displacement of the leaving group (DD) by the conjugate base of a compound $R_1$—H, wherein $R_1$ is as previously defined, using a base in an inert solvent. Exemplary bases include sodium carbonate, potassium carbonate, cesium carbonate, sodium hydride, potassium hydride, or alkyl lithiums. The preferred base is sodium hydride. Exemplary inert solvents include ethers (tetrahydrofuran, 1,4-dioxane, diethyl ether), or N,N-dimethylformamide. The preferred solvent is N,N-dimethylformamide. Exemplary reaction temperatures are between about 0° C. to 154° C., preferably between about 25° C. and 110° C.

Compounds of formula II may also be prepared via a Mitsunobu reaction between a compound of formula XV and the conjugate acid $R_1$—H using a phosphine and oxidizing agent in an inert solvent. Exemplary phosphines include trialkylphosphines, triarylphosphines and polymer supported triarylphosphines. The preferred phosphine is triphenylphosphine. Exemplary oxidizing reagents include diethyl azodicarboxylate, diisopropyl azodicarboxylate, or carbon tetrabromide. The preferred oxidizing reagent is diethyl azodicarboxylate. Exemplary inert solvents include ethers (tetrahydrofuran, 1,4-dioxane, diethyl ether), acetonitrile or N,N-dimethylformamide. The preferred solvent is N,N-dimethylformamide. Exemplary reaction temperatures are between about 0° C. to 154° C., preferably between about 20° C. and 65° C.

Compounds of formula XIV may be prepared from compounds of formula XV using methods well known in the art. For example, compounds of formula XIV (DD=Br) may be prepared by the treatment of compound XV with carbon tetrabromide and triphenylphosphine in a suitable solvent such as toluene or tetrahydrofuran.

Compounds of formula XV may be prepared from reduction of a compound of formula XVI using a suitable reducing agent in an inert solvent. $R_2$ is preferably not an amide, an ester, a carboxylic acid or an aldehyde during this operation.

Compounds of formula XVI may be prepared from a palladium catalyzed coupling of a compound of formula VII with a compound of formula IX in the presence of a suitable base and an inert solvent as described in Scheme I.

Compounds of formula VII are available by means known to one skilled in the art.

SCHEME III

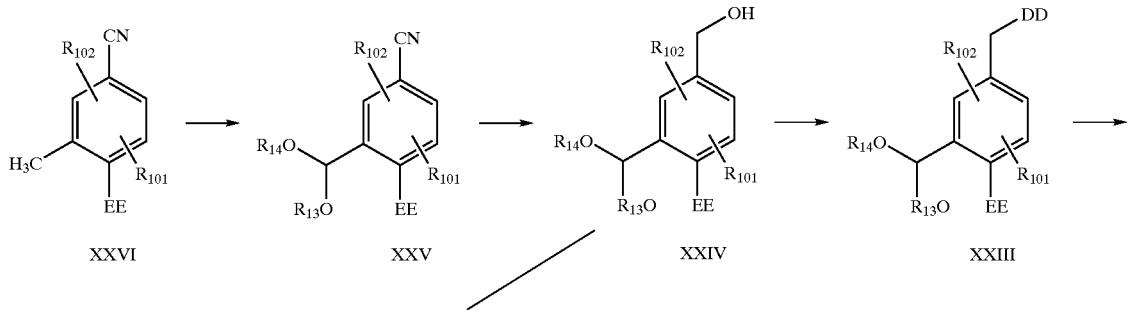

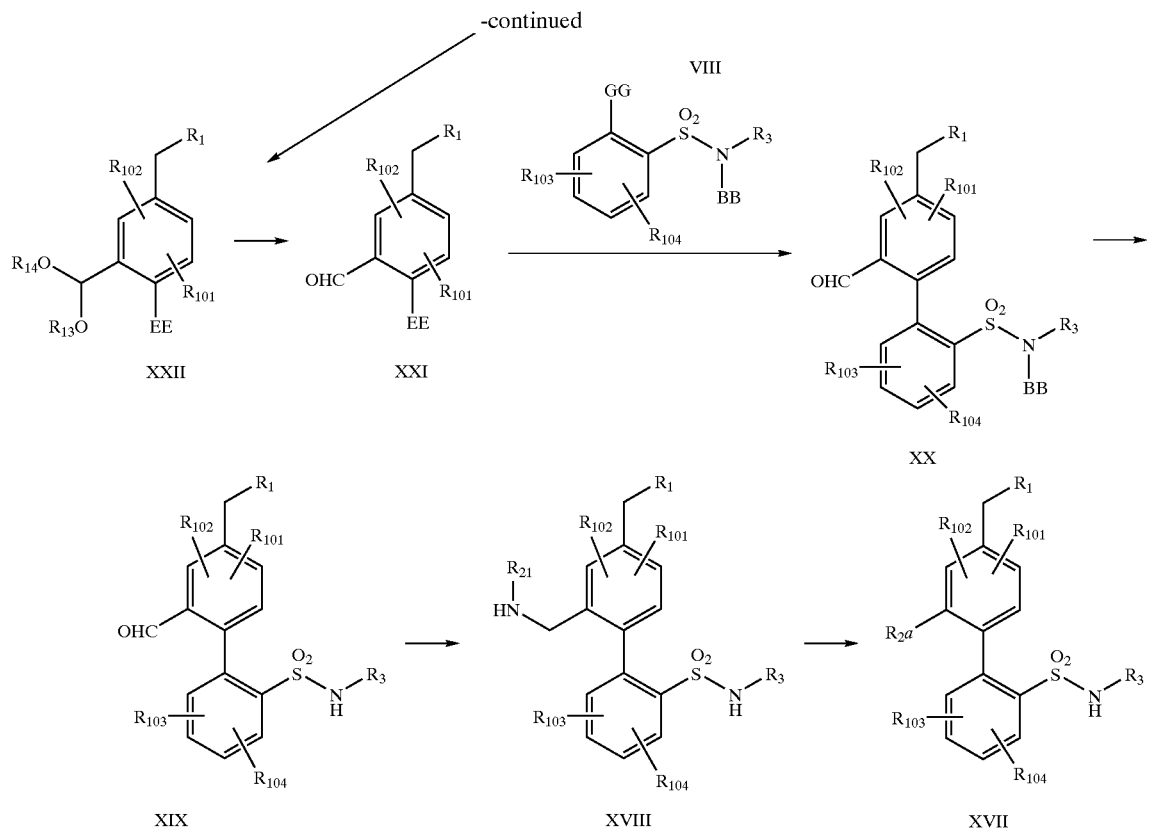

Compounds of formula XVII (which are compounds of formula I wherein $R_2$ is $R_{2a}$ where $R_{2a}$ is —$CH_2N(R_{21})$(C=O)N($R_{19}$)$R_{20}$, —$CH_2N(R_{21})$(C=O)$OR_{18}$ or —$CH_2N$($R_{21}$)(C=O)$R_{22}$), may be prepared from compounds of formula XVIII (also compounds of formula I, where $R_2$ is —$CH_2NHR_{21}$) by reaction of a compound of formula XVIII with an active ester (i.e., from a carboxylic acid such as $R_{22}$COOH in the presence of a suitable coupling agent such as dicyclohexylcarbodimide (DCC)), or an acid chloride (i.e., $R_{22}$(C=O)Cl), or an isocyanate (i.e., $R_{19}$N=C=O), or a chloroformate (i.e., $R_{18}$O(C=O)Cl) in the presence of a suitable base such as triethylamine and catalyst such as 4-dimethylaminopyridine in an inert solvent. This step may, for example, be conducted combinatorially and a library of such compounds created.

Compounds of formula XVIII may be prepared from reductive amination of compounds of formula XIX (compounds of formula I where $R_2$ is —CHO) using a primary amine such as $R_{21}NH_2$ in the presence of a suitable reducing agent such as sodium triacetoxyborohydride in an inert solvent.

Compounds of formula XIX may be prepared by deprotection of compounds of formula XX wherein BB is a suitable nitrogen protecting group as described in Scheme I.

Compounds of formula XX may be prepared from a palladium catalyzed coupling of a compound of formula XXI with a compound of formula VIII in the presence of a suitable base and an inert solvent as described in Scheme I.

Compounds of formula XXI may be prepared in two steps from a compound of formula XXIII, first by displacement of the leaving group (DD) by the conjugate base of a compound $R_1$—H, wherein $R_1$ is as previously defined using a suitable base in an inert solvent as described in Scheme I to provide a compound of formula XXII. Subsequent deprotection of the acetal in a compound of formula XXII using methods known in the art is employed to provide a compound of formula XXI.

Compounds of formula XXII may also be prepared via a Mitsunobu reaction between a compound of formula XXIV and the conjugate acid $R_1$—H using a phosphine and oxidizing agent in an inert solvent. Exemplary phosphines include trialkylphosphines, triarylphosphines and polymer supported triarylphosphines. Exemplary oxidizing reagents include diethyl azodicarboxylate, diisopropyl azodicarboxylate, or carbon tetrabromide. Exemplary inert solvents include ethers (tetrahydrofuran, 1,4-dioxane, diethyl ether), acetonitrile or N,N-dimethylformamide.

Compounds of formula XXIII may be prepared from compounds of formula XXIV using methods well known in the art. For example, compounds of formula XXIII (DD=Br) may be prepared by the treatment of compound XXIV with carbon tetrabromide and triphenylphosphine in a suitable solvent such as toluene or tetrahydrofuran.

Compounds of formula XXIV may be prepared in two steps from compound XXV via a partial reduction of the nitrile group to the aldehyde using a suitable reducing agent such as diisobutylaluminum hydride, with subsequent reduction of the aldehyde to hydroxymethyl using an agent such as sodium borohydride.

Methods for the preparation of compounds XXV and XXVI are known in the art [H.-Y. Zhang, et al., *Tetrahedron*, 50, 11339–11362 (1994)].

SCHEME IV

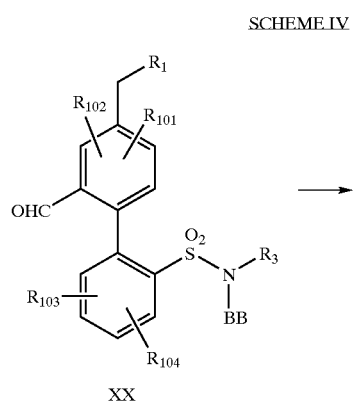

XX

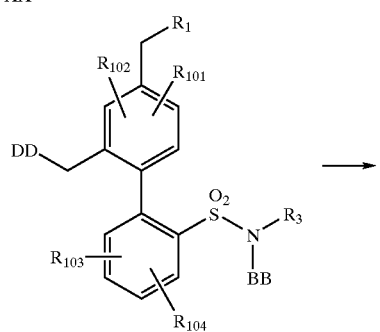

XXXI

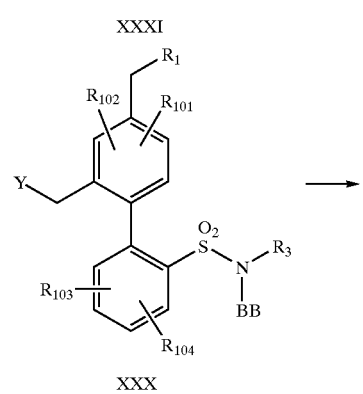

XXX

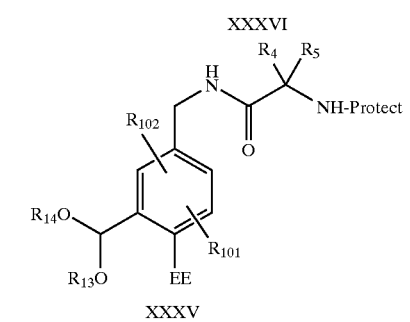

XXIX

Compounds of formula XXIX (which are compounds of formula I where $R_2$ is —$CH_2Y$) may be prepared from the deprotection of a compound of formula XXX such as is described in Scheme I.

Compounds of formula XXX may be prepared from a compound of formula XXI via displacement of the leaving group (DD) by the conjugate base of a compound Y—H, wherein Y is as previously defined using a base in an inert solvent. Exemplary bases include sodium carbonate, potassium carbonate, cesium carbonate, sodium hydride, potassium hydride, or alkyl lithiums. The preferred base is sodium hydride.

Compounds of formula XMI may be prepared from compounds of formula XX using methods well known in the art. For example, compounds of formula XXI (DD=Br) may be prepared from compound XX in two steps: first by reducing the aldehyde to a hydroxymethyl group using a suitable reducing agent such as sodium borohydride, and second, conversion of the hydroxymethyl group to the bromomethyl function using carbon tetrabromide and triphenylphosphine in a suitable solvent such as toluene or tetrahydrofuran.

SCHEME V

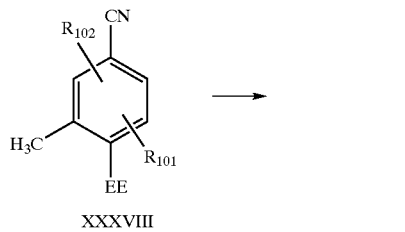

XXXVIII

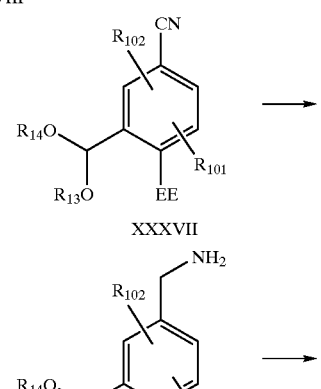

XXXVII

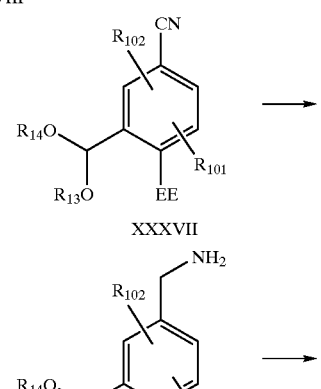

XXXVI

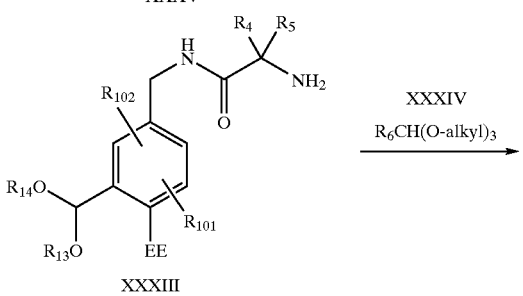

XXXV

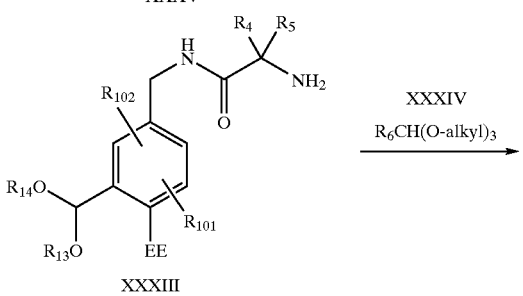

XXXIV $R_6CH(O\text{-alkyl})_3$

XXXIII

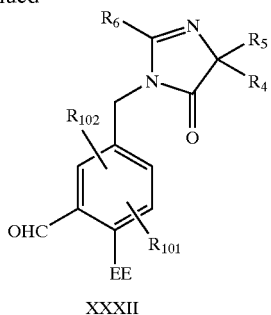

XXXII

Compounds of formula XXII (which may be employed, for example, in the methods of the preceding Schemes) may be prepared by cyclization of compounds of formula XXXII in the presence of orthoester XXIV using a catalytic amount of a weak acid such as acetic acid. Exemplary reaction temperatures are between about 25° C. to 154° C., preferably between about 60° C. and 110° C.

Compounds of formula XXIII (e.g., where $R_{13}$ and $R_{14}$, together with the atoms to which they are bonded, form the five-membered ring

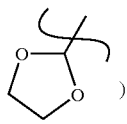

may be prepared from compounds of formula XXXVI in two steps: (1) acylation of compound XXXVI with an N-protected amino acid in the presence of a suitable coupling agent such as dicyclohexylcarbodiimide (DCC) or (benzotriazol-1-yloxy)tripyrrolidinophosphonium hexafluorophosphate (PyBOP) in a suitable solvent such as N,N-dimethylformamide, and (2) removal of the protecting group. Suitable conditions and suitable nitrogen protecting groups and the corresponding deprotection conditions may be found in T. W. Greene and P. G. M. Wuts, *Protecting Groups in Organic Synthesis*, John Wiley & Sons, Inc, New York, 1991, pp. 309–405.

Compounds of formula XXXVI may be prepared via reduction of a compound of formula XXXVII using an appropriate reducing agent such as diborane or lithium aluminum hydride in an appropriate solvent such as tetrahydrofuran.

Compounds of formula XXXVII may be prepared from compounds of formula XXXVIII as described in Scheme III.

Compounds of formula XXXXII may be prepared by methods known in the art.

SCHEME VI

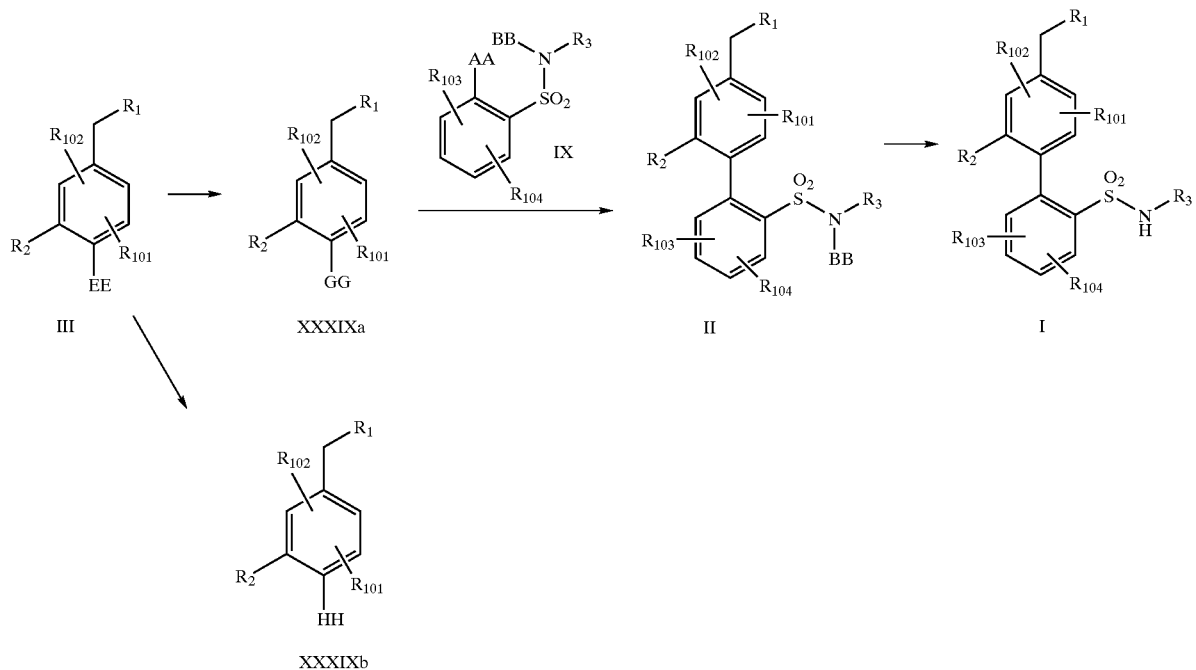

Compounds of formula I may be prepared from the deprotection of a compound of formula II as described in Scheme I.

Compounds of formula II may be prepared by a palladium catalyzed coupling of a compound of formula IX (as described in Scheme I) wherein AA here is —OSO$_2$CF$_3$ or a halogen (chlorine, bromine, or iodine; preferably bromine or iodine) with a compound of formula XXXIXa, wherein GG is a boronic acid or ester, in the presence of a base and an inert solvent as described in Scheme I.

Compounds of formula II may also be prepared by a palladium or nickel catalyzed coupling of a compound of formula IX (as described in Scheme I) wherein AA is a halogen (chlorine, bromine, or iodine; preferably bromine or iodine) with a compound of formula XXXIXb wherein HH is a suitable metal atom bearing appropriate ligands. Exemplary metal atoms include tin, zinc, magnesium, and lithium. Exemplary catalysts include tetrakis(triphenylphosphine)palladium(0) and dichlorobis(triphenylphosphine)nickel(II).

Compounds of formula XXXIXa or XXXIXb may be prepared via lithiation of a compound of formula III wherein EE is a halogen (chlorine, bromine, or iodine; preferably bromine or iodine), then reacting the resulting aryl lithium with an appropriate borate derivative or with an appropriate zinc, tin, or magnesium reagent.

Compounds of formula III may be prepared by the methods described in Scheme I.

SCHEME VII

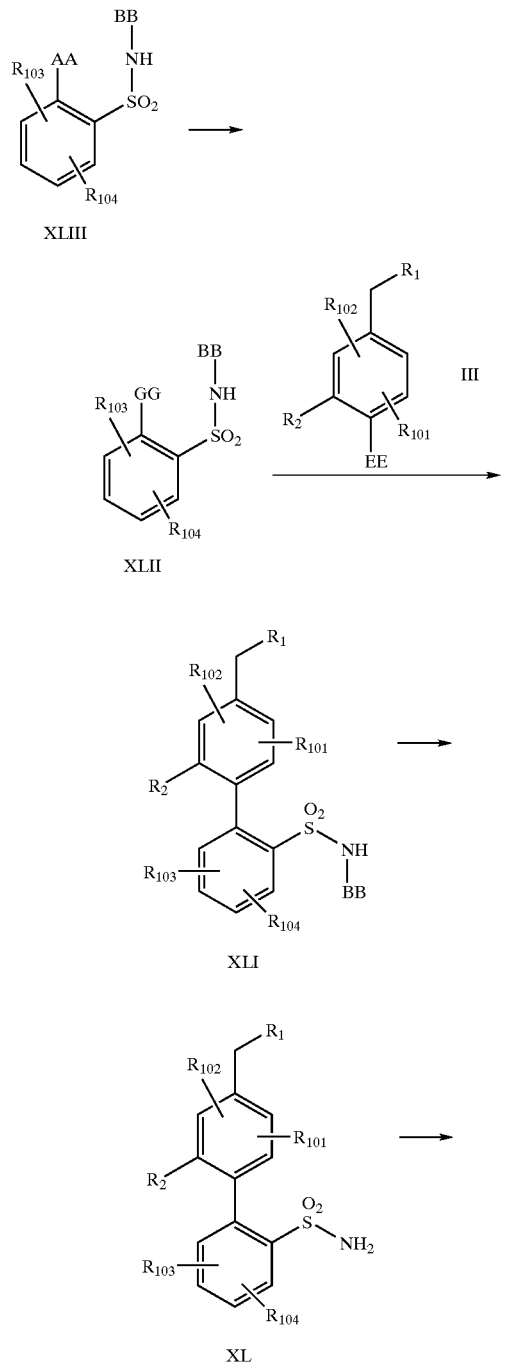

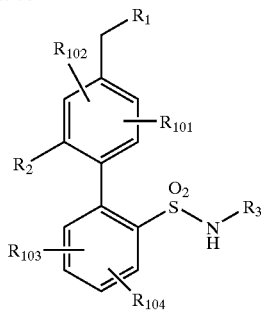

Compounds of formula I may be prepared from the thermal reaction of a compound of formula XL with a heterocyclic compound of formula $R_3$—X, wherein X is a halogen (fluorine, chlorine, bromine, or iodine), in the presence of a base and an inert solvent. Exemplary bases include sodium hydride, potassium carbonate, potassium hydride, and potassium bis(trimethylsilyl)amide, preferably sodium hydride. Exemplary solvents include N,N-dimethylformamide and N,N-dimethylacetamide. Exemplary reaction temperatures are between about 80° C. and 150° C., preferably between 110° C. and 130° C.

Compounds of formula I may also be prepared from the reaction of a compound of formula XL with a heterocyclic compound of formula $R_3$—X, wherein X is a halogen (chlorine, bromine, or iodine), in the presence of a palladium catalyst, a phosphine ligand, a base, and an inert solvent. Exemplary palladium catalysts include palladium acetate and tris(dibenzylideneacetone)palladium(0), and the preferred palladium catalyst is palladium acetate. The preferred phosphine ligand is 2,2'-bis(diphenylphosphino)-1,1'-binaphthyl. Exemplary bases include sodium hydride and sodium t-butoxide. The preferred base is sodium hydride. Exemplary reaction temperatures are between about 20° C. and 110° C., preferably between 85° C. and 110° C.

Compounds of formula XL may be prepared by deprotection of a compound of formula XLI, wherein BB is a suitable nitrogen protecting group. Exemplary conditions for protection and deprotection of nitrogen functionalities may be found in T. W. Greene and P. G. M. Wuts, *Protecting Groups in Organic Synthesis*, John Wiley & Sons, Inc., New York, 1991, pp. 309–405. The preferred protecting group BB for Scheme VII is tertiary-butyl. Exemplary deprotection conditions include the use of acids, such as trifluoroacetic acid.

Compounds of formula XLI may be prepared by a palladium catalyzed coupling of a compound of formula III (as described in Scheme I) wherein EE is a halogen (chlorine, bromine, or iodine; preferably bromine or iodine) with a compound of formula XLII, wherein GG is a boronic acid or ester, in the presence of a base and an inert solvent as described in Scheme I.

Compounds of formula XLII may be prepared via the lithiation of a compound of formula XLIII in an inert solvent, followed by reacting the resulting aryl lithium with an appropriate borate derivative. Exemplary reagents for the lithiation reaction include n-butyllithium and t-butyllithium. Exemplary solvents include ethers such as tetrahydrofuran, either alone or in combination with hydrocarbon solvents such as hexane. The preferred solvent is a mixture of tetrahydrofuran and hexane.

Compounds of formula XLIII are either commercially available or available by means known to one skilled in the art.

SCHEME VIII

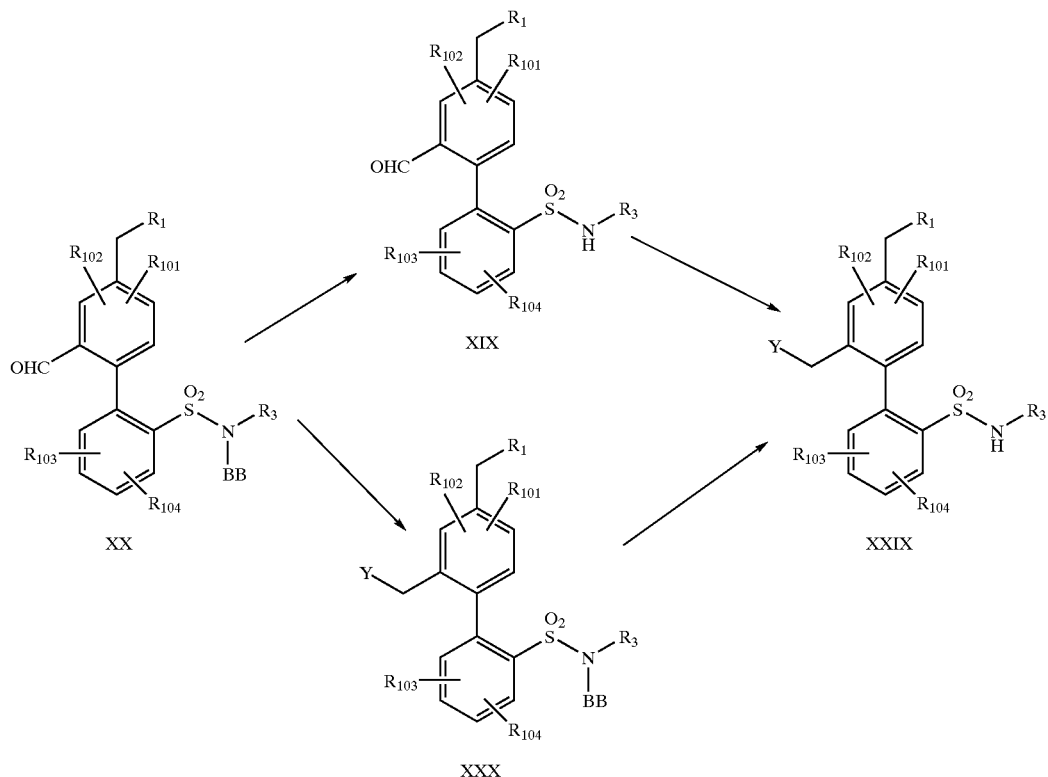

Compounds of formula XXIX (which are certain compounds of formula I where $R_2$ is —$CH_2Y$, as described in Scheme IV) may be prepared from a compound of formula XIX (which is a compound of formula I where $R_2$ is —CHO, as described in Scheme III) via a two step process: 1) reductive amination of XIX in the presence of a primary amine $R_{30}NH_2$, wherein $R_{30}$ is carboxyalkyl, alkoxycarbonylalkyl, hydroxyalkyl, or aminoalkyl, using a suitable reducing agent such as sodium triacetoxyborohydride, yields an intermediate amine; 2) subsequent cyclization using an appropriate cyclization reagent yields a compound of formula XXIX. When $R_{30}$ is carboxyalkyl, appropriate cyclization reagents include carbodiimides such as diisopropylcarbodiimide. When $R_{30}$ is hydroxyalkyl or aminoalkyl, appropriate cyclization reagents include phosgene and 1,1'-carbonyldiimidazole.

When $R_{30}$ is alkoxycarbonylalkyl, appropriate cyclization reagents include tertiary amine bases such as triethylamine and N,N-diisopropylethylamine.

Compounds of formula XIX may be prepared via deprotection of a compound of formula XX as described in Scheme III.

Compounds of formula XXIX may also be prepared by deprotection of a compound of formula XXX as described in Scheme I.

Compounds of formula XXX may be prepared from a compound of formula XX, using the two step process described above for the formation of compounds of formula XXIX from a compound of formula XIX.

SCHEME IX

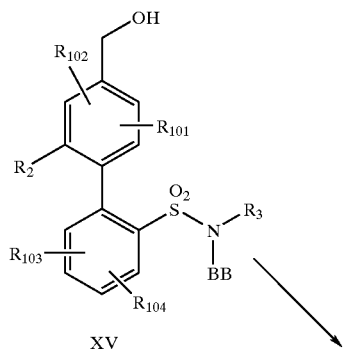

XV

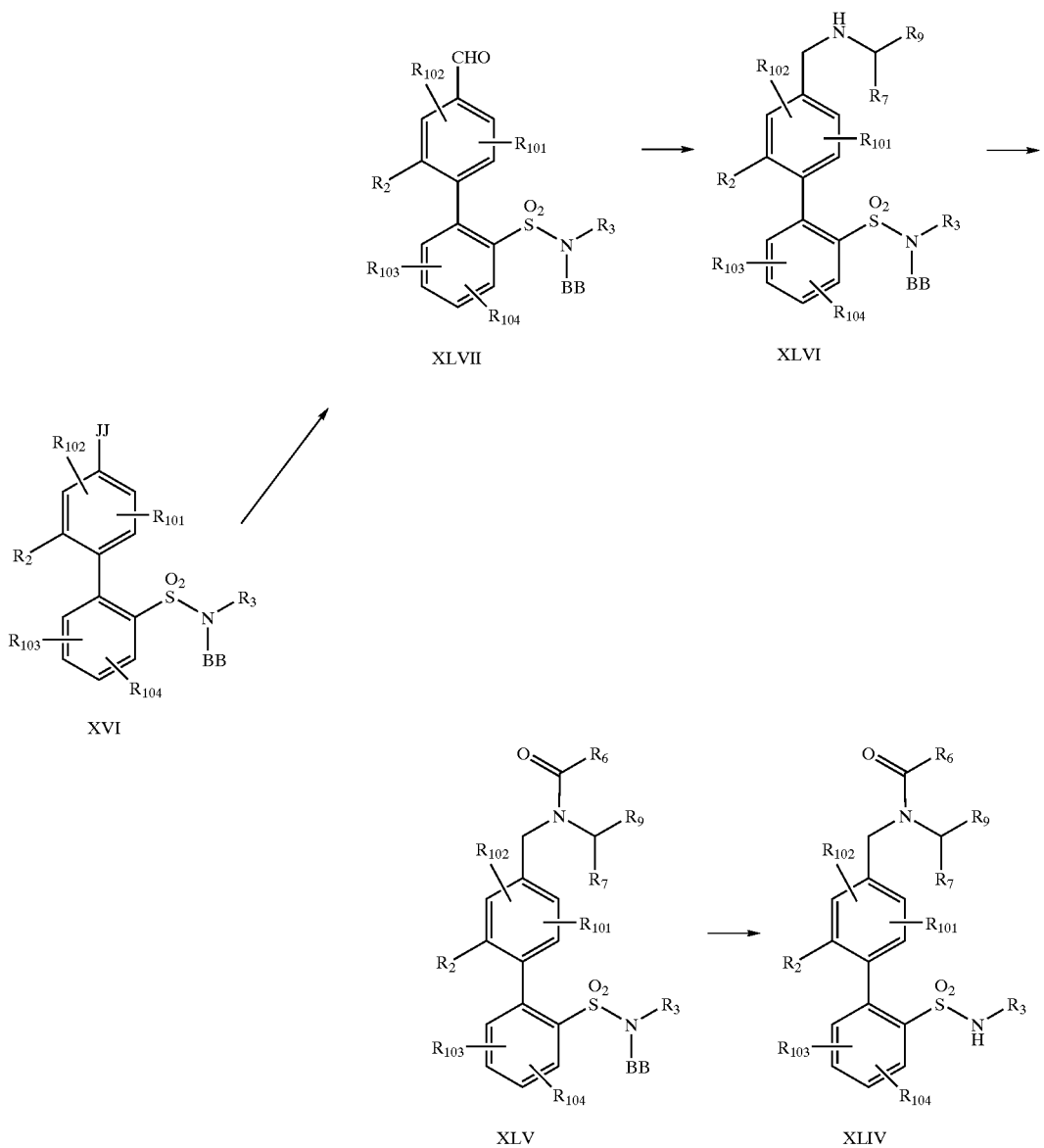

Compounds of formula XLIV (which are compounds of formula I wherein $R_1$ is D as defined for formula I) may be prepared from the deprotection of a compound of formula XLV as described in Scheme I.

Compounds of formula XLV may be prepared via the acylation of a compound of formula XLVI using either a carboxylic acid such as $R_6COOH$ in the presence of a suitable coupling agent such as dicyclohexylcarbodiimide, or the corresponding acid chloride or acid anhydride in the presence of a suitable base such as triethylamine.

Compounds of formula XLVI may be prepared from reduction of a compound of formula XLVII in the presence of a primary amine such as $H_2NCHR_7R_9$ in the presence of a suitable reducing agent such as sodium triacetoxyborohydride.

Compounds of formula XLVII may be prepared via reduction of a compound of formula XVI, as described in Scheme II, wherein JJ is —CN, or —$CO_2R_{20}$ wherein $R_{20}$ is hydrogen or $C_1$ to $C_3$ alkyl, using means known to one skilled in the art.

Compounds of formula XLVII may also be prepared via oxidation of a compound of formula XV, as defined in Scheme II, using means known to one skilled in the art.

SCHEME X

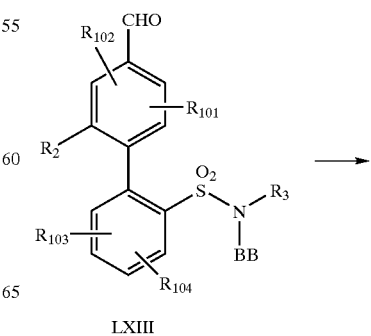

LXIII

SCHEME XI

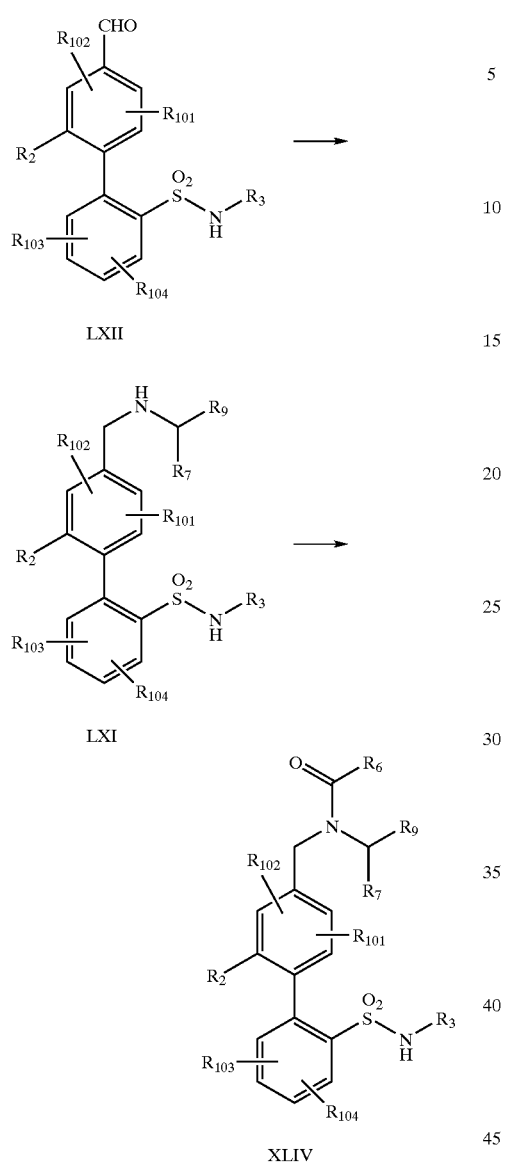
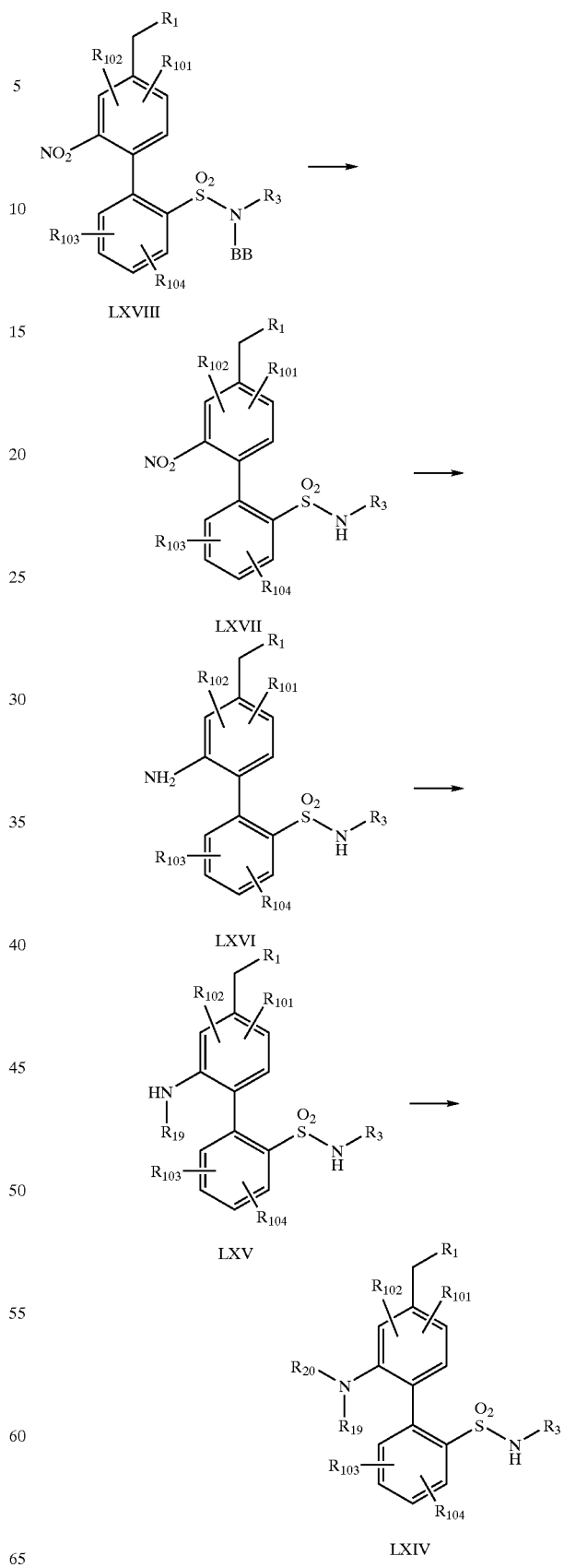

Compounds of formula XLIV (which are compounds of formula I wherein $R_1$ is D as defined for formula I) may be prepared by the acylation of a compound of formula LXI using either a carboxylic acid such as $R_6COOH$ in the presence of a suitable coupling agent such as dicyclohexylcarbodiimide, or the corresponding acid chloride or acid anhydride in the presence of a suitable base such as triethylamine.

Compounds of formula LXI may be prepared by the reduction of a compound of formula LXII in the presence of a primary amine such as $H_2NCHR_7R_9$ in the presence of a suitable reducing agent such as sodium triacetoxyborohydride.

Compounds of formula LXII may be prepared via deprotection of a compound of formula LXIII (which is a compound of formula XVI wherein JJ is CHO), as described in Scheme I.

Compounds of formula LXIV (which are compounds of formula I wherein $R_2$ is $-N(R_{19})R_{20}$) may be prepared via reduction of a compound of formula LXV in the presence of an aliphatic, aromatic, or heteroaromatic aldehyde using a suitable reducing agent such as sodium triacetoxyborohydride.

Compounds of formula LXV (which are compounds of formula I wherein $R_2$ is $-NHR_{19}$) may be similarly prepared via reduction of a compound of formula LXVI in the presence of an aliphatic, aromatic, or heteroaromatic aldehyde using a suitable reducing agent such as sodium triacetoxyborohydride.

Compounds of formula LXVI (which are compounds of formula I wherein $R_2$ is $-NH_2$) may be prepared by reduction of a compound of formula LXVII using a suitable reducing agent such as tin (II) chloride dihydrate in a suitable solvent such as ethyl acetate.

Compounds of formula LXVII (which are compounds of formula I wherein $R_2$ is $-NO_2$) may be prepared by deprotection of a compound of formula LXVIII as described in Scheme I.

Compounds of formula LXVIII (which are compounds of formula II wherein $R_2$ is $-NO_2$) may be prepared by the methods described for the preparation of compounds of formula II in Schemes I and II.

sponding sulfonic anhydride, in the presence of a suitable base such as triethylamine.

SCHEME XIII

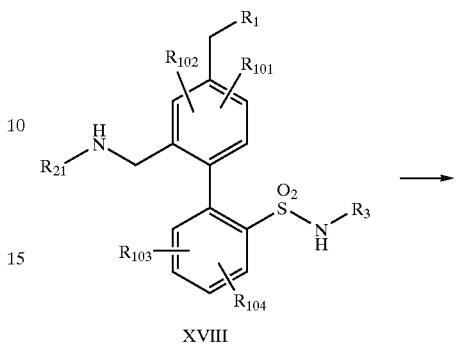

XVIII

SCHEME XII

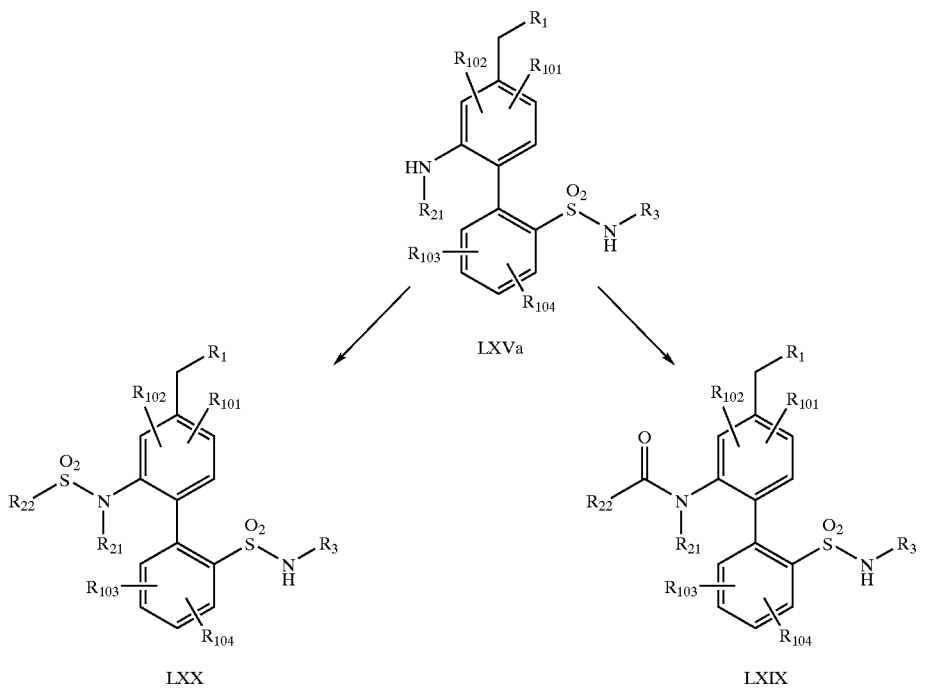

Compounds of formula LXIX (which are compounds of formula I wherein $R_2$ is $-N(R_{21})(C=O)R_{22}$) may be prepared via acylation of a compound of formula LXVa (prepared as described in Scheme XI for a compound of formula LXV) using either a carboxylic acid such as $R_{22}COOH$ in the presence of a suitable coupling agent such as dicyclohexylcarbodiimide, or the corresponding acid chloride or acid anhydride in the presence of a suitable base such as triethylamine.

Compounds of formula LXX (which are compounds of formula I wherein $R_2$ is $-N(R_{21})SO_2R_{22}$) may be prepared via sulfonylation of a compound of formula LXVa using either a sulfonyl chloride such as $R_{22}SO_2Cl$ or the corre- -continued

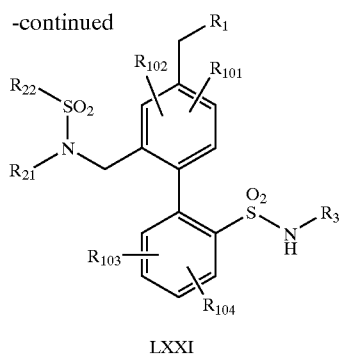

LXXI

Compounds of formula LXXI (which are compounds of formula I wherein $R_2$ is —$CH_2N(R_{21})(SO_2R_{22})$) may be prepared via sulfonylation of a compound of formula XVIII (prepared as described in Scheme III) using either a sulfonyl chloride such as $R_{22}SO_2Cl$ or the corresponding sulfonic anhydride in the presence of a suitable base such as triethylamine.

The present invention further provides the following novel compounds, which may be employed as intermediates in the preparation of compounds of the formula I and salts thereof:

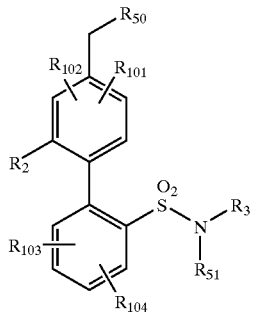

LV wherein $R_2$, $R_3$, $R_{101}$, $R_{102}$, $R_{103}$, and $R_{104}$ are as defined for a compound of formula I, $R_{50}$ is hydroxy, chloro, bromo, iodo, —$OSO_2$-alkyl, or —$OSO_2$-aryl, and $R_{51}$ is hydrogen, —$CH_2OCH_2CH_2OCH_3$, —$CH_2OCH_2CH_2Si(CH_3)_3$, —$CH_2OCH_3$, —$CH_2OCH_2$-aryl, or other suitable nitrogen protecting group;

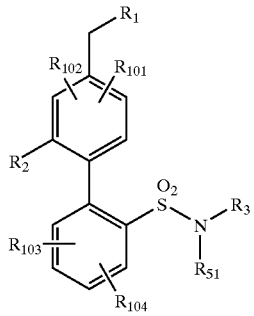

LVI wherein $R_1$, $R_2$, $R_3$, $R_{101}$, $R_{102}$, $R_{103}$, and $R_{104}$ are as defined for a compound of formula I and BB is —$CH_2OCH_2CH_2OCH_3$, —$CH_2OCH_2CH_2Si(CH_3)_3$, —$CH_2OCH_3$, —$CH_2OCH_2$-aryl, or other suitable nitrogen protecting group; and

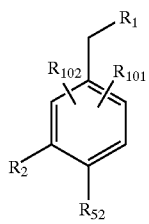

LVII wherein $R_1$, $R_2$, $R_{101}$, and $R_{102}$ are as defined for a compound of formula I, and $R_{52}$ is chloro, bromo, iodo, or —$OSO_2CF_3$.

The present invention also provides the following novel method for the preparation of a compound of the formula I or salt thereof, wherein said method comprises at least one of the following steps:

a) displacement of a leaving group $R_{50}$ via the anion of a compound $R_1$—H from a compound of the formula

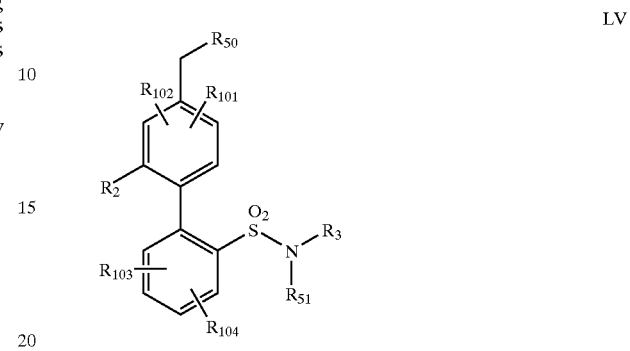

LV wherein $R_1$, $R_2$, $R_3$, $R_{101}$, $R_{102}$, $R_{103}$, and $R_{104}$ are as defined for a compound of formula I, $R_{50}$ is hydroxy, chloro, bromo, iodo, —$OSO_2$-alkyl or —$OSO_2$-aryl, and $R_{51}$ is hydrogen or a suitable nitrogen protecting group, using a Mitsunobu reaction or $S_n1$ or $S_n2$ displacement reaction, with removal of said nitrogen protecting group as appropriate;

b) removal of the nitrogen protecting group $R_{51}$ from a compound of formula

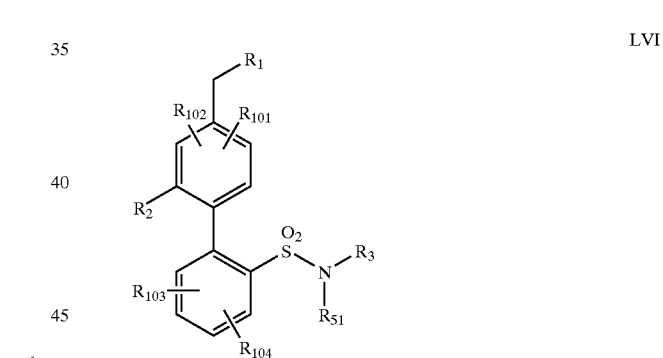

LVI wherein $R_1$, $R_2$, $R_3$, $R_{101}$, $R_{102}$, $R_{103}$, and $R_{104}$ are as defined for a compound of formula I, and $R_{51}$ is a suitable nitrogen protecting group;

c) organometallic coupling of a compound of formula

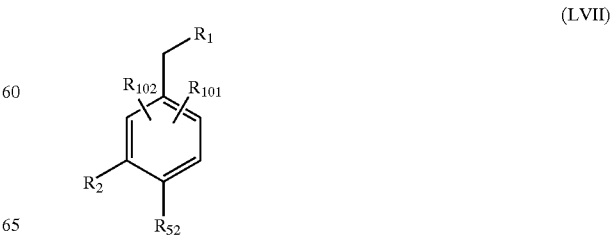

(LVII)

with a compound of formula

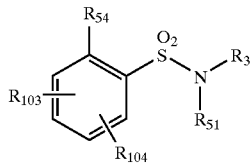
(LIX)

wherein $R_1$, $R_2$, $R_3$, $R_{101}$, $R_{102}$, $R_{103}$, and $R_{104}$ are as defined for a compound of formula I and $R_{51}$ is a suitable nitrogen protecting group. $R_{52}$ is chloro, bromo, iodo or $-OSO_2CF_3$ and $R_{54}$ is a boronic acid, boronic ester or stannane derivative. Or $R_{52}$ is a boronic acid, boronic ester or stannane derivative, and $R_{54}$ is chloro, bromo, iodo or $-OSO_2CF_3$;

d) acylation of a compound of the formula

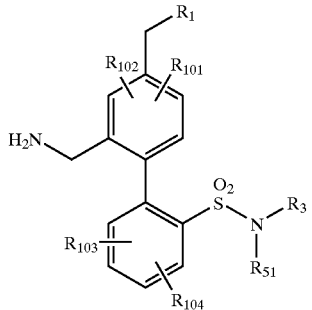
LX wherein $R_1$, $R_3$, $R_{101}$, $R_{102}$, $R_{103}$, and $R_{104}$ are as defined for a compound of formula I, and $R_{51}$ is hydrogen or a suitable nitrogen protecting group, with an acylating agent of the formula $R_{55}-(C=O)R_{22}$, $R_{19}N=C=O$, $R_{55}-CO_2R_{18}$, $R_{55}SO_2R_{22}$, wherein $R_{18}$, $R_{19}$ and $R_{22}$ are as defined for a compound of formula I and $R_{55}$ is an activating group for an acid, or made using an acid activating agent, with removal of said nitrogen protecting group as appropriate; or e) reductive amination of a compound of formula

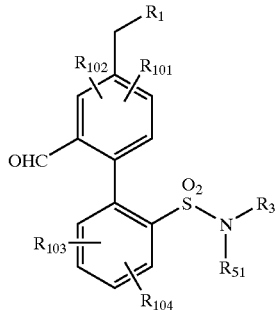
LXI wherein $R_1$, $R_3$, $R_{101}$, $R_{102}$, $R_{103}$, and $R_{104}$ are as defined for a compound of formula I, and $R_{51}$ is hydrogen or a suitable nitrogen protecting group, with an amine of the formula

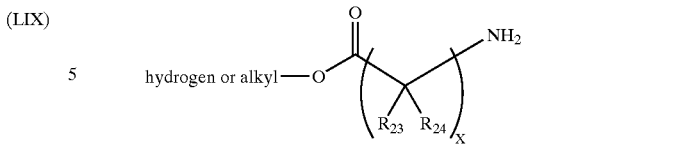
LXII wherein $R_{23}$, $R_{24}$, and x are as defined for a compound of formula I, with removal of said nitrogen protecting group as appropriate.

Utility

The compounds of formula I and salts thereof are antagonists of both endothelin (especially, ET-1) and angiotensin II (especially, subtype $AT_1$) receptors ("dual angiotensin endothelin receptor antagonists") and are useful in treatment of conditions associated with increased ET levels and/or increased angiotensin II levels and of all endothelin-dependent or angiotensin II-dependent disorders. They are thus useful as antihypertensive agents. By the administration of a composition having one (or a combination) of the compounds of this invention, the blood pressure of a hypertensive mammalian (e.g., human) host is reduced. They are also useful in portal hypertension, hypertension secondary to treatment with erythropoietin and low renin hypertension.

The compounds of the present invention are also useful in the treatment of disorders related to renal, glomerular and mesangial cell function, including acute (such as ischemic, nephrotoxic, or glomerulonephritis) and chronic (such as diabetic, hypertensive or immune-mediated) renal failure, diabetic nephropathy, glomerular injury, renal damage secondary to old age or related to dialysis, nephrosclerosis (especially hypertensive nephrosclerosis), nephrotoxicity (including nepuirotoxicity related to imaging and contrast agents and to cyclosporine), renal ischemia, primary vesicoureteral reflux, glomerulosclerosis and the like. The compounds of this invention are also useful in the treatment of disorders related to paracrine and endocrine function. The compounds of this invention are also useful in the treatment of diabetic nephropathy, hypertension-induced nephropathy, and IGA-induced nephropathy.

The compounds of the present invention are also useful in the treatment of endotoxemia or endotoxin shock as well as hemorrhagic shock. The compounds of the present invention are also useful in alleviation of pain associated cancer, such as the pain associated with prostate cancer, and bone pain associated with bone cancer. The compounds of the present invention are further useful in the prevention and/or reduction of end-organ damage associated the cell-poliferative effects of endothelin.

The compounds of the present invention are also useful in hypoxic and ischemic disease and as anti-ischemic agents for the treatment of, for example, cardiac, renal and cerebral ischemia and reperfusion (such as that occurring following cardiopulmonary bypass surgery), coronary and cerebral vasospasm, and the like.

In addition, the compounds of this invention are also useful as anti-arrhythmic agents; anti-anginal agents; anti-fibrillatory agents; antiasthmatic agents; anti-atherosclerotic and anti-arteriosclerotic agents (including anti-transplantation arteriosclerotic agents); additives to cardioplegic solutions for cardiopulmonary bypasses; adjuncts to thrombolytic therapy; and anti-diarrheal agents. The compounds of this invention may be useful in therapy for myocardial infarction; therapy for peripheral vascular disease (e.g., Raynaud's disease, intermittent claudication and Takayashu's disease); treatment of cardiac hypertrophy (e.g., hypertrophic cardiomyopathy); treatment of primary pulmonary hypertension (e.g., plexogenic, embolic) in adults and in the newborn and pulmonary hypertension secondary to heart failure, radiation and chemotherapeutic injury, or other trauma; treatment of central nervous system vascular disorders, such as stroke, migraine and subarachnoid hemorrhage; treatment of central nervous system behavioral disorders; treatment of gastrointestinal diseases such as ulcerative colitis, Crohn's disease, gastric mucosal damage, ulcer, inflammatory bowel disease and ischemic bowel disease; treatment of gall bladder or bile duct-based diseases such as cholangitis; treatment of pancreatitis; regulation of cell growth; treatment of benign prostatic hypertrophy; restenosis following angioplasty or following any procedure including transplantation and stenting; therapy for congestive heart failure including inhibition of fibrosis; inhibition of left ventricular dilatation, remodeling and dysfunction; and treatment of hepatotoxicity and sudden death. The compounds of this invention are useful in the treatment of sickle cell disease including the initiation and/or evolution of the pain crises of this disease; treatment of the deleterious consequences of ET-producing tumors such as hypertension resulting from hemangiopericytoma; treatment of early and advanced liver disease and injury including attendant complications (e.g., hepatotoxicity, fibrosis and cirrhosis); treatment of spastic diseases of the urinary tract and/or bladder; treatment of hepatorenal syndrome; treatment of immunological diseases involving vasculitis such as lupus, systemic sclerosis, mixed cryoglobulinemia; and treatment of fibrosis associated with renal dysfunction and hepatotoxicity. The compounds of this invention are useful in therapy for metabolic and neurological disorders; cancer; insulin-dependent and non insulin-dependent diabetes mellitus; neuropathy; retinopathy; epilepsy; hemorrhagic and ischemic stroke; bone remodeling; psoriasis; and chronic inflammatory diseases such as arthritis, rheumatoid arthritis, osteoarthritis, sarcoidosis and eczematous dermatitis (all types of dermatitis).

The compounds of this invention are additionally useful in the treatment of disorders involving bronchoconstriction and disorders of chronic or acute pulmonary inflammation such as chronic obstructive pulmonary disease (COPD) and adult respiratory distress syndrome (ARDS).

The compounds of this invention are also useful in the treatment of sexual dysfunction in both men (erectile dysfunction, for example, due to diabetes mellitus, spinal cord injury, radical prostatectomy, psychogenic etiology or any other cause) and women by improving blood flow to the genitalia, especially, the corpus cavernosum.

The compounds of this invention are also useful in the treatment of dementia, including Alzheimer's dementia, senile dementia and vascular dementia.

Additionally the compounds of the present invention are further useful in the reduction of general morbidity and/or mortality as a result of the above utilities.

The present invention thus provides methods for the treatment of all endothelin-dependent or angiotensin II-dependent disorders, comprising the step of administering to a subject in need thereof at least one compound of the formula I in an amount effective therefor. Other therapeutic agents such as those described below may be employed with the inventive compounds in the present methods. In the methods of the present invention, such other therapeutic agent(s) may be administered prior to, simultaneously with or following the administration of the compound(s) of the present invention.

The effective amount of a compound of the present invention may be determined by one of ordinary skill in the art, and includes exemplary dosage amounts for a human of from about 0.1 to about 100 mg/kg, preferably about 0.2 to about 50 mg/kg and more preferably from about 0.5 to about 25 mg/kg of body weight (or from about 1 to about 2500 mg, preferably from about 5 to about 500 mg) of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to endothelin-dependent or angiotensin II-dependent disorders.

The present invention also provides pharmaceutical compositions comprising at least one of the compounds of the formula I capable of treating an endothelin-dependent or angiotensin II-dependent disorder in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation or called for by accepted pharmaceutical practice.

The compounds of the formula I may be administered by any suitable means, for example, orally, such as in the form of tablets, capsules, granules or powders; sublingually; buccally; parenterally, such as by subcutaneous, intravenous, intramuscular, or intrasternal injection or infusion techniques (e.g., as sterile injectable aqueous or non-aqueous solutions or suspensions); nasally such as by inhalation spray; topically, such as in the form of a cream or ointment; or rectally such as in the form of suppositories; in dosage unit formulations containing non-toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps. The present compounds may also be administered liposomally. For example, the active substance can be utilized in a composition such as tablet, capsule, solution or suspension containing about 5 to about 500 mg per unit dosage of a compound or mixture of compounds of formula I or in topical form for wound healing (0.01 to 5% by weight compound of formula I, 1 to 5 treatments per day). They may be compounded in a conventional manner with a physiologically acceptable vehicle or carrier, excipient, binder, preservative, stabilizer, flavor, etc., or with a topical carrier. The compounds of formula I can also be formulated in compositions such as sterile solutions or suspensions for parenteral administration. About 0.1 to 500 milligrams of a compound of formula I may be compounded with a physiologically acceptable vehicle, carrier, excipient, binder, preservative, stabilizer, etc., in a unit dosage form as called for by accepted pharmaceutical practice. The amount of active substance in these compositions or preparations is preferably such that a suitable dosage in the range indicated is obtained.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. Molded tablets, compressed tablets or freeze-dried tablets are exemplary forms which may be used. Exemplary compositions include thriose formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene). For example, the compounds of the invention may be administered topically to treat peripheral vascular diseases and as such may be formulated as a cream or ointment.

The compounds of the present invention may be employed alone or in combination with each other and/or other suitable therapeutic agents useful in the treatment of endothelin-dependent or angiotensin II-dependent disorders. For example, the compounds of this invention can be formulated in combination with endothelin converting enzyme (ECE) inhibitors, such as phosphoramidon; thromboxane receptor antagonists such as ifetroban; potassium channel openers; thrombin inhibitors (e.g., hirudin and the like); growth factor inhibitors such as modulators of PDGF activity; platelet activating factor (PAF) antagonists; antiplatelet agents such as GPIIb/IIIa blockers (e.g., abciximab, eptifibatide, and tirofiban), P2Y(AC) antagonists (e.g., clopidogrel, ticlopidine and CS-747), and aspirin; anticoagulants such as warfarin, low molecular weight heparins such as enoxaparin, Factor VIIa inhibitors, and Factor Xa inhibitors such as those described in U.S. Ser. No. 09/496, 571 filed Feb. 2, 2000 (attorney docket HA 723); now U.S. Pat. No. 6,297,233; renin inhibitors; angiotensin converting enzyme (ACE) inhibitors such as captopril, zofenopril, fosinopril, ceranapril, alacepril, enalapril, delapril, pentopril, quinapril, ramipril, lisinopril and salts of such compounds; neutral endopeptidase (NEP) inhibitors; vasopepsidase inhibitors (dual NEP-ACE inhibitors) such as omapatrilat and gemopatrilat; HMG CoA reductase inhibitors such as pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin); squalene synthetase inhibitors; fibrates; bile acid sequestrants such as questran: niacin; anti-atherosclerotic agents such as ACAT inhibitors; MTP inhibitors such as those described in-U.S. Ser. No. 09/007,938 filed Jan. 16, 1998 (attorney docket HX 91); calcium channel blockers such as amlodipine besylate; potassium channel activators; alpha-adrenergic agents. beta-adrenergic agents such as carvedilol and metoprolol; anti-arrhythmic agents; diuretics, such as chlorothiazide, hydrochlorothiazide, flumethiazide, hydroflumethiazide, bendroflumethiazide, methylchlorothiazide, trichloromethiazide, polythiazide or benzothiazide as well as ethacrynic acid, tricrynafen, chlorthalidone, furosemide, musolimine, bumetanide, triamterene, amiloride and spironolactone and salts of such compounds; thrombolytic agents such as tissue plasminogen activator (tPA), recombinant tPA, streptokinase, urokinase, prourokinase and anisoylated plasminogen streptokinase activator complex (APSAC); anti-diabetic agents such as biguanides (e.g. metformin), glucosidase inhibitors (e.g., acarbose), insulins, meglitinides (e.g., repaglinide), sulfonylureas (e.g., glimepiride, glyburide, and glipizide), biguanide/glyburide combinations such as those described in U.S. Ser. No. 09/432,465 filed Nov. 3, 1999 (attorney docket LA 46) and now U.S. Pat. No. 6,586,438, U.S. Ser. No. 09/460,920 filed Dec. 14, 1999 (attorney docket LA 46a); thiozolidinediones (e.g. troglitazone, rosiglitazone and pioglitazone), and PPAR-gamma agonists; mineralocorticoid receptor antagonists such as spironolactone and eplerenone; growth hormone secretagogues such as those described in U.S. Ser. No. 09/417,180 filed Oct. 12, 1999 (attorney docket LA 25) U.S. Pat. No. 6,380,184 and U.S. Ser. No. 09/506,749 filed Feb. 18, 2000 (attorney docket LA 26); U.S. Pat. No. 6,518,292 aP2 inhibitors such as those described in U.S. Ser. No. 09/391,053 filed Sep. 7, 1999 (attorney docket LA 24a) and U.S. Ser. No. 09/390,275 filed Sep. 7, 1999 (attorney docket LA 24b); digitalis; ouabian; non-steroidal antiinflammatory drugs (NSAIDS) such as aspirin and ibuprofen; phosphodiesterase inhibitors such as PDE III inhibitors (e.g., cilostazol) and PDE V inhibitors (e.g., sildenafil); protein tyrosine kinase inhibitors; antiinflammatories; antiproliferatives such as methotrexate, FK506 (tacrolimus, Prograf), mycophenolate and mofetil; chemotherapeutic agents; immunosuppressants; anticancer agents and cytotoxic agents (e.g., alkylating agents, such as nitrogen mustards, alkyl sulfonates, nitrosoureas, ethylenimines, and triazenes);

antimetabolites such as folate antagonists, purine analogues, and pyrimidine analogues; antibiotics, such as anthracyclines, bleomycins, mitomycin, dactinomycin, and plicamycin; enzymes, such as L-asparaginase; farnesyl-protein transferase inhibitors; hormonal agents, such as glucocorticoids (e.g., cortisone), estrogens/antiestrogens, androgens/antiandrogens, progestins, and luteinizing hormone-releasing hormone anatagonists, octreotide acetate; microtubule-disruptor agents, such as ecteinascidins or their analogs and derivatives; microtubule-stabilizing agents such as paclitaxel (Taxol®), docetaxel (Taxotere®), and epothilones A–F or their analogs or derivatives; plant-derived products, such as vinca alkaloids, epipodophyllotoxins, taxanes; and topoisomerase inhibitors; prenyl-protein transferase inhibitors; and miscellaneous agents such as, hydroxyurea, procarbazine, mitotane, hexamethylmelamine, platinum coordination complexes such as cisplatin and carboplatin); cyclosporins; steroids such as prednisone or dexamethasone; gold compounds; cytotoxic drugs such as azathiprine and cyclophosphamide; TNF-alpha inhibitors such as tenidap; anti-TNF antibodies or soluble TNF receptor such as etanercept (Enbrel) rapamycin (sirolimus or Rapamune), leflunimide (Arava); and cyclooxygenase-2 (COX-2) inhibitors such as celecoxib (Celebrex) and rofecoxib (Vioxx).

If formulated as a fixed dose, such combination products employ the compounds of this invention within the dosage range described below and the other pharmaceutically active agent within its approved dosage range. The compounds of this invention may also be formulated with, or useful in conjunction with, antifungal and immunosuppressive agents such as amphotericin B, cyclosporins and the like to counteract the glomerular contraction and nephrotoxicity secondary to such compounds. The compounds of this invention may also be used in conjunction with hemodialysis.

The above other therapeutic agents, when employed in combination with the compounds of the present invention, may be used, for example, in those amounts indicated in the Physicians' Desk Reference (PDR) or as otherwise determined by one of ordinary skill in the art.

The following assays may be employed in ascertaining the degree of activity of a compound ("drug") as an endothelin and angiotensin II receptor antagonist. Compounds described in the following Examples have been tested in these assays, and have shown activity.

ETA$_{A/B}$ Attached Cell Binding Assay

CHO-K1 cells expressing either the human endothelin A or endothelin B receptor were cultured in Ham's F12 media (Gibco/BRL, Grand Island, N.Y.) with 10% fetal bovine serum (Hyclone), supplemented with 300 µg/mL Geneticin (G-418 Gibco BRL Products, Grand Island, N.Y.) and maintained at 37° C. with 5% $CO_2$ in a humidified incubator. Twenty four hours prior to assay, the cells were treated with 0.25% trypsin-EDTA and were seeded in Falcon, 96 well tissue culture plates at a density of $1.8 \times 10^4$ cells/well (the monolayer should reach 80–90% confluency by the day of assay).

In the attached cell assay, culture media was aspirated from each well and the monolayers were washed with 50 µl of PBS ($Mg^{++}$, $Ca^{++}$ free). The binding assay was performed in a total volume of 125 µl consisting of assay buffer (50 mM Tris, pH 7.4, including 1% BSA, and 2 µM phosphoramidon), and 25 µl of either 500 nM ET-1 (to define nonspecific binding) or competing drug. The reaction was initiated with the addition of 25 µl of 0.25 nM [$^{125}$I]-ET-1 (New England Nuclear). Incubation was carried out with gentle orbital shaking, at 4° C., reaching equilibrium at 4 hours. The reaction was terminated by aspiration of the reaction buffer and two subsequent washes with cold PBS ($Mg^{++}$, $Ca^{++}$ free). The cells were dissociated by the addition of 100 µl of 0.5N NaOH followed by incubation for 40 minutes. Samples were then transferred from the 96 well format into tubes for counting in a Cobra gamma counter (Packard). Data was analyzed with curve fitting software by Sigma plot.

RASMC Binding Assay

Assays were conducted in a total volume of 250 µL in 96 well microtitre plates. The incubation mixture contained 50 µL [125]I-Sar-Ile-Angiotensin II (0.2 nM), 25 µL of drug dissolved in DMSO, or angiotensin II (1 µM) to define non-specific binding. Binding to rat aortic smooth muscle cells (RASMCs) was conducted in RPMI media (Gibco BRL Products, Grand Island, N.Y.) containing 0.1% BSA for 2 hours at room temperature with continuous shaking. Unbound radioligand was washed from the wells. The RASMCs with bound radioligand are lysed with 1% Triton X and 0.1% BSA in distilled water for 15 minutes at room temperature with continuous shaking. The solution in each well was transferred to tubes and placed in a gamma counter.

Compounds within the scope of this invention include compounds that have an $IC_{50}$ concentration of less than 100 micromolar versus either or both [125]I-Sar-Ile-Angiotensin II or [$^{125}$I]-ET-1, ideally against both ligands. Preferred compounds within the scope of this invention are compounds that have an $IC_{50}$ concentration of less than 5 micromolar versus either or both [125]I-Sar-Ile-Angiotensin II or [$^{125}$I]-ET-1, ideally against both ligands. More preferred compounds within the scope of this invention are compounds that have an $IC_{50}$ concentration of less than 1 micromolar versus either or both [125]I-Sar-Ile-Angiotensin II or [$^{125}$I]-ET-1, ideally against both ligands.

All documents cited in the present specification are incorporated herein by reference in their entirety.

The following Examples illustrate embodiments of the present invention, and are not intended to limit the scope of the claims. Abbreviations employed herein are defined below. Compounds of the Examples are identified by the example and step in which they are prepared (for example, "1A" denotes the title compound of step A of Example 1), or by the example only where the compound is the title compound of the example (for example, "4" denotes the title compound of Example 4). Compounds prepared for use as synthetic intermediates are identified by the Preparation number and step in which they appear, prefaced by the letter "P." For example, "P1A" denotes the compound generated in step A of Preparation 1, while "P1" denotes the title compound of Preparation 1.

| Abbreviations |
|---|
| Ac = acetyl |
| (S)-BINAP = (S)-(-)2,2'-bis(diphenylphosphino)-1,1'-binaphthyl |
| BOC = t-butoxycarbonyl |
| n-Bu = n-butyl |
| BSA = bovine serum albumin |
| CDI = 1,1' carbonyldiimidazole |
| d = days |
| DBU = 1,8-diazabicyclo[5.4.0]undec-7-ene |
| DIBAL-H = diisobutylaluminum hydride |
| DMF = N,N-dimethylformamide |
| DMSO = dimethylsulfoxide |
| EDCI = 1-ethyl-3-[3-(dimethylamino)propyl]carbodiimide hydrochloride |
| EDTA = ethylenediaminetetraacetic acid |
| eq = equivalents |

-continued

| Abbreviations |
|---|
| Et = ethyl |
| ET = endothelin |
| ET-1 = endothelin-1 |
| EtOAc = ethyl acetate |
| EtOH = ethanol |
| h = hours |
| Me = methyl |
| MEM = methoxyethoxymethyl |
| MeOH = methanol |
| min = minutes |
| mp = melting point |
| Ms = methanesulfonyl |
| NBS = N-bromosuccinimide |
| PBS = phosphate buffered saline |
| Ph = phenyl |
| n-Pr = n-propyl |
| SEM = 2-(trimethylsiloxy)ethoxymethyl |
| Rochelle's salt = potassium sodium tartrate tetrahydrate |
| RT = room temperature |
| TFA = trifluoroacetic acid |
| THF = tetrahydrofuran |

GENERAL METHODS

The following General Methods were Employed in the Preparations and Examples.

General Method 1

Suzuki Coupling of Aryl Bromides with Arylboronic Acids

ArBr+Ar'B(OR)$_2$→Ar—Ar'

R=H, alkyl

A solution of 1.0 eq of an arylboronic acid (or ester) and the appropriate aryl bromide (1.0 eq) in 2:1 toluene:ethanol (0.1 M concentration for each reagent) was sparged with nitrogen for 15 minutes. Tetrakis (triphenylphosphine) palladium (0) (0.05 eq) and 2 M aqueous sodium carbonate (3 eq) were added and the mixture was heated at 85° C. for 3 h under a nitrogen atmosphere. The mixture was cooled and ethyl acetate and water were added. The organic layer was washed once with saturated aqueous sodium carbonate, dried over sodium sulfate, and concentrated. The residue was chromatographed on silica gel using hexanes/ethyl acetate as eluant to yield the biaryl product.

Arylboronic acids used: [2-[[(3,4-dimethyl-5-isoxazolyl)[(2-methoxyethoxy)-methyl]amino]-sulfonyl]phenyl]boronic acid (or the corresponding SEM-protected compound, both of which were prepared as described in U.S. Pat. No. 5,612,359); [2-[[(4,5-dimethyl-3-isoxazolyl)[(2-methoxyethoxy)methyl]amino]-sulfonyl]phenyl]boronic acid (prepared as described in U.S. Pat. No. 5,612,359 and U.S. patent application Ser. No. 09/013,952, filed Jan. 27, 1998); [2-(N-tert-butylsulfamoyl)phenyl]boronic acid (prepared according to Chang, L. L. et al., *J. Med Chem.*, 38, 3741–3758 (1995)).

Arylboronate ester used: N-[(2-methoxyethoxy)methyl]-N-(3,4-dimethyl-5-isoxazolyl)-2-(4,4,5,5-tetramethyl-1,3,2-dioxaborolan-2-yl)benzenesulfonamide (prepared as described in WO 97/29747).

General Method 2

Conversion of Primary Alcohols to Alkyl Bromides

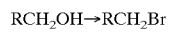

RCH$_2$OH→RCH$_2$Br

To a 0.2 M solution of the alcohol in DMF at 0° C. was added carbon tetrabromide (1.5 eq) followed by triphenylphosphine (1.5 eq). The mixture was stirred at 0° C. for 4 h, diluted with 10 parts 2:1 hexanes/ethyl acetate, and washed with water and brine. The solution was dried over sodium sulfate and concentrated, and the residue chromatographed on silica gel using hexanes/ethyl acetate as eluant to yield the alkyl bromide product.

General Method 3

Conversion of Primary Alcohols to Alkyl Methanesulfonates

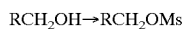

RCH$_2$OH→RCH$_2$OMs

To a 0.15 M solution of the alcohol in dichloromethane at 0° C. was added N,N-diisopropylethylamine (1.5 eq) followed by methanesulfonyl chloride (1.1 eq). The mixture was stirred at 0° C. for 1 to 3 h, and was then treated with 10% aqueous potassium dihydrogensulfate. The aqueous layer was extracted once with dichloromethane and the combined organic layers were dried over sodium sulfate and concentrated to yield the crude alkyl methanesulfonate.

General Method 4

Alkylation of Heterocycles or Aliphatic Alcohols

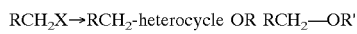

RCH$_2$X→RCH$_2$-heterocycle OR RCH$_2$—OR'

X=Br, OMs

Sodium hydride (60% dispersion in mineral oil, 1.2 eq) was added at 0° C. to a 1.0 M solution or suspension of an appropriate heterocycle or alcohol (1.5 eq) in DMF. The mixture was allowed to warm to RT, was stirred for 20 min, and was then cooled back to 0° C. To the heterocycle mixture was added a solution of the appropriate alkyl bromide or alkyl methanesulfonate (1.0 eq) in a minimal amount of DMF. The resultant mixture was allowed to warm to RT and was stirred for 16–24 h. The reaction mixture was diluted with EtOAc and washed with water and brine. The organic layer was dried over sodium sulfate and concentrated, and the residue chromatographed on silica gel with hexanes/ethyl acetate as eluant to yield the alkylation product.

Heterocycles Used

| Structure | Name | Reference |
|---|---|---|
| 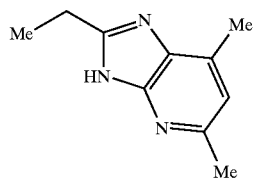 | 2-ethyl-5,7-dimethyl-3H-imidazo[4,5-b]pyridine | Senanayake, C. H., et. al. Heterocycles 1996, 42, 821–830. |
| 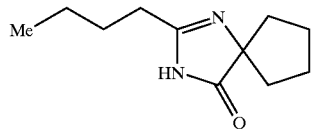 | 2-butyl-1,3-diazaspiro[4.4]non-1-en-4-one | Bernhart, C.A., et. al. J. Med. Chem., 1993, 36, 3371–3380. |
| 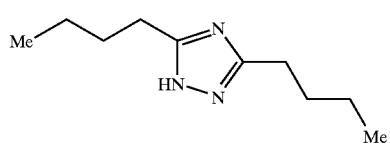 | 3,5-di-n-butyl-1,2,4-triazole | Reitz, D. B., et al. Biorganic & Medicinal chemistry Letters, 1994, 4(1), 99–104 |
| 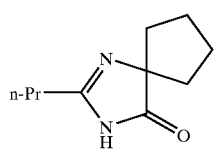 | 2-propyl-1,3-diazaspiro[4.4]non-1-en-4-one | Bernhart, C. A., et. al. J. Med. Chem., 1993, 36, 3371–3380. |
| 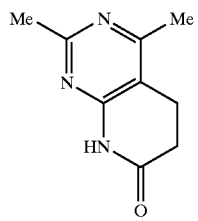 | 7-oxo-2,4-dimethyl-5,6,7,8-tetrahydropyrido[2,3-d]pyrimidine | Hullar, T. L.; French, W. C. J. Med. Chem., 1969, 12, 424–426 |
| 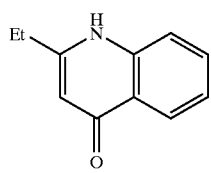 | 2-ethyl-4(1H)-quinolone | Bradbury, R. H.; et. al. J. Med. Chem. 1992, 35, 4027–4038. |
| 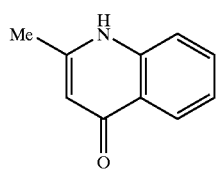 | 2-methyl-4(1H)-quinolone | commercially available |
| 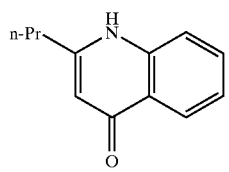 | 2-propyl-4(1H)-quinolone | Bradbury, R. H.; et. al. J. Med. Chem. 1992, 35, 4027–4038. |
| 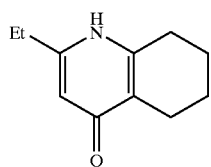 | 2-ethyl-5,6,7,8-tetrahydro-4(1H)-quinolone | Bradbury, R. H.; et. al. J. Med. Chem. 1993, 36, 1245–1254. |

| | | |
|---|---|---|
| -continued | | |
| Structure with pyridine-CO2Me and NH-propyl-Me | methyl 2-(N-propyl[001b]amino)pyridine-3-carboxylate | De, B.; et. at. J. Med. Chem. 1992, 35, 3714–3717 |
| Pyrazolotriazole with Et groups | 2,7-diethyl-5H-pyrazolo[1,5-b][1,2,4]triazole | U.S. Pat. No. 5,475,114 |
| 3-methoxy-2,6-dimethyl-4(4H)-pyridinone structure | 3-methoxy-2,6-dimethyl-4(4H)-pyridinone | Voss, G.; et. al. Liebigs Ann Chem. 1982, 1466–1477 |
| 2-butyl-4(3H)-quinazolinone structure | 2-butyl-4(3H)-quinazolinone | Allen, E. C.; et. al Biorganic & Medicinal Chemistry Let. 1993, 3(6), 1293–1298 |
| N-(2-butyl-3,4-dihydro-4-oxo-6-quinazolinonyl)-N'-isopropyl-N'methylurea structure | N-(2-butyl-3,4-dihydro-4-oxo-6-quinazolinonyl)-N'-isopropyl-N'methylurea | Laszlo, S. E.; et al Biorganic & Medicinal Chemistry Let. 1993, 3(6), 1299–1304 |

General Method 5

Reductive Amination $$ArCHO + RNH_2 \text{ [or } RNH_2 \cdot HCl] \rightarrow ArCH_2\text{—NHR}$$

To a mixture of an aromatic aldehyde (1.0 eq) and a primary amine (1.2 eq) in dichloromethane (0.1 M aldehyde concentration) was added 4 Å molecular sieves (5 g per mmol aldehyde). [Alternately, a primary amine hydrochloride (1.2 eq) and triethylamine (1.2 eq) could be substituted for the primary amine free base.] The mixture was stirred vigorously for 1 h, after which sodium triacetoxyborohydride (1.5 eq) was added. The mixture was stirred vigorously at RT, while the course of the reaction was monitored by HPLC. If the reaction had not reached completion within several hours, additional sodium triacetoxyborohydride (1.0 eq) was added and monitoring was continued. When the reaction was complete the mixture was filtered through celite, aqueous sodium bicarbonate solution was added to the filtrate, and the aqueous layer was extracted with dichloromethane. The combined organic extracts were dried over sodium sulfate and evaporated. The crude residue was carried on without further purification.

In general, reductive amination with a 4-aminobutanoic acid resulted in a lactam product. In a few cases, cyclization was promoted by treatment of a 0.1 M solution of the crude amino acid product in dichloromethane with 1.0 eq of diisopropylcarbodiimide for 1 h at RT.

General Method 6

Amine Acylation

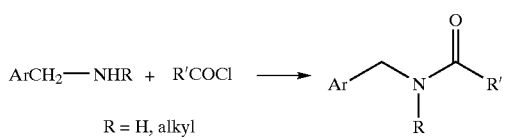

$$ArCH_2\text{—NHR} + R'COCl \rightarrow Ar\text{—}CH_2\text{—N}(R)\text{—C}(O)R'$$

R = H, alkyl

A 0.15 M solution of a primary or secondary amine (1.0 eq) and N,N-diisopropylethylamine (2.0 eq) in dichloromethane was treated at RT with an acyl chloride (1.5 eq). After 1.5 h, methanol (10 eq) was added, followed by aqueous sodium carbonate solution. The aqueous layer was extracted with dichloromethane and the combined organic extracts were combined, dired over sodium sulfate, and concentrated. The residue was chromatographed on silica gel with hexanes/ethyl acetate as eluant to provide the product tertiary amide.

General Method 7

Hydrolysis of SEM or MEM Sulfonamide Protecting Groups Using Hydrochloric Acid/Ethanol

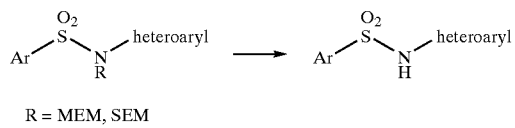

R = MEM, SEM

To a 0.1 M solution of a SEM- or MEM-protected N-heteroaryl sulfonamide in one volume of 95% EtOH was added an equal volume of 6N aqueous HCl, and the resulting solution was heated at reflux for 1 h. The reaction mixture was concentrated and the pH of the solution was adjusted to pH 8 using aqueous sodium bicarbonate solution. It was then reacidified to pH 5 with glacial acetic acid. The mixture was extracted with three portions of ethyl acetate. The combined organic extracts were washed with water and brine, dried over sodium sulfate, and concentrated. The residue was purified by reverse-phase preparative HPLC, or by silica gel chromatography using chloroform/methanol or hexanes/acetone as eluant.

General Method 8

Hydrolysis of SEM or MEM Sulfonamide Protecting Groups Using Hydrogen Chloride in Dioxane/Alcohol

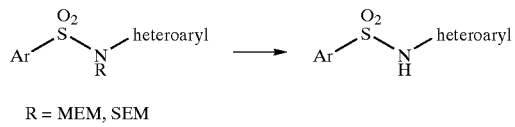

R = MEM, SEM

A solution of a SEM- or MEM-protected N-heteroaryl sulfonamide in one volume of absolute methanol or ethanol was treated with two volumes of 4 N hydrogen chloride/dioxane solution (final substrate concentration 0.05 M). The resulting solution was heated at 55° C. for 16 h and was then concentrated. The residue was purified by reverse-phase preparative HPLC, or by extraction with ethyl acetate from aqueous potassium phosphate adjusted to pH 5–6, followed by silica gel chromatography.

General Method 9

Cleavage of SEM or MEM Sulfonamide Protecting Groups Using Trimethylsilyl Iodide

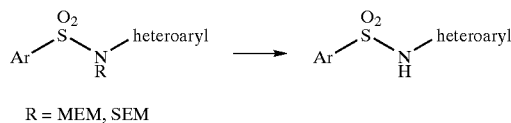

R = MEM, SEM

To a 0.1 M solution of of a SEM- or MEM-protected N-heteroaryl sulfonamide in acetonitrile was added trimethylsilyl chloride (8 eq) followed by sodium iodide (8 eq). The mixture was stirred at RT for 30 min and was then poured onto water and ethyl acetate. The organic layer was washed with saturated sodium sulfite and brine, and was then dried over sodium sulfate and concentrated. The residue was purified by reverse-phase preparative HPLC or by silica gel chromatography.

General Method 10

Cleavage of SEM Sulfonamide Protecting Groups Using Tetrabutylammonium Fluoride

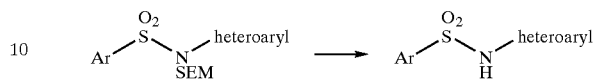

To a 0.05 M solution of a SEM-protected N-heteroaryl sulfonamide in THF was added freshly activated 4 Å molecular sieves (20 g per mmol sulfonamide), followed by tetrabutylammonium fluoride (1.0 M solution in THF, 3 eq). The mixture was heated at 55° C. for 1–2 h, then was cooled and filtered through celite. The filter cake was rinsed with methanol, then aqueous potassium dihydrogen phosphate solution was added to the filtrate and the mixture partially concentrated. The residue was adjusted to pH 4–5 using dilute hydrochloric acid, and the mixture was extracted with two portions of ethyl acetate. The combined organic extracts were dried over sodium sulfate and concentrated. The residue was purified by reverse-phase preparative HPLC or by silica gel chromatography.

General Method 11

Reduction of Aryl Aldehydes to Benzylic Alcohols Using Sodium Borohydride

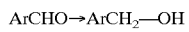

ArCHO→ArCH$_2$—OH

Sodium borohydride (0.5 eq) was added at 0° C. to a 0.2 M solution of an aromatic aldehyde in absolute ethanol or methanol. The mixture was allowed to warm to RT and stirred for 1–2 h. Aqueous potassium dihydrogen phosphate solution (or dilute hydrochloric acid) was added and the mixture was stirred for an additional 15 min. The mixture was partially concentrated and the residue partitioned between ethyl acetate and water. The aqueous layer was extracted twice with ethyl acetate and the combined organic extracts were dried over sodium sulfate and concentrated. The crude benzylic alcohol was either used directly or was purified by silica gel chromatography using hexanes/ethyl acetate as eluant.

General Method 12

Amide Formation using 1,1'-Carbonyldiimidazole

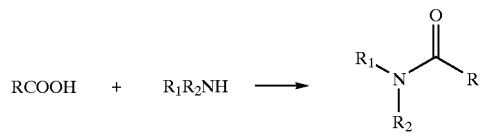

1,1'-Carbonyldiimidazole (2.0 eq) was added to a 0.1 M solution or suspension of an appropriate carboxylic acid (1.0 eq) in THF. The mixture was heated at 50° C. for 1 h, and was then cooled to RT. An appropriate amine (5–10 eq) was then added, and the miture was stirred at RT for 12 h. Ethyl acetate and aqueous sodium bicarbonate solution were added and the aqueous layer was extracted with ethyl acetate. The combined organic layers were dried over sodium sulfate and concentrated. The residue was purified by reverse-phase preparative HPLC or by silica gel chromatography.

General Method 13

Benzylic Bromination Using N-Bromosuccinimide

$ArCH_3 \rightarrow ArCH_2-Br$

To a 0.4 M solution of a methyl-substituted aromatic compound in carbon tetrachloride was added N-bromosuccinimide (1.05 eq) and benzoyl peroxide (0.03 eq), and the mixture was heated at reflux for 8–16 h. The mixture was cooled and filtered and the filtrate concentrated. The residue was purified by trituration with 3:1 hexanes/ethyl acetate, or by silica gel chromatography using hexanes/ethyl acetate as eluant to provide the monobrominated product.

General Method 14

Reduction of an Aromatic Nitrile to an Aromatic Aldehyde Using DIBAL-H

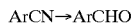

$ArCN \rightarrow ArCHO$

DIBAL-H (1.5 M solution in toluene, 1.5 eq) was added dropwise at 0° C. to a 0.5 M solution of an aromatic nitrile (1.0 eq) in toluene or 9:1 toluene/dichloromethane. The solution was stirred at 0° C. for 1–4 h, and was then treated with excess methanol. After 15 min, 2N hydrochloric acid was added and the mixture was stirred vigorously for an additional 15 min. The layers were separated, and the aqueous layer was extracted with ethyl acetate. The combined organic layers were dried over sodium sulfate and concentrated to yield the crude aldehyde, which was either carried on crude or purified via silica gel chromatography using hexanes/ethyl acetate as eluant.

General Method 15

Ester Hydrolysis Using Lithium Hydroxide

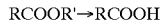

$RCOOR' \rightarrow RCOOH$

A 0.25 M solution of an alkyl ester in 1:1 THF/water was treated with lithium hydroxide hydrate (1.5 eq) at RT. The mixture was stirred for 8–16 h and was then acidified with dilute hydrochloric acid. The product was either isolated by direct filtration from the reaction mixture, or by extraction with ethyl acetate, followed by drying of the organic layers with sodium sulfate, concentration, and silica gel chromatography using methanol/chloroform or hexanes/acetone as eluant.

General Method 16

Displacement of a Benzylic Bromide or Mesylate with Cyanide

$ArCH_2X \rightarrow ArCH_2-CN$

X=Br, OMs

Sodium cyanide (1.2 eq) was added at RT to a 1.0 M solution of a benzylic bromide or mesylate in DMF. The mixture was stirred at RT for 16 h. The reaction mixture was diluted with ethyl acetate and partitioned against aqueous sodium bicarbonate. The organic layer was dried over sodium sulfate and concentrated, and the residue chromatographed on silica gel with hexanes/ethyl acetate as eluant to yield the nitrile product.

General Method 17

Swern Oxidation of a Benzylic Alcohol to an Aromatic Aldehyde

$ArCH_2-OH \rightarrow ArCHO$

Oxalyl chloride (1.5 eq) was added dropwise to a solution of DMSO (2.0 eq) in dichloromethane at −78° C. After 5 min, a solution of benzylic alcohol substrate (1.0 eq) in dichloromethane was added and the mixture (0.2 M final substrate concentration) was stirred at −78° C. for 15 min. Triethylamine (4.0 eq) was added and the mixture was stirred and allowed to warm to RT. Aqueous sodium bicarbonate solution was added, the layers were separated, and the aqueous layer was extracted with one portion of dichloromethane. The combined organic layers were dried over sodium sulfate, concentrated, and the residue was purified by silica gel chromatography using hexanes/ethyl acetate as eluant.

General Method 18

Reduction of an Aromatic Nitro Group to an Aromatic Amine Using Tin (II) Chloride Dihydrate

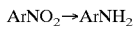

$ArNO_2 \rightarrow ArNH_2$

Tin (II) chloride dihydrate (4.0 eq) was added to a 0.05 M solution of an aromatic nitro compound in ethyl acetate and the resulting mixture was heated at 70° C. for 45 min. The mixture was cooled, half-saturated aqueous sodium carbonate solution was added, and the layers were separated. The aqueous layer was extracted once with ethyl acetate, and the combined organic layers were dried over sodium sulfate and concentrated. The residue was chromatographed on silica gel using hexanes/ethyl acetate as eluant to provide the product aromatic amine.

General Method 19

Hydrolysis of a 2-Aryl-1,3-Dioxolane to an Aromatic Aldehyde

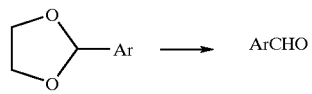

A 0.2 M solution of a 2-aryl-1,3-dioxolane (1.0 eq) in THF was treated with 1N hydrochloric acid (1.5 eq), and the resulting solution was heated at 55° C. for 16 h. The mixture was cooled and neutralized with aqueous sodium bicarbonate solution, then extracted with three portions of ethyl acetate. The combined organic extracts were dried over sodium sulfate and concentrated, and the crude aldehyde was used directly with no further purification.

General Method 20

Ester Formation Using 1,1'-Carbonyldiimidazole and DBU

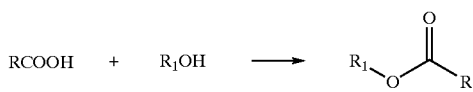

1,1'-Carbonyldiimidazole (2.0 eq) was added to a 0.1 M solution or suspension of an appropriate carboxylic acid (1.0 eq) in THF. The mixture was heated at 50° C. for 1 h. An appropriate alcohol (3.0 eq) was then added, followed by DBU (3.0 eq). The mixture was heated at 50° C. for 16 h and was then cooled. Ethyl acetate and 35% aqueous citric acid solution were added, and the organic layer was dried over sodium sulfate and concentrated. The residue was purified by reverse-phase preparative HPLC or by silica gel chromatography.

General Method 21

Phase-Transfer Alkylation of Imidazoles

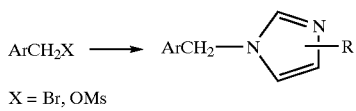

A solution of an appropriate imidazole (0.1 M) in toluene was treated with 50% aqueous sodium hydroxide solution (0.5 ml per mmol imidazole), tetrabutylammonium hydrogen sulfate (0.05 eq), and an appropriate benzylic alkyl bromide or mesylate (0.95 eq). The mixture was stirred vigorously at 40° C. for 24 h and was then cooled and filtered. Water was added and the aqueous layer was extracted with two portions of ethyl acetate. The combined organic extracts were dried over sodium sulfate and concentrated to provide the crude product, which was either purified by silica gel chromatography or was carried on crude. Imidazole used: 2-propyl-4,5,6,7-tetrahydro-8-oxocycloheptimidazole (Yanagisawa, T.; et. al. *Biorg. Med. Chem. Lett.* 1993, 3, 1559–1564).

General Method 22

Imidazole or Phenol Alkylation

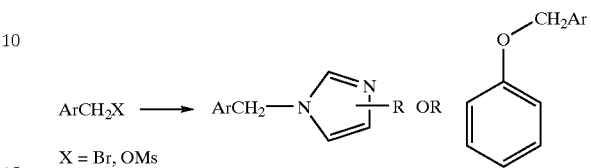

A solution of an appropriate imidazole (0.5 M) in DMF was treated with potassium carbonate (2.0 eq) and a benzylic alkyl bromide or mesylate (1.0 eq) at RT. The mixture was stirred at RT for 16 to 24 h. The solvent was evaporated and the residue was partitioned between ethyl acetate and water. The ethyl acetate layer was dried over sodium sulfate and concentrated to provide the crude product, which was purified by silica gel chromatography or was carried on crude. When mixtures of N-1 and N-3 alkylation products were obtained, the regiochemistry of the alkylation was determined by NOESY spectroscopy.

Imidazoles Used

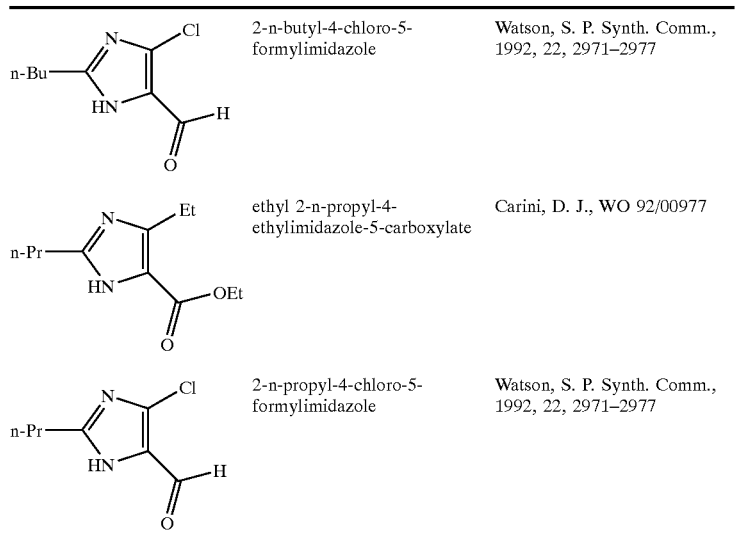

General Method 23

Cleavage of SEM Sulfonamide Protecting Groups Using Cesium Fluoride

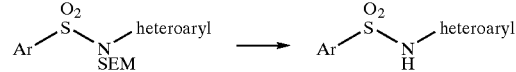

To a 0.05 M solution of a SEM-protected N-heteroaryl sulfonamide in DMF was added cesium fluoride (5.0 eq), and the resulting mixture was heated at 130° C. for 3 h. The reaction mixture was cooled and the solvent evaporated. Aqueous potassium dihydrogen phosphate solution was added (pH 4–5) and the mixture was extracted with three portions of ethyl acetate. The combined organic extracts were dried over sodium sulfate and concentrated. The residue was purified by reverse-phase preparative HPLC or by silica gel chromatography.

General Method 24

Sulfonylation of Aromatic Amines

To a 0.1 M solution of an aromatic amine (1.0 eq.) in dichloromethane at −30° C. was added triethylamine (2.6 eq), followed by a sulfonyl chloride (1.4 eq). The mixture was allowed to warm to RT over 3 hr. Aqueous sodium bisulfate was added (final pH 5) and the aqueous layer was extracted with dichloromethane. The combined organic extracts were washed with water and brine, and were then dried over sodium sulfate and concentrated. The residue was chromatographed on silica gel using dichloromethane/methanol as eluant.

General Method 25

Oxidation of Aromatic Aldehydes to Carboxylic Acids

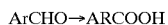

A 0.1 M solution of an aromatic aldehyde in 1:1 THF/water was treated at 0° C. with sulfamic acid (1.5 eq) and sodium chlorite (1.5 eq). After 1 h aqueous potassium bisulfate solution was added and the mixture was extracted with ethyl acetate. The combined organic extracts were washed with brine, dried over sodium sulfate and concentrated to provide the crude carboxylic acid, which was used without further purification.

General Procedure

Purification by Anion Exchange Chromatography

Anion exchange chromatography was performed on Varian SAX cartridges (acetate form, 1.5–3 g) or United Chemical Technologies CUQAX13M6-AC cartridges (acetate form, 3 g). Following a methanol rinse, the cartridge was loaded with a dichloromethane solution of crude product. Elution of impurities with dichloromethane, followed by elution of the desired product with 1–3% TFA in dichloromethane or dichloromethane/methanol, provided the purified product.

General Procedure

Purification by Reverse-Phase Preparative HPLC

Reverse-phase preparative HPLC was performed with Shimadzu 8A liquid chromatographs using YMC S5 ODS columns (20×100, 20×250, or 30×250 mm). Gradient elution was performed with methanol/water mixtures in the presence of 0.1% TFA. In some cases a product eluting as a TFA salt was subsequently converted to the corresponding free base by extraction from aqueous sodium bicarbonate or sodium carbonate solution.

Analytical HPLC Methods Employed in Characterization of Examples

Analytical HPLC was performed on Shimadzu LC10AS liquid chromatographs using the following methods:

A. Linear gradient of 0 to 100% solvent B over 4 min, with 1 min hold at 100% B;
UV visualization at 220 nm
Column: YMC S5 ODS Ballistic 4.6×50 mm
Flowrate: 4 ml/min
Solvent A: 0.1% trifluoroacetic acid, 90% water, 10% methanol
Solvent B: 0.1% trifluoroacetic acid, 90% methanol, 10% water B. Linear gradient of 0 to 100% solvent B over 30 min, with 5 min hold at 100% B;
UV visualization at 254 nm
Column: YMC S3 ODS 6×150 mm
Flowrate: 1.5 ml/min
Solvent A: 0.2% phosphoric acid, 90% water, 10% methanol
Solvent B: 0.2% phosphoric acid, 90% methanol, 10% water C. Linear gradient of 0 to 100% solvent B over 4 min, with 1 min hold at 100% B
UV visualization at 220 nm
Column: YMC S5 ODS Ballistic 4.6×50 mm
Flowrate: 4 ml/min
Solvent A: 0.2% phosphoric acid, 90% water, 10% methanol
Solvent B: 0.2% phosphoric acid, 90% methanol, 10% water D. Linear gradient of 45 to 100% solvent B over 2 min, with 1 min hold at 100% B;
UV visualization at 220 nm
Column: Phenomenex Primesphere 4.6×30 mm
Flowrate: 5 ml/min
Solvent A: 0.2% phosphoric acid, 90% water, 10% methanol
Solvent B: 0.2% phosphoric acid, 90% methanol, 10% water E. Same conditions as (B), but with a linear gradient of 40 to 100% solvent B over 30 min, with 5 min hold at 100% B F. Same conditions as (B), but with a linear gradient of 70 to 100% solvent B over 30 min, with 5 min hold at 100% B G. Same conditions as (D), but with a linear gradient of 40 to 100% solvent B over 2 min, with 1 min hold at 100% B H. Linear gradient of 0 to 100% solvent B over 2 min, with 1 min hold at 100% B;
UV visualization at 220 nm
Column: Phenomenex Primesphere 4.6×30 mm
Flowrate: 5 ml/min
Solvent A: 0.1% trifluoroacetic acid, 90% water, 10% methanol
Solvent B: 0.1% trifluoroacetic acid, 90% methanol, 10% water I. Same conditions as (B), but with a linear gradient of 50 to 100% solvent B over 30 min, with 5 min hold at 100% B J. Same conditions as (C), but with a linear gradient of 0 to 100% solvent B over 8 min, with 1 min hold at 100% B K. Same condidtions as (D), but with a linear gradient of 0 to 100% solvent B over 2 min, with a 1 minute hold at 100% B.

Preparations

Preparation 1

N-(3,4-Dimethyl-5-isoxazolyl)-4'-formyl-2'-(hydroxymethyl)-N-[(2-trimethylsiloxy)ethoxyvmethyl]

[1,1'-biphenyl]-2-sulfonamide

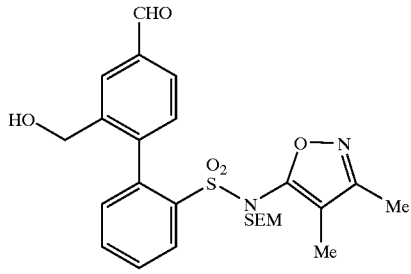

A. 4-Bromo-3-(bromomethyl)benzonitrile

The product was prepared according to General Method 13 starting from 12.0 g 4-bromo-3-methylbenzonitrile. Partial purification of the crude product was performed by trituration with 3:1 hexanes/ethyl acetate to afford 7.3 g of a slightly yellow solid, which was contaminated with approximately 20 mol % of the starting material.

B. 4-Bromo-3-(acetoxymethyl)benzonitrile

A mixture of P1A (7.3 g), potassium acetate (3.4 g), and DMF (10 ml) was stirred at RT for 16 h. Ethyl acetate was added and the mixture was washed with four portions of water, followed by one portion of brine. The ethyl acetate layer was dried over sodium sulfate and concentrated. The solid residue was partially purified by crystallization from ethyl acetate, yielding 4.5 g of a slightly yellow solid.

C. 4-Bromo-3-(hydroxymethyl)benzaldehyde

P1B (4.4 g) was treated with DIBAL-H according to General Method 14, using 3.5 eq of the reducing agent rather than 1.5 eq. The crude product was an orange oil (4.8 g), judged by $^1$H NMR to be approximately 75% pure by weight.

D. N-(3,4-Dimethyl-5-isoxazolyl)-4'-formyl-2'-(hydroxymethyl)-N-[(2-trimethylsiloxy)ethoxymethyl][1,1'-biphenyl]-2-sulfonamide P1C (4.7 g) was subjected to Suzuki coupling according to General Method 1, yielding 7.6 g of the product as an orange oil following silica gel chromatography (2:1 hexanes/ethyl acetate eluant).

Preparation 2

N-(3,4-Dimethyl-5-isoxazolyl)-4'-bromomethyl-2'-(methoxymethyl)-N-[(2-methoxyethoxy)methyl][1,1'-biphenyl]-2-sulfonamide

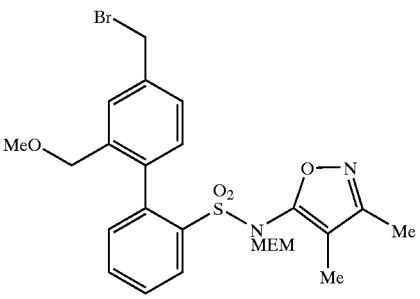

A. 4-Bromo-3-(bromomethyl)benzonitrile

The product was prepared according to General Method 13 starting from 19.6 g 4-bromo-3-methylbenzonitrile. After cooling the mixture was filtered and the filtrate was washed with $H_2O$ and brine, dried and concentrated. The residue was chromatographed on silica gel using 100:3 and then 100:10 hexane/EtOAc to afford P2A (16 g, 58%). $R_f$=0.15, silica gel, 10:1 hexane/EtOAc.

B. 4-Bromo-3-(Methoxymethyl)benzonitrile

To a solution of P2A (6.95 g, 25.28 mmol) in 10 ml DMF, NaOMe (25 wt. % in MeOH, 6.94 ml, 30.3 mmol) was added dropwise. The reaction mixture was stirred at RT for 3 h. Ethyl acetate (100 ml) and hexanes (50 ml) were added, and the mixture was washed twice with water and once with brine. The organic layer was dried over sodium sulfate and concentrated. The residue was chromatographed on silica gel using 100:6 hexane/EtOAc to afford P2B (4.70 g, 82%). $R_f$=0.5, silica gel, 5:1 hexane/EtOAc.

C. 4-Bromo-3-(methoxymethyl)benzaldehyde

P2B (7.0 g) was treated with DIBAL-H according to General Method 14, using THF instead of toluene as solvent. The crude product was purified by silica gel chromatography using 11:1 hexanes/ethyl acetate as eluant to give 6.2 g P2C as a colorless gum. $R_f$=0.4, silica gel, 5:1 Hexane/EtOAc.

D. N-(3,4-Dimethyl-5-isoxazolyl)-4'-formyl-2'-(methoxymethyl)-N-[(2-methoxyethoxy)methyl][1,1'-biphenyl]-2-sulfonamide P2C (6.2 g) was subjected to Suzuki coupling according to General Method 1, giving P2D as an oil in 83% yield after silica gel chromatography.

E. N-(3,4-Dimethyl-5-isoxazolyl)-4'-hydroxymethyl-2'-(methoxymethyl)-N-[(2-methoxyethoxy)methyl][1,1'-biphenyl]-2-sulfonamide P2D (2.8 g) was reduced with sodium borohydride according to General Method 11, to provide 2.8 g P2E.

F. N-(3,4-Dimethyl-5-isoxazolyl)-4'-bromomethyl-2'-(methoxymethyl)-N-[(2-methoxyethoxy)methyl][1,1'-biphenyl]-2-sulfonamide P2E (2.8 g) was treated with triphenylphosphine and carbon tetrabromide according to General Method 2, providing the title compound (2.3 g) in 72% yield.

Preparation 3
2'-Cyano N-(3,4-dimethyl-5-isoxazolyl)-4'-(hydroxymethyl)-N-[(2-trimethylsiloxy)ethoxymethyl][1,1'-biphenyl]-2-sulfonamide

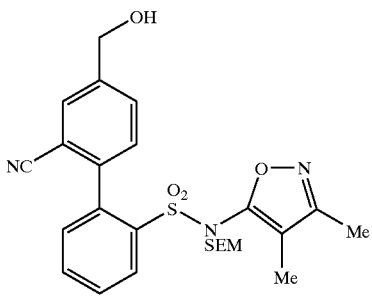

A. 4'-(Acetoxymethyl)-N-(3,4-dimethyl-5-isoxazolyl)-2'-formyl-N-[(2-trimethylsiloxy)ethoxymethyl][1,1'-biphenyl]-2-sulfonamide acetoxime Hydroxylamine hydrochloride (1.13 g) was added to a solution of 7.0 g P4 in 20 ml pyridine and the mixture was stirred at RT for 2 h. Acetic anhydride (5.1 ml) was added and the mixture was stirred for 1 h at RT. Ethanol (5 ml) was added and the mixture was concentrated under reduced pressure. The residue was taken up in ethyl acetate and washed twice with 0.1 N hydrochloric acid, twice with half-saturated aqueous sodium carbonate solution, and once with brine. The ethyl acetate layer was dried over sodium sulfate and concentrated to provide P3A as an orange oil.

B. 4'-(Acetoxymethyl)-2'-cyano-N-(3,4-dimethyl-5-isoxazolyl)-N-[(2-trimethylsiloxy)ethoxymethyl][1,1'-biphenyl]-2-sulfonamide P3A was dissolved in 75 ml acetonitrile, DBU (4.0 ml) was added, and the mixture was stirred at RT for 14 h. The mixture was concentrated, and the residue was taken up in ethyl acetate and washed twice with 0.1 N hydrochloric acid, then once with half-saturated aqueous sodium carbonate solution. The ethyl acetate layer was dried over sodium sulfate and concentrated to give P3B as an orange oil.

C. 2'-Cyano N-(3,4-dimethyl-5-isoxazolyl)-4'-(hydroxymethyl)-N-[(2-trimethylsiloxy)ethoxymethyl][1,1'-biphenyl]-2-sulfonamide P3B was dissolved in 150 ml methanol, potassium carbonate (1.5 g) was added, and the mixture was stirred at RT for 2 h. 2N Hydrochloric acid (5.5 ml) was added and the mixture was concentrated. The residue was taken up in ethyl acetate and partitioned against aqueous sodium bicarbonate solution. The ethyl acetate layer was dried over sodium sulfate and concentrated to yield 5.7 g of the crude title compound, which was used without further purification.

Preparations 4 through 22 were performed by application of the General Methods and are listed in the following Table.

| No. | Structure | Name | Starting Material | Starting Material Reference | General Methods Applied (yield, %) |
|---|---|---|---|---|---|
| P4 | 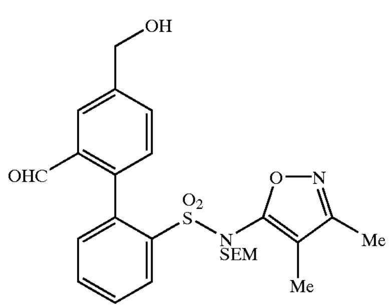 | N-(3,4-Dimethyl-5-iso-xazolyl)-2'-formyl-4'-(hydroxymethyl)-N-[[2-tri-methylsilyl)ethoxy]-methyl][1,1'-biphenyl]-2-sulfonamide |  | Zhang, H.-Y. et al., Tetrahedran, 1994, 50, 11339–11362. | 19 (95); 1 (81) |
| P5 | 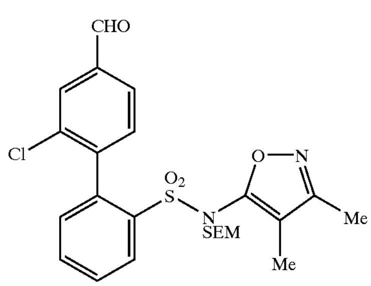 | 2'-Chloro-N-(3,4-dimethyl-5-iso-xazolyl)-4'-formyl-N-[[2-(trimethylsilyl)-ethoxy]-methyl][1,1'-biphenyl]-2-sulfonamide |  | Casida, J. E.; Elliott, M.; Pullmann, D. A., EP 294229 | 1 (83) |

-continued

| No. | Structure | Name | Starting Material | Starting Material Reference | General Methods Applied (yield, %) |
|---|---|---|---|---|---|
| P6 | (structure) | N-(3,4-Dimethyl-5-isoxazolyl(-4'-formyl-2'-(trifluoromethyl)-N[[2-(trimethylsilyl)ethoxy]methyl][1,1'-biphenyl]-2-sulfonamide | (structure) | DoAmaral, J. R.; French, F. A.; Blanz, E. J. Jr.; French, D. A. J. Med. Chem. 1971, 9, 862–866. | 1 (11) |
| P7 | (structure) | N-(3,4-Dimethyl-5-isoxazolyl)-4'-formyl-N-[(2-methoxyethoxy)-methyl]-2'-methyl[1,1'-biphenyl]-2-sulfonamide | (structure) | Pine, S. H.; et. al. J. Org. Chem. 1971, 36, 984–91. | 1 (77) |
| P8 | (structure) | N-(3,4-Dimethyl-5-isoxazolyl)-2'-fluoro-4'-formyl-N-[(2-methoxyethoxy)-methyl][1,1'-biphenyl]-2-sulfonamide | (structure) | Palmer, C. J.; Casida, J. E.; Larkin, J. P. U.S. Pat. No. 5,061,726 | 1 (50) |
| P9 | (structure) | 2'-[[(3,4-Dimethyl-5-isoxazolyl)[2-(trimethylsilyl)ethoxy]methyl]amino]sulfonyl]-2-(trifluoromethyl)[1,1'-biphenyl]-4-methanol methanesulfonate | P6 | | 11 (90); 3 (75) |
| P10 | (structure) | 2-Chloro-2'-[[(3,4-dimethyl-5-isoxazolyl)[[2-(trimethylsilyl)ethoxy]methyl]amino]sulfonyl][1,1'-biphenyl]-4-methanol methanesulfonate | P5 | | 11 (90); 3 (83) |

-continued

| No. | Structure | Name | Starting Material | Starting Material Reference | General Methods Applied (yield, %) |
|---|---|---|---|---|---|
| P11 | 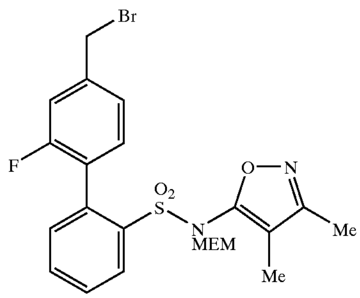 | 4'-(Bromomethyl)-N-(3,4-dimethyl-5-isoxazolyl)-2'-fluoro-N-[(2-methoxyethoxy)methyl][1,1'-biphenyl]-2-sulfonamide | P8 | | 11 (98); 2 (67) |
| P12 | 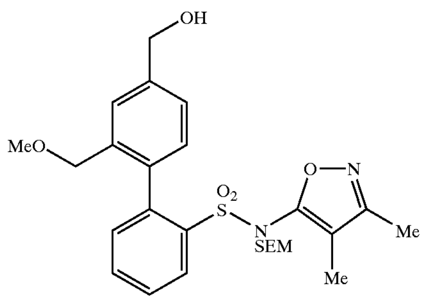 | 2'-[[(3,4-Dimethyl-5-isoxazolyl)[[2-(trimethylsilyl)ethoxy]methyl]amino]sulfonly]-4-(hydroxymethyl)[1,1'-biphenyl]-2-methanol methanesulfonate | P1 | | 3 (99); 11 (76) |
| P13 | 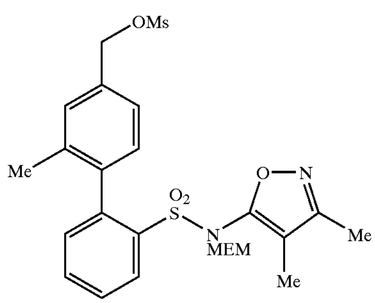 | 4'-[(Methanesulfonyloxy)methyl]-N-(3,4-dimethyl-5-isoxazolyl)-N-[(2-methoxyethoxy)methyl]-2'-methyl[1,1'-biphenyl]-2-sulfonamide | P7 | | 11; 3 (62) |
| P14 | 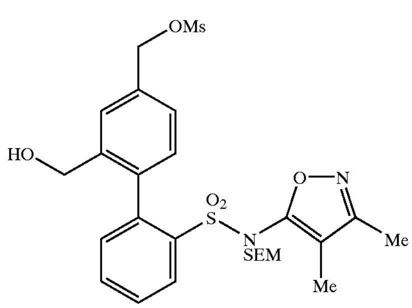 | 2'-[[3,4-Dimethyl-5-isoxazolyl)[[2-(trimethylsilyl)ethoxy]methyl]amino]sulfonyl]-2-(hydroxymethyl)[1,1'-biphenyl]-4-methanol methanesulfonate | P4 | | 3 (90); 11 (35) |
| P15 | 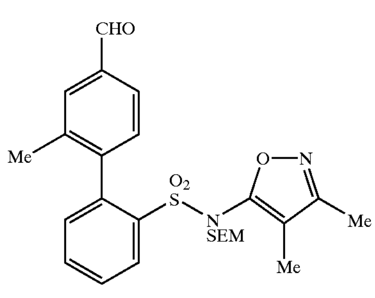 | N-(3,4-Dimethyl-5-isoxazolyl)-4'-formyl-2'-methyl-N-[[2-(trimethylsilyl)ethoxy]methyl][1,1'-biphenyl]-2-sulfonamide | | Pine, S. H.; et. al. J. Org. Chem. 1971, 36, 984–91. | 1 (52) |

-continued

| No. | Structure | Name | Starting Material | Starting Material Reference | General Methods Applied (yield, %) |
|---|---|---|---|---|---|
| P16 | (structure: 4'-CHO biphenyl, 2-SO2-N(SEM)-(3,4-dimethylisoxazol-5-yl)) | N-(3,4-Dimethyl-5-isoxazolyl)-4'-formyl-N-[[2-(trimethylsilyl)ethoxy]methyl][1,1'-biphenyl]-2-sulfonamide | 4-bromo-benzaldehyde | | 1 (67) |
| P17 | (structure: 4'-CHO biphenyl, 2-SO2-N(MEM)-(3,4-dimethylisoxazol-5-yl)) | N-(3,4-Dimethyl-5-isoxazolyl)-4'-formyl-N-[[2-methoxyethosy]methyl][1,1'-biphenyl]-2-sulfonamide | 4-bromo-benzaldehyde | | 1 (80) |
| P18 | (structure: 4'-CH2Br biphenyl, 2-SO2-N(MEM)-(3,4-dimethylisoxazol-5-yl)) | 4'-Bromomomethyl-N-(3,4-dimethyl-5-isoxazolyl)-N-(2-methoxyethoxymethyl) [1,1'-biphenyl]-2-sulfonamide | P17 | | 11, 2 (80) |
| P19 | (structure: 4'-CH2OMs biphenyl, 2-SO2-N(SEM)-(3,4-dimethylisoxazol-5-yl)) | N-(3,4-Dimethyl-5-isoxazolyl)-4'-[(methanesulfonyloxy)methyl]-N-[[2-(trimethylsilyl)ethoxy]methyl][1,1'-biphenyl]-2-sulfonamide | P16 | | 11 (83); 3 (90) |
| P20 | (structure: biphenyl with 4'-CHO, 2'-CH2OMe, 2-SO2-N(SEM)-(3,4-dimethylisoxazol-5-yl)) | N-(3,4-Dimethyl-5-isoxazolyl)-4'-formyl-N-[[2-(trimethylsilyl)ethoxy]methyl][1,1'-biphenyl]-2-sulfonamide | P2C | | 1 (72) |

-continued

| No. | Structure | Name | Starting Material | Starting Material Reference | General Methods Applied (yield, %) |
|---|---|---|---|---|---|
| P21 | 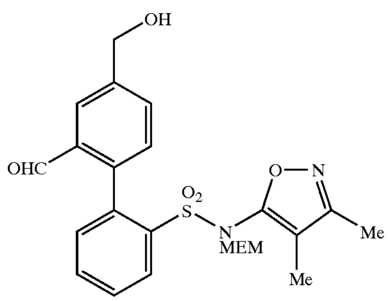 | N-(3,4-Dimethyl-5-isoxazolyl)-2'-formyl-4'-(hydroxymethyl)-N-[[2-methoxyethoxy]methyl][1,1'-biphenyl]-2-sulfonamide | | Zhang, H.-Y. et al., Tetrahedron, 1994, 50, 11339–11362. | 19 (95); 1 (77) |
| P22 | 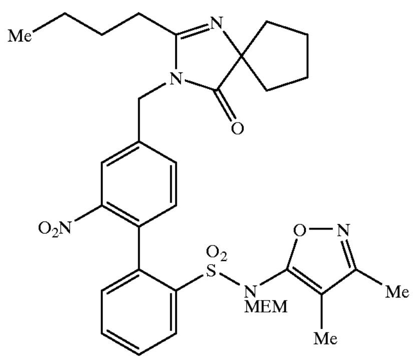 | 4'-[(2-Butyl-4-oxo-1,3-diazaspiro[4.4]non-1-en-3-yl)methyl]-N-(3,4-dimethyl-5-isoxazolyl)-N-[[2-methoxyethoxy]methyl]-2'-nitro[1,1'-biphenyl]-2-sulfonamide | 4-bromo-3-nitrotoluene | | 13 (53); 4 (74); 1 (50) |

EXAMPLES

Example 1

4'-[(2-Butyl-4-oxo-1,3-diazaspiro[4.4]non-1-en-3-yl)methyl]-N-(4,5-dimethyl-3-isoxazolyl)[1,1'-biphenyl]-2-sulfonamide

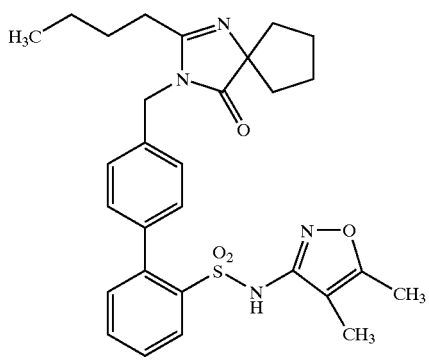

A. N-(4,5-Dimethyl-3-isoxazolyl)-4'-(hydroxymethyl)-N-[(2-methoxyethoxy)methyl][1,1'-biphenyl]-2-sulfonamide 4-Bromobenzyl alcohol (750 mg, 4.0 mmol) was coupled with [2-[[(4,5-dimethyl-3-isoxazolyl)[(2-methoxyethoxy)methyl]amino]sulfonyl]phenyl]boronic acid (1.0 g, 2.7 mmol) according to General Method 1. The crude residue was chromatographed on silica gel using 3:4 hexane/EtOAc to afford 1A (730 mg, 66%) as a colorless gum: $R_f$=0.26, silica gel, 2:3 hexane/EtOAc.

B. 4'-Bromomethyl-N-(4,5-dimethyl-3-isoxazolyl)-N-[(2-methoxyethoxy)methyl][1,1'-biphenyl]-2-sulfonamide 1A (730 mg, 1.64 mmol) was converted to the corresponding bromide according to General Method 2. The crude residue was chromatographed on silica gel using 4:1 hexane/EtOAc to afford 1B (750 mg, 90%) as a colorless gum: $R_f$=0.66, silica gel, 1:1 hexane/EtOAc.

C. 4'-[(2-Butyl-4-oxo-1,3-diazaspiro[4.4]non-1-en-3-yl)methyl]-N-(4,5dimethyl-3-isoxazolyl)-N-(2-methoxyethoxymethyl)[1,1'-biphenyl]-2-sulfonamide 1B (255 mg, 0.5 mmol was reacted with 2-butyl-1,3diazaspiro[4.4]non-1-en-4-one hydrochloride according to General Method 4. The crude residue was chromatographed on silica gel using 3:4 hexane/EtOAc to afford 1C as a gum: $R_f$=0.32, silica gel, 1:1 hexane/EtOAc.

D. 4'-[(2-Butyl-4-oxo-1,3-diazaspiro[4.4]non-1-en-3-yl)methyl]-N-(4.5-dimethyl-3-isoxazolyl)[1,1'-biphenyl]-2-sulfonamide 1C was subjected to deprotection according to General Method 7. The crude residue was purified by preparative HPLC to provide the title compound as a white solid (130 mg, 49%, for two steps): mp 77–81° C. Analysis calculated for $C_{29}H_{34}N_4O_4S \cdot 1.0H_2O$: Calc'd: C, 63.02; H, 6.57; N, 10.14; S, 5.80. Found: C, 62.75; H, 6.16; N, 9.85; S, 5.54.

Example 2
4'-[(2-Butyl-4-oxo-1,3-diazaspiro[4.4]non-1-en-3-yl)methyl]-N-(3,4-dimethyl-5-isoxazolyl)-2'-[(methylamino)methyl][1,1'-biphenyl]-2-sulfonamide

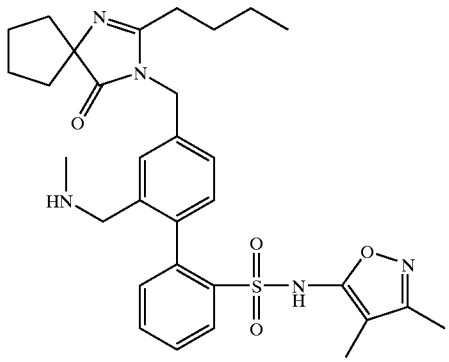

A. 4-Bromo-3-formyl-benzonitrile

To a solution of 4-bromo-3-methyl benzonitrile (14.0 g, 71.4 mmol) in carbon tetrachloride (200 mL), N-bromosuccinimide (13.98 g, 78.55 mmol) and benzoyl peroxide (700 mg) were added, and the mixture was heated at reflux for 8 h while illuminating the solution with a sun lamp. The mixture was cooled and filtered. The filtrate was concentrated to provide a light yellow solid (21 g) which was used in the next step without any further purification.

To a solution of the crude compound (21 g) obtained above in anhydrous DMSO (30 mL) under argon, was added anhydrous trimethylamine N-oxide (6.97 g, prepared as described in Soderquist et al., *Tetrahedron Letters*, 27, 3961 (1986)), and the mixture was stirred at 55° C. for 48 h. The mixture was then cooled and added to ice/water (150 mL) and the resulting aqueous mixture was extracted with EtOAc (3×100 mL). The combined organic extracts were washed once with brine (100 mL), dried and evaporated. The residue was chromatographed on silica gel using 8:1 hexanes/EtOAc to afford 2A as a white solid (6.1 g, 47% for two steps).

B. 4'-Cyano-2'-formyl-N-(3,4-dimethyl-5-isoxazolyl)-N-(2-methoxyethoxymethyl) [1,1'-biphenyl]-2-sulfonamide 2A (3.0 g, 14 mmol) was subjected to Suzuki coupling with N-[(2-methoxyethoxy)methyl]-N-(3,4-dimethyl-5-isoxazolyl)-2-(4,4,5,5-tetramethyl-1,3,2-dioxaborolan-2-yl) benzenesulfonamide according to General Method 1. The crude residue was chromatographed on silica gel using 2:1 hexane/EtOAc to afford 3B (4.5 g, 68%) as a colorless gum.

C. 4'-Cyano-2'-(N-methylaminomethyl)-N-(3,4-dimethyl-5-isoxazolyl)-N-(2-methoxyethoxymethyl)[1,1'-biphenyl]-2-sulfonamide To 2B (2.2 g, 4.69 mmol), MeNH$_2$ (8.03 M in EtOH, 2.33 mL, 18.74 mmol) and 3A molecular sieves in CH$_2$Cl$_2$ (47 mL), glacial acetic acid (1.13 g, 18.74 mmol) was added followed by NaB(AcO)$_3$H (3.98 g, 18.74 mmol). The reaction mixture was stirred at RT overnight, diluted with EtOAc and filtered through celite. The filtrate was washed with H$_2$O, dried and concentrated. The residue was chromatographed on silica gel using 100:5 CH$_2$Cl$_2$/MeOH to afford 2C (1.24 g, 55%) as a colorless gum: R$_f$=0.2, silica gel, 100:5 CH$_2$Cl$_2$/MeOH.

D. 2'-(N-t-Butoxycarbonyl-N-methylaminomethyl)-4'-cyano-N-(3,4-dimethyl-5-isoxazolyl)-N-(2-methoxyethoxymethyl) [1,1'-biphenyl]-2-sulfonamide To 2C (1.3 g, 2.68 mmol), triethylamine (434 mg, 4.3 mmol) and 4-dimethylaminopyridine (33 mg, 0.27 mmol) in THF (10 mL) was added a solution of di-t-butyl dicarbonate (703 mg, 3.22 mmol) in THF (10 mL) dropwise. The reaction mixture was stirred at RT for 3 h. 10% aqueous NH$_4$Cl was added, and the mixture was extracted with EtOAc. The extracts were washed with H$_2$O and brine, dried and concentrated. The residue was chromatographed on silica gel using 7:4 hexane/EtOAc to afford 2D (1.1 g, 70%) as a colorless gum: R$_f$=0.57, silica gel, 2:3 hexane/EtOAc.

E. 2'-(N-t-Butoxycarbonyl-N-methylaminomethyl)-N-(3,4-dimethyl-5-isoxazolyl)-4'-formyl-N-(2-methoxyethoxymethyl) [1,1'-biphenyl]-2-sulfonamide To 2D (1.03 g, 1.76 mmol) in THF (18 mL), diisobutylaluminum hydride (1M in CH$_2$Cl$_2$, 5.29 mL, 5.29 mmol) was added dropwise. The reaction mixture was stirred at RT for 4 h. MeOH (20 mL) was added, and the mixture was stirred for 20 min. The mixture was then added into H$_2$O and extracted with EtOAc. The combined extracts were washed with H$_2$O and brine, dried and concentrated. The residue was chromatographed on silica gel using 5:6 hexane/EtOAc to afford 2E (325 mg, 31%) as a colorless gum: R$_f$=0.37, silica gel, 1:1 hexane/EtOAc.

F. 2'-(N-t-Butoxycarbonyl-N-methylaminomethyl)-4'-Hydroxymethyl-N-(3,4-dimethyl-5-isoxazolyl)-N-(2-methoxyethoxymethyl)[1,1'-biphenyl]-2-sulfonamide 2E was reduced using sodium borohydride according to General Method 11 to provide 2F, which was used in the next reaction step without any purification.

G. 4'-Bromomethyl-2'-(N-t-butoxycarbonyl-N-methylaminomethyl)-N-(3,4-dimethyl-5-isoxazolyl)-N-(2-methoxyethoxymethyl)[1,1'-biphenyl]-2-sulfonamide 2F was treated with carbon tetrabromide and triphenylphosphine according to General Method 2 to provide 2G in 78% yield.

H. 2'-(N-t-Butoxycarbonyl-N-methylaminomethyl)-4'-[(2-butyl-4-oxo-1,3-diazaspiro[4.4]non-1-en-3-yl)methyl]-N-(3,4-dimethyl-5-isoxazolyl)-N-(2-methoxyethoxymethyl)[1,1'-biphenyl]-2-sulfonamide 2G was treated with 2-n-butyl-1,3-diazaspiro[4.4]non-1-en-4-one hydrochloride according to General Method 4 to provide 2H in 79% yield.

I. 4'-[(2-Butyl-4-oxo-1,3-diazaspiro[4.4]non-1-en-3-yl)methyl]-N-(3,4-dimethyl-5-isoxazolyl)-2'[(methylamino)methyl][1,1'-biphenyl]-2-sulfonamide 2H (170 mg, 0.22 mmol) was deprotected according to General Method 7 to provide the title compound in 67% yield: R$_f$=0.39, silica gel, 10:1 CH$_2$Cl$_2$/MeOH; mp: 194–200° C.; LRMS (m/z) 578 (MH$^+$).

Example 3
4'-[(2-Butyl-4-oxo-1,3-diazaspiro[4.4]non-1-en-3-yl)methyl]-2'-formyl-N-(3,4-dimethyl-5-isoxazolyl)-[1,1'-biphenyl]-2-sulfonamide

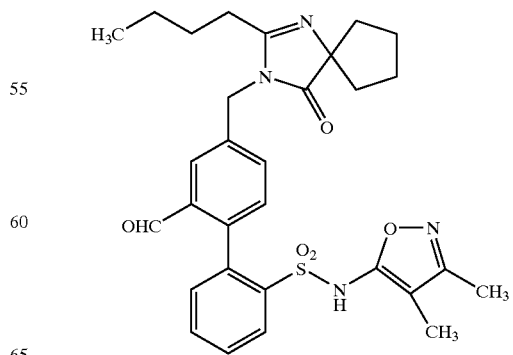

A. 4'-Cyano-2'-(1,3-dioxolan-2-yl)-N-(3,4-dimethyl-5-isoxazolyl)-N-(2-methoxyethoxymethyl) [1,1'-biphenyl]-2-sulfonamide A mixture of 2B (1.28 g, 2.73 mmol), ethylene glycol (1.69 g, 27.3 mmol) and p-toluenesulfonic acid (38 mg) in toluene (30 mL) was heated at 130° C. for 5 h, while a Dean-Stark water separator was used. After cooling, the mixture was diluted with EtOAc. The organic liquid was separated and washed with $H_2O$ and brine, dried and concentrated. The residue was chromatographed on silica gel using 5:4 hexane/EtOAc to afford 3A (1.1 g, 79%) as a colorless gum: $R_f$=0.57, silica gel, 1:2 hexane/EtOAc.

B. 2'-(1,3-Dioxolan-2-yl)-4'-formyl-N-(3,4-dimethyl-5-isoxazolyl)-N-(2-methoxyethoxymethyl)[1,1'-biphenyl]-2-sulfonamide To 3A (1.1 g, 2.14 mmol) in THF (21 mL) at 0° C. was added DIBAL-H (1M in $CH_2Cl_2$, 4.28 mL 4.28 mmol) dropwise. The reaction was stirred at RT overnight. MeOH (20 mL) was added and the reaction was stirred for 5 min. The mixture was poured into cold 0.1 N HCl solution (150 mL), shaken for 5 min, and then extracted with 3:1 EtOAc/hexane. The combined organic extracts were washed with $H_2O$ and brine, dried and concentrated. The residue was chromatographed on silica gel using 3:4 hexane/EtOAc to afford 3B (710 mg, 64%) as a colorless gum: $R_f$=0.45, silica gel, 2:3 hexane/EtOAc.

C. 2'-(1,3-Dioxolan-2-yl)-4'-hydroxymethyl-N-(3,4-dimethyl-5-isoxazolyl)-N-(2-methoxyethoxymethyl)[1,1'-biphenyl]-2-sulfonamide 3B (710 mg, 1.4 mmol) was subjected to sodium borohydride reduction according to General Method 11 to afford 3C, which was used for the next reaction step without further purification.

D. 4'-Bromomethyl-2'-(1,3-dioxolan-2-yl)-N-(3,4-dimethyl-5-isoxazolyl)-N-(2-methoxyethoxymethyl)[1,1'-biphenyl]-2-sulfonamide 3C was treated with carbon tetrabromide and triphenylphosphine according to General Method 2. The crude residue was chromatographed on silica gel using 3:2 hexane/EtOAc to afford 3D (750 mg, 94%) as a colorless gum: $R_f$=0.74, silica gel, 1:2 hexane/EtOAc.

E. 4'-[(2-Butyl-4-oxo-1,3-diazaspiro[4.4]non-1-en-3-yl)methyl]-2'-(1,3-dioxolan-2-yl)-N-(3,4-dimethyl-5-isoxazolyl)-N-(2-methoxyethoxymethyl) [1,1'-biphenyl]-2-sulfonamide 3D (750 mg, 1.3 mmol) was treated with 2-n-butyl-1,3-diazaspiro[4.4]non-1-en-4-one hydrochloride (387 mg, 1.68 mmol) according to General Method 4. The crude residue was chromatographed on silica gel using 100:1.7 $CH_2Cl_2$/MeOH to afford 3E as a gum (830 mg, 93%): $R_f$=0.40, silica gel, 100:5 $CH_2Cl_2$/MeOH.

F. 4'-[(2-Butyl-4-oxo-1,3-diazaspiro[4.4]non-1-en-3-yl)methyl]-2'-formyl-N-(3,4-dimethyl-5-isoxazolyl)-[1,1'-biphenyl]-2-sulfonamide 3E (830 mg, 1.20 mmol) was subjected to deprotection according to General Method 7. The crude residue was chromatographed on silica gel using 100:1.5 and then 100:4 $CH_2Cl_2$/MeOH to afford the title compound as a gum (480 mg, 72%): $R_f$=0.16, silica gel, 100:5 $CH_2Cl_2$/MeOH.

Example 4

4'-[(2-Butyl-4-oxo-1,3-diazaspiro[4.4]non-1-en-3-yl)methyl]-N-(3,4-dimethyl-5-isoxazolyl)-2'-[(3,3-dimethyl-2-oxo-1-pyrrolidinyl)methyl][1,1'-biphenyl]-2-sulfonamide

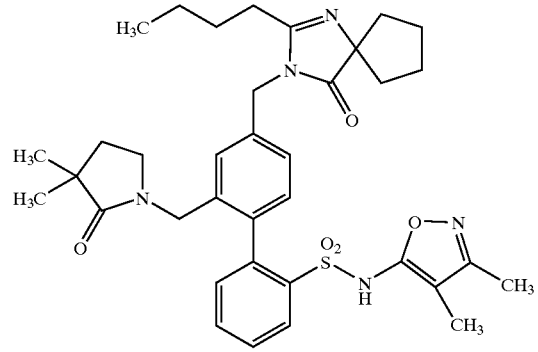

To 3F (110 mg, 0.20 mmol) in $CH_2Cl_2$ (4 mL) was added 4-amino-2,2-dimethylbutanoic acid hydrochloride (98 mg, 0.59 mmol) [Scheinmann, et al., *J. Chem. Research (S)*, 414–415 (1993)] and 3 Å molecular sieves, followed by glacial acetic acid (35 mg, 0.59 mmol) and then sodium acetate (48 mg, 0.59 mmol). The mixture was stirred for 8 minutes, and $NaB(AcO)_3H$ (124 mg, 0.59 mmol) was then added. The reaction mixture was stirred at RT for 2 h, diluted with EtOAc and filtered through celite. The filtrate was washed with $H_2O$ and brine, dried and concentrated. This material was dissolved in $CH_2Cl_2$ (6 mL) and 1,3-diisopropylcarbodiimide (32 mg, 0.25 mmol) was added. The reaction mixture was stirred at RT for 2 h and diluted with $CH_2Cl_2$, washed with $H_2O$ and brine, dried and concentrated. The residue was purified by preparative HPLC to provide the title compound as a white solid (40 mg, 31%, for two steps): mp 104–110° C. Analysis calculated for $C_{36}H_{45}N_5O_5S\cdot0.8\,H_2O$: Calc'd: C, 64.13; H, 6.97; N, 10.39; S, 4.75. Found: C, 64.18; H, 6.60; N, 10.23; S, 4.50.

Example 5

4'-[(2-Butyl-4-oxo-1,3-diazaspiro[4.4]non-1-en-3-yl)methyl]-2'-formyl-N-(3,4-dimethyl-5-isoxazolyl)-[1,1'-biphenyl]-2-sulfonamide (Alternative Preparation for 3F)

A. 2-[(2'-Bromo-5'-formyl)phenyl)]-1,3-dioxolane

DIBAL-H (1.0 M solution in toluene, 445 mL, 445 mmol, 1.1 eq) was added over 30 minutes to a solution of 2-[(2'-bromo-5'-cyano)phenyl)]-1,3dioxolane (103 g, 404 mmol, 1.0 eq) [Zhang, H.-Y. et al., *Tetrahedron*, 50, 11339–11362 (1994)] in toluene (2.0 L) at −78° C. The solution was allowed to warm to 0° C. After 1 hour, a solution of Rochelle's salt (125 g) in water (200 mL) was added, and the mixture was allowed to warm to room temperature and was stirred vigorously for 16 h. The organic layer was concentrated and the residue partitioned between ethyl acetate (1 L) and 1 N hydrochloric acid (800 mL). The organic layer was washed with saturated aqueous sodium bicarbonate (800 mL), dried over sodium sulfate, and then concentrated to give 70.5 g of crude 5A as a yellow solid, which was used without further purification.

B. 2-[(2'-Bromo-5'-hydroxymethyl)phenyl)]-1,3-dioxolane

Sodium borohydride (3.66 g, 96.7 mmol, 0.5 eq) was added to a solution of crude 5A (49.7 g, approximately 193 mmol, 1.0 eq) in absolute ethanol (1300 mL) at 0° C. After 2 hours, a solution of 10% aqueous sodium dihydrogen phosphate (50 mL) was added and the mixture was stirred and allowed to warm to room temperature. The mixture was concentrated, then partitioned between ethyl acetate (800 mL) and saturated aqueous sodium bicarbonate (500 mL). The organic layer was dried over sodium sulfate and concentrated to give 49.0 g of crude 5B as a yellow oil, which was used without further purification.

C. 2-[(2'-Bromo-5'-bromomethyl)phenyl)]-1,3-dioxolane

Triphenylphosphine (52.7 g, 199 mmol, 1.05 eq) was added in portions over 15 minutes to a solution of crude 5B (49.0 g, approximately 189 mmol, 1.0 eq) and carbon tetrabromide (69.0 g, 208 mmol, 1.1 eq) in THF at 0° C. After 2 hours, saturated aqueous sodium bicarbonate solution (20 mL) was added, and the mixture was allowed to warm to room temperature and was then concentrated. Ether (500 mL) was added, and the resulting mixture was filtered. The filtrate was dried over magnesium sulfate and concentrated. The residue was chromatographed on silica gel (8:1 hexanes/ethyl acetate as eluant) to give 5C as a white solid (31.1 g, 51% yield from 2-[(2'-bromo-5'-cyano)phenyl)]-1,3-dioxolane).

D. 2-(1,3-Dioxolan-2-yl)-4-[(2-n-butyl-4-oxo-1,3-diazaspiro[4.4]non-1-en-3-yl)methyl]bromobenzene Sodium hydride (60% dispersion in mineral oil, 9.65 g, 241 mmol, 2.5 eq) was added in portions over 15 minutes to a mixture of 2-n-butyl-1,3-diazaspiro[4.4]non-1-en-4-one hydrochloride (18.7 g, 96.5 mmol, 1.0 eq) in DMF (400 mL) at 0° C. The mixture was stirred and allowed to warm to room temperature over 15 minutes. To this mixture was added via canula a solution of 5C (31.1 g, 96.5 mmol, 1.0 eq) in DMF (100 mL). After 14 hours, the mixture was concentrated in vacuo and partitioned between ethyl acetate (500 mL) and 10% aqueous sodium dihydrogen phosphate (300 mL). The organic layer was dried over sodium sulfate and concentrated to give crude 5D as an orange oil (42.7 g), which was used without further purification.

E. 4-[(2-n-Butyl-4-oxo-1,3-diazaspiro[4.4]non-1-en-3-yl)methyl]-2-formyl-bromobenzene A solution of crude 5D (6.0 g, approximately 13.6 mmol, 1.0 eq) in THF (180 mL) and 1N hydrochloric acid (30 mL) was heated at 65° C. for 1.5 hours. The mixture was cooled and then treated with saturated aqueous sodium carbonate solution (75 mL) and ethyl acetate (200 mL). The organic layer was removed and dried over sodium sulfate, concentrated, and then further dried azeotropically with toluene to give 5E as a crude yellow oil (8.2 g) which contained a small amount of toluene. This material was used without further purification.

F. 4'-[(2-Butyl-4-oxo-1,3-diazaspiro[4.4]non-1-en-3-yl)methyl]-2'-formyl-N-(3,4-dimethyl-5-is oxazolyl)-N-(2-methoxyethoxymethyl) [1 1'-biphenyl]-2-sulfonamide Palladium catalyzed Suzuki coupling of 5E and [2-[[(3,4-dimethyl-5isoxazolyl)[(2-methoxyethoxy)methyl]amino]sulfonyl]phenyl]boronic acid was performed according to General Method 1 to yield 5F in 60% yield.

G. 4'-[(2-Butyl-4-oxo-1,3-diazaspiro[4.4]non-1-en-3-yl)methyl]-2'-formyl-N-(3,4-dimethyl-5-isoxazolyl)-[1,1'-biphenyl]-2-sulfonamide Deprotection of 5F according to General Method 7 provided the title compound (5G=3F) in 73% yield: R$_f$=0.2 (silica gel using CH$_2$Cl$_2$/MeOH [100:5]).

Example 6

4'-[(2-Butyl-4-oxo-1,3-diazaspiro[4.4]non-1-en-3-yl)methyl]-N-(3,4-dimethyl-5-isoxazolyl)-2'-[3,3-dimethyl-2-oxo-1-pyrrolidinyl)methyl][1,1'-biphenyl]-2-sulfonamide (Alternative Preparation for 4)

The title compound (6=4) was obtained as a white solid from 5G using a procedure similar to that described in Example 4 (945 mg, 35%): mp 104–110° C. Analysis calculated for C$_{36}$H$_{45}$N$_5$O$_5$S.0.8 H$_2$O: Calc'd: C, 64.13; H, 6.97; N, 10.39; S, 4,75. Found: C, 64.18; H, 6.60; N, 10.23; S, 4.50.

Example 7

4'-[(2-Butyl-4-oxo-1,3-diazaspiro[4.4]non-1-en-3-yl)methyl]-N-(3,4-dimethyl-5-isoxazolyl)-2'-[(3-methyl-2-oxo-1-imidazolidinyl)methyl][1,1'-biphenyl]-2-sulfonamide

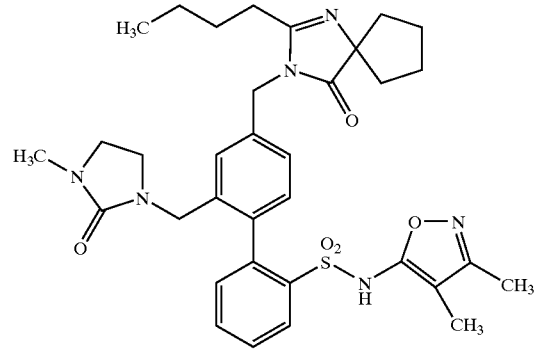

A. 4'-[(2-Butyl-4-oxo-1,3-diazaspiro[4.4]non-1-en-3-yl)methyl]-N-(3,4-dimethyl-5-isoxazolyl)-N-(2-methoxyethoxymethyl)-2'-[(3-methyl-2-oxo-1-imidazolidinyl)methyl][1,1'-biphenyl]-2-sulfonamide To a solution of 0.3 g (0.46 mmol) of 5F in CH$_2$Cl$_2$ (15 mL) was added 3 Å molecular sieves (1 mL), N-methyl ethylenediamine (0.051 g, 0.69 mmol) and glacial acetic acid (0.828 g, 1.38 mmol), and the resulting mixture was stirred under argon for 15 min. Sodium triacetoxyborohydride (0.292 g, 1.38 mmol) was then added to the mixture, and the resulting mixture was stirred at room temperature for 3 h. The solution was then filtered through celite, and the celite was washed with CH$_2$Cl$_2$ (25 mL). The combined filtrates were washed with water (2×50 mL), dried and evaporated to afford a colorless gum (0.32 g). This gum was redissolved in CH$_2$Cl$_2$ (10 mL), and carbonyldiimidazole was then added (0.112 g, 0.69 mmol). The resulting mixture was stirred at room temperature for 24 h. The mixture was then washed with water (15 mL) and dried and evaporated to provide a colorless gum. Purification on silica gel using 1:1 hexane: EtOAc then provided 7A (0.17 g, 50%) as a colorless gum.

B. 4'-[(2-Butyl-4-oxo-1,3-diazaspiro[4.4]non-1-en-3-yl)methyl]-N-(3,4-dimethyl-5-isoxazolyl)-2'-[(3-methyl-2-oxo-1-imidazolidinyl)methyl][1,1'-biphenyl]-2-sulfonamide To a solution of 7A (0.165 g, 0.225 mmol) in 95% EtOH (2 mL) was added 6N aqueous hydrochloric acid (2 mL), and the resulting solution was heated at reflux for 1 h. The mixture was then neutralized with aqueous sodium bicarbonate to pH 7 and then reacidified to pH 6 using aqueous sodium bisulfate. The mixture was then extracted with EtOAc (3×30 mL). The combined organic extracts were then washed once with water and dried and evaporated. The residue was purified on silica gel using 5% MeOH in methylene chloride to provide the title compound (0.13 g, 89%) as a light yellow solid: $^1$H NMR (CDCl$_3$) δ 0.89 (t, J=7.0 Hz, 3H), 1.26–1.60 (m, 4H), 1.87 (s, 3H), 1.97 (m, 8H), 2.16 (s, 3H), 2.35 (t, J=7.6 Hz, 2H), 2.72 (s, 3H), 3.29 (br s, 4H), 4.10 (s, 2H), 4.72 (m, 2H), 7.13–7.92 (m, 7H).

Example 8
4'-[(2-Butyl-4-oxo-1,3-diazaspiro[4.4]non-1-en-3-yl)methyl]-2'-[(3,3dimethyl-2-oxo-1-pyrrolidinyl)methyl]-N-(2-pyrazinyl)[1,1'-biphenyl]-2-sulfonamide

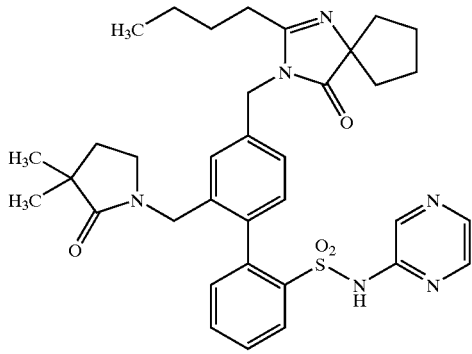

A. N-tert-Butyl-4'-[(2-n-butyl-4-oxo-1,3-diazaspiro[4.4]non-1-en-3-yl)methyl]-2'-formyl[1,1'-biphenyl]-2-sulfonamide Crude 5E (8.3 g, approximately 13.6 mmol) was subjected to Suzuki coupling with [2-(N-tert-butylsulfamoyl)phenyl]boronic acid according to General Method 1. The crude residue was chromatographed on triethylamine-deactivated silica gel (1:1 hexanes/ethyl acetate eluant) to yield 8A (5.03 g, 71% from 5C) as an orange oil.

B. N-tert-Butyl-4'-[(2-n-butyl-4-oxo-1,3-diazaspiro[4.4]non-1-en-3-yl)methyl]-2'-[(3,3-dimethyl-2-oxo-1-pyrrolidinyl)methyl][1,1'-biphenyl]-2-sulfonamide A mixture of 8A (2.0 g, 3.81 mmol, 1.0 eq), 4-amino-2,2-dimethylbutanoic acid hydrochloride (1.28 g, 7.64 mmol, 2.0 eq), freshly-activated 3 Å molecular sieves (5.0 g), and methanol (35 mL) was stirred at room temperature. Solid 85% potassium hydroxide (225 mg) was added to adjust the pH to 6.5. After 1.5 hours, sodium cyanoborohydride (120 mg, 1.91 mmol, 1.5 eq) was added, and the mixture was stirred for an additional two hours. Solid 85% potassium hydroxide (640 mg) was added, the mixture was filtered, and the filtrate concentrated. To the residue was added dry dichloromethane (35 mL) and EDCI (1.10 g, 5.72 mmol, 1.5 eq) and the mixture was stirred at room temperature for 17 hours. Saturated aqueous sodium carbonate solution (100 mL) was added and the aqueous layer was extracted with dichloromethane (3×150 mL). The combined organic extracts were dried over sodium sulfate and concentrated to give 8B (2.50 g) as a crude yellow oil used directly without further purification.

C. 4'-[(2-n-Butyl-4-oxo-1,3-diazaspiro[4.4]non-1-en-3-yl)methyl]-2'-[(3,3-dimethyl-2-oxo-1-pyrrolidinyl)methyl][1,1'-biphenyl]-2-sulfonamide Crude 8B (2.50 g) was dissolved in trifluoroacetic acid (16 mL) and the resulting solution was stirred at room temperature for 7 hours. The resulting mixture was concentrated, and saturated aqueous sodium bicarbonate solution was added to the residue. This mixture was extracted with ethyl acetate (3×50 mL), and the combined organic extracts were dried over sodium sulfate and concentrated. Silica gel chromatography of the residue (5% methanol in dichloromethane as eluant) gave 8C (0.98 g, 45% from 8A) as a yellow solid.

D. 4'-[(2-Butyl-4-oxo-1,3-diazaspiro[4.4]non-1-en-3-yl)methyl]-2'-[(3,3-dimethyl-2-oxo-1-pyrrolidinyl)methyl]-N-(2-pyrazinyl)[1,1'-biphenyl]-2-sulfonamide A solution of 8C (110 mg, 0.19 mmol, 1.0 eq) in DMF (2.5 mL) was treated at room temperature with sodium hydride (60% dispersion in mineral oil, 17 mg, 0.43 mmol, 2.2 eq). After 10 minutes, 2-chloropyrazine (68 μl, 0.76 mmol, 4.0 eq) was added via syringe, and the mixture heated at 120° C. for 2 hours and 130° C. for 6 hours. The solvent was evaporated, and the residue partially purified by preparative reverse-phase HPLC. The fractions containing product were evaporated, and the residue partitioned between dichloromethane and 10% aqueous sodium dihydrogen phosphate. The aqueous phase was adjusted to pH 5 and extracted with two additional portions of dichloromethane. The combined organic extracts were dried over sodium sulfate, evaporated, and the residue chromatographed on silica gel (3% methanol in dichloromethane as eluant) to yield still impure product (70 mg). This material was subjected to ion-exchange chromatography to give the pure title compound (8 mg, 6%) as d white powder after lyophilization: $^1$H NMR (CDCl$_3$, 400 MHz) δ 8.52 (s, 1H), 8.29 (dd, J=1 and 8 Hz, 1H), 8.16 (d, J=3 Hz, 1H), 7.97 (s, 1H), 7.60 (dt, J=1 and 7 Hz, 1H), 7.55 (dt, J=1 and 7 Hz, 1H), 7.20 (dd, J=1 and 7 Hz, 1H), 7.01 (s, 2H), 6.96 (s, 1H), 4.60 (AB quartet, J=16 Hz, 2 H), 4.15 (AB quartet, J=16 Hz, 2 H), 3.16 (m, 2H), 2.34 (dd, J=7 and 8 Hz, 2H), 1.97 (m, 6H), 1.87 (t, J=7 Hz, 2H), 1.82 (m, 2H), 1.61 (m, 2H), 1.36 (sextet, J=7 Hz, 2 H), 1.17 (s, 3H), 1.16 (s, 3H), 0.90 (t, J=7 Hz, 3H); LRMS m/z 643 (ESI+ mode).

Example 9
4'-[(2-Butyl-4-oxo-1,3-diazaspiro[4.4]non-1-en-3-yl)methyl]-N-(3-chloro-2-pyrazinyl)-2'-[(3,3-dimethyl-2-oxo-1-pyrrolidinyl)methyl][1,1'-biphenyl]-2-sulfonamide

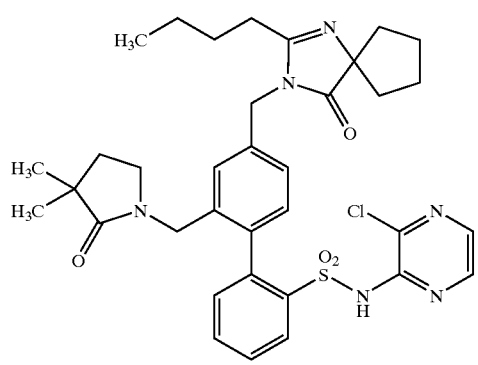

A solution of 8C (100 mg, 0.18 mmol, 1.0 eq) in DMF (1.8 mL) was treated at room temperature with sodium hydride (60% dispersion in mineral oil, 8.5 mg, 0.21 mmol, 1.2 eq). After 10 minutes, 2,3-dichloropyrazine (79 mg, 0.53 mmol, 3.0 eq) was added via syringe, and the mixture heated at 60° C. for 3 hours, then at 85° C. for 14 hours, and then at 120° C. for 5 hours. Workup and purification as described in Example 8 yielded the title compound (7.4 mg, 10%) as a white powder after lyophilization: $^1$H NMR (CDCl$_3$, 400 MHz) δ 8.40 (dd, J=1 and 8 Hz, 1H), 8.0 (m, 2H), 7.68 (dt, J=1 and 7 Hz, 1H), 7.61 (dt, J=1 and 7 Hz, 1H), 7.22 (dd, J=1 and 7 Hz, 1H), 7.16 (s, 1H), 7.05 (d, J=8 Hz, 1H), 6.89 (d, J=8 Hz, 1H), 6.85 (br s, 2H), 4.87 (AB quartet, J=16 Hz, 2 H), 4.31 (d, J=16 Hz, 1H), 4.15 (d, J=16 Hz, 1H), 3.16 (m, 2H), 2.82 (t, J=7 Hz, 2H), 1.90–2.20 (m, 8H), 1.82 (m, 2H), 1.66 (m, 2H), 1.38 (sextet, J=7 Hz, 2H), 1.22 (s, 3H), 1.14 (s, 3H), 0.92 (t, J=7 Hz, 3H) ppm; LRMS m/z 677, 679 (ESI+ mode); m/z 675, 677 (ESI− mode).

Example 10
4'-[(2-Butyl-4-oxo-1,3-diazaspiro[4.4]non-1-en-3-yl)methyl]-N-(3,4-dimethyl-5-isoxazolyl)-2'-[(2-oxo-1-pyrrolidinyl)methyl][1,1'-biphenyl]-2-sulfonamide

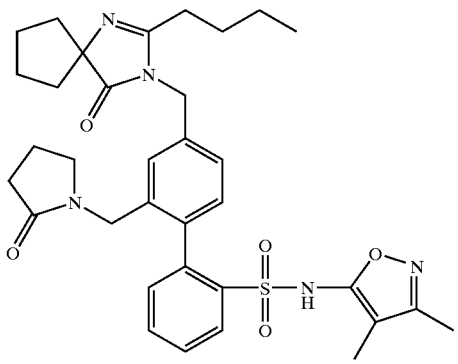

The title compound was prepared in 51% yield starting from 3F and 4-aminobutyric acid as described in Example 4 as a white solid: mp 95–100° C.; $^1$H NMR (CDCl$_3$) δ 0.90 (t, J=7.3 Hz, 3H), 1.36 (m, 2H), 1.61 (m, 2H), 1.82–2.10 (m, 15H), 2.17 (s, 3H), 2.36 (m, 2H), 3.41 (m, 2H), 4.20 (m, 2H), 4.72 (s, 2H), 7.00–7.90 (m, 7H).

Example 11
4'-[(2-Butyl-4-oxo-1,3-diazaspiro[4.4]non-1-en-3-yl)methyl]-2'-[(3,3dimethyl-2-oxo1-pyrrolidinyl)methyl]-N-(3,6-dimethyl-2-pyrazinyl)[1,1'-biphenyl]-2-sulfonamide

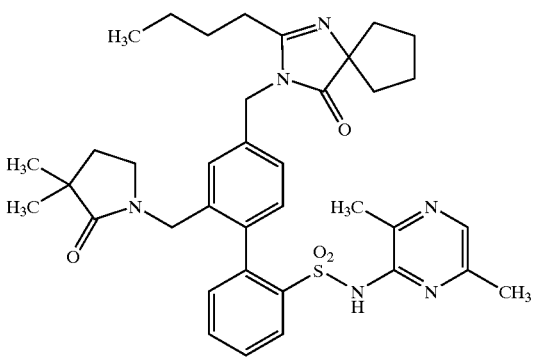

A mixture of 8C (200 mg, 0.36 mmol, 1.0 eq), palladium acetate (4 mg, 0.02 mmol, 0.05 eq), (S)-BINAP (2.5 mg, 0.02 mmol, 0.05 eq), and toluene (5 mL) was sparged with nitrogen for 10 minutes. 2-Chloro-3,6-dimethylpyrazine (83 μl, 0.71 mmol, 2.0 eq) was added via syringe, followed by sodium hydride (60% dispersion in mineral oil, 28 mg, 0.71 mmol, 2.0 eq). The mixture was heated at 80° C. for 15 hours. After cooling, the mixture was diluted with ethyl acetate and partitioned against 10% aqueous sodium phosphate adjusted to pH 5–6, and the aqueous layer was extracted with two additional portions of ethyl acetate. The combined organic extracts were dried over sodium sulfate, concentrated, and evaporated to a yellow oil, which was chromatographed on silica gel (1:3 hexanes/ethyl acetate eluant) to yield the title compound (50 mg, 21%) as an off-white solid: $^1$H NMR (CD$_3$OD, 400 MHz) δ 8.14 (d, J=7 Hz, 1H), 7.75 (br s, 1H), 7.49 (m, 2H), 7.11 (dd, J =1 and 7 Hz, 1H), 6.87 (s, 2H), 6.70 (s, 1H), 4.65 (br s, 2 H), 4.11 (s, 2H), 3.95 (m, 2H), 2.92 (m, 2H), 2.29 (br s, 2H), 2.17 (s, 3H), 2.06 (s, 3H), 1.79 (m, 6H), 1.68 (m, 2H), 1.65 (m, 2H), 1.41 (m, 2H), 1.17 (m, 2H), 1.03 (s, 3H), 1.00 (s, 3H), 0.72 (t, J=7 Hz, 3H); LRMS m/z 671 (ESI+ mode); m/z 669 (ESI– mode).

Example 12
N-[[4-[(2-Butyl-4-oxo-1,3-diazaspiro[4.4]non-1-en-3-yl)methyl[-2'-[[(3,4-dimethyl-5-isoxazolyl)amino]sulfonyl][1,1'-biphenyl]-2-yl]methyl]-N,N',N'-trimethylurea

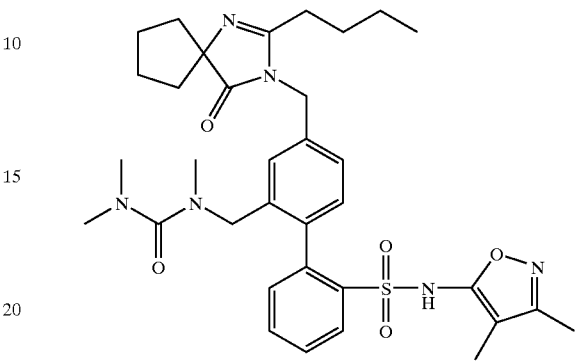

To 2I (34.7 mg, 0.06 mmol) in CH$_2$Cl$_2$ (0.6 mL) and DMF (0.15 mL) was added dimethylcarbamyl chloride (6.5 mg, 0.06 mmol) followed by triethyl amine (6.7 mg, 0.066 mmol). The resulting mixture was stirred at RT for two days. The mixture was purified by anion-exchange chromatography to provide the title compound (90%). Characterization recorded with Example 73.

Example 13
N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N'-(1,1-dimethylethyl)-N-methylurea

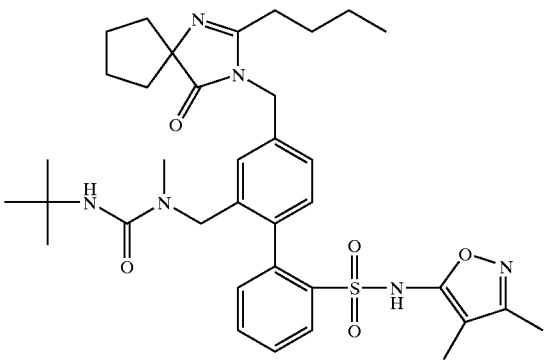

To 2I (34.7 mg, 0.06 mmol) in CH$_2$Cl$_2$ (0.6 mL) and DMF (0.15 mL), t-butylisocyanate (6.0 mg, 0.06 mmol) was added, and the resulting mixture was stirred at RT for two days. The mixture was was purified by anion-exchange chromatography to provide the title compound (90%). Characterization recorded with Example 74.

Example 14

[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]methylcarbamic acid ethyl ester

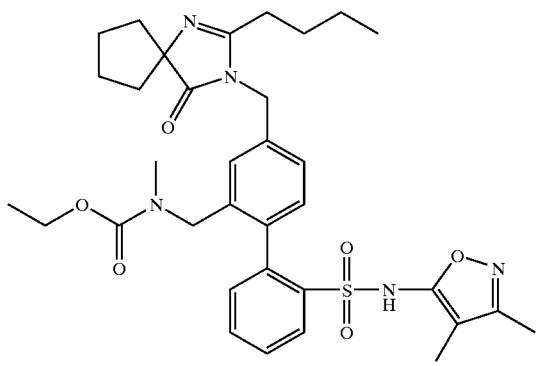

The title compound was prepared from 2I and ethyl chloroformate using a procedure similar to the one described in Example 12 (90%). Characterization recorded with Example 75.

Example 15

[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]methylcarbamic acid 2-methylpropyl ester

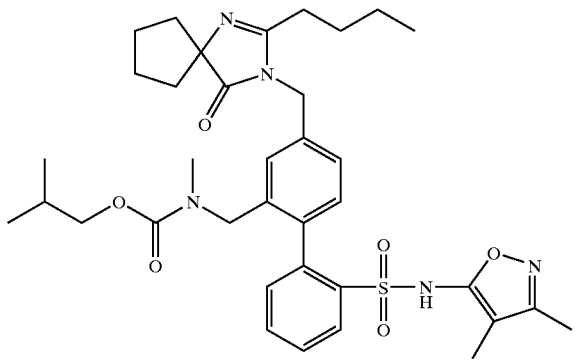

The title compound was prepared from 2I and isobutyl chloroformate using a procedure similar to the one described in Example 12 (90%). Characterization recorded with Example 76.

Example 16

4'-[(2-Butyl-4-oxo-1,3-diazaspiro[4.4]non-1-en-3-yl)methyl]-2'-[(3,3-dimethyl-2-oxo-1-pyrrolidinyl)methyl]-N-(3-methoxy-2-pyrazinyl)[1,1'-biphenyl]-2-sulfonamide

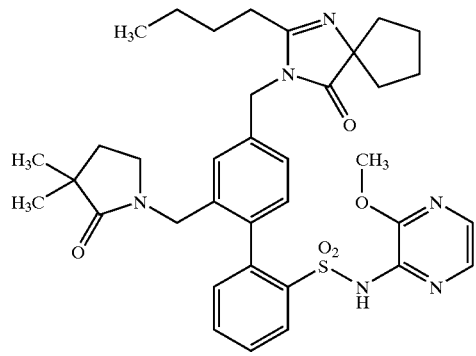

The title compound was prepared from 8C (486 mg, 0.86 mmol) and 2-chloro-3-methoxypyrazine (250 mg, 1.72 mmol) [Uchimaru, F. et al., *Chem. Pharm. Bull.*, 20, 2204–2208 (1972)] using a procedure similar to the one used in Example 9. Preparative reverse-phase HPLC of the crude product after extractive workup gave the title compound (24 mg, 4%) as an off-white solid after lyophilization: $^1$H NMR (CDCl$_3$, 400 MHz) δ 10.8 (br s, 2H), 8.36 (dd, J=1 and 8 Hz, 1H), 7.50–7.65 (m, 4H), 7.19 (dd, J=1 and 7 Hz, 1H), 7.15 (s, 1H), 7.01 (s, 2H), 4.92 (AB quartet, J=16 Hz, 2H), 4.20 (AB quartet, J=16 Hz, 2H), 3.99 (s, 3H), 3.18 (m, 2H), 2.82 (m, 2H), 2.18 (m, 4H), 1.96 (m, 4H), 1.82 (m, 2H), 1.63 (m, 2H), 1.32 (m, 2H), 1.21 (s, 3H), 1.12 (s, 3H), 0.87 (t, 3H, J=7 Hz, 3H); LRMS m/z 673 (ESI+ mode); m/z 671 (ESI– mode); HPLC retention time 25.52 minutes (Method B).

Example 17

4'-[(2-Butyl-4-oxo-1,3-diazaspiro[4.4]non-1-en-3-yl)methyl]-2'-formyl-N-(4,5-dimethyl-3-isoxazolyl)-[1,1'-biphenyl]-2-sulfonamide

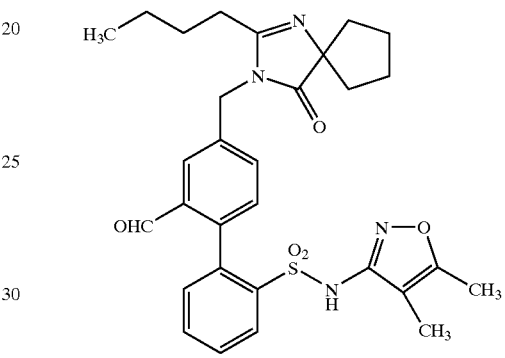

A. 4'-[(2-Butyl-4-oxo-1,3-diazaspiro[4.4]non-1-en-3-yl)methyl]-2'-formyl-N-(4,5-dimethyl-3-isoxazolyl)-N-(2-methoxyethoxymethyl) [1,1'-biphenyl]-2-sulfonamide Palladium catalyzed Suzuki coupling of 5E and [2-[[(4,5-dimethyl-3-isoxazolyl)[(2-methoxyethoxy)methyl]amino]sulfonyl]phenyl]boronic acid was performed according to General Method 1 to afford 17A (81%) following silica-gel chromatography.

B. 4'-[(2-Butyl-4-oxo-1,3-diazaspiro[4.4]non-1-en-3-yl)methyl]-2'-formyl-N-(4,5-dimethyl-3-isoxazolyl)-[1,1'-biphenyl]-2-sulfonamide Treatment of 17A with 6N aqueous hydrochloric acid according to General Method 7 provided the title compound (85%): R$_f$=0.38, 5% MeOH in methylene chloride.

Example 18

4'-[(2-Butyl-4-oxo-1,3-diazaspiro[4.4]non-1-en-3-yl)methyl]-N-(4,5-dimethyl-3-isoxazolyl)-2'-[(2-oxo-1-pyrrolidinyl)methyl][1,1'-biphenyl]-2-sulfonamide

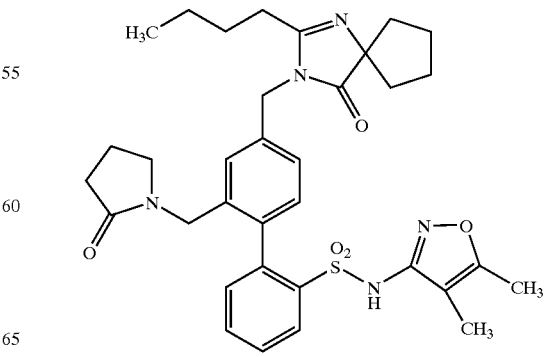

The title compound was obtained as a white solid using 17B and 4-aminobutyric acid as described in Example 4 (25%): mp 97–103° C.; $^1$H NMR (CDCl$_3$) δ 0.90 (t, J=7 Hz, 3H), 1.36 (m, 2H), 1.62 (m, 2H), 1.80–2.10 (m, 13H), 2.26 (s, 3H), 2.39 (m, 4H), 3.31 (m, 2H), 4.20 (s, 2H), 4.73 (s, 2H), 7.05–8.10 (m, 7H).

Example 19

(S)-N-[[2'-[[(3,4-Dimethyl-5-isoxazolyl)amino]sulfonyl][1,1'-biphenyl]-4-yl]methyl]-N-[2-methyl-1-(3-methyl-1,2,4-oxadiazol-5-yl)propyl]pentanamide

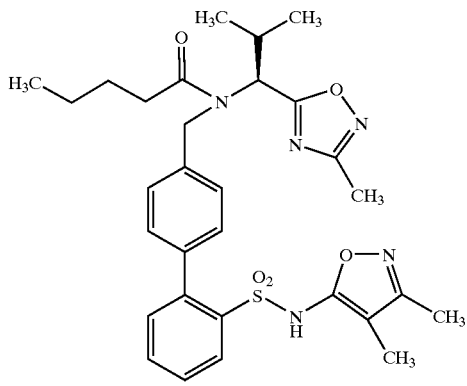

A. (S)-5-(1-amino-2-methylpropyl)-3-methyl-1,2,4-oxadiazole

A solution of BOC-L-valine (4.34 g, 20.0 mmol) in dichloromethane (20 mL) was cooled to 0° C. and treated dropwise with a solution of dicyclohexylcarbodiimide (2.06 g, 10.0 mmol) in dichloromethane (5 mL). After 1 hour the white solid which had formed was removed by filtration and the filtrate concentrated under reduced pressure. The residue was dissolved in pyridine (15 mL) and treated with acetamidoxime (488 mg, 6.6 mmol) in pyridine (5 mL) and the mixture heated at reflux for 1 hour. The pyridine was evaporated under reduced pressure and the residue partitioned between ethyl acetate and water. The organic phase was washed several times with water, dried over magnesium sulfate and concentrated. The residue was chromatographed on silica gel using 10% ethyl acetate in hexanes to elute the product (0.62 g, 25%) as a white solid.

A solution of the above product in 3 M hydrochloric acid (10 mL) was stirred at room temperature for 1 hour. The mixture was evaporated to dryness under reduced pressure and then azeotroped with toluene. This gave 19A as a white solid (100%).

B. 2'-[[(3,4-Dimethyl-5-isoxazolyl)amino]sulfonyl][1,1'-biphenyl]-4-carboxaldehyde P17 (0.35 g, 0.79 mmol) was subjected to deprotection according to General Method 7. Extraction and concentration gave 200 mg (71%) of 19B as a yellow solid which was used without purification.

C. (S)-[[1-[2'-[(3,4-Dimethyl-5-isoxazolyl)amino]sulfonyl][1,1'-biphenyl]-4-ylmethylamino]-2-methylpropyl]-3-methyl-1,2,4-oxadiazole A mixture of 19B (100 mg, 0.28 mmol) and 19A (53 mg, 0.28 mmol) in dichloroethane (8 mL) was treated with sodium triacetoxyborohydride (74 mg, 0.35 mmol) in one portion and the mixture stirred under argon at room temperature. After 1 hour more sodium triacetoxyborohydride (32 mg, 0.15 mmol) was added to the mixture which stirred for 45 minutes more and the mixture was adjusted to pH 6 with saturated sodium bicarbonate solution. The mixture was diluted with 50 mL dichloromethane and the organic phase washed with water, dried over magnesium sulfate and concentrated to give crude 19C (110 mg, 79%) which was used without purification in the next step.

D. (S)-N-[[2'-[[(3,4-Dimethyl-5-isoxazolyl)amino]sulfonyl][1,1'-biphenyl]-4-yl]methyl]-N-[2-methyl-1-(3-methyl-1,2,4-oxadiazol-5-yl)propyl]pentanamide A mixture of 19C (100 mg, 0.20 mmol), dichloromethane (5 mL) and triethylamine (70 mL, 0.5 mmol) was treated with valeryl chloride (60 mg, 0.5 mmol) and the mixture stirred under argon for 16 hours. The reaction mixture was concentrated under reduced pressure and the residue treated with 2 M sodium hydroxide (1 mL) and 2-propanol (2 mL) and stirred at room temperature for 1.5 hours. Citric acid was added to adjust the pH to 5–6 and the mixture extracted with dichloromethane. The residue obtained after drying the extract over magnesium sulfate and concentrating under reduced pressure was chromatographed on silica gel using 30 to 50% ethyl acetate in hexanes to elute the title product (73 mg, 63%) as a white foam: ESIMS (NH$_3$) m/z 580 (MH$^+$, 100), 597 (M+NH$_4^+$, 20), 1176 (2M+NH$_4^+$, 10); HRMS calcd for C$_{30}$H$_{37}$N$_5$O$_5$S (MH$^+$) 580.2593, found 580.2619.

Example 20

N-(3,4-Dimethyl-5-isoxazolyl)-2'-[(3,3-dimethyl-2-oxo-1-pyrrolidinyl)methyl]-4'-[(2-ethyl-5,7-dimethyl-3H-imidazo[4,5-b]pyridin-3-yl)methyl][1,1'-biphenyl]-2-sulfonamide

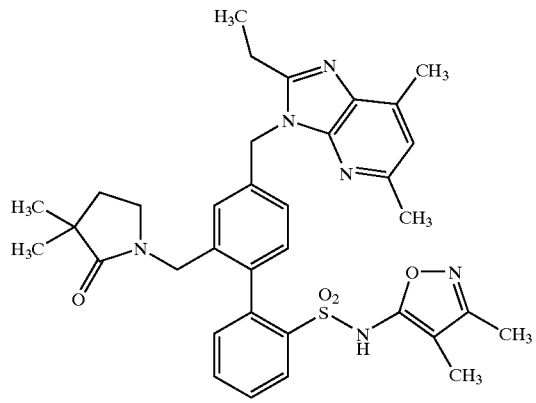

A. N-(3,4-Dimethyl-5-isoxazolyl)-2'-[(3,3-dimethyl-2-oxo-1-pyrrolidinyl)methyl]-4'-hydroxymethyl-N-(2-methoxyethoxymethyl)[1,1'-biphenyl]-2-sulfonamide Preparation P21 (4.25 g, 9.0 mmol) was reacted with ethyl 4-amino-2,2-dimethylbutanoate hydrochloride (2.13 g, 10.9 mmol) according to General Method 5. The crude residue was chromatographed on silica gel (5% methanol in dichloromethane eluant) to yield 3.05 g of 20A (59%) as an orange oil.

B. N-(3,4-Dimethyl-5-isoxazolyl)-2'-[(3,3-dimethyl-2-oxo-1-pyrrolidinyl)methyl]-4'-[(2-ethyl-5,7-dimethyl-3H-imidazo[4,5-b]pyridine-3-yl)methyl]-N-(2-methoxyethoxymethyl)[1,1'-biphenyl]-2-sulfonamide A solution of 20A (500 mg, 0.87 mmol, 1.0 eq), triphenylphosphine (344 mg, 1.3 mmol, 1.5 eq), and 2-ethyl-5,7-dimethyl-3H-imidazo[4,5-b]pyridine (184 mg, 1.1 mmol, 1.2 eq) in tetrahydrofuran (5 mL) was treated at 0° C. with diethylazodicarboxylate (206 μl, 1.3 mmol, 1.5 eq). The mixture was allowed to warm to room temperature, was stirred for 16 hr, and then concentrated. The residue was chromatographed on silica gel (3:2 hexanes/acetone as eluant) to give 320 mg of a mixture containing 20B and 2-ethyl-5,7-dimethyl-3H-imidazo[4,5-b]pyridine (approximately 3:1 ratio by weight).

C. N-(3,4-Dimethyl-5-isoxazolyl)-2'-[(3,3-dimethyl-2-oxo-1-pyrrolidinyl)methyl]-4'-[(2-ethyl-5,7-dimethyl-3H-imidazo[4,5-b]pyridine-3-yl)methyl][1,1'-biphenyl]-2-sulfonamide 20B (320 mg) was deprotected according to General Method 8 (ethanol). The crude residue was purified by reverse-phase preparative HPLC followed by extraction (3×50 mL ethyl acetate) of the product from brine adjusted to pH 4 with hydrochloric acid, to provide 135 mg of the title compound (24% from 20A) as a white solid after lyophilization; mp 95–104° C.; MS m/e 641 (ESI+ mode); MS m/e 639 (ESI– mode); HPLC retention time 3.43 minutes (Method C).

Example 21
N-(3,4-Dimethyl-5-isoxazolyl)-4'-[2-(2-methoxyethyl)-4-oxo-1,3-diazaspiro[4.4]non-1-en-3-yl)methyl][1,1'-biphenyl]-2-sulfonamide

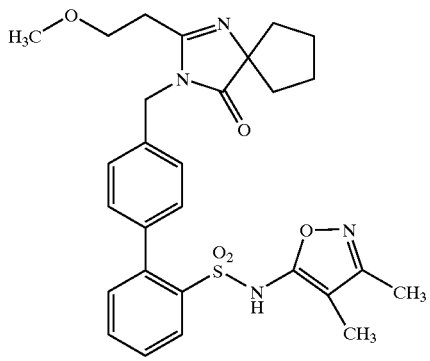

A. Methyl 1-[(3-methoxy-1-oxopropyl)amino]cyclopentane-1-carboxylate

3-Methoxypropanoic acid (1.65 mL, 17.6 mmol, 2.1 eq) was added to a mixture of EDCI (1.77 g, 9.24 mmol, 1.1 eq), triethylamine (3.5 mL, 25.2 mmol., 3.0 eq), 4-dimethylaminopyridine (20 mg, 0.18 mmol, 0.02 eq), and dichloromethane (100 mL) at room temperature. After 5 minutes, methyl 1-aminocyclopentane-1-carboxylate hydrochloride (1.50 g, 8.4 mmol, 1.0 eq) was added and the mixture was stirred at room temperature for 18 hours. The reaction mixture was partitioned against 1N hydrochloric acid and the aqueous phase was extracted once with dichloromethane. The combined organic extracts were dried over sodium sulfate and concentrated. Silica gel chromatography of the residue (1:3 hexanes/ethyl acetate as eluant) yielded 1.30 g of 21A (67%) as a colorless oil.

B. 1-[(3-Methoxy-1-oxopropyl)amino]cyclopentane-1-carboxylic acid

A mixture of 21A (1.25 g, 5.5 mmol, 1.0 eq), lithium hydroxide hydrate (300 mg, 7.1 mmol, 1.3 eq), THF (10 mL), and water (10 mL) was stirred at room temperature for 5.5 hours. 1N hydrochloric acid (10 mL) was added and the mixture was saturated with solid sodium chloride, then extracted with ethyl acetate (3×30 mL). The combined organic extracts were dried over sodium sulfate and concentrated to provide 0.95 g of 21B (80%) as a white solid.

C. 1-[(3-Methoxy-1-oxopropyl)amino]cyclopentane-1-carboxamide

A suspension of 21B (0.95 g, 4.4 mmol, 1.0 eq) in THF (20 mL) was treated with 1,1'-carbonyldiimidazole (930 mg, 5.7 mmol, 1.3 eq) at room temperature. After 30 minutes, the mixture was cooled to −78° C. and ammonia gas was introduced. The resulting heterogeneous mixture was allowed to warm to room temperature and was stirred for 16 hours. The solvent was evaporated and 1N hydrochloric acid saturated with sodium chloride was added to the residue. The aqueous mixture was extracted with ethyl acetate (6×50 mL), and the combined organic layers were dried over sodium sulfate and concentrated to yield 500 mg of 21C (53%) as a white solid.

D. 2-(2-Methoxyethyl)-1,3-diazaspiro[4.4]non-1-en-4-one

A solution of 21C (460 mg, 2.15 mmol, 1.0 eq), potassium hydroxide (288 mg, 4.30 mmol, 2.0 eq) and methanol (15 mL) was heated at reflux for 20 hours. The mixture was cooled, solid ammonium chloride was added, and the solvent was evaporated. Water was added and the mixture was extracted with ethyl acetate (3×30 mL). The combined organic extracts were dried over sodium sulfate, concentrated, and the residue chromatographed on silica gel (4% methanol in dichloromethane as eluant) to yield 162 mg of 21D (38%) as an amber oil.

E. N-(3,4-Dimethyl-5-isoxazolyl)-4'-[2-(2-methoxyethyl)-4-oxo-1,3-diazaspiro[4.4]non-1-en-3-yl)methyl][1,1'-biphenyl]-2-sulfonamide 21D (75 mg, 0.38 mmol, 1.0 eq) was alkylated with P18 (195 mg, 0.38 mmol, 1.0 eq) according to General Method 4. The resulting crude orange oil was dissolved in methanol (7 mL). Concentrated hydrochloric acid (7 mL) was added and the solution was heated at 55° C. for 14 hours. The reaction mixture was concentrated and then partitioned between ethyl acetate and pH 5 sodium phosphate buffer. The organic layer was dried over sodium sulfate and concentrated to provide a crude residue. The title compound (7 mg, 3% yield) was obtained as a white powder following silica gel chromatography (4% methanol in chloroform as eluant), preparative reverse-phase HPLC, and lyophilization: MS m/e 537 (ESI+ mode); MS m/e 535 (ESI– mode); HPLC retention time 3.35 minutes (Method A).

Example 22
N-(3,4-Dimethyl-5-isoxazolyl)-4'-[2-(ethoxymethyl)-4-oxo-1,3-diazaspiro [4.4]non-1-en-3-yl)methyl][1,1'-biphenyl]-2-sulfonamide

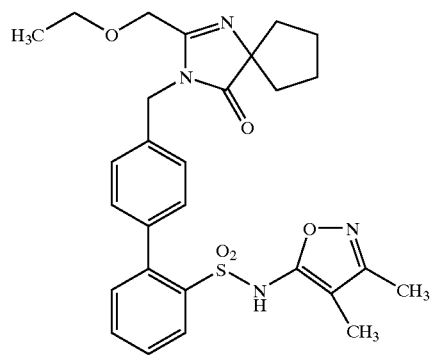

A. Methyl 1-[(2-ethoxyethanoyl)amino]cyclopentane-1-carboxylate

2-Ethoxyacetic acid (3.3 mL, 35 mmol, 2.1 eq) was added to a mixture of EDCI (3.38 g, 18 mmol, 1.1 eq), triethylamine (7.0 mL, 50 mmol, 3.0 eq), 4-dimethylaminopyridine (20 mg, 0.18 mmol, 0.01 eq), and dichloromethane (100 mL) at room temperature. After 5 minutes, methyl 1-aminocyclopentane-1-carboxylate hydrochloride (3.0 g, 17 mmol, 1.0 eq) was added and the mixture was stirred at room temperature for 18 hours. The solvent was evaporated and the residue partitioned between ether and 1N hydrochloric acid. The organic layer was washed once with 1N hydrochloric acid, then twice with saturated aqueous sodium bicarbonate, and once with brine. The organic layer was dried over magnesium sulfate and concentrated to give 2.0 g of 22A (52%) as a pink oil.

B. 2-(Ethoxymethyl)-1,3-diazaspiro[4.4]non-1-en-4-one

A mixture of 22A (2.0 g, 8.7 mmol, 1.0 eq), lithium hydroxide hydrate (440 mg, 10.5 mmol, 1.2 eq), THF (10 mL), and water (3 mL) was stirred at room temperature for 16 hours. 2N hydrochloric acid (6 mL) was added and the solvents were evaporated. The residue was dried azeotropically with toluene, then dissolved in THF (15 mL) and treated with 1,1'-carbonyldiimidazole (2.8 g, 17.3 mmol, 2.1 eq) at room temperature. After 2 hours, the mixture was cooled to −78° C. and ammonia gas was introduced. The resulting mixture was allowed to warm to room temperature and was stirred for 16 hours, after which the solvent was evaporated. The residue was suspended in methanol (15 mL), solid potassium hydroxide (2.9 g, 43 mmol, 5 eq) was added, and the mixture was heated at reflux for 72 hours. After cooling, the mixture was treated with solid ammonium chloride and the solvent was evaporated. Water was added and the mixture was extracted with ethyl acetate (3×30 mL). The combined organic extracts were dried over sodium sulfate, concentrated, and the residue chromatographed on silica gel (4% methanol in chloroform as eluant) to yield 370 mg of 22B (22%) as an orange oil.

C. N-(3,4-Dimethyl-5-isoxazolyl)-4'-[2-(ethoxymethyl)-4-oxo-1,3-diazaspiro[4.4]non-1-en-3-yl)methyl][1,1'-biphenyl]-2-sulfonamide The title compound was prepared from 22B (80 mg, 0.41 mmol) and P18 (209 mg, 0.41 mmol) according to the procedure described in Example 61, Step E, substituting ethanol for methanol in the deprotection reaction. The crude residue was chromatographed twice on silica gel (4% methanol in chloroform as eluant, followed by 25:75:1 hexanes/ethyl acetate/acetic acid as eluant), then was further purified by reverse-phase preparative HPLC to provide 42 mg of the title compound (19%) as a white solid after lyophilization; MS m/e 537 (ESI+ mode); MS m/e 535 (ESI− mode); HPLC retention time 3.51 minutes (Method A).

Example 23

4'-[(2-Ethyl-5,7-dimethyl-3H-imidazo[4,5-b]pyridin-3-yl)methyl]-2'-[(2-oxo-1-pyrrolidinyl)methyl]-N-(3,4-dimethyl-5-isoxazolyl)[1,1'-biphenyl]-2-sulfonamide

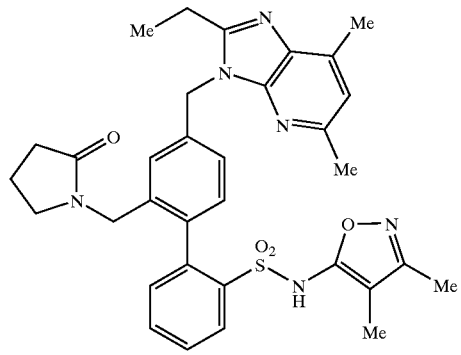

A. 2'-Formyl-N-(3,4-dimethyl-5-isoxazolyl)-4'-[(methanesulfonyl)oxy]-N-(2-methoxyethoxymethyl)[1,1'-biphenyl]-2-sulfonamide P21 (2.4 g) was converted to the corresponding mesylate according to General Method 3. The crude product (2.7 g) was carried on without further purification.

B. 4'-[(2-Ethyl-5,7-dimethyl-3H-imidazo[4,5-b]pyridin-3-yl)methyl]-2'-formyl-N-(3,4-dimethyl-5-isoxazolyl)-N-(2-methoxyethoxymethyl)[1,1'-biphenyl]-2-sulfonamide 23A (2.7 g) was used to alkylate 2-ethyl-5,7-dimethyl-3H-imidazo[4,5-b]pyridine according to General Method 4. The crude product was chromatographed on silica gel using 1:3 hexanes/ethyl acetate as eluant to provide 1.8 g 23B as a colorless oil.

C. 4'-[(2-Ethyl-5,7-dimethyl-3H-imidazo[4,5-b]pyridin-3-yl)methyl]-2'-[(2-oxo-1-pyrrolidinyl)methyl-N-(3,4-dimethyl-5-isoxazolyl)-N-(2-methoxyethoxymethyl)[1,1'-biphenyl]-2-sulfonamide 23B (1.5 g) was subjected to reductive amination with ethyl 4-aminobutanoate hydrochloride according to General Method 5. The reaction mixture was allowed to stir for 24 h to allow time for cyclization of the amino ester to the corresponding lactam. The crude product after workup was purified by silica gel chromatography (1:1 hexanes/acetone eluant) to provide 23C (0.50 g) as a yellow oil.

D. 4'-[(2-Ethyl-5,7-dimethyl-3H-imidazo[4,5-b]pyridin-3-yl)methyl]-2'-[(2-oxo-1-pyrrolidinyl)methyl]-N-(3,4-dimethyl-5-isoxazolyl)[1,1'-biphenyl]-2-sulfonamide 23C (0.50 g) was subjected to sulfonamide deprotection using HCl/dioxane/ethanol according to General Method 8. The crude product was purified by silica gel chromatography (90:9:1 dichloromethane/methanol/ammonium hydroxide eluant), and the purified product was partitioned between ethyl acetate and pH 5 potassium phosphate buffer. The ethyl acetate layer was dried over sodium sulfate and concentrated to provide 310 mg of the title compound as a white solid; mp 98–102° C.; MS m/e 613 (ESI+ mode); HPLC retention time 3.09 min (Method A); HPLC purity 97%.

Example 24

4'-[(2-Ethyl-5,7-dimethyl-3H-imidazo[4,5-b]pyridin-3-yl)methyl]-2'-[(3-methyl-2-oxo-1-imidazolidinyl)methyl]-N-(3,4-dimethyl-5-isoxazolyl)[1,1'-biphenyl]-2-sulfonamide

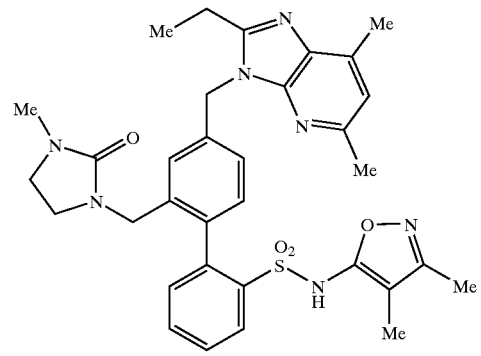

A. 4'-[(2-Ethyl-5,7-dimethyl-3H-imidazo[4,5-b]pyridin-3-yl)methyl]-2'-[(3-methyl-2-oxo-1-imidazolidinyl)methyl]-N-(3,4-dimethyl-5-isoxazolyl)-N-(2-methoxyethoxymethyl)[1,1'-biphenyl]-2-sulfonamide 23B (2.0 g) was subjected to reductive amination with N-methylethylenediamine according to General Method 5. The crude product following extractive workup was dissolved in dichloromethane (25 ml) and treated with CDI (0.77 g). The mixture was stirred at RT for 24 h, and was then washed once with water and once with brine. The dichloromethane layer was dried over sodium sulfate and concentrated. The residue was chromatographed on silica gel using 95:5 chloroform/methanol as eluant to give 24A (0.53 g) as a slightly yellow oil.

B. 4'-[(2-Ethyl-5,7-dimethyl-3H-imidazo[4,5-b]pyridin-3-yl)methyl]-2'-[(3-methyl-2-oxo-1-imidazolidinyl)methyl]-N-(3,4-dimethyl-5-isoxazolyl)[1,1'-biphenyl]-2-sulfonamide 24A (0.50 g) was subjected to sulfonamide deprotection according to General Method 8. The crude product was purified by reverse-phase preparative HPLC to yield 140 mg of the title compound as a white solid following lyophilization; MS m/e 628 (ESI+ mode); HPLC retention time 3.03 min (Method A); HPLC purity 97%.

Example 25
(S)-2-[N-[2'-[[N-(3-Methyl-5-isoxazolyl)amino]sulfonyl][1,1'-biphenyl]-4-yl[methyl]-N-(1-oxopentyl)amino]-3,N-dimethylbutanamide

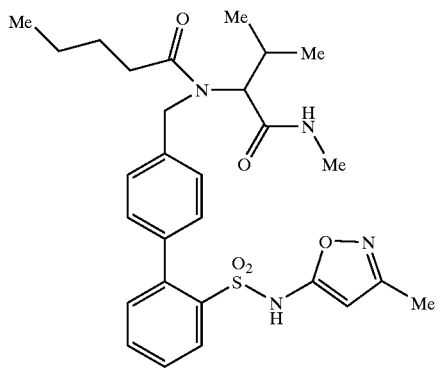

A. N-(3-Methyl-5-isoxazolyl)-2-bromobenzenesulfonamide

5-Amino-3-methylisoxazole (3.84 g) was added at RT in portions to a solution of 2-bromobenzenesulfonyl chloride (10.0 g) in pyridine (40 ml). The mixture was heated at 60° C. for 16 h, then the solvent was evaporated. The residue was taken up in ethyl acetate and washed three times with 1 N hydrochloric acid. The ethyl acetate layer was dried over sodium sulfate and concentrated to give 25A (8.8 g).

B. N-[(2-Trimethylsilyl)ethoxymethyl]-N-(3-methyl-5-isoxazolyl)-2-bromobenzenesulfonamide 2-(Trimethylsilyl)ethoxymethyl chloride (5.2 ml) was added to a mixture of 25A (8.8 g), potassium carbonate (7.7 g), and DMF (40 ml) at 0° C. The mixture was allowed to warm to RT and was then stirred for 16 h. The solvent was evaporated, and the residue was taken up in ethyl acetate and washed with water and brine. The ethyl acetate layer was dried over sodium sulfate and concentrated. The residue was purified by silica gel chromatography using 3:2 hexanes/ethyl acetate as eluant to provide 25B (6.6 g) as an oil.

C. 4'-Formyl-N-(3-methyl-5-isoxazolyl)-N-[(2-trimethylsilyl)ethoxymethyl][1,1'-biphenyl]-2-sulfonamide 25B (2.0 g) and 4-formylphenylboronic acid (1.5 g) were subjected to Suzuki coupling according to General Method 1. The crude product was chromatographed on silica gel using 9:1 hexanes/ethyl acetate as eluant to yield 0.75 g 25C as a colorless oil.

D. (S)-2-[N-[2'-[[N-(3-Methyl-5-isoxazolyl)-N-[(2-trimethylsilyl)ethoxymethyl]amino]sulfonyl][1,1'-biphenyl]-4-yl]methyl]-amino]-3,N-dimethylbutanamide 25C (0.75 g) was subjected to reductive amination with L-valine N-methyl amide hydrochloride according to General Method 5. Crude 25D (0.93 g) was obtained as an orange oil.

E. (S)-2-[N-[[2'-[[N-(3-Methyl-5-isoxazolyl)-N-[(2-trimethylsilyl)ethoxymethyl]amino]sulfonyl][1,1'-biphenyl]-4yl]methyl]-N-(1-oxopentyl)amino]-3,N-dimethylbutanamide 25D (0.93 g) was subjected to acylation with valeryl chloride according to General Method 6. The crude product was chromatographed on silica gel using 2:3 hexanes/ethyl acetate as eluant to yield 0.78 g 25E as a colorless oil.

F. (S)-2-[N-[2'-[[N-(3-Methyl-5-isoxazolyl)amino]sulfonyl][1,1'-biphenyl]-4-yl]methyl]-N-(1-oxopentyl)amino]-3,N-dimethylbutanamide 25E (0.78 g) was deprotected with HCl/methanol according to General Method 8. The crude product was purified by silica gel chromatography using 3:7 hexanes/ethyl acetate as eluant, providing the title compound (210 mg) as a white solid; MS m/e 541 (ESI+ mode); HPLC retention time 31.32 min (Method B); HPLC purity >98%.

Example 26
(S)-2-[N-[2'-[[N-(4-Bromo-3-methyl-5-isoxazolyl)amino]sulfonyl][1,1'-biphenyl]-4-yl]methyl]-N-(1-oxopentyl)amino]-3,N-dimethylbutanamide

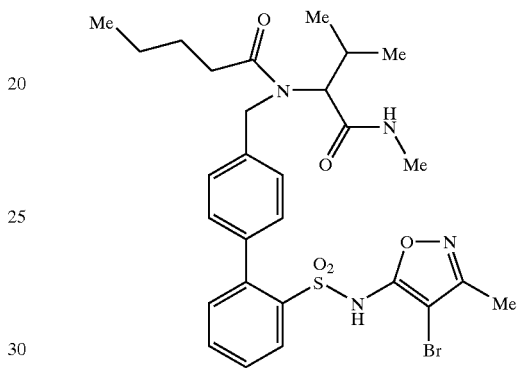

A solution of 25 (75 mg) in chloroform (1.5 ml) was treated with NBS (25 mg) at RT. After 1 h, the mixture was diluted with dichloromethane and partitioned against water. The organic layer was dried over sodium sulfate and concentrated, and the residue was chromatographed on silica gel using 3:7 hexanes/ethyl acetate as eluant to provide the title compound (25 mg) as a white solid; MS m/e 619, 621 (ESI+ mode); HPLC retention time 31.83 min (Method B); HPLC purity >99%.

Example 27
4'-[(2-Butyl-4-oxo-1,3-diazaspiro[4.4]non-1-en-3-yl)methyl]-N-(3,4-dimethyl-5-isoxazolyl)-2'-propyl[1,1'-biphenyl]-2-sulfonamide

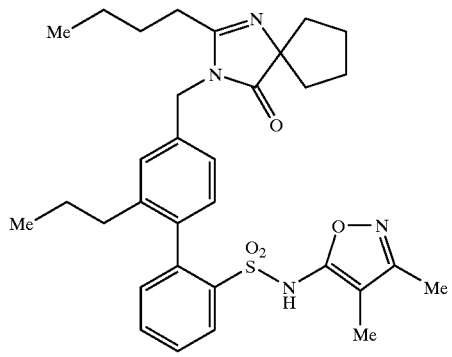

A. 4-Bromo-3-(1-propen-1-yl)benzonitrile n-Butyllithium (2.5M solution in hexane, 7.6 ml, 19 mmol) was added dropwise to a solution of ethyltriphenylphosphonium bromide (6.42 g, 17.3 mmol) in 100 ml of 1:1 THF/ether at –15° C. The mixture was stirred for 3 h at RT and then was cooled to –50° C. 2A (4.0 g, 19.0 mmol)

in THF (10 ml) was added and the mixture was allowed to warm to RT and was stirred for 16 h. The mixture was added to water and extracted with EtOAc (3×50 mL) and the combined organic extracts were washed with water, dried over magnesium sulfate, and evaporated. The residue was chromatographed on silica gel using 95:5 hexane/EtOAc to afford 27A as an E/Z mixture (3.5 g, 83%).

B. 4-Bromo-3-propylbenzonitrile

A mixture of 27A (1.5 g) and 150 mg of $PtO_2$ in 40 ml EtOH was hydrogenated at 35 PSI for 40 min. Filtration and concentration gave 1.44 g of 27B (85%).

C. 4-Bromo-3-propylbenzaldehyde 27B (1.44 g) was treated with DIBAL-H according to General Method 14 to provide crude 27C (1.4 g, 97%) as an oil.

D. N-(3,4-Dimethyl-5-isoxazolyl)-4'-formyl-2'-propyl-N-[(2-methoxyethoxy)methyl][1,1'-biphenyl]-2-sulfonamide 27C (1.4 g) was subjected to Suzuki coupling according to General Method 1 to provide 27D (27%) as an oil.

E. N-(3,4-Dimethyl-5-isoxazolyl)-4'-hydroxymethyl-2'-propyl-N-[(2-methoxyethoxy)methyl][1,1'-biphenyl]-2-sulfonamide 27D (810 mg) was reduced with sodium borohydride in methanol according to General Method 11 to provide 27E (32%) as an oil.

F. N-(3,4-Dimethyl-5-isoxazolyl)-4'-(methanesulfonyl)oxymethyl-2'-propyl-N-[(2-methoxyethoxy)methyl][1,1'-biphenyl]-2-sulfonamide 27E (250 mg) was converted to the corresponding methanesulfonate ester according to General Method 3 to provide 27F (68%) as an oil.

G. 4'-[(2-Butyl-4-oxo-1,3-diazaspiro[4.4]non-1-en-3-yl)methyl]-2'-propyl-N-[(2-methoxyethoxy)methyl]-N-(3,4-dimethyl-5-isoxazolyl)[1,1'-biphenyl]-2-sulfonamide 27F (100 mg) was used to alkylate 2-butyl-1,3-diazaspiro[4.4]non-1-en-4-one according to General Method 4. 27G (100 mg, 85%) was produced as an oil.

H. 4'-[(2-Butyl-4-oxo-1,3-diazaspiro[4.4]non-1-en-3-yl)methyl]-2'-propyl-N-(3,4-dimethyl-5-isoxazolyl)[1,1'-biphenyl]-2-sulfonamide 27G (100 mg) was deprotected according to General Method 7. The crude product was purified by preparative HPLC to provide the title compound (57 mg, 66%) as a solid; MS m/e 577 (ESI+ mode); HPLC retention time 29.11 min (Method B); HPLC purity >98%.

Example 28

4'-[(7-Methoxycarbonyl-2-ethoxybenzimidazol-1-yl)methyl]-N-(3,4-dimethyl-5-isoxazolyl)-[1,1'-biphenyl]-2-sulfonamide

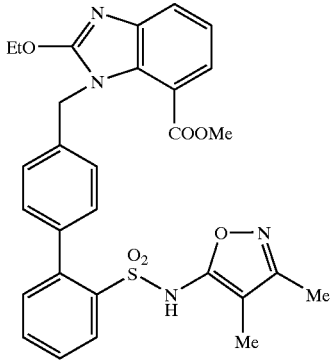

A. N-(2-Methoxycarbonyl-6-nitrophenyl)-4-bromobenzylamine

Triethylamine (5.2 ml, 37 mmol) was added to a mixture of methyl 2-chloro-3-nitrobenzoate (3.2 g, 15 mmol) and 4-bromobenzylamine hydrochloride (3.4 g, 15 mmol) in acetonitrile (75 ml). The mixture was heated at reflux for 48 hr, then was cooled and concentrated. 10% Aqueous sodium dihydrogen phosphate solution was added and the mixture was extracted with 2 portions of ethyl acetate. The combined organic extracts were dried over sodium sulfate and concentrated, and the residue was crystallized from ethyl acetate to give 28A (3.2 g) as a yellow solid.

B. 4'-[(2-Methoxycarbonyl-6-nitrophenyl)aminomethyl]-N-(3,4-dimethyl-5-isoxazolyl)-N-(2-trimethylsiloxymethyl)[1,1'-biphenyl]-2-sulfonamide 28A (3.5 g, 9.6 mmol) was subjected to Suzuki coupling according to General Method 1, providing 28B as a yellow oil (3.1 g) following silica gel chromatography using 5:1 hexanes/ethyl acetate as eluant.

C. 4'-[(2-Methoxycarbonyl-6-aminophenyl)aminomethyl]-N-(3,4-dimethyl-5-isoxazolyl)-N-(2-trimethylsiloxymethyl)[1,1'-biphenyl]-2-sulfonamide 28B (2.4 g, 3.6 mmol) was treated with tin (II) chloride dihydrate (3.3 g) in ethyl acetate (80 ml) according to General Method 18. The crude product was purified by silica gel chromatography using 2:1 hexanes/ethyl acetate as eluant to provide 28C (1.3 g) as a pale yellow oil.

D. 4'-[(7-Methoxycarbonyl-2-ethoxybenzimidazol-1-yl)methyl]-N-(3,4-dimethyl-5-isoxazolyl)-N-(2-trimethylsiloxymethyl)[1,1'-biphenyl]-2-sulfonamide 28C (1.3 g), tetraethylorthocarbonate (6 ml), and acetic acid (0.2 ml) was heated under a nitrogen atmosphere at 70° C. for 2 h. The mixture was cooled and concentrated, and the residue was chromatographed on silica gel using 1:1 hexanes/ethyl acetate as eluant to provide 28D (1.1 g) as a brown oil.

E. 4'-[(7-Methoxycarbonyl-2-ethoxybenzimidazol-1-yl)methyl]-N-(3,4-dimethyl-5-isoxazolyl)-[1,1'-biphenyl]-2-sulfonamide 28D (1.1 g) was subjected to sulfonamide deprotection using TBAF in THF according to General Method 10. The crude product was purified by silica gel chromatography using 2:1 hexanes/acetone as eluant to provide 0.75 g of the title compound as a white solid; mp 105–110° C.; MS m/e 561 (ESI+ mode); HPLC retention time 3.96 min (Method A); HPLC purity 96%.

Example 29

4'-[(7-Carboxy-2-ethoxybenzimidazol-1-yl)methyl]-N-(3,4-dimethyl-5-isoxazolyl)-[1,1'-biphenyl]-2-sulfonamide

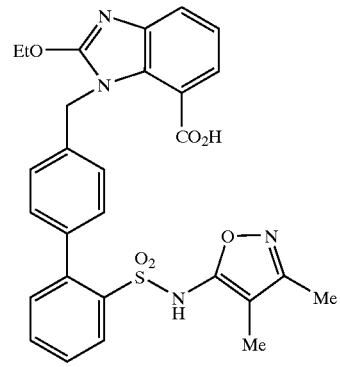

28 (0.70 g) was subjected to ester hydrolysis according to General Method 15 to provide the crude product (0.66 g). Purification of a portion by reverse-phase preparative HPLC provided the title compound (9 mg, white solid); MS m/e 547 (ESI+ mode); HPLC retention time 3.79 min (Method A); HPLC purity 91%.

Example 30
4'-[(7-Methoxycarbonyl-2-ethylbenzimidazol-1-yl)methyl]-N-(3,4-dimethyl-5-isoxazolyl)-[1,1'-biphenyl]-2-sulfonamide

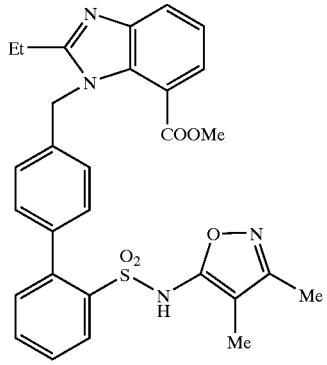

A solution of 28C (3.8 g, 5.9 mmol) and triethylamine (1.7 ml, 12 mmol) in dichlroromethane (25 ml) was treated at 0° C. with propionyl chloride (0.67 ml, 10 mmol), and the mixture was allowed to come to RT. After 2.5 h, aqueous sodium bicarbonate solution was added to the mixture and the aqueous layer was extracted with two portions of dichloromethane. The combined organic extracts were dried over sodium sulfate and concentrated to provide an orange oil.

To this residue was added methanolic hydrogen chloride (prepared from 100 ml methanol and 11 ml (200 mmol) acetyl chloride), and the resulting solution was heated at 50° C. for 16 h. The mixture was cooled and concentrated, and the residue was extracted with two portions of ethyl acetate from sodium phosphate buffer adjusted to pH 4. The combined ethyl acetate extracts were dried over sodium sulfate and concentrated. The residue was chromatographed on silica gel using 1:2 hexanes/acetone as eluant to provide the title compound (2.6 g) as a slightly orange solid; MS m/e 545 (ESI+ mode); HPLC retention time 3.32 min (Method C); HPLC purity 95%.

Example 31
4'-[(7-Carboxy-2-ethylbenzimidazol-1-yl)methyl]-N-(3,4-dimethyl-5-isoxazolyl)-[1,1'-biphenyl]-2-sulfonamide

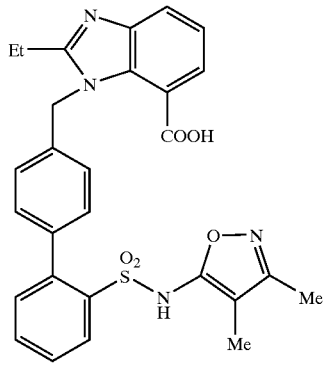

30 (2.6 g, 4.8 mmol) was subjected to ester hydrolysis according to General Method 15. The THF was evaporated and the residue was treated with 6 ml of 2N hydrochloric acid, resulting in the precipitation of a white solid. The solid was collected on a filter, rinsed with water, and dried to provide 2.4 g of the title compound; MS m/e 531 (ESI+ mode); HPLC retention time 2.94 min (Method A); HPLC purity 95%.

Example 32
2'-[(3,3-Dimethyl-2-oxopyrrolidin-1-yl)methyl]-4'-[(2-ethoxy-7-(methoxycarbonyl)benzimidazol-1-yl)methyl]-N-(3,4-dimethyl-5-isoxazolyl)-[1,1'-biphenyl]-2-sulfonamide

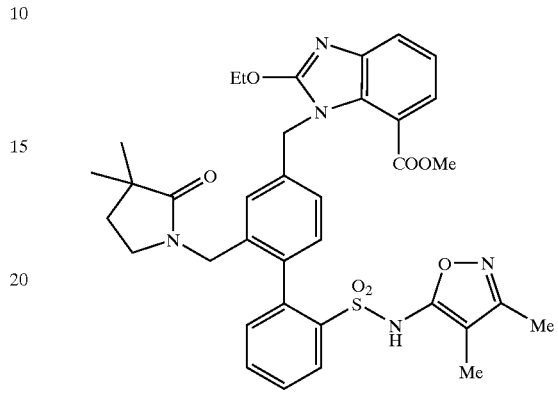

A. 2-[(5'-Aminomethyl-2'-bromo)phenyl)-1,3-dioxolane

Borane.THF (100 ml of a 1.0 M solution in THF, 100 mmol) was added at 0° C. to a solution of 2-[(2'-Bromo-5'-cyano)phenyl)]-1,3-dioxolane [Zhang, H.-Y. et al., Tetrahedron, 50, 11339–11362 (1994)] (10.8 g, 43 mmol) in 25 ml THF. The mixture was allowed to warm to RT and was stirred for 18 h. After cooling to 0° C., the mixture was treated carefully with 10 ml methanol and was then evaporated. The residue was taken up in 150 ml ethyl acetate and was washed with 1N aqueous sodium hydroxide, followed by water and brine. The organic layer was dried over magnesium sulfate and concentrated to give crude 32A (11.0 g) as an amber oil, which was estimated (HPLC) to be 80% pure.

B. N-(2-Methoxcyarbonyl-6-nitrophenyl)-4-bromo-3-(1,3-dioxolan-2-yl)benzylamine

Triethylamine (4.8 ml, 34 mmol) was added to a mixture of methyl 2-chloro-3-nitrobenzoate (4.9 g, 23 mmol) and 32A (5.9 g of a 65% pure mixture, 15 mmol) in acetonitrile (150 ml). The mixture was heated at reflux for 24 h and was then cooled and concentrated. Ethyl acetate was added and the solution was washed twice with 10% aqueous potassium dihydrogen phosphate solution and once with aqueous sodium bicarbonate solution. The organic layer was concentrated and the residue purified by silica gel column chromatography using 3:1 hexanes/ethyl acetate as eluant, followed by trituration with 3:1 hexanes/ethyl acetate. 32B was a yellow solid (6.6 g).

C. N-(2-Methoxycarbonyl-6-nitrophenyl)-4-bromo-3-(formyl)benzylamine 32B (6.6 g, 15 mmol) was subjected to acetal hydrolysis according to General Method 19, providing 32C as a crude yellow solid following extractive workup.

D. 2'-Formyl-4'-[(2-methoxycarbonyl-6-nitrophenyl)aminomethyl]-N-(3,4-dimethyl-5-isoxazolyl)-N-(2-trimethylsiloxymethyl)[1,1'-biphenyl]-2-sulfonamide Crude 32C was subjected to Suzuki coupling according to General Method 1, providing 32D (5.9 g) as a yellow oil following silica gel chromatography using 2:1 hexanes/ethyl acetate as eluant.

E. 2'-[(3,3-Dimethyl-2-oxopyrrolidin-1-yl)methyl]-4'-[(2-methoxycarbonyl-6-nitrophenyl)aminomethyl]-N-(3,4- dimethyl-5-isoxazolyl)-N-(2-trimethylsiloxymethyl)[1,1'-biphenyl]-2-sulfonamide 32D (4.3 g) was subjected to reductive amination with ethyl 4amino-2,2-dimethylbutanoate hydrochloride according to General Method 5. The reaction mixture was allowed to stir for 60 h at RT to allow time for cyclization of the amino ester to the corresponding lactam. The crude product after workup was purified by silica gel chromatography, using 3:2 hexanes/ethyl acetate as eluant, to provide 32E (2.8 g) as a yellow oil.

F. 2'-[(3,3-Dimethyl-2-oxopyrrolidin-1-yl)methyl]-4'-[(2-methoxycarbonyl-6-aminophenyl)aminomethyl]-N-(3,4-dimethyl-5-isoxazolyl)-N-(2-trimethylsiloxymethyl)[1,1'-biphenyl]-2-sulfonamide 32E (2.8 g, 3.6 mmol) was treated with tin (II) chloride dihydrate (3.2 g) in ethyl acetate (200 ml) according to General Method 18. The crude product (3.5 g) was used without further purification.

G. 2'-[(3,3-Dimethyl-2-oxopyrrolidin-1-yl)methyl]-4'-[((7-methoxycarbonyl)benzimidazol-1-yl)methyl]-N-(3,4-dimethyl-5isoxazolyl)-N-(2-trimethylsiloxymethyl)[1,1'-biphenyl]-2-sulfonamide A mixture of 32F (1.5 g, 2.0 mmol), tetraethylorthocarbonate (6 ml), and acetic acid (0.15 ml) was heated under a nitrogen atmosphere at 70° C. for 2 h. The mixture was cooled and concentrated, and the residue chromatographed on silica using 1:2 hexanes/ethyl acetate as eluant to provide 32G (0.80 g) as a yellow oil.

H. 2'-[(3,3-Dimethyl-2-oxopyrrolidin-1-yl)methyl]-4'-[(2-ethoxy-7-(methoxycarbonyl)benzimidazol-1-yl)methyl]-N-(3,4-dimethyl-5-isoxazolyl)-[1,1'-biphenyl]-2-sulfonamide 32G (0.80 g) was subjected to sulfonamide deprotection using TBAF in THF according to General Method 10. The crude product was purified by silica gel chromatography using 3:2 hexanes/acetone as eluant to provide 0.55 g of the title compound as a white solid; mp 101–103° C. (decomp); MS m/e 686 (ESI+ mode); HPLC retention time 3.91 min (Method A); HPLC purity >98%.

Example 33

2'-[(3,3-Dimethyl-2-oxopyrrolidin-1-yl)methyl]-4'-[(2-ethoxy-7-(carboxy)benzimidazol-1-yl)methyl]-N-(3,4-dimethyl-5-isoxazolyl)-[1,1'-biphenyl]-2-sulfonamide

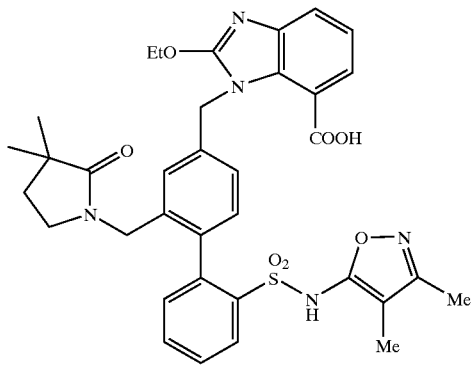

32 (0.31 g) was subjected to ester hydrolysis according to General Method 15. Purification by reverse-phase preparative HPLC provided the title compound (14 mg) as a white solid; MS m/e 672 (ESI+ mode); HPLC retention time 3.61 min (Method A); HPLC purity 82%.

Example 34

2'-[(3,3-Dimethyl-2-oxopyrrolidin-1-yl)methyl]-4'-[(2-ethoxy-7-(N-methylcarbamoyl)benzimidazol-1-yl)methyl]-N-(3,4-dimethyl-5-isoxazolyl)-[1,1'-biphenyl]-2-sulfonamide

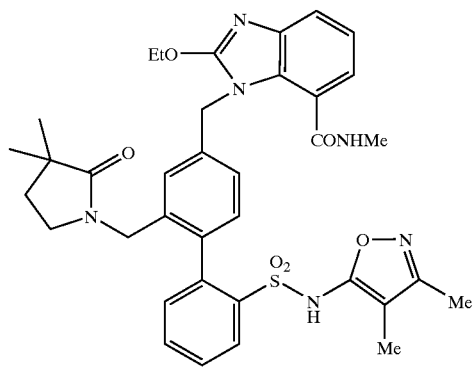

33 (80 mg) was subjected to amide formation according to General Method 12 using methylamine as the amine component. The product was purified by reverse-phase preparative HPLC: white solid (7 mg); MS m/e 685 (ESI+ mode); HPLC retention time 3.39 min (Method A); HPLC purity 81%.

Example 35

2'-[(3,3-Dimethyl-2-oxopyrrolidin-1-yl)methyl]-4'-[(2-ethoxy-7-(N,N-dimethylcarbamoyl)benzimidazol-1-yl)methyl]-N-(3,4-dimethyl-5isoxazolyl)-[1,1'-biphenyl]-2-sulfonamide

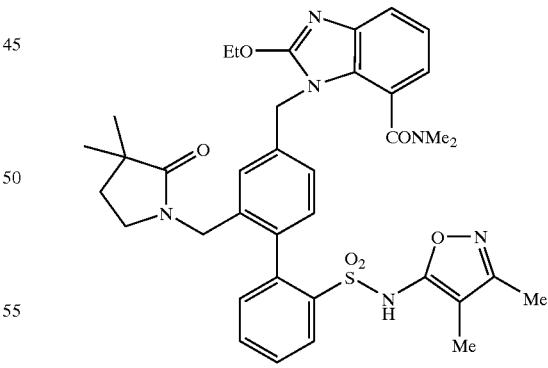

33 (80 mg) was subjected to amide formation according to General Method 12 using dimethylamine as the amine component. The crude product was subjected to reverse-phase preparative HPLC to give the title compound as a white solid (6 mg); MS m/e 699 (ESI+ mode); HPLC retention time 3.46 min (Method A); HPLC purity 66% [contaminant (34%) is the corresponding imidazolin-2-one].

Example 36
4'-[(2-Ethylquinolin-4-yl)oxymethyl]-N-(1,3,5-trimethylpyrazol-4-yl) [1,1'-biphenyl]-2-sulfonamide

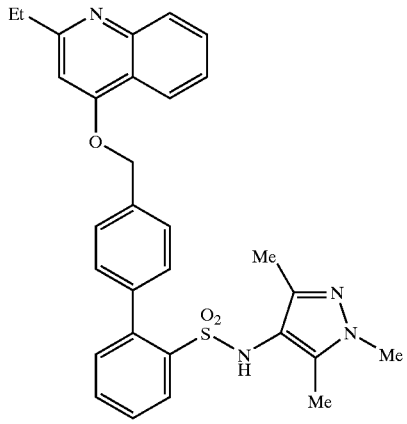

A. 4-[(4-Bromophenyl)methoxy]-2-ethylquinoline

A mixture of 2-ethyl-4-quinolone (1.0 g, 5.8 mmol), 4-bromobenzyl bromide (1.7 g, 6.9 mmol), potassium carbonate (1.6 g, 11.6 mmol), and DMF (10 ml) was stirred at RT for 16 h. Ethyl acetate (100 ml) was added and the mixture was washed four times with water, then once with brine. The organic layer was dried over sodium sulfate and evaporated, and the residue was triturated with 1:1 hexanes/ethyl acetate to provide 1.6 g 36A as a white solid.

B. 4-[(2-Ethylquinolin-4-yl)oxymethyl]-N-(tert-butyl)-1,1'-biphenyl]-2-sulfonamide

A mixture of 36A (1.5 g, 4.4 mmol) and [2-(N-tert-butylsulfamoyl)phenyl]boronic acid (2.3 g, 8.7 mmol) was subjected to Suzuki coupling according to General Method 1. The crude product was chromatographed on silica gel using 1:1 hexanes/ethyl acetate as eluant to provide the 36B (1.8 g) as a yellow solid.

C. 4'-[(2-Ethylquinolin-4-yl)oxymethyl]-[1,1'-biphenyl]-2-sulfonamide

A solution of 36B (1.8 g, 3.8 mmol) in 4 ml dichloromethane and 8 ml TFA was stirred at RT for 14 h, then was heated at reflux for 8 h. The solvent was evaporated and the residue partitioned between ethyl acetate and aqueous sodium bicarbonate. A small amount of a solid precipitate was retained with the organic layer. The organic layer was washed twice with water, then was concentrated. The crude product was crystallized from 1:1 toluene/ethyl acetate to provide 36C (1.2 g) as a yellow solid.

D. 4'-[(2-Ethylquinolin-4-yl)oxymethyl][1,1'-biphenyl]-2-sulfonic acid

A suspension of 36C (1.1 g, 2.7 mmol) in 25 ml acetonitrile was treated at 0° C. with nitrosonium tetrafluoroborate (370 mg, 3.2 mmol). After 30 min the mixture was allowed to warm to RT and was stirred at RT for 4 h. The mixture was concentrated to provide 36D (1.2 g) as a crude white solid.

E. 4'-[(2-Ethylquinolin-4-yl)oxymethyl]-N-(1,3,5-trimethylpyrazol-4yl)[1,1'-biphenyl]-2-sulfonamide

A suspension of 36D (100 mg, 0.24 mmol) in thionyl chloride (4 ml) was treated with DMF (10 μl). The resulting mixture was refluxed for 45 min, then the solvent was evaporated. The residue was twice taken up in toluene and evaporated to dryness. Pyridine (2.5 ml) and 4-amino-1,3,5-trimethylpyrazole (90 mg, 0.72 mmol) were added and the mixture was stirred at RT for 14 h, then the solvent was evaporated. The residue was purified by silica gel chromatography (100:1 chloroform/methanol eluant), followed by silica gel thin-layer chromatography (1:1 hexanes/acetone eluant) to provide the title compound (24 mg) as an amorphous white solid: mp 212–215° C. (decomp); MS m/e 527 (ESI+ mode); HPLC retention time 3.18 min (Method C); HPLC purity 94%.

Example 37
4'-[(2-Ethylquinolin-4-yl)oxymethyl]-N-(3-methylisoxazol-5-yl) [1,1'-biphenyl]-2-sulfonamide

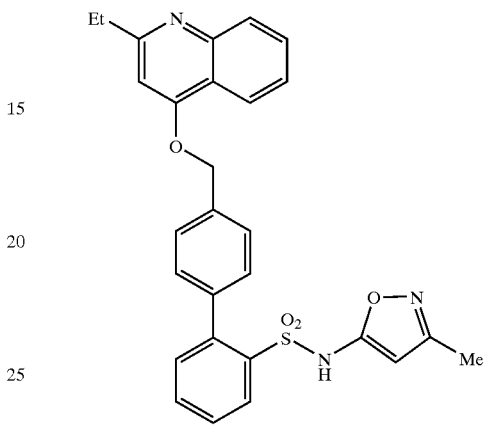

A suspension of the product of 36D (370 mg, 0.88 mmol) was subjected to the procedure used for Example 36, Step E, substituting 5amino-3-methylisoxazole as the amine component. The crude product was purified by reverse-phase preparative HPLC to provide the title compound (8 mg) as an amorphous tan solid: MS m/e 500 (ESI+ mode); HPLC retention time 3.32 min (Method A); HPLC purity >98%.

Example 38
4'-[(5-Acetyl-2-n-propyl-4-chloroimidazol-1-yl)methyl]-N-(3,4-dimethyl-5-isoxazolyl)-[1,1'-biphenyl]-2-sulfonamide

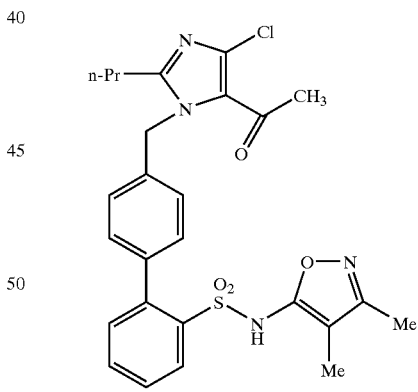

A. 5-(1-Hydroxyethyl)-2-n-propyl-4-chloroimidazole

A solution of 2-n-propyl-4-chloroimidazole-5-carboxaldehyde (Watson, S. P. *Synth. Comm.*, 1992, 22, 2971–2977) (1.5 g, 8.7 mmol) in THF (50 ml) was treated dropwise at 0° C. with methylmagnesium bromide (8.7 ml of a 3.0 M solution in ether). Upon completion of the addition, the mixture was allowed to warm to RT and was stirred for 2 h. The mixture was cooled again to 0° C. and was quenched with the addition of 1N hydrochloric acid. The mixture was adjusted to pH 8–9 by the addition of aqueous dipotassium hydrogen phosphate solution, then was partitioned against ethyl acetate. The ethyl acetate layer and an accompanying precipitate were collected and the solvent was evaporated to provide 38A (1.6 g) as a slightly yellow solid.

B. 5-Acetyl-4-chloro-2-n-propyl-imidazole

A mixture of 38A (1.6 g), activated manganese dioxide (5.7 g), and dioxane (20 ml) was heated at 55° C. for 48 h. The mixture was cooled and filtered through celite, and the filter cake was rinsed with dichloromethane. The combined filtrates were evaporated and the residue was chromatographed on silica gel using 3:1 hexanes/ethyl acetate as eluant. The product was further purified by trituration with 9:1 hexanes/ethyl acetate, providing 0.6 g 38B as an orange solid.

C. 4'-[(5-Acetyl-2-n-propyl-4-chloroimidazol-1-yl) methyl]-N-(3,4-dimethyl-5-isoxazolyl)-N-(2-trimethylsiloxymethyl)[1,1'-biphenyl]-2-sulfonamide 38B (148 mg, 0.79 mmol) was alkylated with P19 (300 mg, 0.53 mmol) according to General Method 22. The crude product was purified by silica gel chromatography using 2:1 hexanes/ethyl acetate as eluent to provide 38C (89 mg) as a yellow oil.

D. 4'-[(5-Acetyl-2-n-propyl-4-chloroimidazol-1-yl) methyl]-N-(3,4-dimethyl-5-isoxazolyl)-[1,1'-biphenyl]-2-sulfonamide Deprotection of 38C (60 mg) according to General Method 8, followed by preparative thin-layer chromatography using 1:1 hexanes/acetone as eluant, provided the title compound (24 mg) as a white solid: MS m/e 528 (ESI+ mode); HPLC retention time 3.75 min (Method A); HPLC purity 98%.

Example 39
4'-[(5-Methoxycarbonyl-2-n-propyl-4-chloroimidazol-1-yl) methyl]-N-(3,4-dimethyl-5-isoxazolyl)-[1,1'-biphenyl]-2-sulfonamide

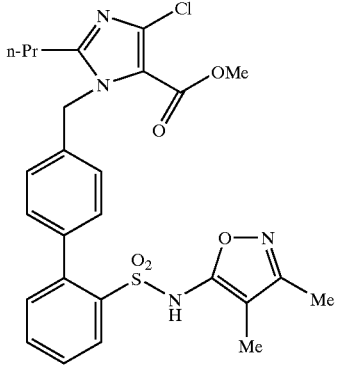

A. 4'-[(5-Formyl-2-n-propyl-4-chloroimidazol-1-yl) methyl]-N-(3,4-dimethyl-5-isoxazolyl)-N-(2-timethylsiloxymethyl)[1,1'-biphenyl]-2-sulfonamide P19 (300 mg) was used to alkylate 2-n-propyl-4-chloroimidazole-5-carboxaldehyde according to General Method 22. The crude product was chromatographed on silica gel using 4:1 hexanes/ethyl acetae as eluant to provide 39A (200 mg) as a yellow oil.

B. 4'-[(5-Carboxy-2-n-propyl-4-chloroimidazol-1-yl) methyl]-N-(3,4-dimethyl-5-isoxazolyl)-N-(2-trimethylsiloxymethyl)[1,1'-biphenyl]-2-sulfonamide Sodium chlorite (19 mg, 0.21 mmol) was added to a mixture of 39A (90 mg, 0.14 mmol) and sulfamic acid (20 mg, 0.21 mmol) in 1:1 THF/water (8 ml) at 0° C. The mixture was stirred at 0° C. for 1 h, then saturated potassium bisulfate solution was added. The aqueous layer was extracted twice with ethyl acetate. The combined organic extracts were washed once with brine, then were dried over sodium sulfate and concentrated to provide 39B (62 mg) as a yellow oil.

C. 4'-[(5-Carboxy-2-n-propyl-4-chloroimidazol-1-yl) methyl]-N-(3,4-dimethyl-5-isoxazolyl) 1,1'-biphenyl]-2-sulfonamide 39B (62 mg) was deprotected according to General Method 8, using water in place of an alcohol as co-solvent. Crude 39C (54 mg) was a yellow oil.

D. 4'-[(5-Methoxycarbonyl-2-n-propyl-4-chloroimidazol-1-yl)methyl]-N-(3,4-dimethyl-5-isoxazolyl) 1,1'-biphenyl]-2-sulfonamide 39C (54 mg) was subjected to ester formation according to General Method 20. Reverse-phase preparative HPLC provided the title compound (9 mg) as a white solid: MS m/e 544 (ESI+ mode); HPLC retention time 3.94 min (Method A); HPLC purity >98%.

Example 40
4'-[(5-(N,N-dimethylcarbamoyl)-2-n-propyl-4-chloroimidazol-1-yl)methyl]-N-(3,4-dimethyl-5-isoxazolyl)-[1,1'-biphenyl]-2-sulfonamide

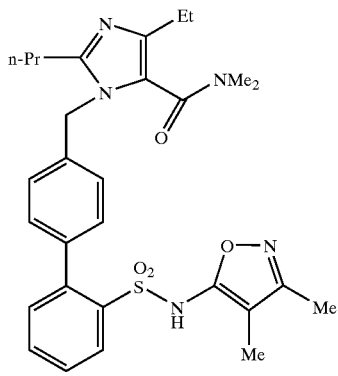

A. 4'-[(5-Ethoxycarbonyl-2-n-propyl-4-ethylimidazol-1-yl)methyl]-N-(3,4-dimethyl-5-isoxazolyl)-N-(2-methoxyethoxymethyl)[1,1'-biphenyl]-2-sulfonamide Ethyl 2-n-propyl-4-ethylimidazole-5-carboxylate (94 mg, 0.45 mmol) was alkylated with P18 (380 mg, 0.37 mmol), according to General Method 22 to provide crude 40A as a 3:1 mixture of N-1 and N-3 regioisomeric alkylation products.

B. 4'-[(5-Carboxy-2-n-propyl-4-ethylimidazol-1-yl) methyl]-N-(3,4-dimethyl-5-isoxazolyl)-[1,1'-biphenyl]-2-sulfonamide A solution of 40A (0.45 g) in dioxane (3 ml) and 6N hydrochloric acid (3 ml) was heated at 70° C. for 2 h. The mixture was cooled to RT and made basic (pH>14) with the addition of 45% aqueous potassium hydroxide solution. Additional dioxane and water were added to obtain a clear solution and the mixture was stirred at RT for 16 h, followed by heating at 70° C. for 3 h. The pH was adjusted to 2–3 with the addition of 6N hydrochloric acid and solid trisodium phosphate, and the mixture was extracted with three portions of ethyl acetate. The combined organic extracts were dried over sodium sulfate and evaporated to give 40B (0.33 g) as a crude oil.

C. 4'-[(5-(N,N-dimethylcarbamoyl)-2-n-propyl-4-ethylimidazol-1-yl)methyl]-N-(3,4-dimethyl-5-isoxazolyl)-[1,1'-biphenyl]-2-sulfonamide 40B (110 mg) was subjected to amide formation according to General Method 12 using dimethylamine as the amine component. The crude material was subjected to reverse-phase preparative HPLC to provide the title compound (19 mg) as a white solid: MS m/e 550 (ESI+ mode); HPLC retention time 19.54 min (Method B); HPLC purity 74%. The contaminant (24%) is the isomeric product arising from N-3 alkylation of the imidazole in Step A (HPLC retention time 19.77 min).

Example 41
4'-[(2-Butyl-4-oxo-1,3-diazaspiro[4.4]non-1-en-3-yl)methyl]-N-(3,4-dimethyl-5-isoxazolyl)-2'-hydroxymethyl[1,1'-biphenyl]-2-sulfonamide

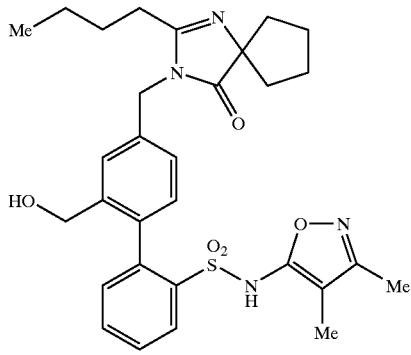

A. 4'-[(2-Butyl-4-oxo-1,3-diazaspiro[4.4]non-1-en-3-yl)methyl]-N-(3,4-dimethyl-5-isoxazolyl)-N-[(2-trimethylsilylethoxy)methyl]-2'-hydroxymethyl[1,1'-biphenyl]-2-sulfonamide P14 (243 mg, 0.41 mmol) was used to alkylate 2-butyl-4-oxo-1,3-diazaspiro[4.4]non-1-ene hydrochloride according to General Method 4. 41A (100 mg, 35% yield) was isolated as a slightly yellow oil after silica gel chromatography using 1:1 hexanes/ethyl acetate as eluant.

B. 4'-[(2-Butyl-4-oxo-1,3-diazaspiro[4.4]non-1-en-3-yl)methyl]-N-(3,4-dimethyl-5-isoxazolyl)-2'-hydroxymethyl[1,1'-biphenyl]-2-sulfonamide Deprotection of 41A (100 mg, 0.14 mmol) according to General Method 8 (ethanol) gave the title compound as white solid in 46% yield following silica gel chromatography (96:4 methanol/chloroform eluant): MS m/e 565 (ESI+ mode); HPLC retention time 3.21 min (Method A); HPLC purity >98%.

Example 42
4'-[(2-Butyl-4-oxo-1,3-diazaspiro[4.4]non-1-en-3-yl)methyl]-N-(3,4-dimethyl-5-isoxazolyl)-2'-ethoxymethyl[1,1'-biphenyl]-2-sulfonamide

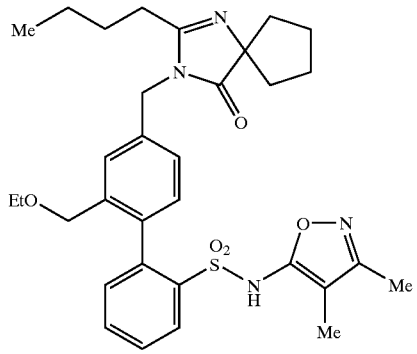

A. 4'-[(2-Butyl-4-oxo-1,3-diazaspiro[4.4]non-1-en-3-yl)methyl]-N-(3,4-dimethyl-5-isoxazolyl)-N-[(2-methoxyethoxy)methyl]-2'-hydroxymethyl[1,1'-biphenyl]-2-sulfonamide Triethylsilane (6 ml) and TFA (6 ml) were added to a solution of 5F (960 mg, 1.5 mmol) in 15 ml dichloromethane at RT. The mixture was stirred at RT for 2 h and was then concentrated. The residue was taken up in ethyl acetate and was washed successively with aqueous sodium bicarbonate, water, and brine. The organic layer was dried over sodium sulfate and concentrated. The residue was chromatographed on silica gel using 100:2 dichloromethane/methanol to afford 42A (740 mg, 77%) as a colorless gum. Rf=0.13, silica gel, 100:5 dichloromethane/methanol.

B. 4'-[(2-Butyl-4-oxo-1,3-diazaspiro[4.4]non-1-en-3-yl)methyl]-N-(3,4-dimethyl-5-isoxazolyl)-N-[(2-methoxyethoxy)methyl]-2'-ethoxymethyl[1,1'-biphenyl]-2-sulfonamide A mixture of 42A (100 mg, 0.15 mmol), iodoethane (960 mg, 6.1 mmol) and silver (I) oxide (180 mg, 0.77 mmol) in 0.7 ml DMF was heated at 40° C. for 16 h. Additional iodoethane (190 mg, 1.2 mmol) and silver (I) oxide (71 mg, 0.31 mmol) were added and the reaction mixture was heated at 40° C. for an additional 4 h. The mixture was diluted with 1:4 hexanes/ethylacetate and was then washed with water and brine. The organic layer was dried over sodium sulfate and was then concentrated. The residue was chromatographed on silica gel using 200:3 dichloromethane/methanol as eluant to afford 42B (51 mg, 49%) as a colorless gum. Rf=0.35, silica gel, 100:5 dichloromethane/methanol.

C. 4'-[(2-Butyl-4-oxo-1,3-diazaspiro[4.4]non-1-en-3-yl)methyl]-N-(3,4dimethyl-5-isoxazolyl)-2'-ethoxymethyl[1,1'-biphenyl]-2-sulfonamide 42B (51 mg) was deprotected according to General Method 7 to afford the title compound in 80% yield following preparative reverse-phase HPLC purification: white solid; m.p. 74–80° C. (amorphous); 1H NMR (CDCl$_3$)δ0.87 (tr, J=7Hz, 3H), 0.99(tr, J=7Hz, 3H), 1.32(m, 2H), 1.59(m, 2H), 1.75–2.02(m, 11H), 2.16(s, 3H), 2.35(m, 2H), 3.38 (m, 2H), 4.23(m, 2H), 4.73(s, 2H), 7.11–7.85 (m, 7H); MS m/e 593 (ESI+ mode); HPLC retention time 18.22 min. (Method E); HPLC purity >97%.

Example 43
4'-[(2-Butyl-4-oxo-1,3-diazaspiro[4.4]non-1-en-3-yl)methyl]-N-(3,4-dimethyl-5-isoxazolyl)-2'-propyl[1,1'-biphenyl]-2-sulfonamide

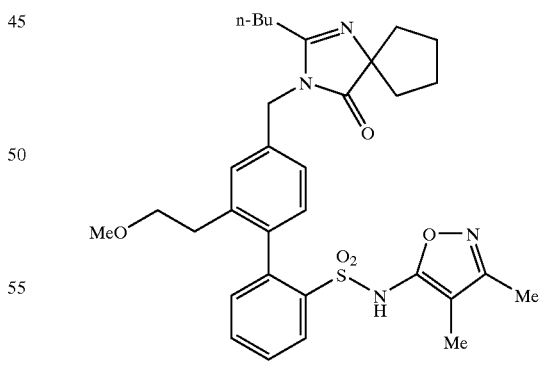

A. 4'-[(2-Butyl-4-oxo-1,3-diazaspiro[4.4]non-1-en-3-yl)methyl]-N-[(2methoxyethoxy)methyl]-N-(3,4-dimethyl-5-isoxazolyl)-2'-(2-methoxyvinyl)[1,1'-biphenyl]-2-sulfonamide 5F was treated with methoxymethyltriphenylphosphonium bromide according to the procedure used in Example 27, Step A. The product (34%) was generated as a mixture of E and Z isomers.

B. 4'-[(2-Butyl-4-oxo-1,3-diazaspiro[4.4]non-1-en-3-yl)methyl]-N-(3,4dimethyl-5-isoxazolyl)-2'-methoxyethyl[1,1'-biphenyl]-2-sulfonamide 43A (18 mg) was treated with triethylsilane and TFA according to the procedure of Example 42, Step B, to provide the title compound (6 mg, 45%) as an oil: MS m/e 593 (ESI+ mode); HPLC retention time 24.74 min. (Method B); HPLC purity >98%.

Example 44
4'-[(2-Butyl-4-oxo-1,3-diazaspiro[4.4]non-1-en-3-yl)methyl]-2'-[(3,3-dimethyl-2-oxo-1-pyrrolidinyl)methyl]-N-(3-methoxy-5-methyl-2-pyrazinyl)[1,1'-biphenyl]-2-sulfonamide

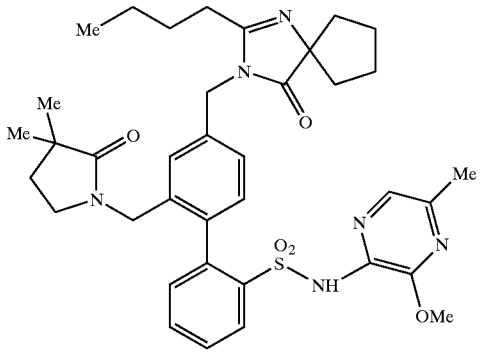

A. N-(3-Methoxy-5-methyl-2-pyrazinyl)-2-bromobenzenesulfonamide 2-amino-3-methoxy-5-methylpyrazine (1.50 g, 10.8 mmol; synthesized according to Bradbury, R. H., et. al. *J. Med. Chem.* 1997, 40, 996–1004) and 2-bromobenzenesulfonyl chloride (2.80 g, 11.0 mmol) were reacted according to the procedure of Example 25, Step A. 44A was a pink solid, 2.0 g (52%).

B. N-(3-Methoxy-5-methyl-2-pyrazinyl)-N-[2-(trimethylsilyl)ethoxymethyl]-2-bromobenzenesulfonamide 44A (2.0 g) was reacted with 2-(trimethylsilyl)ethoxymethyl chloride (1.15 ml) according to the procedure of Example 25, Step B. The crude residue was chromatographed on silica gel using 4:1 hexanes/ethyl acetate to give 44B (2.37 g, 86%) as a yellow oil.

C. 4'-[(2-Butyl-4-oxo-1,3-diazaspiro[4.4]non-1-en-3-yl)methyl]-2'-(1,3-dioxolan-2-yl)-N-[2-(trimethylsilyl)ethoxymethyl]-N-(3-methoxy-5-methyl-2-pyrazinyl)[1,1'-biphenyl]-2-sulfonamide A solution of 5E (2.0 g, 4.6 mmol) in ether (45 ml) was treated at −78° C. with t-butyllithium (1.7 M in pentane, 5.9 ml, 10.1 mmol). After stirring at −78° C. for 10 min, the mixture was treated with trimethylborate (1.3 ml, 11.5 mmol) and was then allowed to warm to RT. The mixture was concentrated and the residue azeotroped twice with methanol to produce a pale yellow solid (3.5 g).

The crude solid was subjected to Suzuki coupling with 44B (2.37 g) according to General Method 1. Silica gel chromatography using 1:1 hexanes/ethyl acetate as eluant provide 1.45 g 44C (39%) as a yellow oil.

D. 4'-[(2-Butyl-4-oxo-1,3-diazaspiro[4.4]non-1-en-3-yl)methyl]-2'-formyl-N-(3-methoxy-5-methyl-2-pyrazinyl)[1,1'-biphenyl]-2-sulfonamide 44C (1.45 g, 1.9 mmol) was treated with 2M sulfuric acid (11 ml) and ethanol (11 ml) at RT for 6 h. Aqueous sodium bicarbonate was added (final pH 7) and the mixture was extracted with ethyl acetate. The combined organic extracts were dried over sodium sulfate and concentrated to provide crude 44D (0.91 g) as an off-white solid.

E. 4'-[(2-Butyl-4-oxo-1,3-diazaspiro[4.4]non-1-en-3-yl)methyl]-2'-[(3,3dimethyl-2-oxo-1-pyrrolidinyl)methyl]-N-(3-methoxy-5-methyl-2-pyrazinyl)[1,1'-biphenyl]-2-sulfonamide 44D (0.91 g) was reacted with ethyl 4-amino-2,2-dimethylbutanoate hydrochloride according to General Method 5. The crude residue was purified by silica gel colunm chromatography using 1:3 hexanes/ethyl acetate as eluant to provide the title compound (230 mg, 18% over two steps) as a yellow solid: MS m/e 687 (ESI+ mode); HPLC retention time 3.58 min (Method A); HPLC purity 95%.

Example 45
4'-[(2-Butyl-4-oxo-1,3-diazaspiro[4.4]non-1-en-3-yl)methyl]-N-(4-bromo-3-methyl-5-isoxazolyl)-2'-[(3,3-dimethyl-2-oxo-1-pyrrolidinyl)methyl][1,1'-biphenyl]-2-sulfonamide

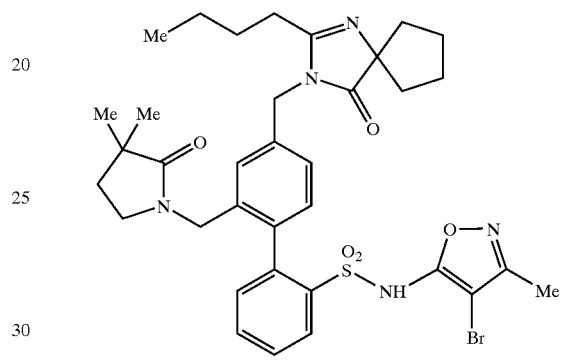

A. N-(2-methoxyethoxymethyl)-N-(3-methyl-5-isoxazolyl)-2-bromobenzenesulfonamide 25A (10.0 g, 31.5 mmol) was reacted with MEM chloride according to the procedure of Example 25, Step B. The crude residue was chromatographed on silica gel using 2:1 hexanes/ethyl acetate to give 4.8 g 45A (38%) as a yellow oil.

B. [2-[[(3-methyl-5-isoxazolyl)[(2-methoxyethoxy)methyl]amino]sulfonyl]phenyl]boronic acid n-Butyllithium (1.35 M solution in hexanes, 9.7 ml, 13 mmol) was added dropwise over 5 min to a 0.2 M solution of the45A (4.8 g, 12 mmol) in THF at −90° C. After 10 min, trimethylborate (1.6 ml, 14 mmol) was added and the mixture was allowed to warm to RT and stirred for 30 min. The mixture was cooled to 0° C. and treated with 21 ml of 3N hydrochloric acid, after which it was allowed to warm to RT over 30 min. Brine was added and the mixture was extracted with dichloromethane. The combined extracts were dried over sodium sulfate and concentrated to give 45B (5.3 g) as a yellow oil.

C. 4'-[(2-Butyl-4-oxo-1,3-diazaspiro[4.4]non-1-en-3-yl)methyl]-N-(2-methoxyethoxymethyl)-N-(3-methyl-5isoxazolyl)-2'-formyl[1,1'-biphenyl]-2-sulfonamide 45B (4.5 g) was subjected to Suzuki coouplilng with 5E according to General Method 1. Silica gel chromatography using 1:2 hexanes/ethyl acetate as eluant provide 45C (1.30 g, 17%) as a yellow oil.

D. 4'-[(2-Butyl-4-oxo-1,3-diazaspiro[4.4]non-1-en-3-yl)methyl]-N-(3-methyl-5-isoxazolyl)-N-[2-methoxyethoxy)methyl]-2'-[(3,3-dimethyl-2-oxo-1-pyrrolidinyl)methyl][1,1'-biphenyl]-2-sulfonamide 45C (420 mg, 0.66 mmol) was reacted with ethyl 4-amino-2,2-dimethylbutanoate hydrochloride and sodium cyanoborohydride using a procedure similar to that of Example 8, Step B. The crude residue was chromatographed on silica gel using 1:3 hexanes/ethyl acetate as eluant to provide 45D (150 mg) as a yellow oil.

E. 4'-[(2-Butyl-4-oxo-1,3-diazaspiro[4.4]non-1-en-3-yl)methyl]-N-(3-methyl-5-isoxazolyl)-2'-[(3,3-dimethyl-2-oxo-1-pyrrolidinyl)methyl][1,1'-biphenyl]-2-sulfonamide 45D (110 mg) was deprotected according to General Method 7. The crude residue was chromatographed on silica gel using 95:5 chloroform/methanol as eluant to provide 45E (50 mg) as a white solid.

F. 4'-[(2-Butyl-4-oxo-1,3-diazaspiro[4.4]non-1-en-3-yl)methyl]-N-(4-bromo-3-methyl-5-isoxazolyl)-2'-[(3,3-dimethyl-2-oxo-1-pyrrolidinyl)methyl][1,1'-biphenyl]-2-sulfonamide 45E (33 mg) was brominated using NBS according to the procedure used for Example 26. Preparative TLC purification of the crude residue provided the title compound (4 mg) as a white powder: MS m/e 724, 726 (ESI+ mode); HPLC retention time 3.53 min (Method A); HPLC purity 98%.

Examples 46 to 97

The following compounds 46 to 97 were prepared by a solution phase combinatorial chemistry method using 21 and the corresponding carboxylic acid in the presence of diisopropylcarbodiimide. The products were purified by ion-exchange chromatography according to the General Method. HLPC retention times were determined using HPLC Method C.

| Ex. No. | Compound Name | J | HPLC Retention Time (min) | LRMS m/z [MH+] |
|---|---|---|---|---|
| 46 | 4'-[(2-Butyl-4-oxo-1,3-diazaspiro[4.4]non-1-en-3-yl)methyl]-N-(3,4-dimethyl-5-isoxazolyl)-2'-[(formylmethylamino)-methyl][1,1'-biphenyl]-2-sulfonamide | Me-N(Me)-CHO | 3.23 | 606 |
| 47 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methylpropanamide | Me-N(Me)-C(O)Et | 3.28 | 634 |
| 48 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methylcyclopropanecarbox-amide | Me-N(Me)-C(O)-cyclopropyl | 3.33 | 646 |
| 49 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,2-dimethylpropanamide | Me-N(Me)-C(O)-iPr | 3.41 | 648 |
| 50 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methylbutanamide | Me-N(Me)-C(O)Pr | 3.45 | 648 |

-continued

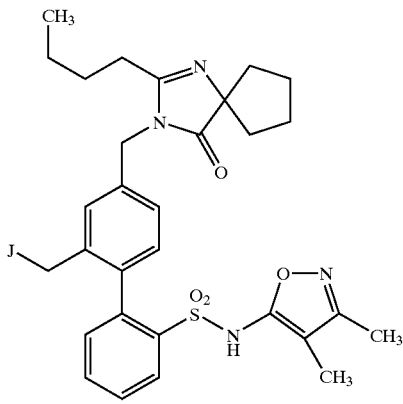

| Ex. No. | Compound Name | J | HPLC Retention Time (min) | LRMS m/z [MH+] |
|---|---|---|---|---|
| 51 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-2-methoxy-N-methylacetamide | 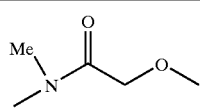 | 3.29 | 650 |
| 52 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methyl-4-pentynamide | 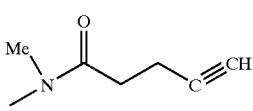 | 3.32 | 658 |
| 53 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methylcyclobutanecarbox-amide | 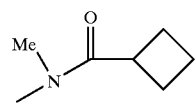 | 3.50 | 660 |
| 54 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,3-dimethylbutanamide | 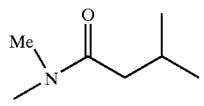 | 3.57 | 662 |
| 55 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,2,2-trimethylpropanamide | 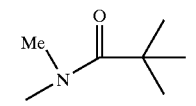 | 3.80 | 662 |
| 56 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-3-methoxy-N-methylproprnamide | 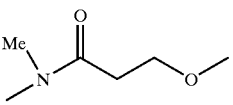 | 3.38 | 664 |
| 57 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-2-ethoxy-N-methylacetamide | 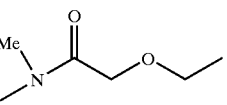 | 3.25 | 664 |
| 58 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methyl-2-furancarboxamide | 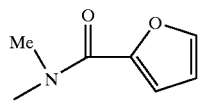 | 3.30 | 672 |

-continued

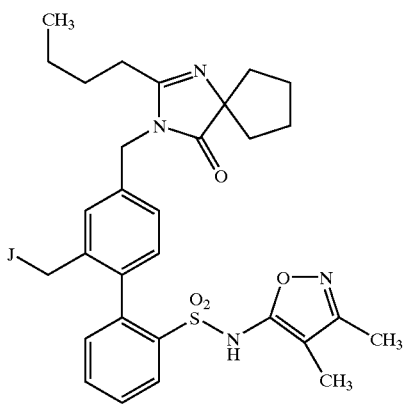

| Ex. No. | Compound Name | J | HPLC Retention Time (min) | LRMS m/z [MH+] |
|---|---|---|---|---|
| 59 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,4-dimethylpentanamide | | 3.95 | 676 |
| 60 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methylbenzamide | | 3.66 | 682 |
| 61 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methyl-3-thiophenecarboxamide | | 3.59 | 688 |
| 62 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methylcyclopentaneacet-amide | | 3.82 | 688 |
| 63 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methylcyclohexanecarbox-amide | | 3.76 | 688 |
| 64 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,3-dimethylbenzamide | | 3.82 | 696 |
| 65 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methylbenzeneacetamide | | 3.78 | 696 |

-continued

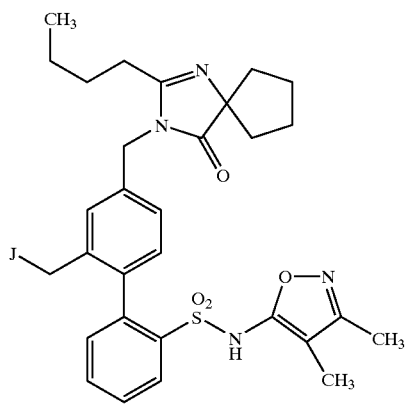

| Ex. No. | Compound Name | J | HPLC Retention Time (min) | LRMS m/z [MH+] |
|---|---|---|---|---|
| 66 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-2-fluoro-N-methylbenzamide | 2-F-C6H4-C(O)-N(Me)- | 3.46 | 700 |
| 67 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-3-fluoro-N-methylbenzamide | 3-F-C6H4-C(O)-N(Me)- | 3.53 | 700 |
| 68 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-4-fluoro-N-methylbenzamide | 4-F-C6H4-C(O)-N(Me)- | 3.72 | 700 |
| 69 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methylcyclohexaneacet-amide | Cyclohexyl-CH2-C(O)-N(Me)- | 3.96 | 702 |
| 70 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-2-fluoro-N-methylbenzeneacetamide | 2-F-C6H4-CH2-C(O)-N(Me)- | 3.79 | 714 |
| 71 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-3-fluoro-N-methylbenzeneacetamide | 3-F-C6H4-CH2-C(O)-N(Me)- | 3.82 | 714 |
| 72 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-4-fluoro-N-methylbenzeneacetamide | 4-F-C6H4-CH2-C(O)-N(Me)- | 3.82 | 714 |

-continued

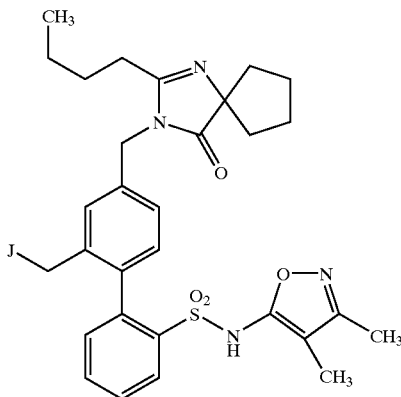

| Ex. No. | Compound Name | J | HPLC Retention Time (min) | LRMS m/z [MH⁺] |
|---|---|---|---|---|
| 73 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,N',N'-trimethylurea | Me-N(Me)-C(O)-N(Me)Me | 3.44 | 649 |
| 74 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N'-(1,1-dimethylethyl)-N-methylurea | Me-N(Me)-C(O)-NH-C(Me)₃ | 3.74 | 677 |
| 75 | [[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]methylcarbamic acid ethyl ester | Me-N(Me)-C(O)-O-Et | 3.69 | 650 |
| 76 | [[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]methylcarbamic acid 2-methylpropyl ester | Me-N(Me)-C(O)-O-CH₂CH(Me)₂ | 4.01 | 678 |
| 77 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,3,3-trimethylbutanamide | (Me)₃C-CH₂-C(O)-N(Me)Me | 3.85 | 676 |
| 78 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methyl-2-pyridinecarboxamide | 2-pyridyl-C(O)-N(Me)Me | 3.33 | 683 |

-continued

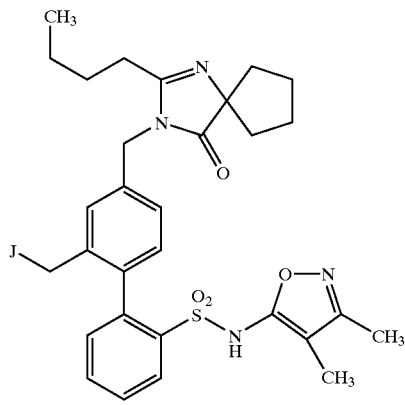

| Ex. No. | Compound Name | J | HPLC Retention Time (min) | LRMS m/z [MH+] |
|---|---|---|---|---|
| 79 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methyl-3-pyridinecarboxamide | 3-pyridyl-C(O)-N(Me)- | 3.16 | 683 |
| 80 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methyl-2-pyrazinecarboxamide | 2-pyrazinyl-C(O)-N(Me)- | 3.27 | 684 |
| 81 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,1-dimethyl-1H-pyrrole-2-carboxamide | 1-methylpyrrol-2-yl-C(O)-N(Me)- | 3.64 | 685 |
| 82 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methyl-1,2,3-thiadiazole-4-carboxamide | 1,2,3-thiadiazol-4-yl-C(O)-N(Me)- | 3.36 | 690 |
| 83 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,5-dimethyl-2-pyrazinecarboxamide | 5-methylpyrazin-2-yl-C(O)-N(Me)- | 3.37 | 698 |
| 84 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,3,5-trimethyl-4-isoxazolecarboxamide | 3,5-dimethylisoxazol-4-yl-C(O)-N(Me)- | 3.42 | 701 |

-continued

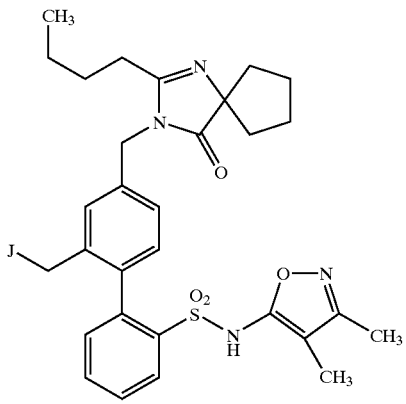

| Ex. No. | Compound Name | J | HPLC Retention Time (min) | LRMS m/z [MH+] |
|---|---|---|---|---|
| 85 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,3-dimethyl-2-thiophenecarboxamide | | 3.66 | 702 |
| 86 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N,5-dimethyl-2-thiophenecarboxamide | | 3.72 | 702 |
| 87 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-3-cyano-N-methylbenzamide | | 3.45 | 707 |
| 88 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-4-cyano-N-methylbenzamide | | 3.49 | 707 |
| 89 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-2-methoxy-N-methylbenzamide | | 3.63 | 712 |
| 90 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-2-chloro-N-methylbenzamide | | 3.77 | 717 |

-continued

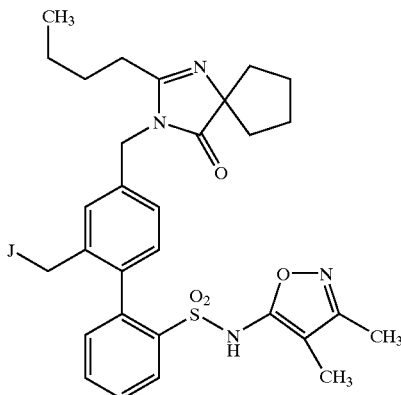

| Ex. No. | Compound Name | J | HPLC Retention Time (min) | LRMS m/z [MH+] |
|---|---|---|---|---|
| 91 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-3-chloro-N-methylbenzamide | 3-chloro-N-methylbenzamide group | 3.84 | 717 |
| 92 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-4-chloro-N-methylbenzamide | 4-chloro-N-methylbenzamide group | 3.87 | 717 |
| 93 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-2,3-difluoro-N-methylbenzamide | 2,3-difluoro-N-methylbenzamide group | 3.66 | 718 |
| 94 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-3,4-difluoro-N-methylbenzamide | 3,4-difluoro-N-methylbenzamide group | 3.76 | 718 |
| 95 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-3,5-difluoro-N-methylbenzamide | 3,5-difluoro-N-methylbenzamide group | 3.76 | 718 |

-continued

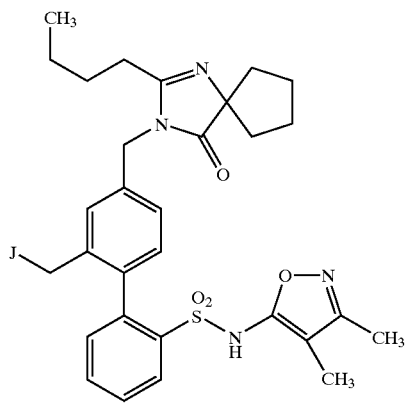

| Ex. No. | Compound Name | J | HPLC Retention Time (min) | LRMS m/z [MH+] |
|---|---|---|---|---|
| 96 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-N-methylbenzamide | | 3.48 | 724 |
| 97 | N-[[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]methyl]-3-ethoxy-N-methyl-2-thiophenecarboxamide | | 3.63 | 732 |

The following examples were synthesized by combinations of the General Methods.

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 98 | 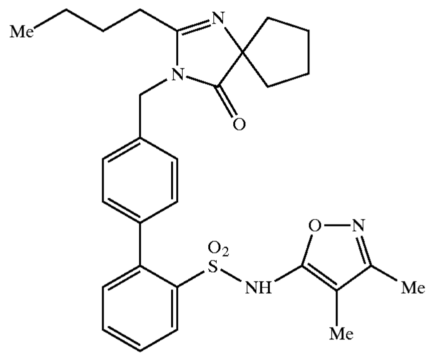 | 4'-[(2-Butyl-4-oxo-1,3-diazaspiro[4.4]non-1-en-3-yl)methyl]-N-(3,4-dimethyl-5-isoxazolyl)[1,1'-biphenyl]-2-sulfonamide | P18 | 4, 7 (32) | 535 | >98 | 15.00 (I) |
| 99 | 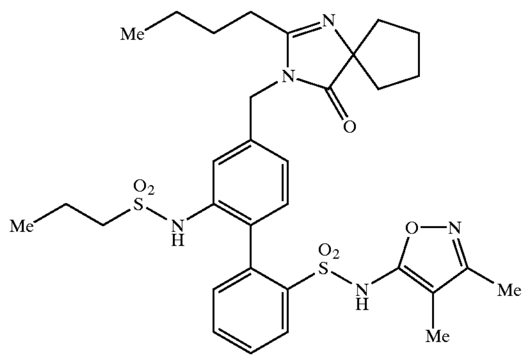 | 4'-[(2-Butyl-4-oxo-1,3-diazaspiro[4.4]non-1-en-3-yl)methyl]-N-(3,4-dimethyl-5-isoxazolyl)-2-[(propylsulfonyl)amino][1,1'-biphenyl]-2-sulfonamide | 123 | 24 (67) | 656 | 98 | 14.58 (E) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 100 | 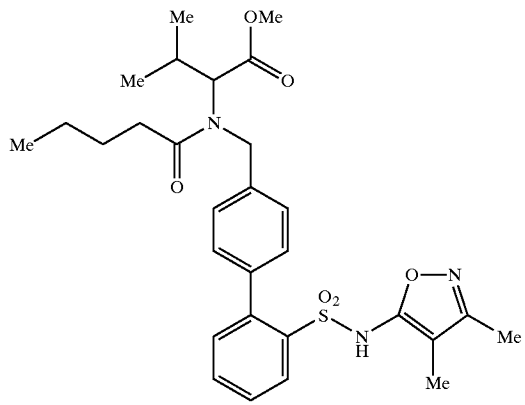 | N-[[2'-[[(3,4-Dimethyl-5-isoxazolyl)amino]sulfonyl][1,1'-biphenyl]-4-yl]methyl]-N-(1-oxopentyl)-L-valine methyl ester | P17 | 5, 6 (16); 9 (60) | 556 | >98 | 16.27 (F) |
| 101 | 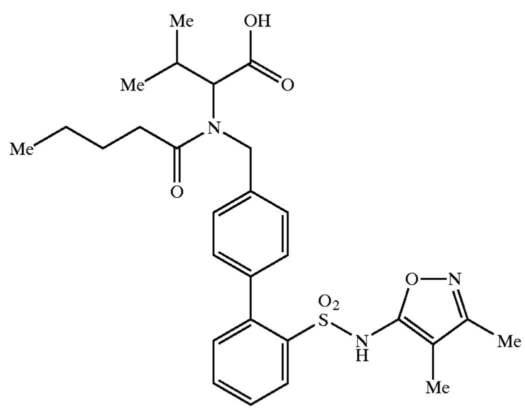 | N-[[2'-[[(3,4-Dimethyl-5-isoxazolyl)amino]sulfonyl][1,1'-biphenyl]-4-yl]methyl]-N-(1-oxopentyl)-L-valine | 100 | 15 (40) | 542 | >98 | 13.55 (F) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 102 | 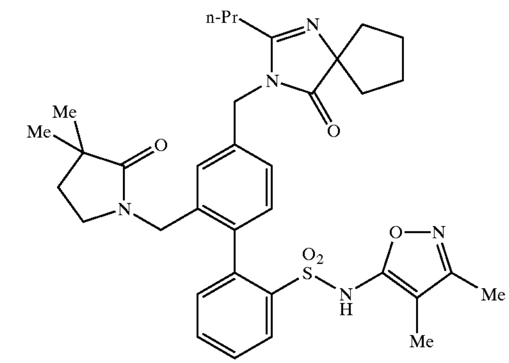 | N-(3,4-Dimethyl-5-isoxazolyl)-2'-[(3,3-dimethyl-2-oxo-1-pyrrolidinyl)methyl]-4'-[(2-propyl-4-oxo-1,3-diazaspiro[4.4]non-1-en-3-yl)methyl][1,1'-biphenyl]-2-sulfonamide | 5C | 4 (65); 19, 1 (70); 5 (36); 9 (50) | 646 | 97 | 7.92 (E) |
| 103 | 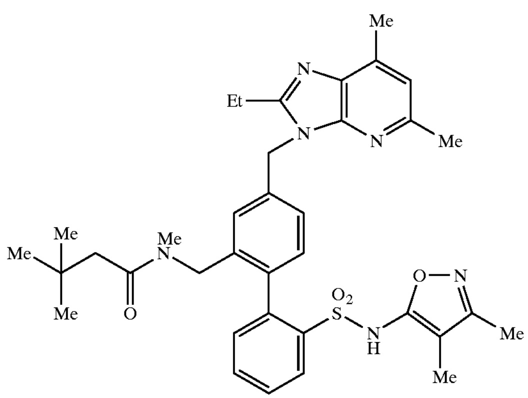 | N-[[2'-[[(3,4-Dimethyl-5-isoxazolyl)amino]sulfonyl]-4-[(2-ethyl-5,7-dimethyl-3H-imidazo[4,5-b]pyridin-3-yl]methyl][1,1'-biphenyl]-2-yl]methyl]-N,3,3-trimethylbutanamide | 2G | 4 (32); 7, 6 (80) | 657 | >98 | 25.45 (B) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 104 | 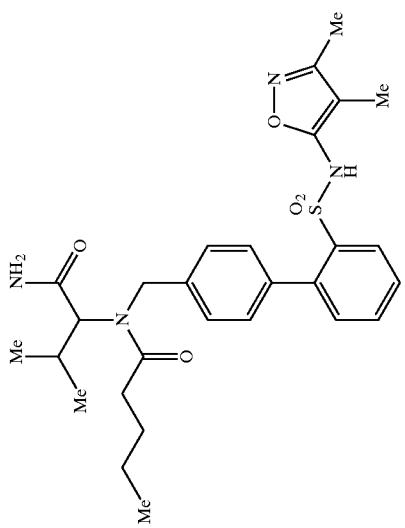 | N²-[[2'-[[(3,4-Dimethyl-5-isoxazolyl)amino]sulfonyl][1,1'-biphenyl]-4-yl]methyl]-N²-(1-oxopentyl)-L-valinamide | 101 | 12, NH₃ (70) | 541 | 98 | 11.39 (B) |
| 105 | 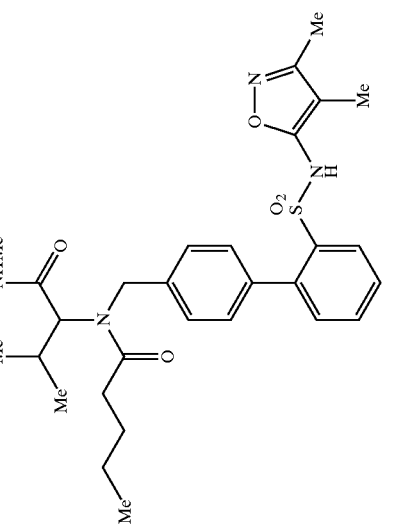 | N²-[[2'-[[(3,4-Dimethyl-5-isoxazolyl)amino]sulfonyl][1,1'-biphenyl]-4-yl]methyl]-N-methyl-N²-(1-oxopentyl)-L-valinamide | 101 | 12, MeNH₂ (67) | 555 | 98 | 11.27 (F) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 106 | 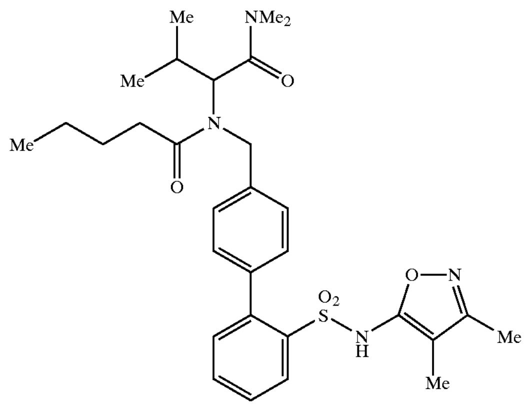 | N²-[[2'-[[(3,4-Dimethyl-5-isoxazolyl)amino]sulfonyl][1,1'-biphenyl]-4-yl]methyl]-N,N-dimethyl-N²-(1-oxopentyl)-L-valinamide | 101 | 12, Me₂NH (12) | 569 | 94 | 12.28 (F) |
| 107 | 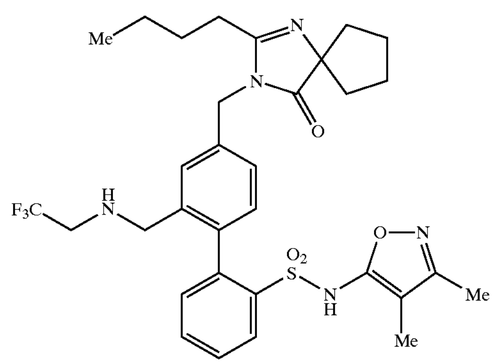 | 4'-[(2-Butyl-4-oxo-1,3-diazaspiro[4.4]non-1-en-3-yl)methyl]-N-(3,4-dimethyl-5-isoxazolyl)-2'-[[(2,2,2-trifluoroethyl)amino]methyl][1,1'-biphenyl]-2-sulfonamide | P4 | 3 (90); 4 (37); 5 (56); 8, EtOH (31) | 646 | >99 | 3.46 (A) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 108 | 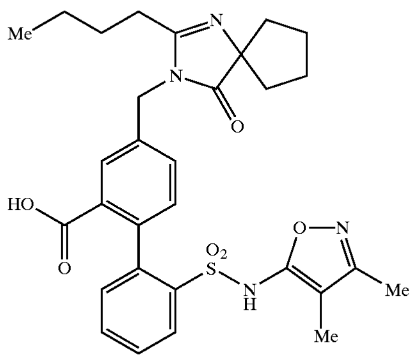 | 4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-carboxylic acid | 110 | 15 (62) | 578 | 95 | 3.16 (A) |
| 109 | 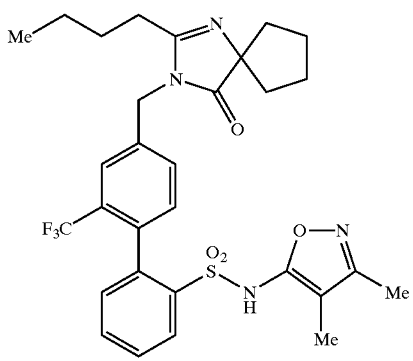 | 4'-[(2-Butyl-4-oxo-1,3-diazaspiro[4.4]non-1-en-3-yl)methyl]-N-(3,4-dimethyl-5-isoxazolyl)-2'-(trifluoromethyl)[1,1'-biphenyl]-2-sulfonamide | P9 | 4 (60); 10 (90) | 603 | 94 | 2.33 (D) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 110 | 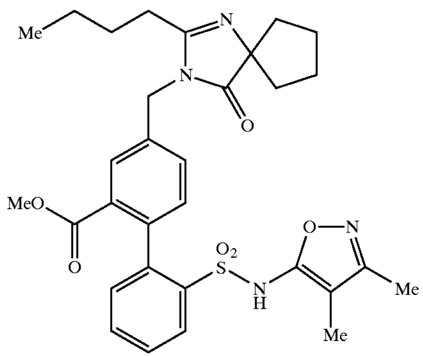 | 4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-carboxylic acid methyl ester | methyl 2-bromo-5-methyl-benzoate | 13, 4 (61); 1 (50); 8, MeOH (34) | 593 | 96 | 3.42 (A) |
| 111 | 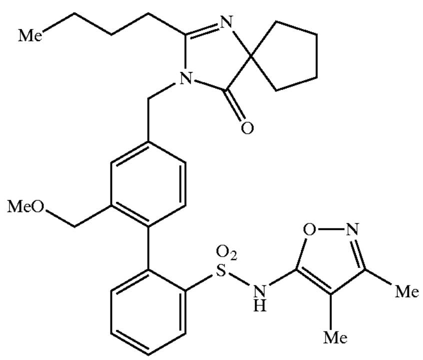 | 4'-[(2-Butyl-4-oxo-1,3-diazaspiro[4.4]non-1-en-3-yl)methyl]-N-(3,4-dimethyl-5-isoxazolyl)-2-(methoxymethyl)[1,1'-biphenyl]-2-sulfonamide | P2 | 4 (53); 7 (58) | 579 | >98 | 16.26 (E) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 112 | 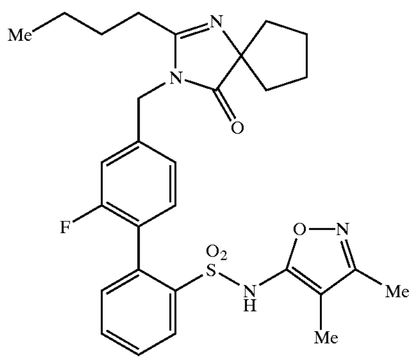 | 4'-[(2-Butyl-4-oxo-1,3-diazaspiro[4.4]non-1-en-3-yl)methyl]-N-(3,4-dimethyl-5-isoxazolyl)-2'-fluoro[1,1'-biphenyl]-2-sulfonamide | P11 | 4 (82); 7 (85) | 553 | >99 | 25.90 (B) |
| 113 | 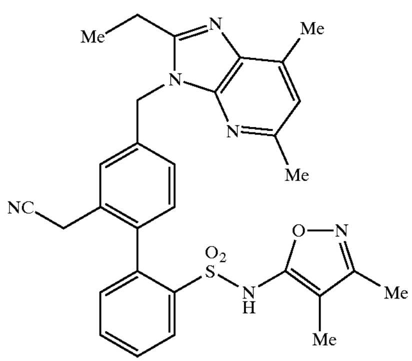 | 2'-(Cyanomethyl)-N-(3,4-dimethyl-5-isoxazolyl)-4'-[(2-ethyl-5,7-dimethyl-3H-imidazo[4,5-b]pyridin-3-yl)methyl][1,1'-biphenyl]-2-sulfonamide | P12 | 16, 3, 4 (35); 8, EtOH (81) | 555 | 97 | 3.16 (A) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 114 | 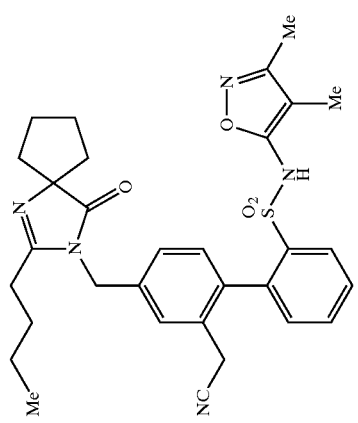 | 4'-[(2-Butyl-4-oxo-1,3-diazaspiro[4.4]non-1-en-3-yl)methyl]-2'-(cyanomethyl)-N-(3,4-dimethyl-5-isoxazolyl)[1,1'-biphenyl]-2-sulfonamide | P12 | 16, 3, 4 (35); 8, EtOH (52) | 574 | 96 | 3.36 (A) |
| 115 | 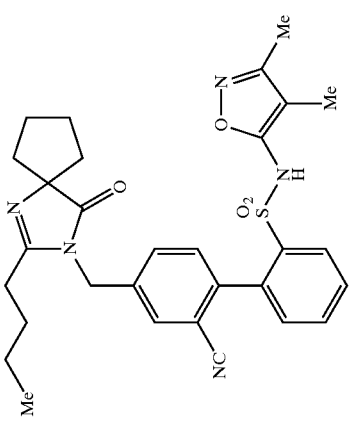 | 4'-[(2-Butyl-4-oxo-1,3-diazaspiro[4.4]non-1-en-3-yl)methyl]-2'-cyano-N-(3,4-dimethyl-5-isoxazolyl)[1,1'-biphenyl]-2-sulfonamide | P3 | 3 (88); 4 (45); 10 (40) | 560 | >97 | 3.31 (C) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 116 | 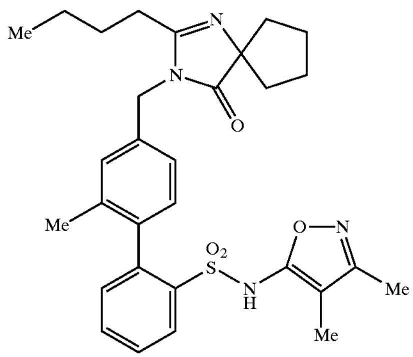 | 4'-[(2-Butyl-4-oxo-1,3-diazaspiro[4.4]non-1-en-3-yl)methyl]-N-(3,4-dimethyl-5-isoxazolyl)-2'-methyl[1,1'-biphenyl]-2-sulfonamide | P7 | 11 (83); 2 (87); 4 (70); 1 (35); 7 (20) | 549 | 98 | 27.21 (B) |
| 117 | 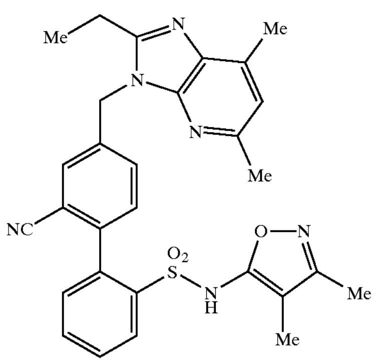 | 2'-Cyano-N-(3,4-dimethyl-5-isoxazolyl)-4'-[(2-ethyl-5,7-dimethyl-3H-imidazo[4,5-b]pyridin-3-yl)methyl][1,1'-biphenyl]-2-sulfonamide | P3 | 3 (88); 4 (45); 10 (38) | 541 | 98 | 3.10 (A) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 118 | 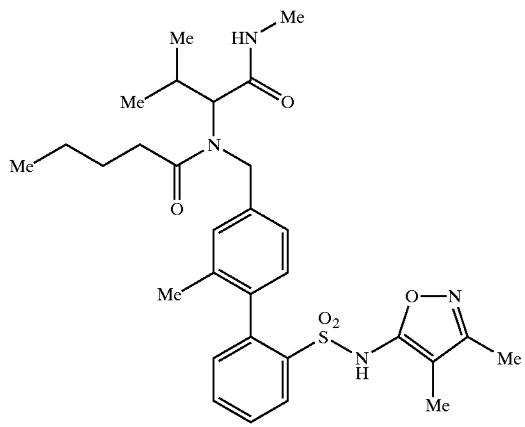 | N²-[[2'-[[(3,4-Dimethyl-5-isoxazolyl)amino]sulfonyl]-2-methyl[1,1'-biphenyl]-4-yl]methyl]-N²-(1-oxopentyl)-L-valinamide | P15 | 5 (39); 6 (92); 10 (30) | 569 | >99 | 2.15 (H) |
| 119 | 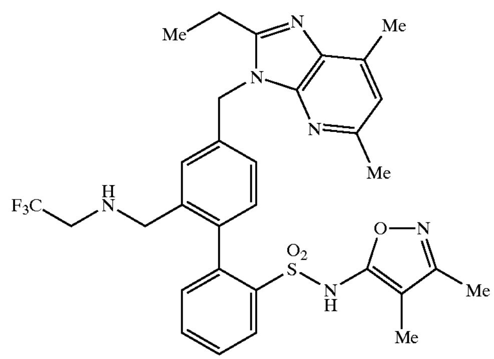 | N-(3,4-Dimethyl-5-isoxazolyl)-4-[(2-ethyl-5,7-dimethyl[4,5-b]pyridin-3-yl)methyl]-2-[[(2,2,2-trifluoroethyl)amino]methyl][1,1'-biphenyl]-2-sulfonamide | P4 | 3 (90); 4 (49); 5 (83); 10 (15) | 627 | 89 | 3.10 (A) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 120 | 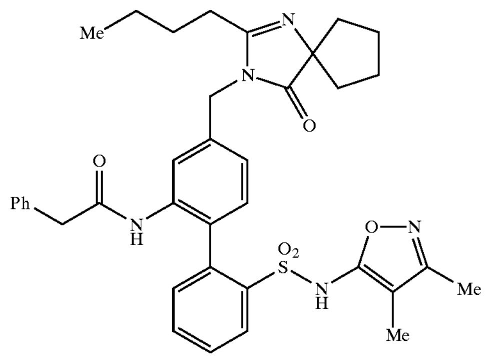 | N-[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]benzeneacetamide | 122 | 6 (27) | 668 | 97 | 14.97 (I) |
| 121 | 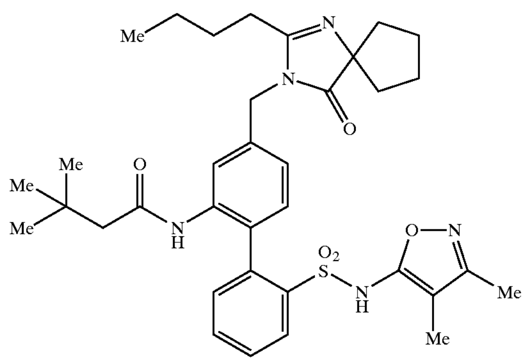 | N-[4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-yl]-3,3-dimethylbutanamide | 122 | 6 (36) | 648 | >98 | 16.38 (I) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 122 | 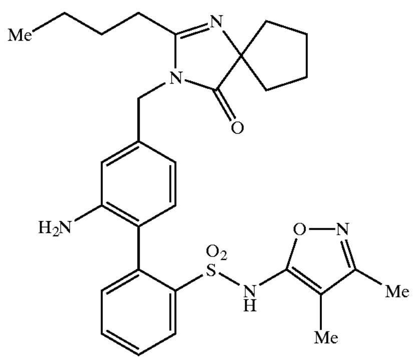 | 2'-Amino-4'-[(2-butyl-4-oxo-1,3-diazaspiro[4.4]non-1-en-3-yl)methyl]-N-(3,4-dimethyl-5-isoxazolyl)[1,1'-biphenyl]-2-sulfonamide | 123 | 18 (75) | 550 | >98 | 8.39 (I) |
| 123 | 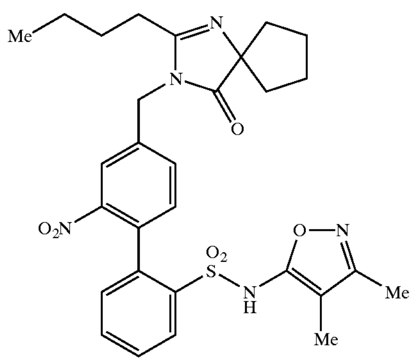 | 4'-[(2-Butyl-4-oxo-1,3-diazaspiro[4.4]non-1-en-3-yl)methyl]-N-(3,4-dimethyl-5-isoxazolyl)-2'-nitro[1,1'-biphenyl]-2-sulfonamide | P22 | 7 (93) | 580 | >98 | 11.17 (I) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 124 | 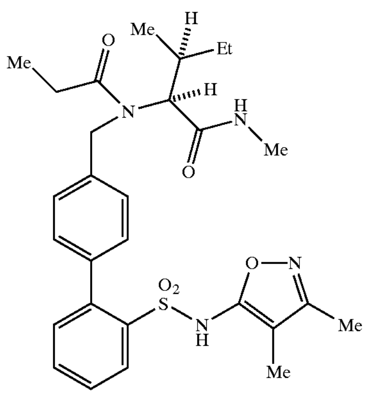 | $N^2$-[[2'-[[(3,4-Dimethyl-5-isoxazolyl)amino]sulfonyl][1,1'-biphenyl]-4-yl]methyl]-N-methyl-$N^2$-(1-oxopropyl)-L-isoleudinamide | P16 | 5 (85); 6, 10 (62) | 541 | 96 | 1.00 (G) |
| 125 | 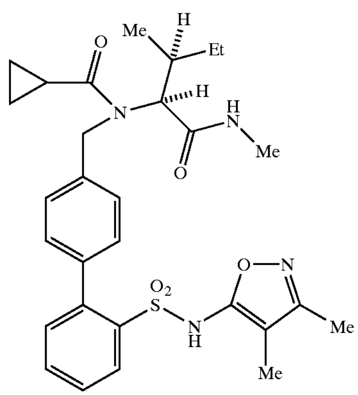 | $N^2$-(Cyclopropylcarbonyl)-$N^2$-[[2'-[[(3,4-dimethyl-5-isoxazolyl)amino]sulfonyl][1,1'-biphenyl]-4-yl]methyl]-N-methyl-L-isoleucinamide | P16 | 5 (85); 6, 10 (62) | 553 | 96 | 1.09 (G) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 126 | 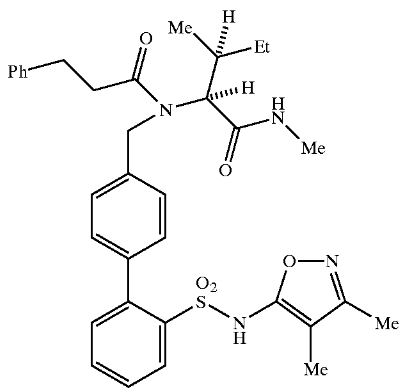 | N²-[[2'-[[(3,4-Dimethyl-5-isoxazolyl)amino]sulfonyl][1,1'-biphenyl]-4-yl]methyl]-N-methyl-N²-(1-oxo-3-phenylpropyl)-L-isoleucinamide | P16 | 5 (85); 6, 10 (64) | 617 | 95 | 1.63 (G) |
| 127 | 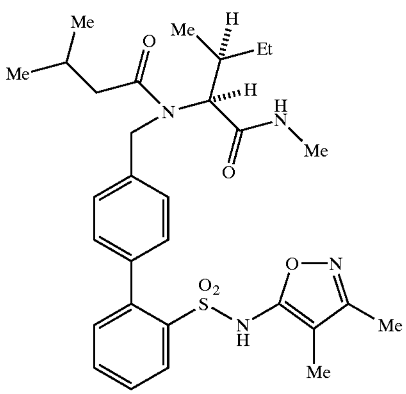 | N²-[[2'-[[(3,4-Dimethyl-5-isoxazolyl)amino]sulfonyl][1,1'-biphenyl]-4-yl]methyl]-N-methyl-N²-(3-methyl-1-oxobutyl)-L-isoleucinamide | P16 | 5 (85); 6, 10 (58) | 569 | 98 | 1.47 (G) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 128 | 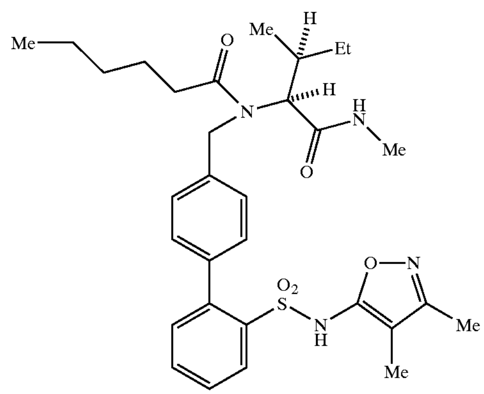 | N²-[[2'-[[(3,4-Dimethyl-5-isoxazolyl)amino]sulfonyl][1,1'-biphenyl]-4-yl]methyl]-N-methyl-N²-(1-oxohexyl)-L-isoleucinamide | P16 | 5 (85); 6, 10 (75) | 583 | 98 | 1.74 (G) |
| 129 | 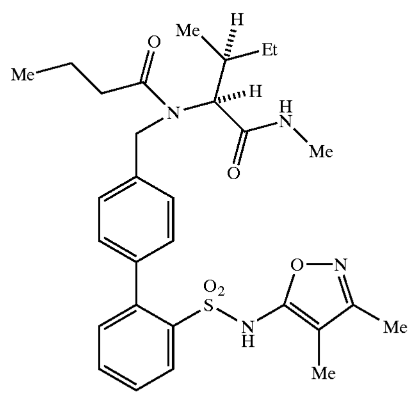 | N²-[[2'-[[(3,4-Dimethyl-5-isoxazolyl)amino]sulfonyl][1,1'-biphenyl]-4-yl]methyl]-N-methyl-N²-(1-oxobutyl)-L-isoleucinamide | P16 | 5 (85); 6, 10 (62) | 555 | 95 | 1.31 (G) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 130 | 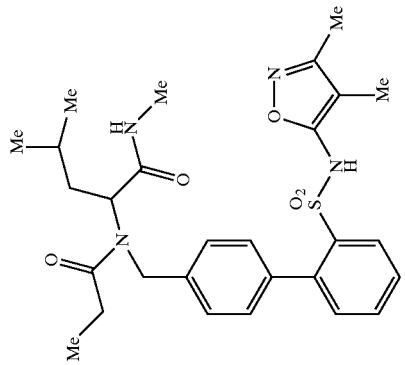 | N²-[[2'-[[(3,4-Dimethyl-5-isoxazolyl)amino]sulfonyl][1,1'-biphenyl]-4-yl]methyl]-N-methyl-N²-(1-oxopropyl)-L-leucinamide | P16 | 5 (83); 6, 10 (75) | 541 | 90 | 1.01 (G) |
| 131 | 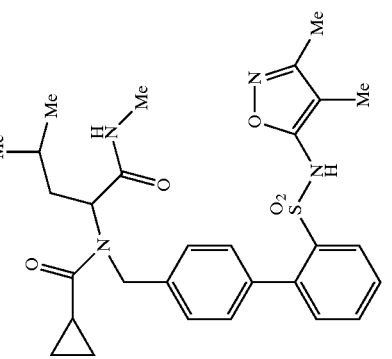 | N²-(Cyclopropylcarbonyl)-N²-[[2'-[[(3,4-dimethyl-5-isoxazolyl)amino]sulfonyl][1,1'-biphenyl]-4-yl]methyl]-N-methyl-L-leucinamide | P16 | 5 (83); 6, 10 (79) | 553 | 95 | 1.11 (G) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 132 | 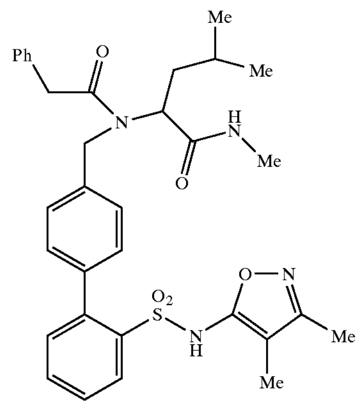 | N²-[[2'-[[(3,4-Dimethyl-5-isoxazolyl)amino]sulfonyl][1,1'-biphenyl]-4-yl]methyl]-N-methyl-N²-(1-oxo-3-phenylpropyl)-L-leucinamide | P16 | 5 (83); 6, 10 (20) | 617 | 95 | 1.08 (G) |
| 133 | 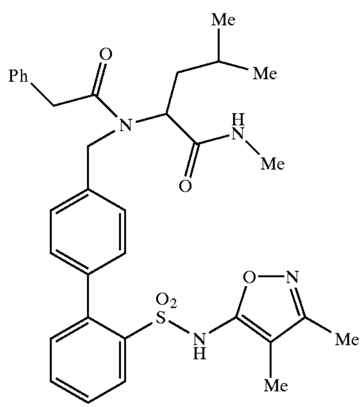 | N²-[[2'-[[(3,4-Dimethyl-5-isoxazolyl)amino]sulfonyl][1,1'-biphenyl]-4-yl]methyl]-N-methyl-N²-(phenylacetyl)-L-leucinamide | P16 | 5 (83); 6, 10 (20) | 603 | 95 | 1.68 (G) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 134 | 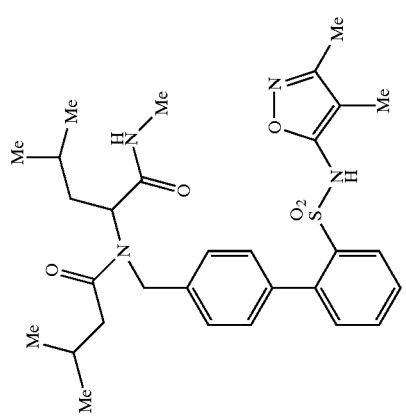 | N²-[[2'-[[(3,4-Dimethyl-5-isoxazolyl)amino]sulfonyl][1,1'-biphenyl]-4-yl]methyl]-N-methyl-N²-(3-methyl-1-oxobutyl)-L-leucinamide | P16 | 5 (83); 6, 10 (62) | 569 | 90 | 1.51 (G) |
| 135 | 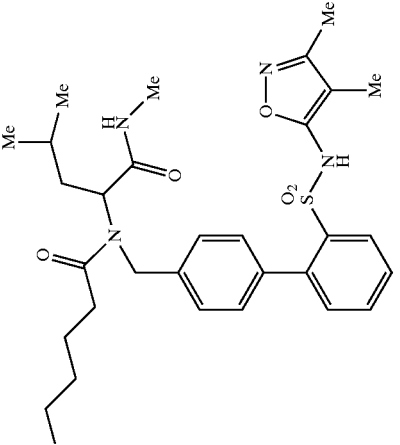 | N²-[[2'-[[(3,4-Dimethyl-5-isoxazolyl)amino]sulfonyl][1,1'-biphenyl]-4-yl]methyl]-N-methyl-N²-(1-oxohexyl)-L-leucinamide | P16 | 5 (83); 6, 10 (47) | 583 | 97 | 1.76 (G) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 136 | 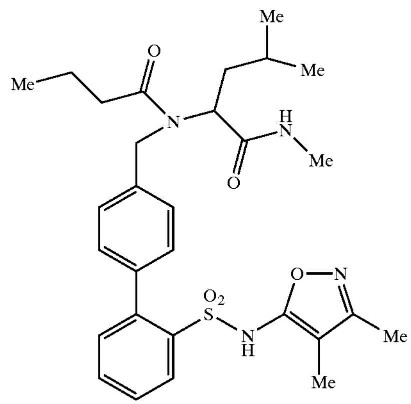 | N²-[[2'-[[(3,4-Dimethyl-5-isoxazolyl)amino]sulfonyl][1,1'-biphenyl]-4-yl]methyl]-N-methyl-N²-(1-oxobutyl)-L-leucinamide | P16 | 5 (83); 6, 10 (64) | 555 | 94 | 1.29 (G) |
| 137 | 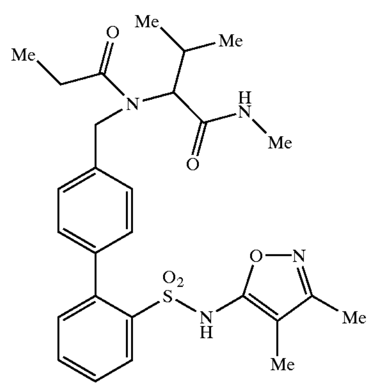 | N²-[[2'-[[(3,4-Dimethyl-5-isoxazolyl)amino]sulfonyl][1,1'-biphenyl]-4-yl]methyl]-N-methyl-N²-(1-oxopropyl)-L-valinamide | P16 | 5 (89); 6, 10 (39) | 527 | 90 | 0.73 (G) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 138 | 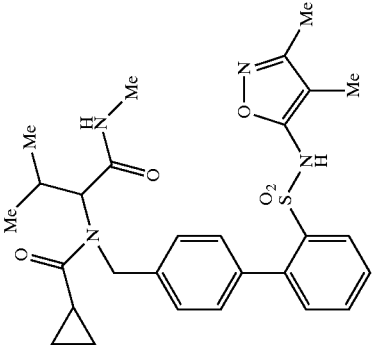 | N²-(Cyclopropylcarbonyl)-N²-[[2'-[[(3,4-dimethyl-5-isoxazolyl)amino]sulfonyl][1,1'-biphenyl]-4-yl]methyl]-N-methyl-L-valinamide | P16 | 5 (89); 6, 10 (66) | 539 | 98 | 0.89 (G) |
| 139 | 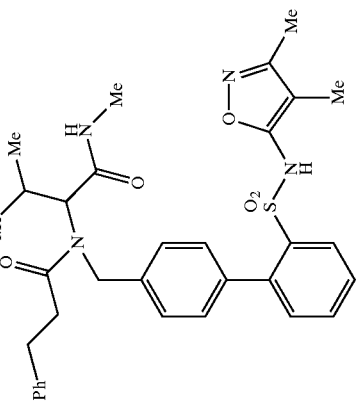 | N²-[[2'-[[(3,4-Dimethyl-5-isoxazolyl)amino]sulfonyl][1,1'-biphenyl]-4-yl]methyl]-N-methyl-N²-(1-oxo-3-phenylpropyl)-L-valinamide | P16 | 5 (89); 6, 10 (6) | 603 | 95 | 1.63 (G) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 140 | 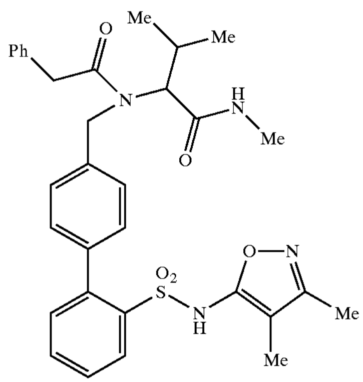 | N²-[[2'-[[(3,4-Dimethyl-5-isoxazolyl)amino]sulfonyl][1,1'-biphenyl]-4-yl]methyl]-N-methyl-N²-(phenylacetyl)-L-valinamide | P16 | 5 (89); 6, 10 (54) | 589 | 93 | 1.53 (G) |
| 141 | 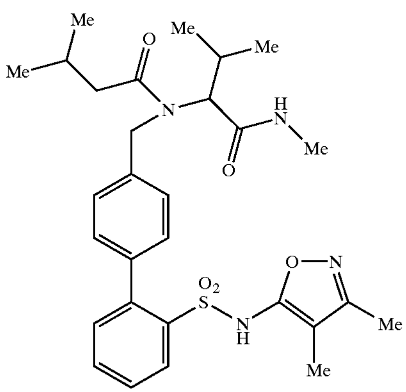 | N²-[[2'-[[(3,4-Dimethyl-5-isoxazolyl)amino]sulfonyl][1,1'-biphenyl]-4-yl]methyl]-N-methyl-N²-(3-methyl-1-oxobutyl)-L-valinamide | P16 | 5 (89); 6, 10 (45) | 555 | 98 | 1.37 (G) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 142 | 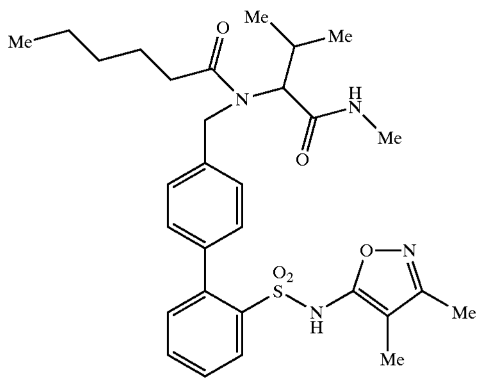 | N²-[[2'-[[(3,4-Dimethyl-5-isoxazolyl)amino]sulfonyl][1,1'-biphenyl]-4-yl]methyl]-N-methyl-N²-(1-oxohexyl)-L-valinamide | P16 | 5 (89); 6, 10 (61) | 569 | 98 | 1.58 (G) |
| 143 | 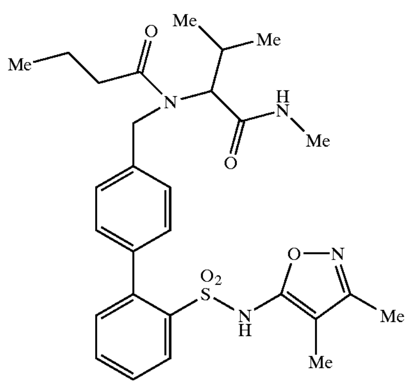 | N²-[[2'-[[(3,4-Dimethyl-5-isoxazolyl)amino]sulfonyl][1,1'-biphenyl]-4-yl]methyl]-N-methyl-N²-(1-oxobutyl)-L-valinamide | P16 | 5 (89); 6, 10 (43) | 541 | 98 | 1.65 (G) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 144 | 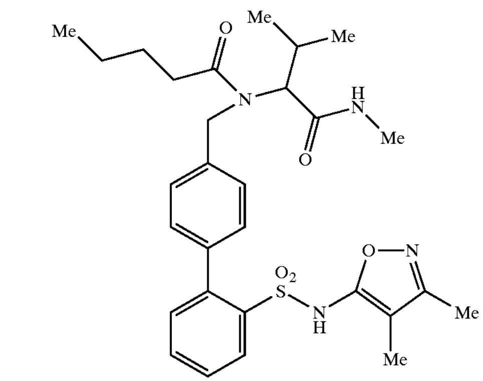 | N²-[[2'-[[(3,4-Dimethyl-5-isoxazolyl)amino]sulfonyl][1,1'-biphenyl]-4-yl]methyl]-N-ethyl-N²-(1-oxopentyl)-L-valinamide | P17 | 5 (87); 6 (93); 9 (65); 15 (85); 12 (65) | 569 | >97 | 12.94 (F) |
| 145 | 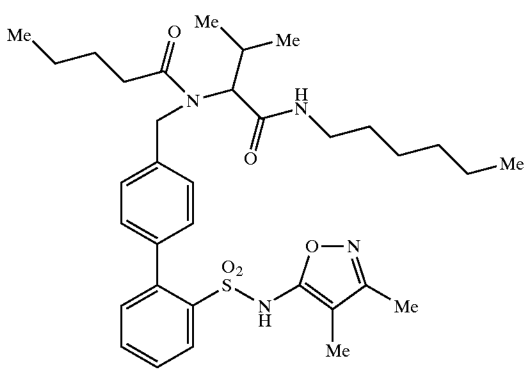 | N²-[[2'-[[(3,4-Dimethyl-5-isoxazolyl)amino]sulfonyl][1,1'-biphenyl]-4-yl]methyl]-N-henyl-N²-(1-oxopentyl)-L-valinamide | P17 | 5 (87); 6 (93); 9 (65); 15 (85); 12 (65) | 625 | >98 | 22.19 (F) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 146 | 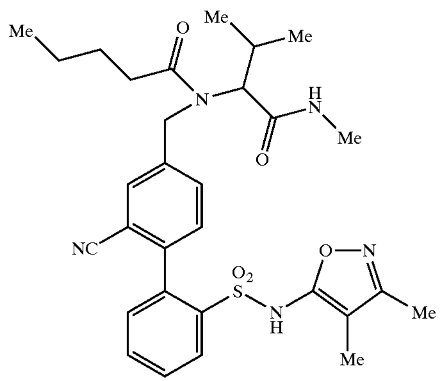 | N²-[[2'-[[(3,4-Dimethyl-5-isoxazolyl)amino]sulfonyl]-2-cyano [1,1'-biphenyl]-4-yl]methyl]-N-methyl-N²-(1-oxopentyl)-L-valinamide | P3 | 17 (58); 5, 6 (49); 10 (14) | 580 | >98 | 3.78 (C) |
| 147 | 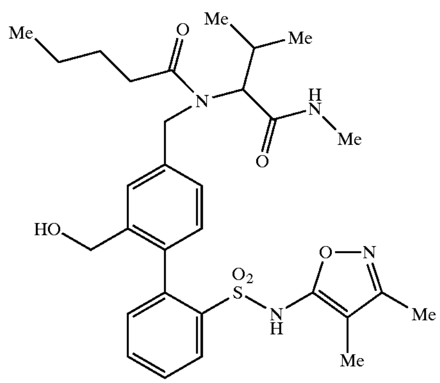 | N²-[[2'-[[(3,4-Dimethyl-5-isoxazolyl)amino]sulfonyl]-2-hydroxymethyl[1,1'-biphenyl]-4-yl]methyl]-N-methyl-N²-(1-oxopentyl)-L-valinamide | P1 | 5 (77); 6 (92); 10 (17) | 585 | 94 | 3.82, 3.90 (A) (two diastereomers) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 148 | 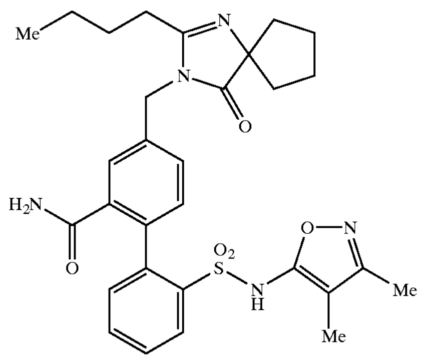 | 4-[(2-Butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-carboxamide | 108 | 12 (33) | 578 | 99 | 3.16 (A) |
| 149 | 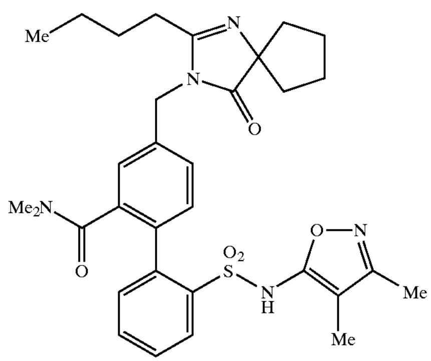 | N,N-Dimethyl-4-[(2-butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-carboxamide | 108 | 12 (61) | 606 | 99 | 3.22 (A) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 150 | 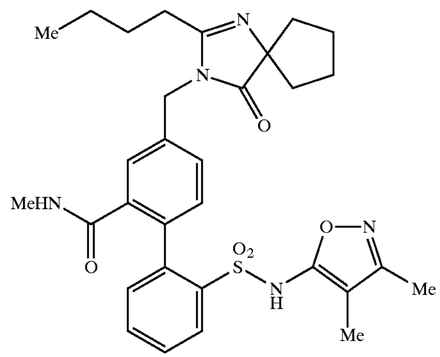 | N-Methyl-4-[[2-butyl-4-oxo-1,3-diazaspiro[4.4]non-1-en-3-yl)methyl]-2'-[[(3,4-dimethyl-5-isoxazolyl)amino]sulfonyl][1,1'-biphenyl]-2-carboxamide | 108 | 12 (93) | 592 | 99 | 3.17 (A) |
| 151 | 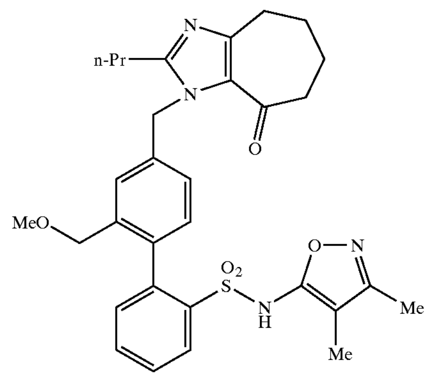 | N-(3,4-Dimethyl-5-isoxazolyl)-4-[(1,4,5,6,7,8-hexahydro-8-oxo-2-propyl-1-cycloheptimidazolyl)methyl]-2'-(methoxymethyl)[1,1'-biphenyl]-2-sulfonamide | P2 | 11 (87; 3 (38); 8 (42) | 577 | >98 | 11.58 (E) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 152 | 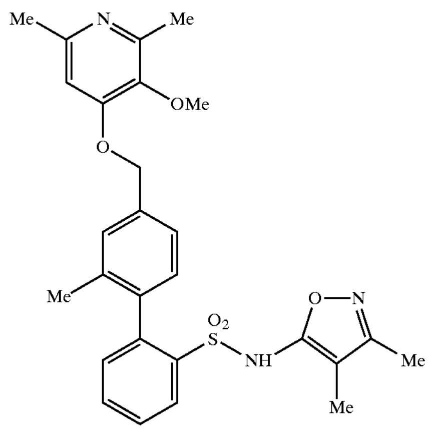 | N-(3,4-Dimethyl-5-isoxazolyl)-4'-[[(3-methoxy-2,6-dimethyl-4-pyridinyl)oxy]methyl]-2'-methyl[1,1'-biphenyl]-2-sulfonamide | P13 | 4 (20); 7 (27) | 508 | >98 | 22.83 (B) |
| 153 | 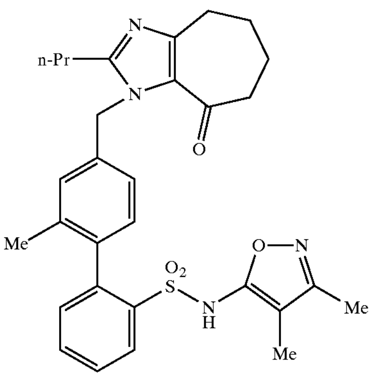 | N-(3,4-Dimethyl-5-isoxazolyl)-4'-[(1,4,5,6,7,8-hexahydro-8-oxo-2-propyl-1-cycloheptimidazolyl)methyl]-2'-methyl[1,1'-biphenyl]-2-sulfonamide | P13 | 21 (60); 7 (20) | 547 | >98 | 23.29 (B) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 154 | 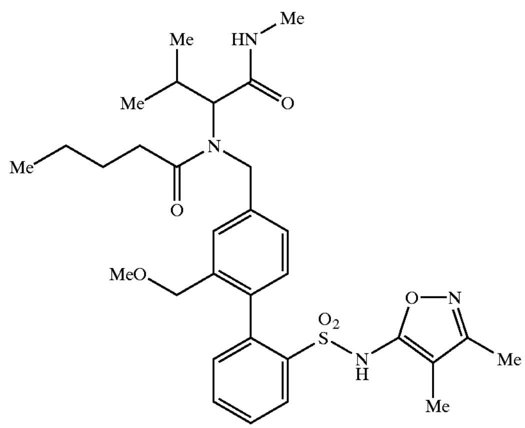 | $N^2$-[[2'-[[(3,4-Dimethyl-5-isoxazolyl)amino]sulfonyl]-2-(methoxymethyl)[1,1'-biphenyl]-4-yl]methyl]-N-methyl-$N^2$-(1-oxopentyl)-L-valinamide | P20 | 5 (90); 6 (90); 7 (42) | 599 | >98 | 12.71, 12.95 (F), migrates as diastereomers |
| 155 | 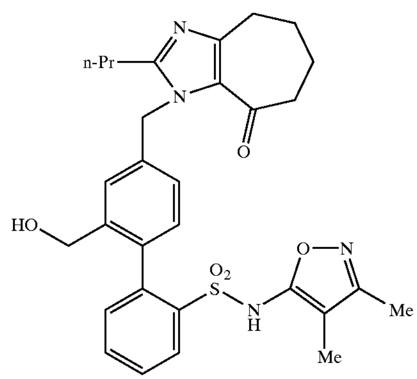 | N-(3,4-Dimethyl-5-isoxazolyl)-4'-[(1,4,5,6,7,8-hexahydro-8-oxo-2-propyl-1-cycloheptimidazolyl)methyl]-2'-(hydroxymethyl)[1,1'-biphenyl]-2-sulfonamide | P14 | 21 (29); 8, EtOH (32) | 563 | >98 | 2.99 (A) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 156 | 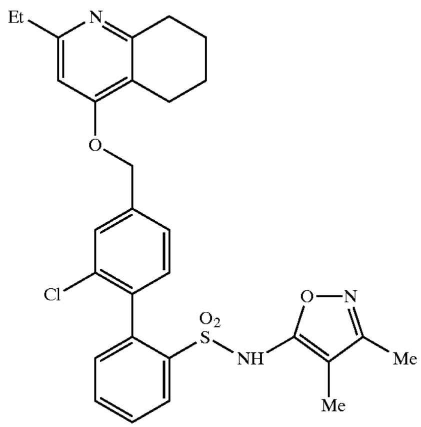 | 2'-Chloro-N-(3,4-dimethyl-5-isoxazolyl)-4'-[[(5,6,7,8-tetrahydro-2-ethyl-4-quinolinyl)oxy]methyl][1,1'-biphenyl]-2-sulfonamide | P10 | 4, 8 (33) | 553 | 97 | 1.69 (D) |
| 157 | 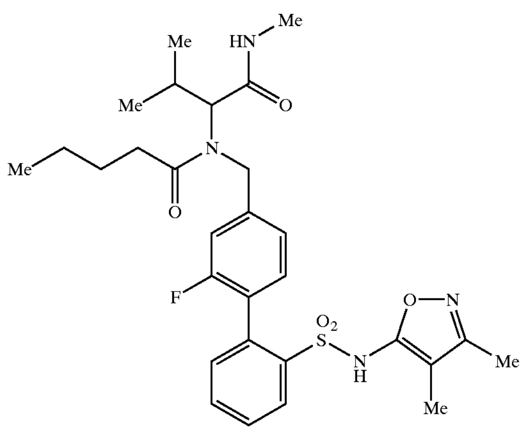 | $N^2$-[[2'-[[(3,4-Dimethyl-5-isoxazolyl)amino]sulfonyl]-2-fluoro[1,1'-biphenyl]-4-yl]methyl]-N-methyl-$N^2$-(1-oxopentyl)-L-valinamide | P8 | 5 (30); 6 (34); 7 (45) | 573 | >98 | 30.02 (B) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 158 | 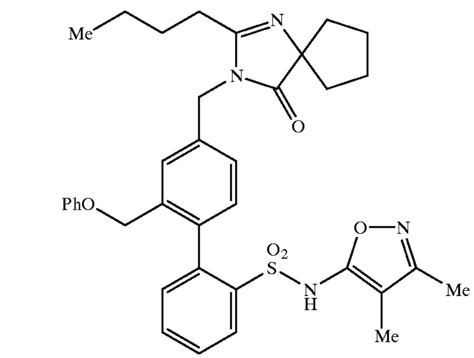 | 4'-[(2-Butyl-4-oxo-1,3-diazaspiro[4.4]non-1-en-3-yl)methyl]-N-(3,4-dimethyl-5-isoxazolyl)-2'-(phenoxymethyl)[1,1'-biphenyl]-2-sulfonamide | 42A | 3 (70); 22 (68); 7 (76) | 641 | 94 | 19.91 (I) |
| 159 | 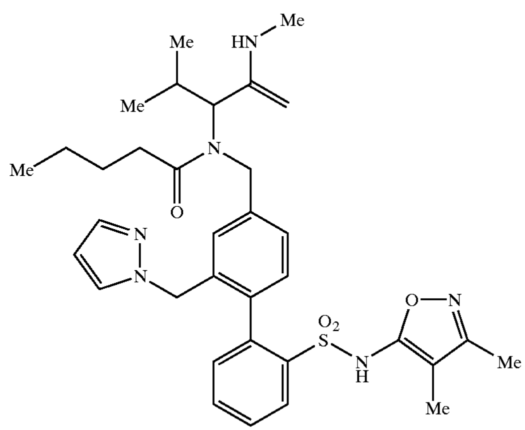 | $N^2$-[[2'-[[(3,4-Dimethyl-5-isoxazolyl)amino]sulfonyl]-2-(1H-ylmethyl)[1,1'-biphenyl]-4-yl]methyl]-N-methyl-$N^2$-(1-oxopentyl)-L-valinamide | P1 | 5 (77); 6 (92); 3 (99); 4 (69); 23 (18) | 635 | 95 | 4.08 (A) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 160 | 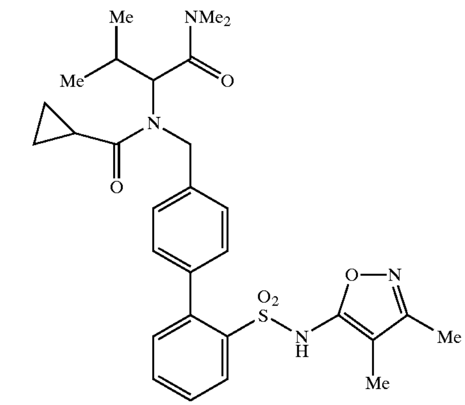 | N²-(Cyclopropylcarbonyl)-N²-[[2'-[[(3,4-dimethyl-5-isoxazolyl)amino]sulfonyl][1,1'-biphenyl]-4-yl]methyl]-N,N-dimethyl-L-valinamide | P16 | 5 (85); 6, 10 (28) | 553 | 88 | 2.58 (D) |
| 161 | 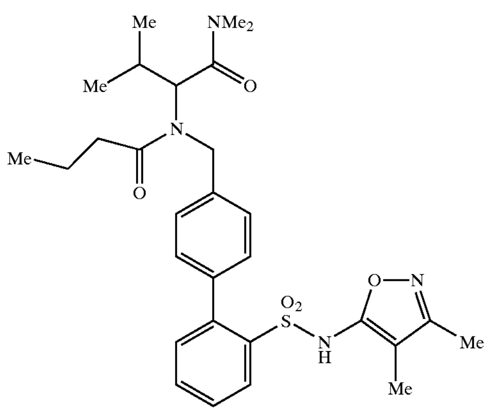 | N²-[[2'-[[(3,4-Dimethyl-5-isoxazolyl)amino]sulfonyl][1,1'-biphenyl]-4-yl]methyl]-N,N-dimethyl-N²-(1-oxobutyl)-L-valinamide | P16 | 5 (85); 6, 10 (33) | 555 | 93 | 2.82 (D) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 162 | 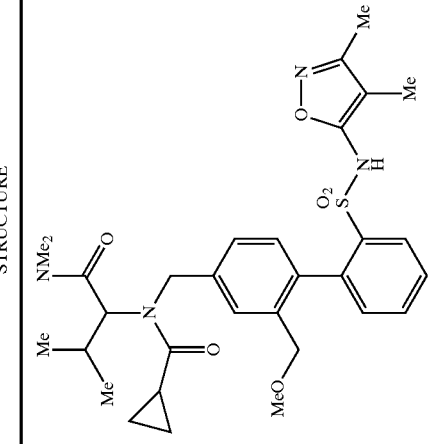 | N²-(Cyclopropylcarbonyl)-N²-[[2'-[[(3,4-dimethyl-5-isoxazolyl)amino]sulfonyl][1,1'-biphenyl]-4-yl]methyl]-2-(methoxymethyl)]-N,N-dimethyl-L-valinamide | P2 | 5 (50); 6, 8, EtOH (56) | 597 | >98 | 2.50, 2.63 (D) (migrates as diastereomers) |
| 163 | 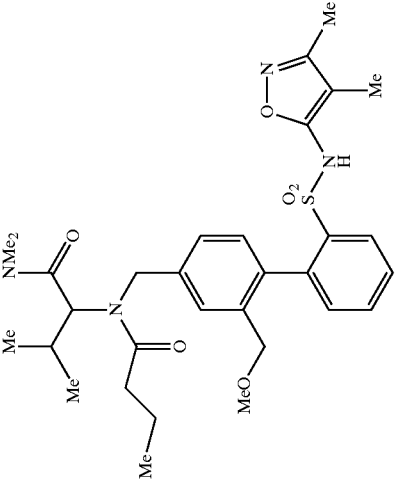 | N²-[[2'-[[(3,4-Dimethyl-5-isoxazolyl)amino]sulfonyl][1,1'-biphenyl]-4-yl]methyl]-2-(methoxymethyl)]-N,N-dimethyl-N²-(1-oxobutyl)-L-valinamide | P2 | 5 (50); 6, 8 EtOH (59) | 599 | 96 | 2.92, 3.02 (D) (migrates as diastereomers) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 164 | 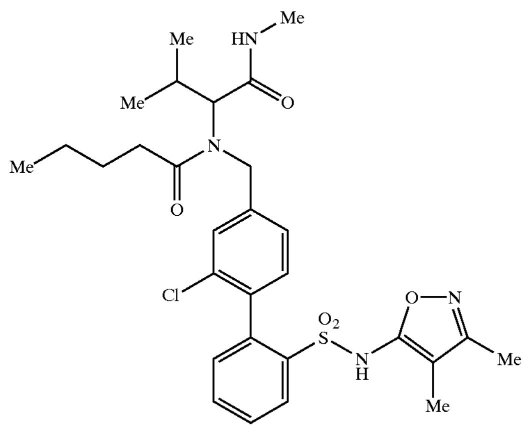 | N²-[[2-Chloro-2'-[[(3,4-dimethyl-5-isoxazolyl)amino]sulfonyl][1,1'-biphenyl]-4-yl]methyl]-N²-(1-oxopentyl)-L-valinamide | P5 | 5 (69); 6, 10 (50) | 590 | 96 | 3.03 (D) |
| 165 | 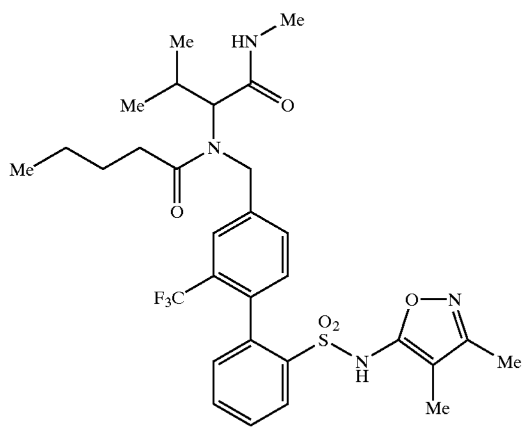 | N²-[[2'-[[(3,4-Dimethyl-5-isoxazolyl)amino]sulfonyl]]-2-(trifluoromethyl)[1,1'-biphenyl]-4-yl]methyl]-N²-(1-oxopentyl)-L-valinamide | P6 | 5 (80); 6, 10 (83) | 623 | 95 | 2.93, 3.05 (D) (migrates as diastereomers) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 166 | 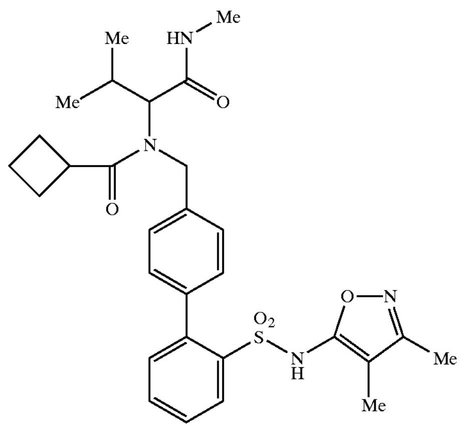 | N²-(Cyclobutylcarbonyl)-N²-[[2'-[[(3,4-dimethyl-5-isoxazolyl)amino]sulfonyl][1,1'-biphenyl]-4-yl]methyl]-N-methyl-L-valinamide | P16 | 5 (85); 6, 10 (35) | 553 | 98 | 2.82 (D) |
| 167 | 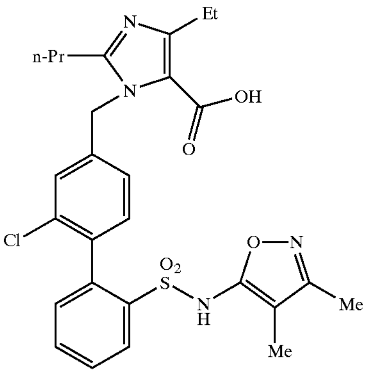 | 1-[[2-Chloro-2'-[[(3,4-dimethyl-5-isoxazolyl)amino]sulfonyl][1,1'-biphenyl]-4-yl]methyl]-4-ethyl-2-propyl-1H-imidazole-5-carboxylic acid | P10 | 22 (60); 8, EtOH (90); 15 (99) | 558 | >98 | 3.04 (A) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 168 | 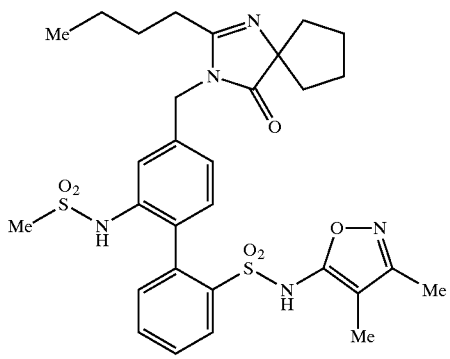 | 4'-[(2-Butyl-4-oxo-1,3-diazaspiro[4.4]non-1-en-3-yl)methyl]-N-(3,4-dimethyl-5-isoxazolyl)-2'-[(methylsulfonyl)amino][1,1'-biphenyl]-2-sulfonamide | 122 | 24 (25) | 628 | >98 | 11.48 (E) |
| 169 | 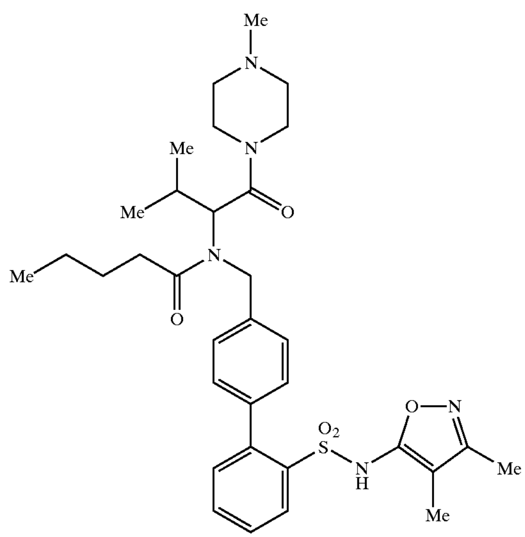 | (S)-N-[[2'-[[(3,4-Dimethyl-5-isoxazolyl)amino]sulfonyl][1,1'-biphenyl]-4-yl]methyl]-N-[2-methyl-1-[(4-methyl-1-piperazinyl)carbonyl]propyl]pentanamide | 101 | 12 (43) | 624 | >98 | 28.26 (B) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 170 | 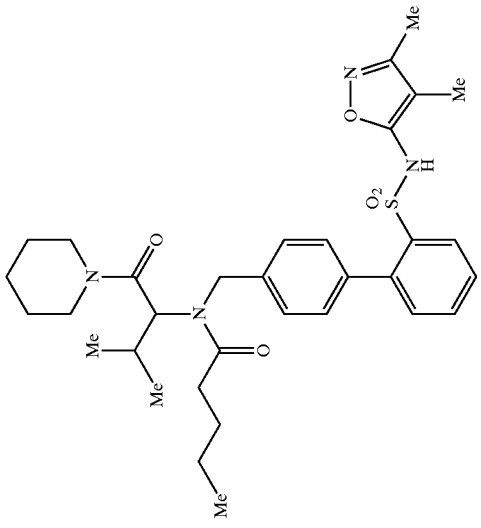 | (S)-N-[[2'-[[(3,4-Dimethyl-5-isoxazolyl)amino]sulfonyl][1,1'-biphenyl]-4-yl]methyl]-N-(1-piperidinyl)carbonyl]propyl]pentanamide | 101 | 12 (30) | 609 | >98 | 34.45 (B) |
| 171 | 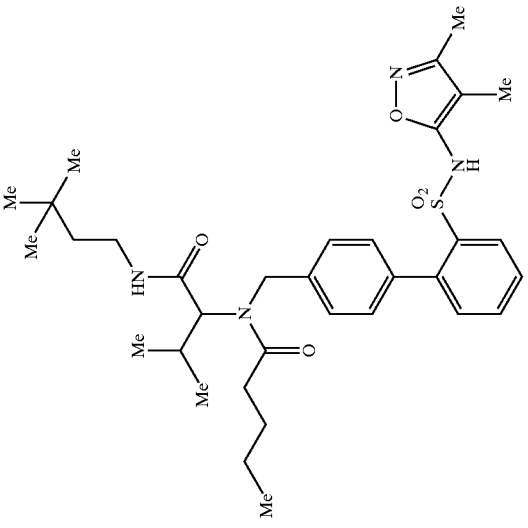 | N-(3,3-Dimethylbutyl)-N²-[[2'-[[(3,4-dimethyl-5-isoxazolyl)amino]sulfonyl][1,1'-biphenyl]-N²-(1-oxopentyl)-L-valinamide | 101 | 12 (38) | 625 | >98 | 33.97 (B) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 172 | 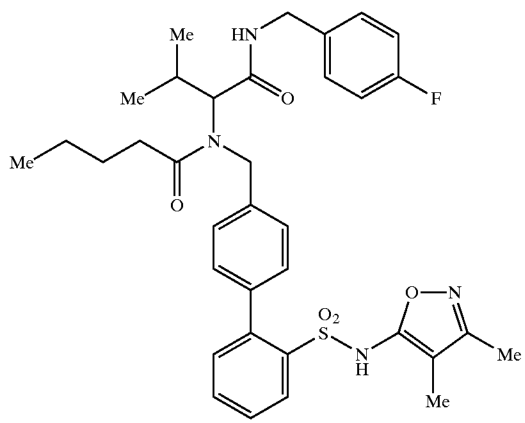 | $N^2$-[[2'-[[(3,4-Dimethyl-5-isoxazolyl)amino]sulfonyl][1,1'-biphenyl]-4-yl]methyl]-N-[(4-fluorophenyl)methyl]-$N^2$-(1-oxopentyl)-L-valinamide | 101 | 12 (38) | 649 | >98 | 32.90 (B) |
| 173 | 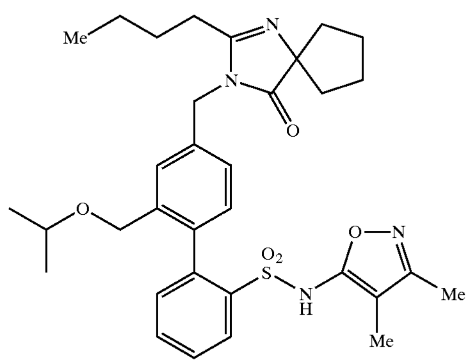 | $N'$-[(2-Butyl-4-oxo-1,3-diazaspiro[4.4]non-1-en-3-yl)methyl]-N-(3,4-dimethyl-5-isoxazolyl)-2'-[(methylethoxy)methyl][1,1'-biphenyl]-2-sulfonamide | 42A | 2 (67); 4 (51); 7 (62) | 607 | 97 | 13.59 (E) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 174 | 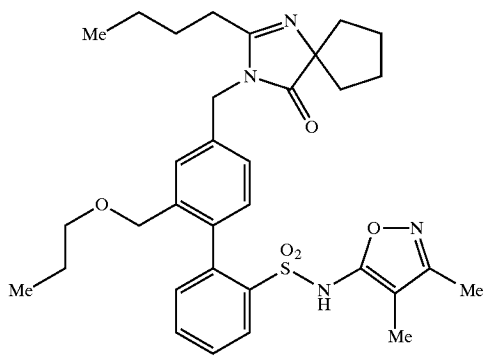 | 4'-[(2-Butyl-4-oxo-1,3-diazaspiro[4.4]non-1-en-3-yl)methyl]-N-(3,4-dimethyl-5-isoxazolyl)-2'-(propoxymethyl)[1,1'-biphenyl]-2-sulfonamide | 42A | 2 (67); 4 (49); 7 (68) | 607 | >97 | 20.61 (E) |
| 175 | 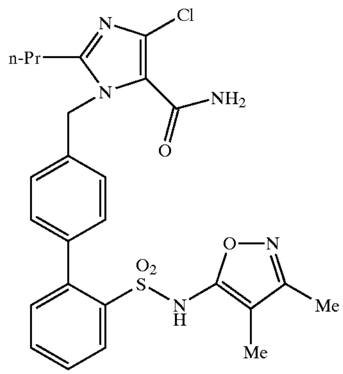 | 4-Chloro-1-[[2'-[[(3,4-dimethyl-5-isoxazolyl)amino]sulfonyl][1,1'-biphenyl]-4-yl]methyl]-2-propyl-1H-imidazole-5-carboxamide | P19 | 22 (87); 25 (47); 8, H$_2$O (99); 12 (35) | 529 | >98 | 3.69 (A) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 176 | 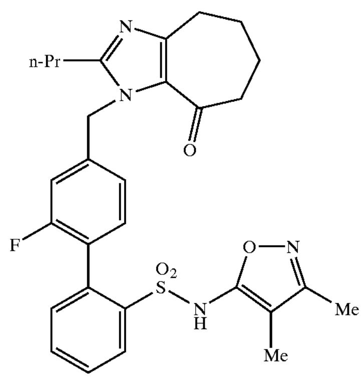 | N-(3,4-Dimethyl-5-isoxazolyl)-2'-fluoro-4'-[(1,4,5,6,7,8-hexahydro-8-oxo-2-propyl-1-cycloheptimidazolyl)methyl][1,1'-biphenyl]-2-sulfonamide | P8 | 21 (15); 7 (16) | 551 | >98 | 5.78 (J) |
| 177 | 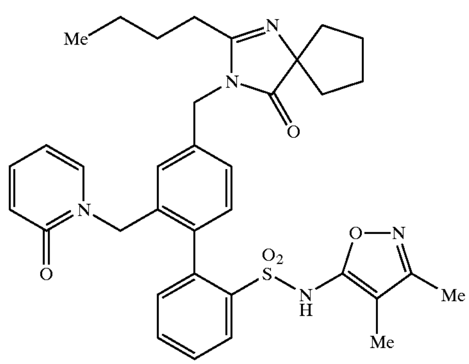 | 4'-[(2-Butyl-4-oxo-1,3-diazaspiro[4.4]non-1-en-3-yl)methyl]-2'-[(1,2-dihydro-2-oxo-1-pyridinyl)methyl]-N-(3,4-dimethyl-5-isoxazolyl)[1,1'-biphenyl]-2-sulfonamide | 42A | 2 (67); 4 (72); 7 (21) | 642 | >97 | 13.59 (E) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 178 | 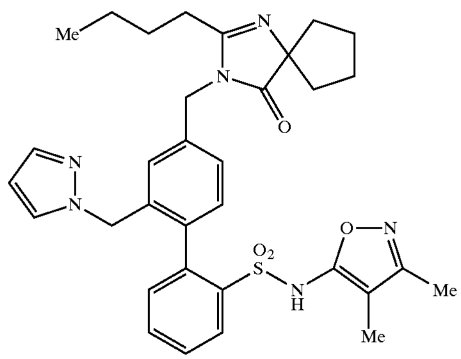 | 4'-[(2-Butyl-4-oxo-1,3-diazaspiro[4.4]non-1-en-3-yl)methyl]-N-(3,4-dimethyl-5-isoxazolyl)-2'-(1H-pyrazol-1-ylmethyl)[1,1'-biphenyl]-2-sulfonamide | P1 | 3 (98); 4, 11 (35); 3, 4, 7 (13) | 615 | 97 | 3.42 (A) |
| 179 | 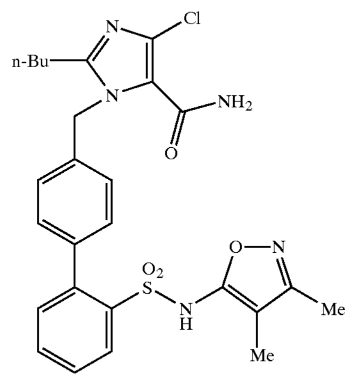 | 2-Butyl-4-chloro-1-[[2'-[[(3,4-dimethyl-5-isoxazolyl)amino]sulfonyl][1,1'-biphenyl]-4-yl]methyl]-1H-imidazole-5-carboxamide | P19 | 22 (43); 25; 8, H₂O; 12 (19) | 543 | 94 | 3.82 (A) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 180 | 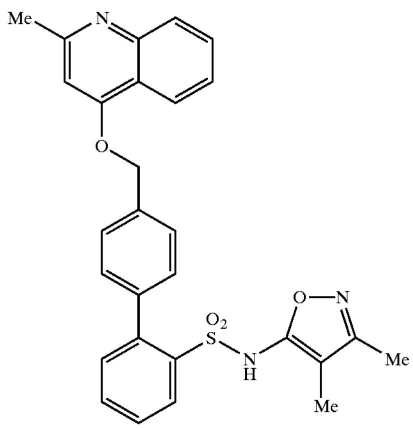 | N-(3,4-Dimethyl-5-isoxazolyl)-4'-[[(2-methyl-4-quinolinyl)oxy]methyl]-[1,1'-biphenyl]-2-sulfonamide | P18 | 4 (79); 8, EtOH (26) | 500 | 98 | 22.4 (B) |
| 181 | 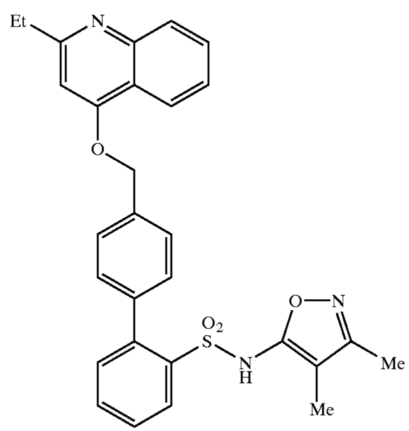 | N-(3,4-Dimethyl-5-isoxazolyl)-4'-[[(2-ethyl-4-quinolinyl)oxy]methyl]-[1,1'-biphenyl]-2-sulfonamide | P18 | 4 (49); 8, EtOH (30) | 514 | 93 | 23.25 (B) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 182 | 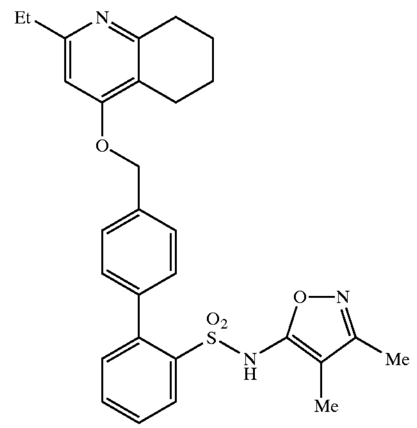 | N-(3,4-Dimethyl-5-isoxazolyl)-4'-[[(2-ethyl-5,6,7,8-tetrahydro-4-quinolinyl)osy]methyl][1,1'-biphenyl]-2-sulfonamide | P18 | 4 (79); 8, EtOH (3) | 518 | 93 | 3.49 (A) |
| 183 | 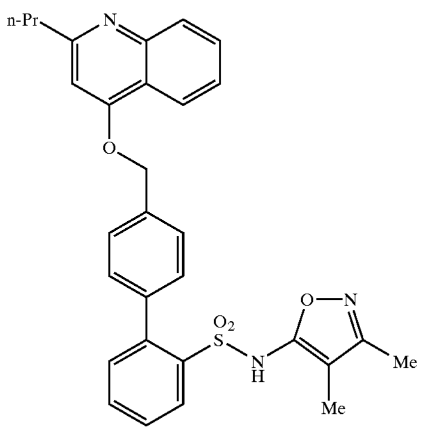 | N-(3,4-Dimethyl-5-isoxazolyl)-4'-[[(2-propyl-4-quinolinyl)oxy]methyl][1,1'-biphenyl]-2-sulfonamide | P18 | 4 (47); 8, EtOH (20) | 528 | 97 | 3.50 (A) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 184 | 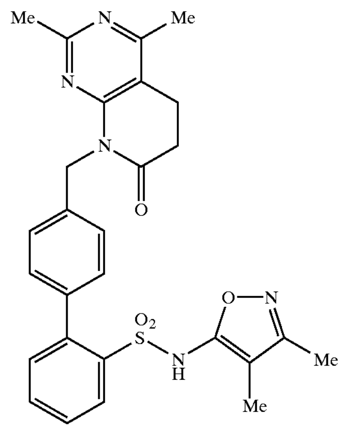 | N-(3,4-Dimethyl-5-isoxazolyl)-4'-[(5,6,7,8-tetrahydro-2,4-dimethyl-7-oxopyrido[2,3-d]pyrimidin-8-yl)methyl][1,1'-biphenyl]-2-sulfonamide | P18 | 4 (79) 8, EtOH (20) | 518 | >98 | 3.05 (A) |
| 185 | 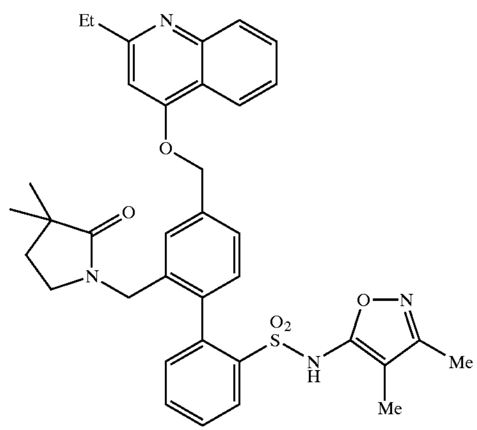 | 4'-[[(2-Ethyl-4-quinolinyl)oxy]methyl]-N-(3,4-dimethyl-5-isoxazolyl)-2'-[(3,3-dimethyl-2-oxo-1-pyrrolidinyl)methyl][1,1'-biphenyl]-2-sulfonamide | P18 | 4 (20); 8, EtOH (33) | 639 | 93 | 3.43 (A) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 186 | 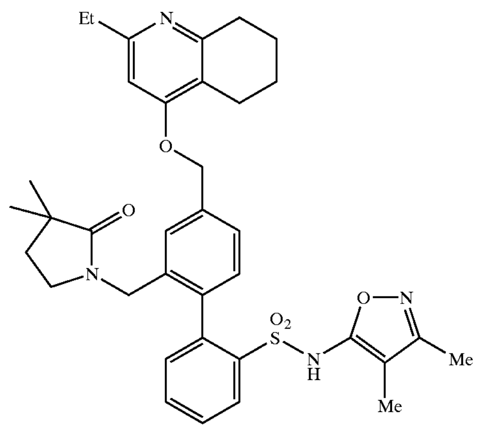 | N-(3,4-Dimethyl-5-isoxazolyl)-2'-[[(3,3-dimethyl-2-oxo-1-pyrrolidinyl)methyl]-4'-[[(5,6,7,8-tetrahydro-2-ethyl-4-quinolinyl)oxy]methyl][1,1'-biphenyl]-2-sulfonamide | P18 | 4 (63); 8, EtOH (8) | 643 | 92 | 3.79 (C) |
| 187 | 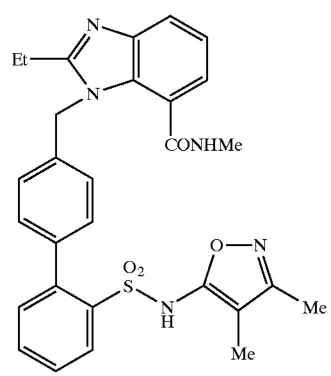 | 3-[[2'-[[[(3,4-Dimethyl-5-isoxazolyl)amino]sulfonyl][1,1'-biphenyl]-4-yl]methyl]-2-ethyl-N-methyl-3H-benzimidazole-4-carboxamide | 31 | 12 (12) | 544 | 92 | 2.80 (A) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 188 | 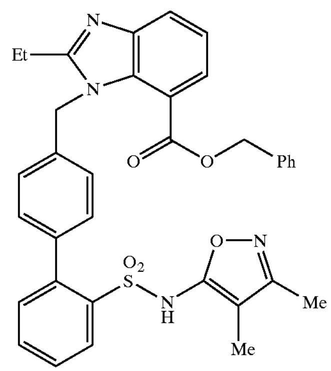 | 1-[[2'-[[(3,4-Dimethyl-5-isoxazolyl)amino]sulfonyl][1,1'-biphenyl]-4-yl]methyl]-2-ethyl-1H-benzimidazole-7-carboxylic acid phenylmethyl ester | 31 | 20 (55) | 621 | 96 | 3.95 (C) |
| 189 | 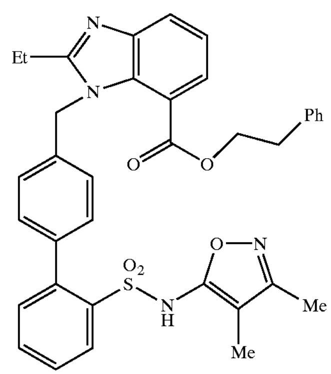 | 1-[[2'-[[(3,4-Dimethyl-5-isoxazolyl)amino]sulfonyl][1,1'-biphenyl]-4-yl]methyl]-2-ethyl-1H-benzimidazole-7-carboxylic acid 2-phenylethyl ester | 31 | 20 (12) | 635 | >98 | 4.03 (C) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 190 | 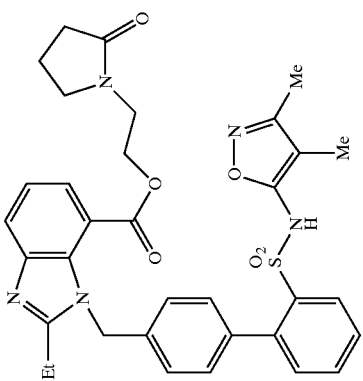 | 1-[[2'-[[(3,4-Dimethyl-5-isoxazolyl)amino]sulfonyl][1,1'-biphenyl]-4-yl]methyl]-2-ethyl-1H-benzimidazole-7-carboxylic acid 2-(2-oxo-1-pyrrolidinyl)ethyl ester | 31 | 20 (45) | 642 | >98 | 3.15 (C) |
| 191 | 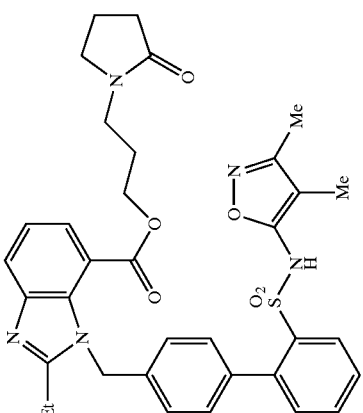 | 1-[[2'-[[(3,4-Dimethyl-5-isoxazolyl)amino]sulfonyl][1,1'-biphenyl]-4-yl]methyl]-2-ethyl-1H-benzimidazole-7-carboxylic acid 3-(2-oxo-1-pyrrolidinyl)propyl ester | 31 | 20 (30) | 656 | >98 | 3.21 (C) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 192 | 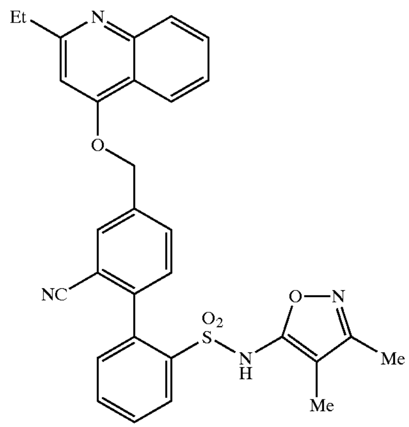 | 2'-Cyano-N-(3,4-dimethyl-5-isoxazolyl)-4'-[[(2-ethyl-4-quinolinyl)oxy]methyl][1,1'-biphenyl]-2-sulfonamide | P3 | 3, 4 (59); 10 (60) | 539 | >98 | 3.01 (C) |
| 193 | 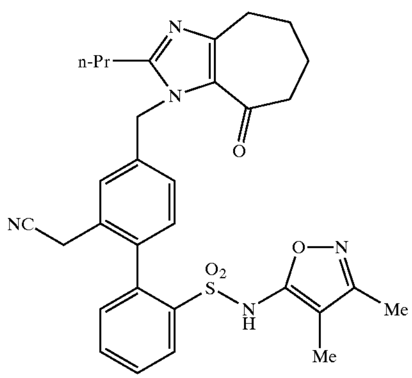 | 2'-(Cyanomethyl)-N-(3,4-dimethyl-5-isoxazolyl)-4'-[(1,4,5,6,7,8-hexahydro-8-oxo-2-propyl-1-cycloheptimidazolyl)methyl][1,1'-biphenyl]-2-sulfonamide | P12 | 16, 3 (73); 21 (46); 8, EtOH (16) | 572 | 96 | 2.95 (A) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 194 | 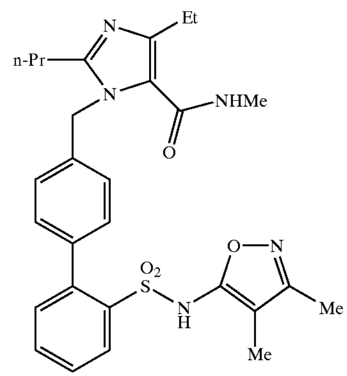 | 3-[[2'-[[(3,4-Dimethyl-5-isoxazolyl)amino]sulfonyl][1,1'-biphenyl]-4-yl]methyl]-5-ethyl-N-methyl-2-propyl-3H-imidazole-4-carboxamide | 40B | 12, MeNH$_2$ (12) | 536 | >98 | 2.88 (C) |
| 195 | 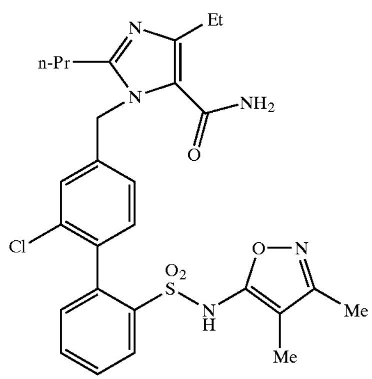 | 1-[[2'-Chloro-2'-[[(3,4-dimethyl-5-isoxazolyl)amino]sulfonyl][1,1'-biphenyl]-4-yl]methyl]-4-ethyl-2-propyl-1H-imidazole-5-carboxamide | 167 | 12, NH$_3$ (17) | 557 | >98 | 3.08 (A) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 196 | 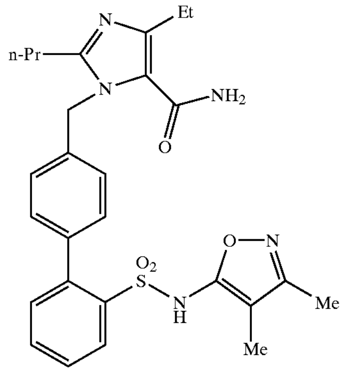 | 3-[[2'-[[(3,4-Dimethyl-5-isoxazolyl)amino]sulfonyl][1,1'-biphenyl]-4-yl]methyl]-5-ethyl-2-propyl-3H-imidazole-4-carboxamide | 40B | 12, $NH_3$ (16) | 522 | >98 | 2.79 (C) |
| 197 | 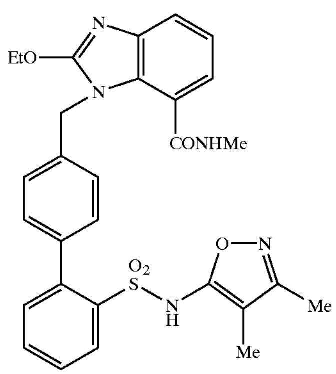 | 3-[[2'-[[(3,4-Dimethyl-5-isoxazolyl)amino]sulfonyl][1,1'-biphenyl]-4-yl]methyl]-2-ethoxy-N-methyl-3H-benzimidazole-4-carboxamide | 29 | 12, $MeNH_2$ (32) | 560 | >98 | 3.31 (A) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 198 | 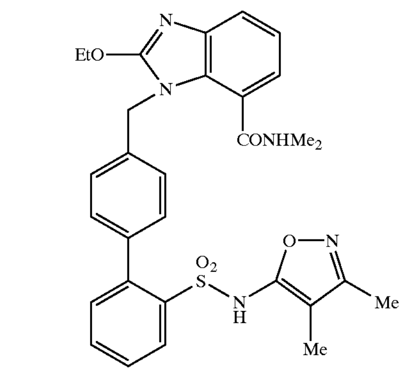 | 3-[[2'-[[(3,4-Dimethyl-5-isoxazolyl)amino]sulfonyl][1,1'-biphenyl]-4-yl]methyl]-2-ethoxy-N,N-dimethyl-3H-benzimidazole-4-carboxamide | 29 | 12, Me₂NH (5) | 574 | >98 | 3.42 (A) |
| 199 | 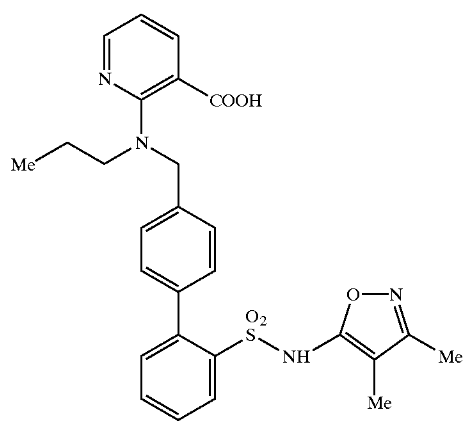 | 2-[[[2'-[[(3,4-Dimethyl-5-isoxazolyl)amino]sulfonyl][1,1'-biphenyl]-4-yl]methyl]propylamino]-3-pyridinecarboxylic acid | P18 | 4, 15, 7 (34) | 521 | 99 | 23.4 (B) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 200 | 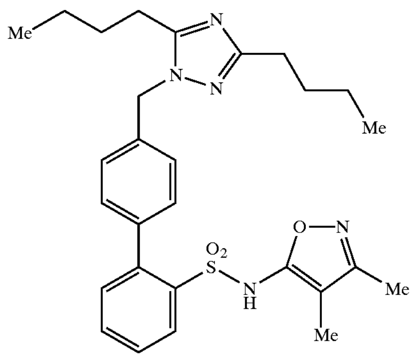 | 4'-[(3,5-Dibutyl-1H-1,2,4-triazol-1-yl)methyl]-N-(3,4-dimethyl-5-isoxazolyl)[1,1'-biphenyl]-2-sulfonamide | P18 | 4, 7 (77) | 522 | 99 | 28.4 (B) |
| 201 | 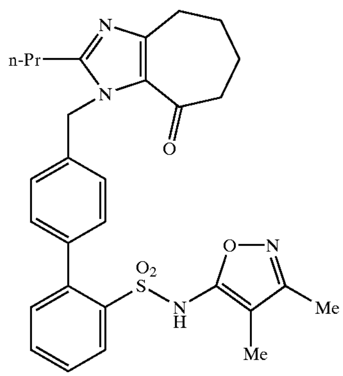 | N-(3,4-Dimethyl-5-isoxazolyl)-4'-[(1,4,5,6,7,8-hexahydro-8-oxo-2-propyl-1-cycloheptimidazolyl)methyl][1,1'-biphenyl]-2-sulfonamide | P18 | 21, 7 (55) | 533 | 99 | 21.5 (B) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 202 | 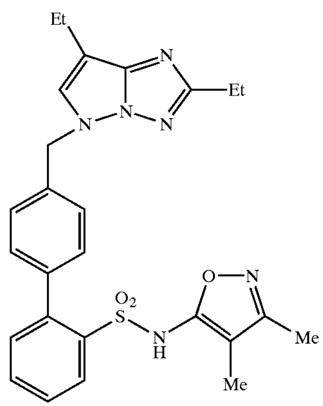 | 4'-[(2,7-Diethyl-5H-pyrazolo[1,5-b][1,2,4]triazol-5-yl)methyl]-N-(3,4-dimethyl-5-isoxazolyl)[1,1'-biphenyl]-2-sulfonamide | P18 | 4, 7 (33) | 505 | 99 | 21.8 (B) |
| 203 | 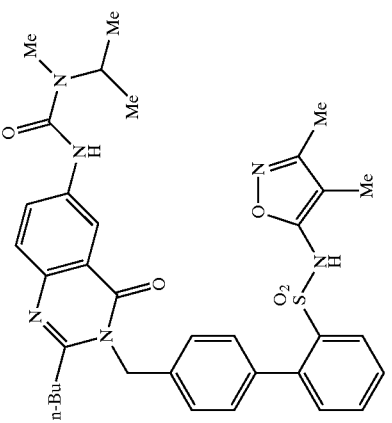 | N-[2-Butyl-3-[[2'-[[(3,4-dimethyl-5-isoxazolyl)amino]sulfonyl][1,1'-biphenyl]-4-yl]methyl]-3,4-dihydro-4-oxo-6-quinazolinyl]-N'-methyl-N'-(1-methylethyl)urea | P18 | 4, 7 (71) | 657 | 99 | 28.7 (B) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 204 | 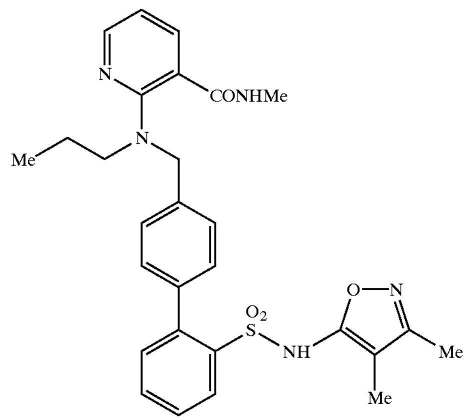 | 2'-[[2'-[[(3,4-Dimethyl-5-isoxazolyl)amino]sulfonyl][1,1'-biphenyl]-4-yl]methyl]propylamino]-N-methyl-3-pyridinecarboxamide | 199 | 12 (98) | 534 | 99 | 23.8 (B) |
| 205 | 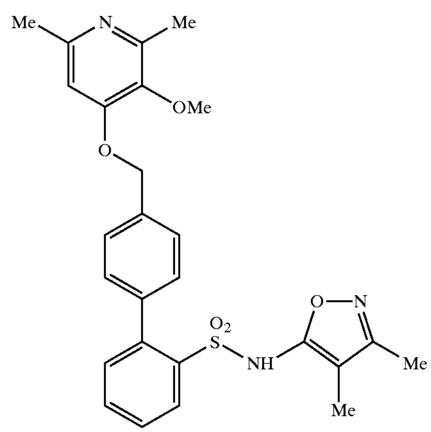 | 4'-[[(3-Methoxy-2,6-dimethyl-4-pyridinyl)oxy]methyl]-N-(3,4-dimethyl-5-isoxazolyl)[1,1'-biphenyl]-2-sulfonamide | P18 | 4 (59); 8 (74) | 494 | 98 | 6.99 (I) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 206 | 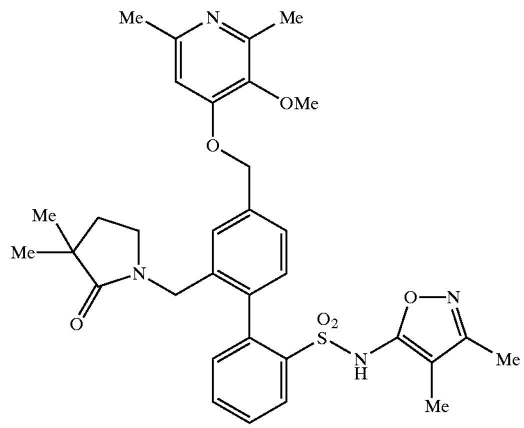 | N-(3,4-Dimethyl-5-isoxazolyl)-2'-[(3,3-dimethyl-2-oxo-1-pyrrolidinyl)methyl]-4'-[[(3-methoxy-2,6-dimethyl-4-pyridinyl)oxy]methyl][1,1'-biphenyl]-2-sulfonamide | 20A | 2 (82); 4 (82); 8 (31) | 619 | 96 | 14.02 (E) |
| 207 | 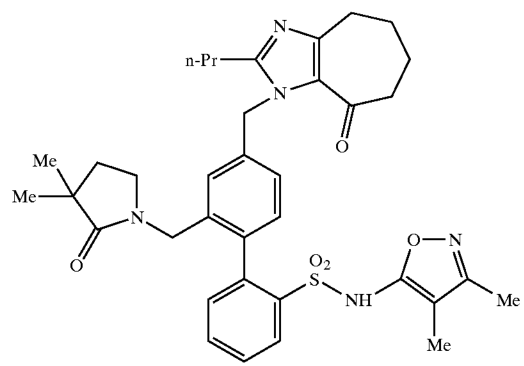 | N-(3,4-Dimethyl-5-isoxazolyl)-2'-[(3,3-dimethyl-2-oxo-1-pyrrolidinyl)methyl]-4'-[(1,4,5,6,7,8-hexahydro-8-oxo-2-propyl-1-cycloheptimidazolyl)methyl][1,1'-biphenyl]-2-sulfonamide | 20A | 2 (82); 21, 9 (54) | 658 | 97 | 15.56 (E) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 208 | 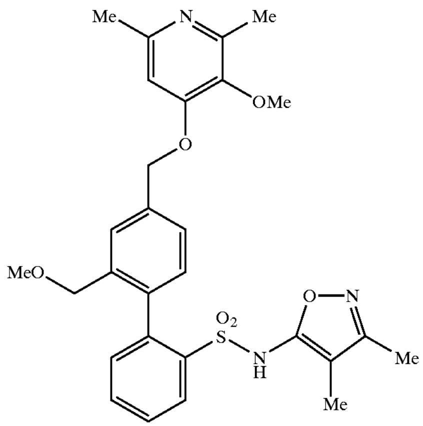 | N-(3,4-Dimethyl-5-isoxazolyl)-4'-[[(3-methoxy-2,6-dimethyl-4-pyridinyl)oxy]methyl]-2'-(methoxymethyl)[1,1'-biphenyl]-2-sulfonamide | P2 | 4 (45); 8 (63) | 538 | 99 | 10.60 (E) |
| 209 | 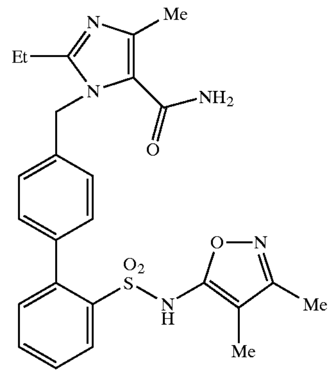 | 3-[[2'-[[(3,4-Dimethyl-5-isoxazolyl)amino]sulfonyl][1,1'-biphenyl]-4-yl]methyl]-2-ethyl-5-methyl-3H-imidazole-4-carboxamide | P19 | 22 (35); 7 (67) | 494 | >97 | 7.96 (E) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 210 | 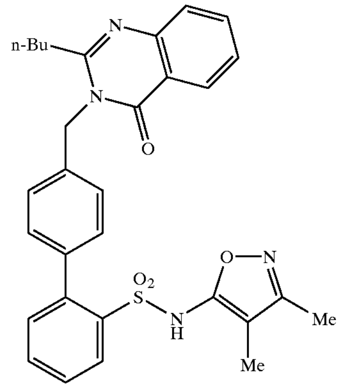 | 4'-[(2-Butyl-3,4-dihydro-4-oxo-3-quinazolinyl)methyl]-N-(3,4-dimethyl-5-isoxazolyl)[1,1'-biphenyl]-2-sulfonamide | P18 | 4, 7 (13) | 543 | 98 | 25.52 (I) |
| 211 | 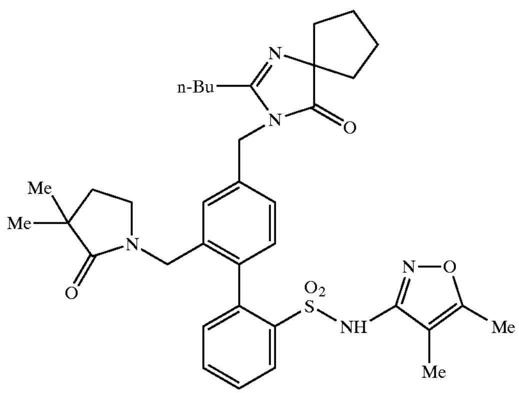 | 4'-[(2-Butyl-4-oxo-1,3-diazaspiro[4.4]non-1-en-3-yl)methyl]-N-(4,5-dimethyl-3-isoxazolyl)-2'-[(3,3-dimethyl-2-oxo-1-pyrrolidinyl)methyl][1,1'-biphenyl]-2-sulfonamide | 17 | 5 (36) | 660 | 98 | 14.51 (I) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 212 | 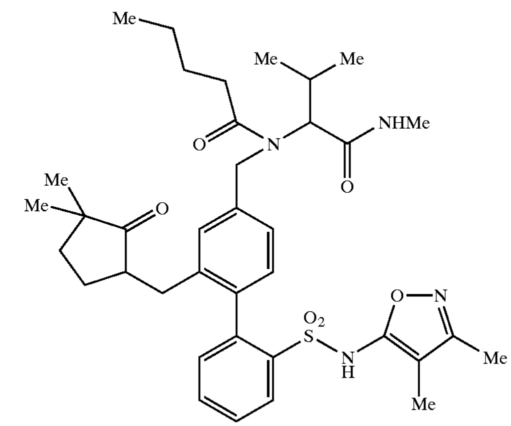 | N²-[[2'-[[(3,4-Dimethyl-5-isoxazolyl)amino]sulfonyl]-2-[(3,3-dimethyl-2-oxo-1-pyrrolidinyl)methyl][1,1'-biphenyl]-4-yl]methyl]-N-methyl-N²-(1-oxopentyl)-L-valinamide | 20A | 17 (80); 5 (95); 6 (95); 7 (42) | 680 | 97 | 13.13, 14.66 (F) migrates as diastereomers |
| 213 | 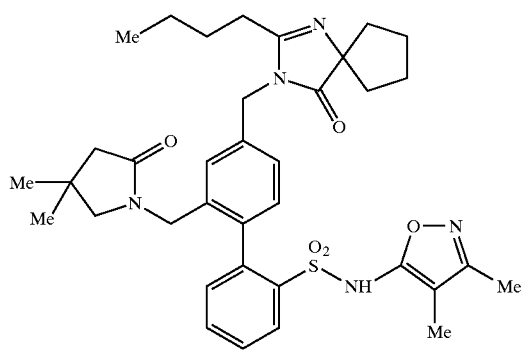 | 4'-[(2-Butyl-4-oxo-1,3-diazaspiro[4.4]non-1-en-3-yl)methyl]-N-(3,4-dimethyl-5-isoxazolyl)-2'-[(4,4-dimethyl-2-oxo-1-pyrrolidinyl)methyl][1,1'-biphenyl]-2-sulfonamide | 3 | 5 (58) | 660 | >98 | 24.60 (B) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 214 | 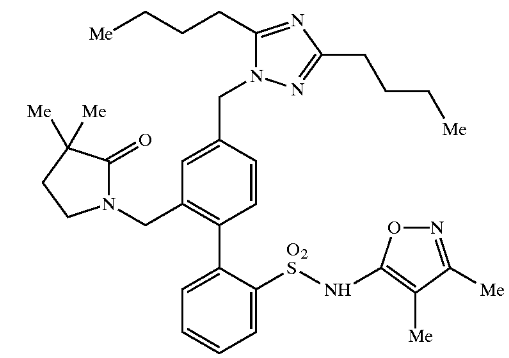 | 4'-[(3,5-Dibutyl-1H-1,2,4-triazol-1-yl)methyl]-N-(3,4-dimethyl-5-isoxazolyl)-2'-[(3,3-dimethyl-2-oxo-1-pyrrolidinyl)methyl][1,1'-biphenyl]-2-sulfonamide | 20A | 4 (52); 9 (57) | 647 | 97 | 23.53 (I) |
| 215 | 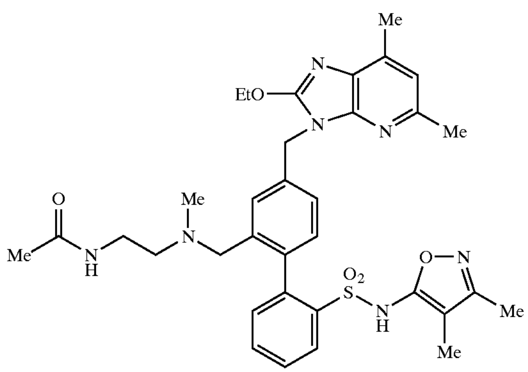 | N-[2-[[[2'-[[(3,4-Dimethyl-5-isoxazolyl)amino]sulfonyl]-4-[(2-ethyl-5,7-dimethyl-3H-imidazo[4,5-b]pyridin-3-yl)methyl][1,1'-biphenyl]-2-yl]methyl]methylamino]ethyl]acetamide | 23B | 5, 12 (4); 8 (15) | 644 | 89 | 2.69 (A) |

| EXAMPLE | NAME | STRUCTURE | STARTING MATERIAL | General Methods Applied (yield, %) | M/z (MH)+ | HPLC % Purity | HPLC ret time, min (method) |
|---|---|---|---|---|---|---|---|
| 216 | 4-[(2-Ethyl-5,7-dimethyl-3H-imidazo[4,5-b]pyridin-3-yl)methyl]-2'-[[(3,4-dimethyl-5-isoxazolyl)amino]sulfonyl]-[1,1'-biphenyl]-2-acetic acid ethyl ester | 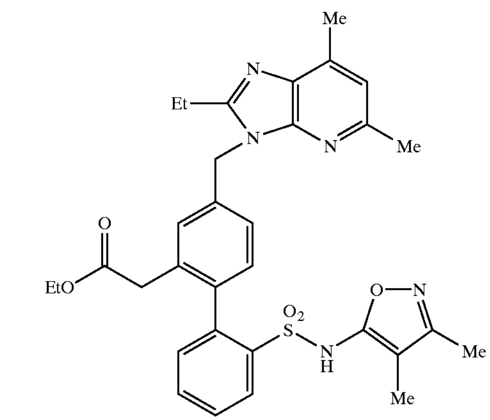 | 113 | 8, EtOH (13) | 602 | 90 | 3.41 (A) |
| 217 | N²-[[2'-[[(3,4-Dimethyl-5-isoxazolyl)amino]sulfonyl][1,1'-biphenyl]-4-yl]methyl]-N²-(1-oxopentyl)-N-propyl-L-valinamide | 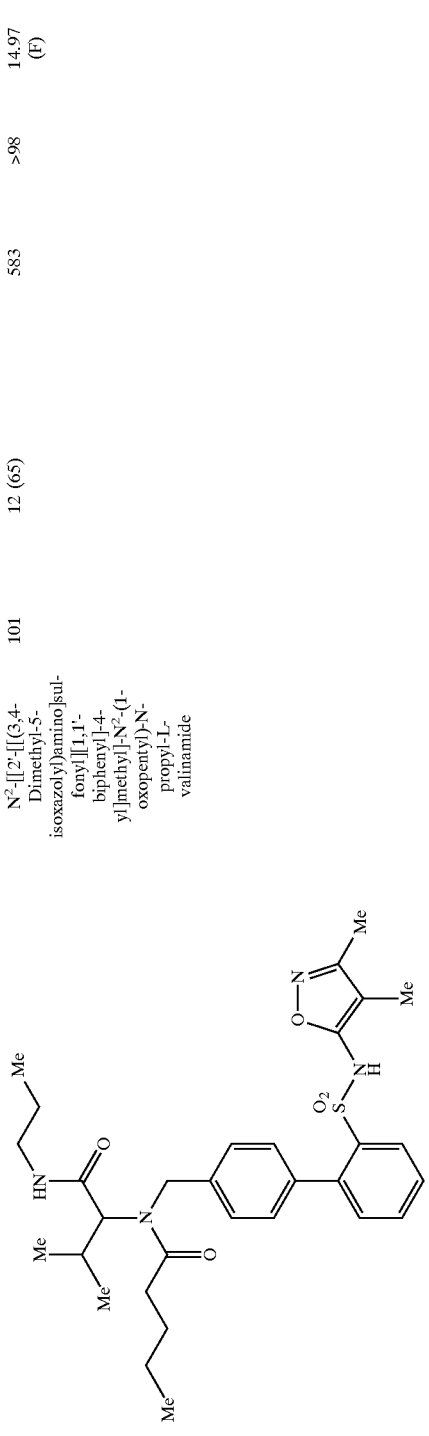 | 101 | 12 (65) | 583 | >98 | 14.97 (F) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 218 | 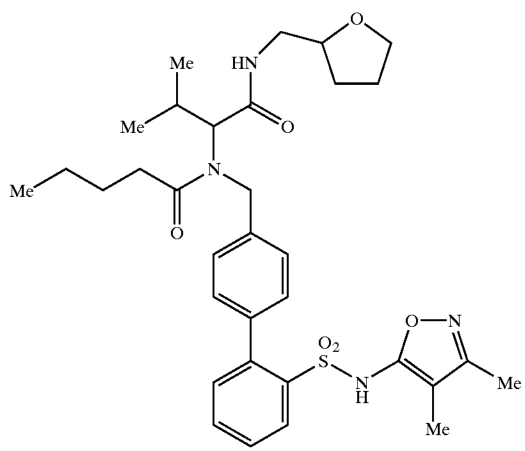 | $N^2$-[[2'-[[(3,4-Dimethyl-5-isoxazolyl)amino]sulfonyl][1,1'-biphenyl]-4-yl]methyl]-$N^2$-(1-oxopentyl)-N-[(tetrahydro-2-furanyl)methyl]-L-valinamide | 101 | 12 (43) | 625 | >98 | 14.06 (F) |
| 219 | 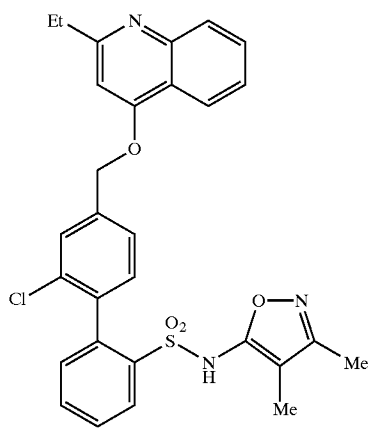 | 2'-Chloro-N-(3,4-dimethyl-5-isoxazolyl)-4'-[[(2-ethyl-4-quinolinyl)oxy]methyl][1,1'-biphenyl]-2-sulfonamide | P10 | 4 (90); 8 (65) | 549 | 98 | 1.68 (D) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 220 | 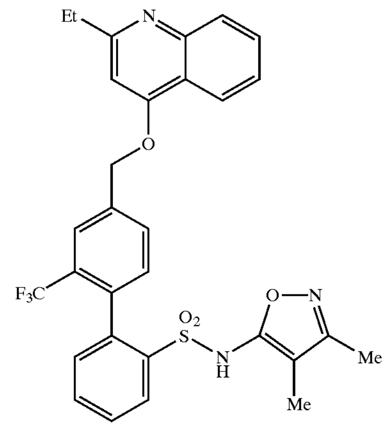 | N-(3,4-Dimethyl-5-isoxazolyl)-4'-[[(2-ethyl-4-quinolinyl)oxy]methyl]-2'-(trifluoromethyl)[1,1'-biphenyl]-2-sulfonamide | P9 | 4, 8 (30) | 582 | 97 | 1.75 (D) |
| 221 | 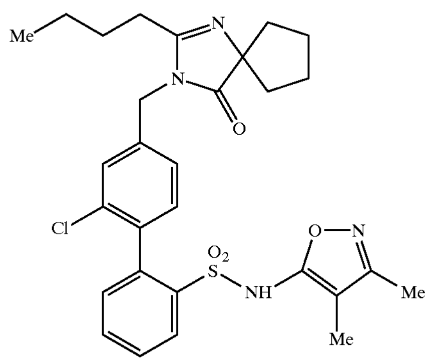 | 4'-[(2-Butyl-4-oxo-1,3-diazaspiro[4.4]non-1-en-3-yl)methyl]-2'-chloro-N-(3,4-dimethyl-5-isoxazolyl)[1,1'-biphenyl]-2-sulfonamide | P10 | 4, 8 (42) | 570 | 98 | 2.13 (D) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 222 | 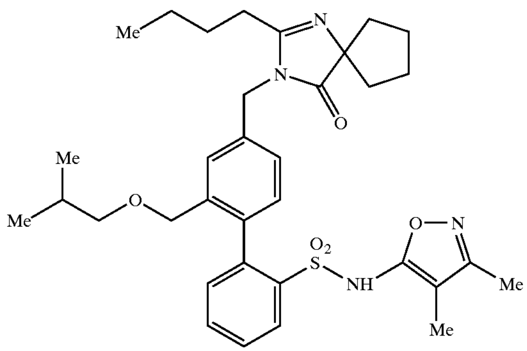 | 4'-[(2-Butyl-4-oxo-1,3-diazaspiro[4.4]non-1-en-3-yl)methyl]-N-(3,4-dimethyl-5-isoxazolyl)-2'-[(2-methylproposy)methyl][1,1'-biphenyl]-2-sulfonamide | 42A | 2 (67); 4 (49); 7 (85) | 621 | >98 | 23.07 (B) |
| 223 | 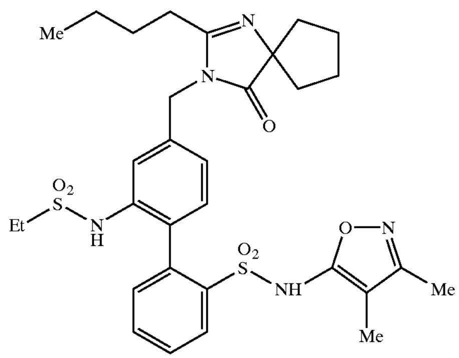 | 4'-[(2-Butyl-4-oxo-1,3-diazaspiro[4.4]non-1-en-3-yl)methyl]-N-(3,4-dimethyl-5-isoxazolyl)-2'-[(ethylsulfonyl)amino][1,1'-biphenyl]-2-sulfonamide | 123 | 24 (33) | 642 | 98 | 14.32 (E) |

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 224 | 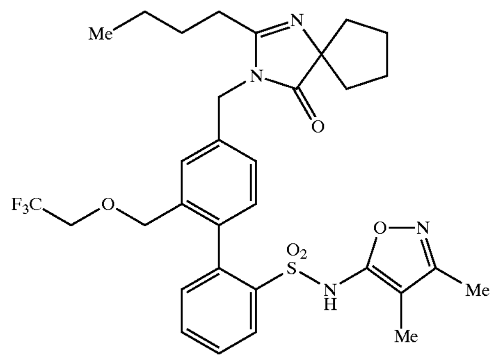 | 4'-[(2-Butyl-4-oxo-1,3-diazaspiro[4.4]non-1-en-3-yl)methyl]-N-(3,4-dimethyl-5-isoxazolyl)-2'-[(2,2,2-trifluoroethoxy)methyl][1,1'-biphenyl]-2-sulfonamide | P2A | 4, F$_3$CCH$_2$OH (89); 14 (76); 1 (67); 11 (95); 2 (90); 4 (85); 7 (85) | 647 | >97 | 20.15 (E) |
| 225 | 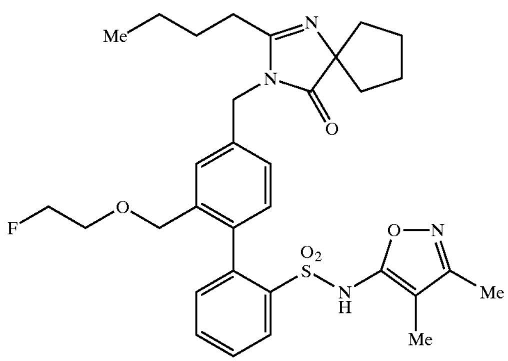 | 4'-[(2-Butyl-4-oxo-1,3-diazaspiro[4.4]non-1-en-3-yl)methyl]-N-(3,4-dimethyl-5-isoxazolyl)-2'-[(2-fluoroethoxy)methyl][1,1'-biphenyl]-2-sulfonamide | P2A | 4, FCH$_2$CH$_2$OH (72); 14 (65); 1 (68); 11 (95); 2 (85); 4 (80); 7 (90) | 611 | >97 | 15.94 (E) |

-continued

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 226 | 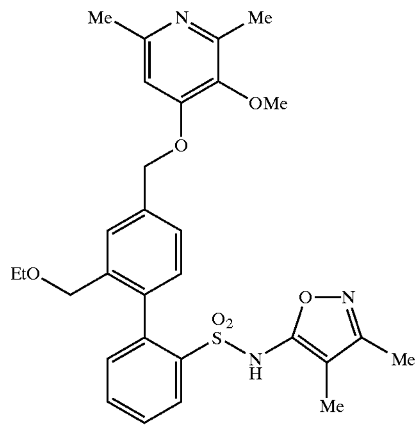 | N-(3,4-Dimethyl-5-isoxazolyl)-4'-[[(3-methoxy-2,6-dimethyl-4-pyridinyl)oxy]methyl]-2'-ethoxymethyl[1,1'-biphenyl]-2-sulfonamide | P2A | 4, EtOH (77); 14 (80); 1 (75); 11 (95); 2 (77); 22 (43); 7 (74) | 552 | 97 | 12.60 (E) |
| 227 | 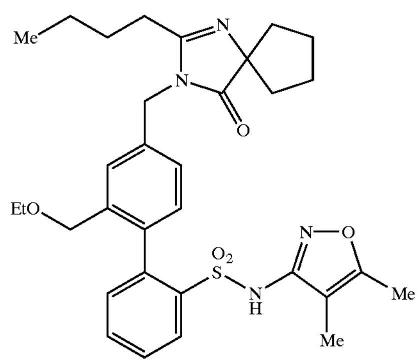 | 4'-[(2-Butyl-4-oxo-1,3-diazaspiro[4.4]non-1-en-3-yl)methyl]-N-(4,5-dimethyl-3-isoxazolyl)-2'-(ethoxymethyl)[1,1'-biphenyl]-2-sulfonamide | P2A | 4, EtOH (77); 14 (80); 1 (70); 11 (98); 2 (80); 4 (83); 7 (86) | 593 | >98 | 18.75 (E) |

-continued
| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 228 | 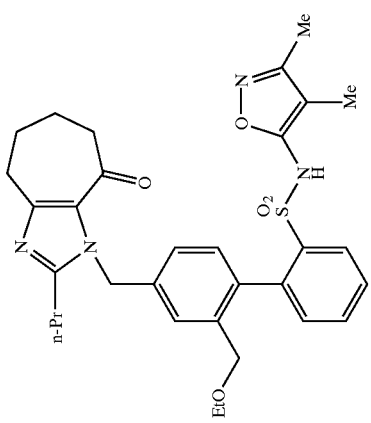 | N-(3,4-Dimethyl-5-isoxazolyl)-4'-[(1,4,5,6,7,8-hexahydro-8-oxo-2-propyl-1-cycloheptimidazolyl) methyl]-2'-(ethoxymethyl)[1,1'-biphenyl]-2-sulfonamide | P2A | 4, EtOH (77); 14 (80); 1 (75); 11 (95); 2 (77); 21 (); 7 () | 591 | >98 | 20.07 (B) |

Example 229

4'-[(2-Butyl-4-oxo-1,3-diazaspiro[4.4]non-1-en-3-yl)methyl]-N-(3,4-dimethylisoxazol-5yl)-2'-(3,3,3-trifluoropropyl)[1,1'-biphenyl]-2-sulfonamide

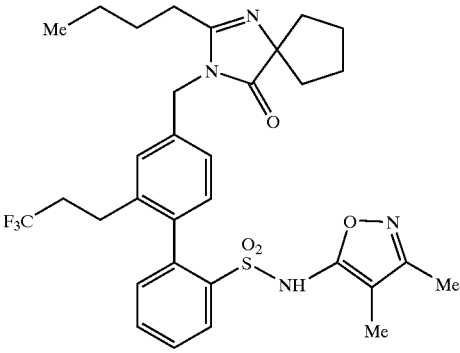

A. 3-Bromo-4-methoxybenzaldehyde dimethyl acetal

A solution of 3-bromo-4-methoxybenzaldehyde (19.2 g, 89 mmol) and trimethylorthoformate (14.8 ml, 140 mmol) in 150 ml methanol was treated at RT with concentrated sulfuric acid (10 μl). After stirring for 16 h, the mixture was treated with potassium carbonate (70 mg) and the solvent was evaporated. The residue was partitioned between dichloromethane and aqueous sodium bicarbonate. The organic layer was dried over sodium sulfate and concentrated to provide 229A (22.6 g) as a brown oil, which was used without further purification.

B. 4-Methoxy-3-(3,3,3-trifluoropropyl)benzaldehyde dimethyl acetal

A solution of 229A (15.8 g, 60 mmol) in dry THF (120 ml) was added to magnesium turnings (4.1 g, 170 mmol) at RT. The mixture was heated to 60° C. for 5 min, which initiated an exothermic reaction. The heating bath was removed and the mixture was allowed to reflux gently. Upon subsidence of the reaction (approximately 5 min), the mixture was heated to reflux for an additional 20 min and then was allowed to cool to RT. The clear green supernatant was transferred via canula away from excess magnesium and into a separate flask containing copper (I) iodide (575 mg, 3.0 mmol) under a nitrogen atmosphere. To this mixture was added 1-iodo-3,3,3-trifluoropropane (15 g, 67 mmol) and the resulting mixture was allowed to stir for 16 h, during which time a thick white precipitate developed. Aqueous ammonium chloride solution, ethyl acetate, and hexanes were added, and the organic layer was dried over sodium sulfate. Evaporation followed by silica gel chromatography of the residue using 3:1 hexanes/ethyl acetate as eluant provided 7.7 g of a mobile, slightly yellow oil, which was a 6:1 (mol ratio) mixture of 229B and 4-methoxybenzaldehyde dimethyl acetal, as determined by proton NMR. This mixture was used without further purification.

C. 4-Methoxy-3-(3,3,3-trifluoropropyl)benzaldehyde

The 229B mixture (7.7 g) was subjected to hydrochloric acid hydrolysis according to General Method 19. The resulting crude yellow oil (8.0 g) was a 6:1 mixture (mol ratio) of 229C and 4-methoxybenzaldehyde, and was used without further purification.

D. 4-Hydroxy-3-(3,3,3-trifluoropropyl)benzaldehyde

A solution of the 229C mixture (8.0 g, 35 mmol) in dichloromethane (5 ml) was treated at 0° C. with boron tribromide (55 ml of a 1.0 M solution in dichloromethane). The mixture was allowed to warm to RT and was stirred for 2 h. Aqueous 10% dipotassium hydrogen phosphate solution was added, and the aqueous layer was extracted with two portions of dichloromethane. The combined organic extracts were dried over sodium sulfate and evaporated. The residue was chromatographed on silica gel using 3:1 hexanes/ethyl acetate as eluant to provide 2.0 g of 229D as an orange solid (contaminated with 4-hydroxybenzaldehyde).

E. 4-(trifluoromethanesulfonyloxy)-3-(3,3,3-trifluoropropyl)benzaldehyde

A solution of the 229D mixture (2.0 g, 9 mmol) and N,N-diisopropylethylamine (2.4 ml, 14 mmol) in dichloromethane (40 ml) was treated dropwise at −78° C. with trifluoromethanesulfonic anhydride (1.9 ml, 11 mmol). The mixture was stirred at that temperature for 15 min following the completion of the addition. Aqueous sodium bicarbonate solution was added and the mixture was stirred and allowed to warm to RT. The layers were separated and the aqueous layer was extracted with two portions of dichloromethane. The combined organic extracts were dried over sodium sulfate, evaporated, and the residue was chromatographed on silica gel using hexanes/ethyl acetate as eluant to provide first recovered 229D (540 mg), and then the product fraction (380 mg) as an orange oil. The product fraction was a 2:1 mixture (mol ratio) of 229E and 4-(trifluormethanesulfonyloxy)benzaldehyde, as determined by proton NMR.

F. N-(3,4-Dimethyl-5-isoxazolyl)-4'-formyl-2'-(3,3,3-trifluoropropyl)-N-[(2-trimethylsilyl)ethoxymethyl][1,1'-biphenyl]-2-sulfonamide A solution of 229E (380 mg, 1.1 mmol) and [2-[[(3,4-dimethyl-5-isoxazolyl[(2-(trimethylsilyl)ethoxy)methyl]amino]-sulfonyl]phenyl]boronic acid (925 mg, 2.2 mmol) in dioxane (10 ml) was sparged with nitrogen for 15 min. Tetrakis(triphenylphosphine)palladium(0) (130 mg, 0.11 mmol) was added, followed by powdered potassium phosphate (460 mg, 2.2 mmol). The mixture was heated at 85° C. for 5 h, then the solvent was evaporated. The residue was chromatographed on silica gel using hexanes/ethyl acetate as eluant to provide the product fraction (550 mg) as an orange oil. The product fraction was a 2:1 mixture (mol ratio) of 229F and the corresponding 2'-H product, as judged by proton NMR.

G. N-(3,4-Dimethyl-5-isoxazolyl)-4'-hydroxymethyl-2'-(3,3,3trifluoropropyl)-N-[(2-trimethylsilyl)ethoxymethyl][1,1'-biphenyl]-2-sulfonamide The 229F mixture (550 mg, 0.9 mmol) was subjected to sodium borohydride reduction according to General Method 14. The crude residue was chromatographed directly on silica gel using 3:1 hexanes/ethyl acetate as eluant to provide the product fraction (355 mg) as an amber oil. The product fraction was a 2:1 mixture (mol ratio) of 229G and the corresponding 2'-H product, as judged by proton NMR.

H. N-(3,4-Dimethyl-5-isoxazolyl)-4'-(methanesulfonyloxy)methyl-2'-(3,3,3-trifluoropropyl)-N-[(2-trimethylsilyl)ethoxymethyl][1,1'-biphenyl]-2-sulfonamide The 229G mixture (350 mg, 0.63 mmol) was converted to the corresponding methanesulfonate ester according to General Method 3. The entire crude product 229H was used directly in the next step.

I. 4'-[(2-Butyl-4-oxo-1,3-diazaspiro[4.4]non-1-en-3-yl)methyl]-N-(3,4-dimethyl-5-isoxazolyl)-2'-(3,3,3-trifluoropropyl)-N-[(2-trimethylsilyl)ethoxymethyl] [1,1'-biphenyl]-2-sulfonamide 229H was used to alkylate 2-butyl-1,3-diazaspiro[4.4]non-1-en-4one according to General Method 4. The crude residue was chromatographed on silica gel using 2:1 hexanes/ethyl acetate as eluant to provide the product fraction (370 mg) as a slightly orange oil. The product fraction was a 2:1 mixture (mol ratio) of 229I and the corresponding 2'-H product, as judged by proton NMR J. 4'-[(2-Butyl-4-oxo-1,3-diazaspiro[4.4]non-1-en-3-yl) methyl]-N-(3,4-dimethylisoxazol-5-yl)-2'-3,3,3-trifluoropropyl)[1,1'-biphenyl]-2-sulfonamide The 229I mixtue was deprotected according to General Method 8. The crude product (which contained the 2'-H contaminant) was purified by reverse-phase preparative HPLC, followed by extraction with ethyl acetate from pH 8 potassium phosphate buffer. Finally, silica gel chromatography using 2:1 hexanes/acetone as eluant provided the title compound (120 mg) as a white foam; LRMS m/z 631 (ESI+ mode); HPLC retention time 3.78 min (Method C); HPLC purity >98%.

Example 230
4'-[(2-Butyl-4-oxo-1,3-diazaspiro[4.4]non-1-en-3-yl) methyl]-N-(3,4-dimethylisoxazol-5-yl)-2'-(3-fluoropropyl) [1,1'-biphenyl]-2-sulfonamide

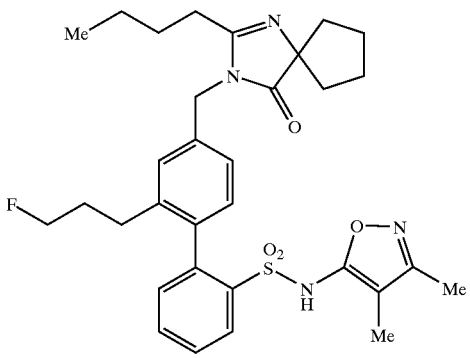

A. Methyl 3-(2-propenyl)-4-(trifluoromethanesulfonyloxy)benzoate

Methyl 4-hydroxy-3-(2-propenyl)benzoate (12.0 g, 62.4 mmol, prepared according to W. J. Greenlee, et. al., WO 91/11999) was treated with trifluoromethanesulfonic anhydride according to the procedure of Example 229, Step E. The crude product was chromatographed on silica gel using 3:1 hexanes/ethyl acetate as eluant to yield 17.4 g of 230A as a yellow oil.

B. Methyl 3-(3-hydroxypropyl)-4-(trifluoromethanesulfonyloxy)benzoate

Borane-THF complex (1.0 M solution in THF, 32 ml,32 mmol) was added to a solution of 230A (8.5 g, 26 mmol) in THF at 0° C. The mixture was stirred at RT for 16 h and then cooled to 0° C. A 1.0 M solution of sodium/potassium phoshate buffer (pH 7, 50 ml) was added, followed by 30% aqueous hydrogen peroxide (9.0 ml). The mixture was allowed to warm to RT, then water and EtOAc were added. The organic layer was dried over sodium sulfate and evaporated. The crude product was chromatographed on silica gel using 1:1 hexanes/ethyl acetate as eluant to yield 4.3 g of 230B as a yellow oil.

C. N-(3,4-Dimethyl-5-isoxazolyl)-2'-(3-hydroxypropyl)-4'-(methoxycarbonyl)-N-[(2-trimethylsilyl)ethoxymethyl] [1,1'-biphenyl]-2-sulfonamide Suzuki coupling of 230B (1.3 g, 3.8 mmol) according to the procedure of Example 229, step F, provided 230C (750 mg) as an orange oil following silica gel chromatography using1:1hexanes/ethyl acetate as eluant.

D. N-(3,4-Dimethyl-5-isoxazolyl)-2'-(3-fluoropropyl)-4'-(methoxycarbonyl)-N-[(2-trimethylsilyl)ethoxymethyl][1,1'-biphenyl]-2-sulfonamide A solution of 230C (750 mg,1.3 mmol) in dichloromethane (3 ml) was treated at −78° C. with (diethylamino) sulfur trifluoride (0.21 ml, 1.6 mmol). The mixture was allowed to warm to RT. After 15 min, water was added and the aqueous layer was extracted with two portions of dichloromethane. The organic extracts were dried over sodium sulfate, concentrated, and the residue was chromatographed on silica gel using 2:1 hexanes/ethyl acetate as eluant to provide 230D (175 mg) as a yellow oil.

E. N-(3,4-Dimethyl-5-isoxazolyl)-2'-(3-fluoropropyl)-4'-(hydroxymethyl)-N-[(2-trimethylsilyl)ethoxymethyl][1,1'-biphenyl]-2-sulfonamide A solution of 230D (175 mg,0.3 mmol) in THF (5 ml) was treated with DIBAL-H (0.53 ml of a 1.5 M solution in toluene, 0.8 mmol) at −78° C. The temperature was allowed to rise to −25° C. and the mixture was stirred for 2 h. Water (2 ml) and ether (10 ml) were added and the mixture was stirred at RT for 2 h. The mixture was filtered and the filtrate concentrated to provide crude 230E (110 mg) as a colorless oil.

F. N-(3,4-Dimethyl-5-isoxazolyl)-2'-(3-fluoropropyl)-4'-(methanesulfonyloxy)methyl-N-[(2-trimethylsilyl) ethoxymethyl][1,1'-biphenyl]-2-sulfonamide 230E (110 mg,0.2 mmol) was converted to the corresponding methanesulfonate ester according to General Method 3. The entire crude product 230F was used directly in the next step.

G. 4'-[(2-Butyl-4-oxo-1,3-diazaspiro[4.4]non-1-en-3-yl) methyl]-N-(3,4-dimethyl-5-isoxazolyl)-2'-(3-fluoropropyl)-N-[(2-trimethylsilyl)ethoxymethyl][1,1'-biphenyl]-2-sulfonamide 230F was used to alkylate 2-butyl-1,3-diazaspiro[4.4] non-1-en-4-one according to General Method 4, to provide 230G (124 mg) as a colorless oil, which was used without further purification.

H. 4'-[(2-Butyl-4-oxo-1,3-diazaspiro[4.4]non-1-en-3-yl) methyl]-N-(3,4-dimethylisoxazol-5-yl)-2'-(3-fluoropropyl) [1,1'-biphenyl]-2-sulfonamide 230G (124 mg, 0.2 mmol) was deprotected according to General Method 8 (EtOH). The crude product was purified by silica gel chromatography using 1:1 hexanes/ethyl acetate as eluant provided the title compound (23 mg) as a white foam; LRMS m/z 595 (ESI+ mode); HPLC retention time 2.10 min (Method D); HPLC purity >98%.

Example 231
4'-[(2-Butyl-4-oxo-1,3-diazaspiro[4.4]non-1-en-3-yl) methyl]-2'-(1,1-difluoroethyl)-N-(3,4-dimethylisoxazol-5-yl)[1,1'-biphenyl]-2-sulfonamide

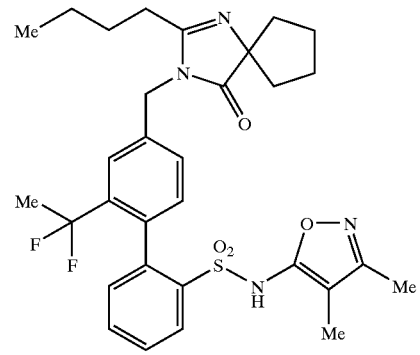

A. 5-Bromo-2-(trifluoromethanesulfonyloxy) acetophenone

5-Bromo-2-hydroxyacetophenone (3.3 g, 15 mmol) was treated with trifluoromethanesulfonic anhydride according to the procedure of Example 229, Step E. The crude residue was taken up in ether and washed twice with 10% aqueous potassium dihydrogenphosphate solution and once with brine. The ether solution was dried over magnesium sulfate and concentrated to provide crude 231A (4.7 g) as an orange oil, which was used without further purification.

B. 3-(1,1,-Difluoroethyl)-4-(trifluoromethanesulfonyloxy)bromobenzene 231A (4.4 g, 13 mmol) was treated at RT with neat (diethylamino)sulfur trifluoride (2.5 ml, 19 mmol) and the resulting solution was stirred at RT for 40 h. The mixture was poured onto ice, aqueous sodium bicarbonate solution was added, and the mixture was extracted with three portions of dichloromethane. The combined extracts were dried over sodium sulfate and concentrated, and the residue was chromatographed on silica gel using 5:1 hexanes/ethyl acetate as eluant to provide 231B (4.0 g) as an orange oil.

C. 3-(1,1,-Difluoroethyl)-4-(trifluoromethanesulfonyloxy)benzaldehyde

A solution of 231B (3.8 g, 10 mmol) and DMF (1.2 ml, 15 mmol) in dry THF (60 ml) was treated dropwise at −78° C. with n-butyllithium (5.0 ml of a 2.5 M solution in hexanes, 13 mmol). 10% aqueous potassium dihydrogenphosphate solution was added and the resulting mixture was allowed to warm to RT. 1:1 hexanes/ethyl acetate and brine were added and the organic layer was collected, dried over sodium sulfate, and evaporated. The residue was chromatographed on silica gel using 3:1 hexanes/ethyl acetate as eluant to provide recovered 231B (1.4 g), followed by 231C (1.0 g), which was an orange oil.

D. 2'-(1,1-Difluoroethyl)-N-(3,4-dimethylisoxazol-5-yl)-4'-formyl-N-[(2-trimethylsilyl)ethoxymethyl][1,1'-biphenyl]-2-sulfonamide Suzuki coupling of 231C (1.0 g, 3.2 mmol) according to the procedure of Example 229, step F, provided 231D (640 mg) as an orange oil following silica gel chromatography using 3:1 hexanes/ethyl acetate as eluant.

E. 2'-(1,1-Difluoroethyl)-N-(3,4-dimethylisoxazol-5-yl)-4'-hydroxymethyl-N-[(2-trimethylsilyl)ethoxymethyl][1,1'-biphenyl]-2-sulfonamide 231D (640 mg, 1.2 mmol) was subjected to sodium borohydride reduction according to General Method 14. The crude residue was chromatographed on silica gel using 1:1 hexanes/ethyl acetate as eluant to provide 231E (550 mg) as a brown oil.

F. 2'-(1,1-Difluoroethyl)-N-(3,4-dimethylisoxazol-5-yl)-4'-(methanesulfonyloxy)methyl-N-[(2-trimethylsilyl)ethoxymethyl][1,1'-biphenyl]-2-sulfonamide 231E (360 mg, 0.7 mmol) was converted to the corresponding methanesulfonate ester according to General Method 3. The entire crude product 231F was used directly in the next step.

G. 4'-[(2-Butyl-4-oxo-1,3-diazaspiro[4.4]non-1-en-3-yl)methyl]-2'-(1,1-difluoroethyl)-N-(3,4-dimethylisoxazol-5-yl)-N-[(2-trimethylsilyl)ethoxymethyl][1,1'-biphenyl]-2-sulfonamide 231F was used to alkylate 2-butyl-1,3-diazaspiro[4.4]non-1-en-4-one according to General Method 4. The crude residue was chromatographed on silica gel using 1:1 hexanes/ethyl acetate as eluant to provide 231G (170 mg) as a yellow oil.

H. 4'-[(2-Butyl-4-oxo-1,3-diazaspiro[4.4]non-1-en-3-yl)methyl]-2'-(1,1-difluoroethyl)-N-(3,4-dimethylisoxazol-5-yl)-[1,1'-biphenyl]-2-sulfonamide 231G (150 mg, 0.2 mmol) was deprotected according to General Method 8 (EtOH). The crude product was chromatographed on silica gel using 1:1 hexanes/ethyl acetate as eluant to provide the title compound (36 mg) as a white foam; LRMS m/z 599 (ESI+ mode); HPLC retention time 3.58 min (Method A); HPLC purity >98%.

Example 232

4'-[(2-Butyl-4-oxo-1,3-diazaspiro[4.4]non-1-en-3-yl)methyl]-2'-(2,2,2-trifluoroethyl)-N-(3,4-dimethylisoxazol-5-yl)[1,1'-biphenyl]-2-sulfonamide

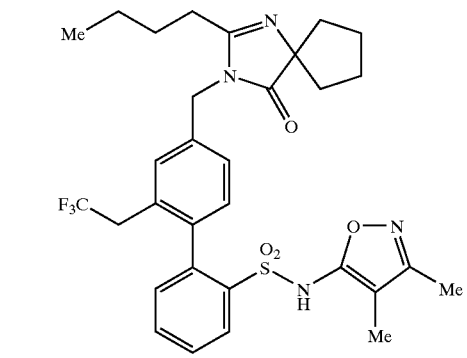

A. Methyl 4-bromo-3-(bromomethyl)benzoate

Methyl 4-bromo-3-methylbenzoate (20 g, 87 mmol) was brominated according to General Method 13. The crude orange solid was triturated with 4:1 hexanes/ethyl acetate to provide 232A (14.7 g) as a white solid.

B. Methyl 4-bromo-3-(2,2,2-trifluoroethyl)benzoate

Methyl 2,2-difluoro-2-(fluorosulfonyl)acetate (3.1 ml, 25 mmol) was added to a mixture of 232A (7.0 g, 22 mmol) and copper(I) iodide (420 mg, 2.2 mmol) in DMF (45 ml) under a nitrogen atmosphere. The mixture was heated to 85° C. for 16 h. The mixture was cooled to RT and the solvent was evaporated. Hexanes and brine were added, and the organic layer was dried over sodium sulfate and concentrated to give a yellow solid (6.0 g), which contained 232A and 232B.

The solid was dissolved in DMF (15 ml) and stirred at RT with potassium acetate (1.0 g, 10 mmol) for 3 h. The solvent was evaporated and the residue partitioned between ethyl acetate and water. The organic layer was dried over sodium sulfate and concentrated, and the residue was chromatographed on silica gel using 4:1 hexanes/ethyl acetate as eluant to provide 232B (3.4 g) as a white solid.

C. N-(3,4-Dimethylisoxazol-5-yl)-4'-(methoxycarbonyl)-2'-(2,2,2-trifluoroethyl)-N-[(2-trimethylsilyl)ethoxymethyl][1,1'-biphenyl]-2-sulfonamide Suzuki coupling of 232B (1.8 g, 5.9 mmol) according to the procedure of Example 229, step F, provided 232C (1.3 g) as a yellow solid following silica gel chromatography using 3:1 hexanes/ethyl acetate as eluant.

D. N-(3,4-Dimethylisoxazol-5-yl)-4'-hydroxymethyl-2'-(2,2,2-trifluoroethyl)-N-[(2-trimethylsilyl)ethoxymethyl][1,1'-biphenyl]-2-sulfonamide 232C (1.3 g, 2.2 mmol) was treated with DIBAL-H according to the procedure of Example 230, step E, to provide 232D (650 mg) as an oil following silica gel chromatography using 3:1 hexanes/ethyl acetate as eluant.

E. N-(3,4-Dimethylisoxazol-5-yl)-4'-(methanesulfonyloxy)methyl-2'-(2,2,2-trifluoroethyl)-N-[(2-trimethylsilyl)ethoxymethyl][1,1'-biphenyl]-2-sulfonamide 232D (650 mg, 1.1 mmol) was converted to the corresponding methanesulfonate ester according to General Method 3. The entire crude product 232E was used directly in the next step.

F. 4'-[(2-Butyl-4-oxo-1,3-diazaspiro[4.4]non-1-en-3-yl)methyl]-N-(3,4-dimethylisoxazol-5-yl)-2'-(2,2,2- trifluoroethyl)-N-[(2-trimethylsilyl)ethoxymethyl][1,1'-biphenyl]-2-sulfonamide 232E was used to alkylate 2-butyl-1,3-diazaspiro[4.4]non-1-en-4-one according to General Method 4. The crude residue was chromatographed on silica gel using 2:1 hexanes/ethyl acetate as eluant to provide 232F (440 mg) as a yellow oil.

G. 4'-[(2-Butyl-4-oxo-1,3-diazaspiro[4.4]non-1-en-3-yl)methyl]-N-(3,4-dimethylisoxazol-5-yl)-2'-(2,2,2-trifluoroethyl)[1,1'-biphenyl]-2-sulfonamide 232F was deprotected according to General Method 8 (EtOH). The crude product was purified by reverse-phase preparative HPLC, followed by an extraction with ethyl acetate from pH 5 sodium phoshpate buffer to provide the title compound (78 mg) as a white foam; LRMS m/z 617 (ESI+ mode); HPLC retention time 1.69 min (Method H); HPLC purity >98%.

Example 233

4'-[(2-Butyl-4-oxo-1,3-diazaspiro[4.4]non-1-en-3-yl)methyl]-N-(3,4-dimethylisoxazol-5-yl)-2'-[(2-methyl)propoxy][1,1'-biphenyl]-2-sulfonamide

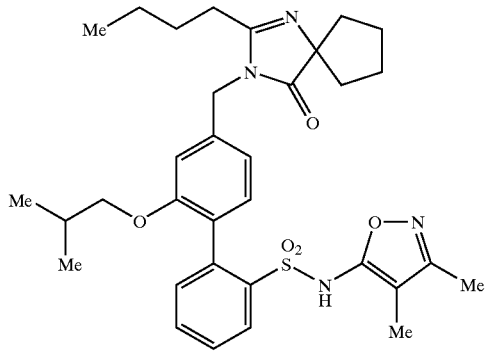

A. 2-Bromo-5-methylphenol

A solution of sodium nitrite (2.8 g, 41 mmol) in 5 ml water was added rapidly with stirring to an ice-cooled mixture of 6-amino-m-cresol (5.0 g, 41 mmol) and 48% hydrobromic acid (17 ml, 100 mmol). The temperature was kept below 10° C. by addition of ice chips. The diazonium salt solution was then added in portions over a period of 30 min to a boiling mixture of copper(I) bromide (6.4 g, 22 mmol) and 48% hydrobromic acid (5 ml). The resulting mixture was refluxed for an additional 30 min, then was cooled and extracted with ether (2×100 ml). The combined organic extracts were washed with water, dried over magnesium sulfate, and evaporated. The residue was chromatographed on silica gel using 98:2 hexanes/ethyl acetate to afford 233A (1.6 g, 20%) as an oil.

B. 4-Bromo-3-(2-methylpropoxy)toluene

Isobutyl bromide (0.70 ml, 6.4 mmol) was added to a mixture of 233A (800 mg, 4.3 mmol), potassium carbonate (1.2 g, 8.5 mmol), and DMF (2 ml). The mixture was stirred for 36 h at 45° C. and was then cooled and concentrated under vacuum. The residue was added to water and extracted with ethyl acetate (3×50 ml). The combined organic extracts were washed with water and dried over sodium sulfate to give 233B (960 mg, 93%) as an oil.

C. 4-Bromomethyl-2-(2-methylpropoxy)-1-bromobenzene 233B (960 mg, 3.9 mmol) was subjected to NBS bromination according to General Method 13. The crude 233C (1.1 g, 86%) was used without further purification.

D. 4-[(2-Butyl-4-oxo-1,3-diazaspiro[4.4]non-1-en-3-yl)methyl]-2-(2-methylpropoxy)-1-bromobenzene 233C (1.1 g, 3.4 mmol) was used to alkylate 2-butyl-1,3-diazaspiro[4.4]non-1-en-4-one according to General Method 4. The crude residue was chromatographed on silica gel using 1:1 hexanes/ethyl acetate as eluant to provide 233D (550 mg, 40%) as an oil.

E. 4'-[(2-Butyl-4-oxo-1,3-diazaspiro[4.4]non-1-en-3-yl)methyl]-N-(3,4-dimethylisoxazol-5-yl)-2'-[(2-methyl)propoxy]-N-[(2-trimethylsilyl)ethoxymethyl][1,1'-biphenyl]-2-sulfonamide Suzuki coupling of 233D (550 mg, 1.3 mmol) according to General Method 1 provided 233E (660 mg, 60%) as an oil following silica gel chromatography using 2:3 hexanes/ethyl acetate as eluant.

F. 4'-[(2-Butyl-4-oxo-1,3-diazaspiro[4.4]non-1-en-3-yl)methyl]-N-(3,4-dimethylisoxazol-5-yl)-2'-[(2-methyl)propoxy][1,1'-biphenyl]-2-sulfonamide 233E (660 mg) was deprotected according to General Method 8 (EtOH). Water was added to the crude residue and the mixture was extracted with ethyl acetate (3×50 ml). The combined organic extracts were washed with water and dried and evaporated. The residue was chromatographed on silica gel using 1:1 hexanes/ethyl acetate to provide the title compound (270 mg, 60%) as a white solid, mp 58–61° C.; LRMS m/e 607 (ESI+ mode); HPLC retention time 26.32 min (Method B); HPLC purity >98%.

Example 234

4'-[(2-Butyl-4-oxo-1,3-diazaspiro[4.4]non-1-en-3-yl)methyl]-N-(3,4-dimethylisoxazol-5-yl)-2'-(2-methoxyethoxy)[1,1'-biphenyl]-2-sulfonamide

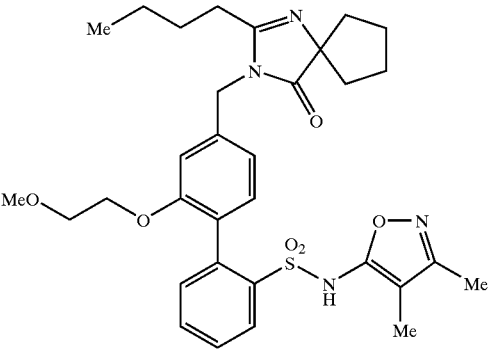

A. 4-Bromo-3-(2-methoxyethoxy)toluene 233A (800 mg, 4.3 mmol) was alkylated with 1-bromo-2-methoxyethane (0.89 g, 6.4 mmol) according to the procedure of Example 233, step B, to give 234A (840 mg, 81%) as an oil.

B. 4-Bromomethyl-2-(2-methoxyethoxy)-1-bromobenzene 234A (840 mg, 3.4 mmol) was subjected to NBS bromination according to General Method 13. The crude 234B (510 mg, 46%) was used without further purification.

C. 4-[(2-Butyl-4-oxo-1,3-diazaspiro[4.4]non-1-en-3-yl)methyl]-2-(2-methoxyethoxy)-1-bromobenzene 234B (510 mg, 1.6 mmol) was used to alkylate 2-butyl-1,3-diazaspiro[4.4]non-1-en-4-one according to General Method 4. The crude residue was chromatographed on silica gel using 4:1 hexanes/ethyl acetate as eluant to provide 234C (600 mg, 88%) as an oil.

D. 4'-[(2-Butyl-4-oxo-1,3-diazaspiro[4.4]non-1-en-3-yl)methyl]-N-(3,4-dimethylisoxazol-5-yl)-2'-(2-methoxyethoxy)-N-[(2-trimethylsilyl)ethoxymethyl][1,1'-biphenyl]-2-sulfonamide Suzuki coupling of 234C (600 mg, 1.4 mmol) according to General Method 1 provided 234D (550 mg, 54%) as an oil following silica gel chromatography using 2:3 hexanes/ethyl acetate as eluant.

E. 4'-[(2-Butyl-4-oxo-1,3-diazaspiro[4.4]non-1-en-3-yl)methyl]-N-(3,4-dimethylisoxazol-5-yl)-2'-(2-methoxyethoxy)[1,1'-biphenyl]-2-sulfonamide 234D (550 mg, 0.8 mmol) was deprotected according to General Method 8 (EtOH). Water was added to the crude residue and the mixture was extracted with ethyl acetate (3×50 ml). The combined organic extracts were washed with water and dried and evaporated. The residue was purified by reverse-phase preparative HPLC to provide the title compound (125 mg, 30%) as a white solid, mp 55–58° C.; MS m/e 609 (ESI+ mode); HPLC retention time 22.75 min (Method B); HPLC purity >98%.

Example 235
4'-[(2-Butyl-4-oxo-1,3-diazaspiro[4.4]non-1-en-3-yl)methyl]-2'-butyl-N-(3,4-dimethylisoxazol-5-yl)[1,1'-biphenyl]-2-sulfonamide

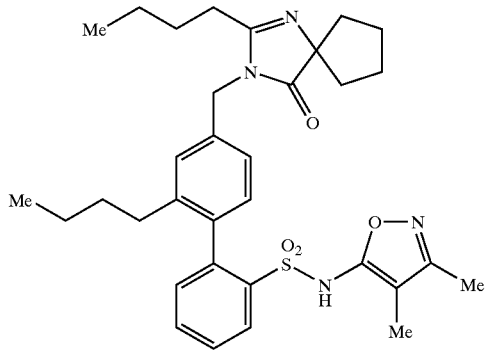

A. 4-Bromo-3-(1-butenyl)benzonitrile 2A (4.0 g, 19 mmol) was reacted with propyltriphenylphosphonium bromide following the procedure of Example 27, step A. The crude residue was chromatographed on silica gel using 9:1 hexanes/ethyl acetate to afford 235A (2.2 g, 49%) as an E/Z mixture.

B. 4-Bromo-3-butylbenzonitrile

A mixture of 235A (2.2 g, 9.3 mmol) and 210 mg of $PtO_2$ in 40 ml EtOH was hydrogenated at 35 PSI for 40 min. Filtration and concentration gave 1.4 g of 235B (62%).

C. 4-Bromo-3-butylbenzaldehyde 235B (1.4 g, 5.8 mmol) was treated with DIBAL-H according to General Method 14 to provide crude 235C (1.2 g, 90%) as an oil.

D. N-(3,4-Dimethyl-5-isoxazolyl)-2'-butyl-4'-formyl-N-[(2-trimethylsilyl)ethoxymethyl][1,1'-biphenyl]-2-sulfonamide 235C (1.2 g, 5.1 mmol) was subjected to Suzuki coupling according to General Method 1 to provide 235D as a crude oil.

E. N-(3,4-Dimethyl-5-isoxazolyl)-2'-butyl-4'-hydroxymethyl-N-[(2-trimethylsilyl)ethoxymethyl][1,1'-biphenyl]-2-sulfonamide 235D (entire sample) was reduced with sodium borohydride in methanol according to General Method 11 to provide 235E (1.4 g, 50% from 235C) as an oil.

F. N-(3,4-Dimethyl-5-isoxazolyl)-4'-(methanesulfonyl)oxymethyl-2'-butyl-N-[(2-trimethylsilyl)ethoxymethyl][1,1'-biphenyl]-2-sulfonamide 235E (1.4 g, 2.5 mmol) was converted to the corresponding methanesulfonate ester according to General Method 3 to provide 235F (1.4 g, 90%) as an oil.

G. 4'-[(2-Butyl-4-oxo-1,3-diazaspiro[4.4]non-1-en-3-yl)methyl]-2'-butyl-N-[(2-trimethylsilyl)ethoxymethyl]-N-(3,4-dimethyl-5-isoxazolyl)[1,1'-biphenyl]-2-sulfonamide 235F (1.3 g, 2.1 mmol) was used to alkylate 2-butyl-1,3-diazaspiro[4.4]non-1-en-4-one according to General Method 4. 235G (1.3 g, 85%) was produced as an oil.

H. 4'-[(2-Butyl-4-oxo-1,3-diazaspiro[4.4]non-1-en-3-yl)methyl]-2'-butyl-N-(3,4-dimethyl-5-isoxazolyl)[1,1'-biphenyl]-2-sulfonamide 235G (1.2 g, 1.7 mmol) was deprotected according to General Method 7. The crude product was purified by reverse-phase preparative HPLC to provide the title compound (620 mg, 62%) as a solid, mp 58–61° C.; MS m/e 591 (ESI+ mode); HPLC retention time 26.67 min (Method B); HPLC purity >98%.

Example 236
4'-[(2-Butyl-4-oxo-1,3-diazaspiro[4.4]non-1-en-3-yl)methyl]-N-(3-methylisoxazol-5-yl)-2'-trifluoromethyl[1,1'-biphenyl]-2-sulfonamide

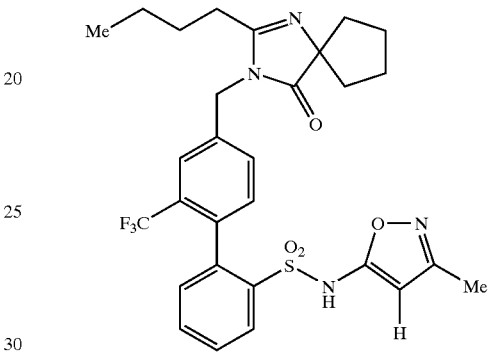

A. [2-[[(3-methyl-5-isoxazolyl)[[(2-trimethylsilyl)ethoxy]methyl]amino]sulfonyl]phenyl]boronic acid 25B (14 g, 31 mmol) was converted to the corresponding boronic acid according to the procedure of Example 45, step B. The crude product 236A (16.5 g, estimated purity 60%) was produced as an amber oil, and was used without further purification.

B. 4'-Formyl-N-(3-methyl-5-isoxazolyl)-2'-trifluoromethyl-N-[(2-trimethylsilyl)ethoxymethyl][1,1'-biphenyl]-2-sulfonamide 236A (8.0 g, 20 mmol) was subjected to Suzuki coupling with P6 according to General Method 1. Silica gel chromatography using 2:1 hexanes/ethyl acetate as eluent provided 1.8 g of a mixture of 236B and a highly crystalline impurity. Trituration with 2:1 hexanes/ethyl acetate to remove this impurity provided 236B (1.0 g) as an orange oil.

C. 4'-Hydroxymethyl-N-(3-methyl-5-isoxazolyl)-2'-trifluoromethyl-N-[(2-trimethylsilyl)ethoxymethyl][1,1'-biphenyl]-2-sulfonamide 236B (880 mg, 1.6 mmol) was reduced with sodium borohydride (0.3 eq.) in ethanol according to General Method 11. The crude residue was chromatographed on silica gel using 2:1 hexanes/ethyl acetate as eluant to provide 236C (450 mg) as a yellow oil.

D. 4'-(Methanesulfonyloxy)methyl-N-(3-methyl-5-isoxazolyl)-2'-trifluoromethyl-N-[(2-trimethylsilyl)ethoxymethyl][1,1'-biphenyl]-2-sulfonamide 236C (450 mg) was converted to the corresponding methanesulfonate ester according to General Method 3. The entire crude product 236D was used in the next reaction step.

E. 4'-[(2-Butyl-4-oxo-1,3-diazaspiro[4.4]non-1-en-3-yl)methyl]N-(3-methyl-5-isoxazolyl)-2'-trifluoromethyl-N-[(2-trimethylsilyl)ethoxymethyl][1,1'-biphenyl]-2-sulfonamide 236D was used to alkylate 2-butyl-1,3-diazaspiro[4.4]non-1-en-4-one according to General Method 4. The crude residue was chromatographed on silica gel using 2:1 hexanes/acetone as eluant to provide 236E (170 mg) as a yellow oil.

F. 4'-[(2-Butyl-4-oxo-1,3-diazaspiro[4.4]non-1-en-3-yl)methyl] N-(3-methyl-5-isoxazolyl)-2'-trifluoromethyl[1,1'-biphenyl]-2-sulfonamide 236E (100 mg) was deprotected according to General Method 8 (ethanol) to provide the title compound as the hydrochloride salt (77 mg), which required no additional purification: MS m/e 589 (ESI+ mode); HPLC retention time 3.72 min (Method C); HPLC purity 97%.

Example 237
N-(4-Bromo-3-methyl-5-isoxazolyl)-4'-[(2-butyl-4-oxo-1,3-diazaspiro[4.4]non-1-en-3-yl)methyl]-2'-trifluoromethyl[1,1'-biphenyl]-2-sulfonamide

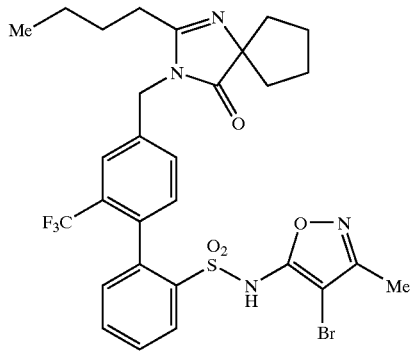

Bromine (33 mg/ml solution in acetic acid, 18 mg, 0.11 mmol) was added in portions to a solution of 236 (53 mg, 0.09 mmol) and sodium acetate (35 mg, 0.42 mmol) in acetic acid (4 ml) at RT. The solvent was evaporated, aqueous potassium phosphate solution was added, and the pH was adjusted to 8. The mixture was extracted with ethyl acetate, and the combined organic layers were dried over sodium sulfate. The residue was chromatographed on silica gel using 1:3 hexanes/acetone as eluant to provide the title compound (31 mg) as a white powder following lyophilization: MS m/e 667, 669 (ESI+ mode); HPLC retention time 3.83 min (Method C); HPLC purity 94%.

Example 238
4'-[(2-Butyl-4-oxo-1,3-diazaspiro[4.4]non-1-en-3-yl)methyl]-N-(4-chloro-3-methyl-5-isoxazolyl)-2'-trifluoromethyl[1,1'-biphenyl]-2-sulfonamide

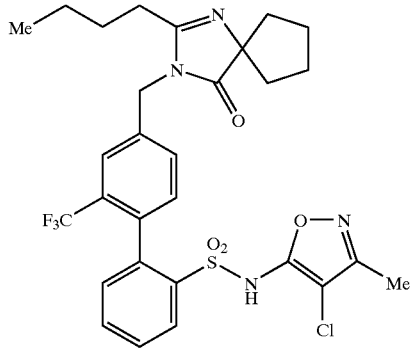

Clorox bleach (5.25% sodium hypochlorite solution, 225 μl) was added in portions to a solution of 236 (32 mg, 0.054 mmol) in THF (2 ml) at RT. The solvent was evaporated and the residue was purified by reverse-phase preparative HPLC, followed by preparative thin-layer silica gel chromatography using 10% methanol in dichloromethane as eluant, providing the title compound (1.0 mg) as a white powder following lyophilization: MS m/e 624 (ESI+ mode); HPLC retention time 3.53 min (Method A); HPLC purity 95%.

Example 239

4'-[(2-Butyl-4-oxo-1,3-diazaspiro[4.4]non-1-en-3-yl)methyl]-N-(3,4-dimethyl-5-isoxazolyl)-2'-(N-methoxy-N-methylaminomethyl)[1,1'-biphenyl]-2-sulfonamide

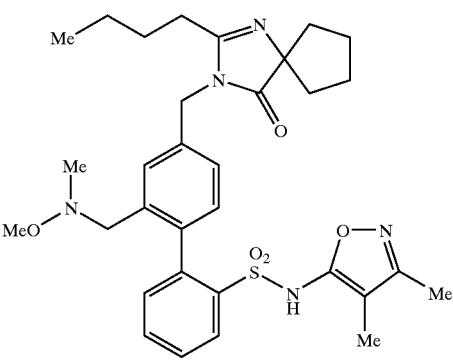

A. N-(3,4-Dimethyl-5-isoxazolyl)-4'-hydroxymethyl-2'-(N-methoxy-N-methylaminomethyl)-N-[(2-methoxyethoxy)methyl][1,1'-biphenyl]-2-sulfonamide P21 (230 mg, 0.48 mmol) was subjected to reductive amination with N-methoxy-N-methylamine according to General Method 5, yielding 239A (169 mg, 69%) as an oil.

B. 4'-Bromomethyl-N-(3,4-dimethyl-5-isoxazolyl)-2'-(N-methoxy-N-methylaminomethyl)-N-[(2-methoxyethoxy)methyl][1,1'-biphenyl]-2-sulfonamide 239A (165 mg, 0.33 mmol) was converted to the corresponding bromide according to General Method 2, yielding 239B (174 mg, 92%) as an oil following silica gel chromatography using hexanes/ethyl acetate as eluant.

C. 4'-[(2-Butyl-4-oxo-1,3-diazaspiro[4.4]non-1-en-3-yl)methyl]-N-(3,4-dimethyl-5-isoxazolyl)-2'-(N-methoxy-N-methoxyaminomethyl)-N-[(2-methoxyethoxy)methyl][1,1'-biphenyl]-2-sulfonamide 239B (170 mg, 0,30 mmol) was used to alkylate 2-butyl-1,3-diazaspiro[4.4]non-1-en-4-one according to General Method 4. The crude residue was chromatographed on silica gel using hexanes/ethyl acetate as eluant to provide 239C (155 mg, 72%) as a yellow oil.

D. 4'-[(2-Butyl-4-oxo-1,3-diazaspiro[4.4]non-1-en-3-yl)methyl]-N-(3,4-dimethyl-5-isoxazolyl)-2'-(N-methoxy-N-methylaminomethyl)[1,1'-biphenyl]-2-sulfonamide 239C (150 mg) was deprotected according to General Method 7. The crude product was purified by reverse-phase preparative HPLC to provide the title compound (117 mg, 89%) as a white solid: MS m/e 608 (ESI+ mode); HPLC retention time 17.75 min (Method E); HPLC purity >97%.

Example 240
4'-[(2-Butyl-4-oxo-1,3-diazaspiro[4.4]non-1-en-3-yl)methyl]-2'-(2,2-difluoroethoxymethyl)-N-(3,4-dimethylisoxazol-5-yl)[1,1'-biphenyl]-2-sulfonamide

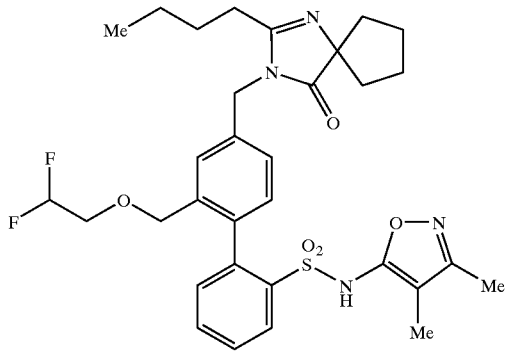

A. Methyl 4-bromo-3-(hydroxymethyl)benzoate

A mixture of methyl 4-bromo-3-methylbenzoate (168 g, 735 mmol), N-bromosuccinimide (141 g, 792 mmol), benzoyl peroxide (3.5 g, 15 mmol), and carbon tetrachloride (900 ml) was refluxed for 17 h. The mixture was cooled and filtered, and the filtrate was washed once with water and once with brine. The filtrate was then dried over sodium sulfate and concentrated to provide an orange oil (261 g), which was judged ($^1$H NMR) be about 70 mol % methyl 4-bromo-3-(bromomethyl)benzoate.

The crude orange oil (261 g) was dissolved in 400 ml DMF and treated with potassium acetate (74 g, 750 mmol) at 0° C. The mixture was allowed to warm to RT and was stirred for 54 h. The solvent was evaporated and the residue was taken up in 1:1 hexanes ethyl acetate and washed twice with half-saturated brine, then once with saturated brine. The organic layer was dried over sodium sulfate and concentrated to provide a new orange oil (208 g), which was judged to contain about 70 mol % methyl 4-bromo-3-(acetoxymethyl)benzoate.

The crude acetate mixture (208 g) was dissolved in methanol (1 l) and treated with potassium carbonate (12 g, 87 mmol) at 0° C. The mixture was allowed to warm to RT and was stirred for 18 h. The solvent was evaporated and the residue was treated with 130 ml 1N hydrochloric acid at 0° C. The mixture was extracted once with 1:3 hexanes/ethyl acetate, once with 1:1 hexanes/ethyl acetate, and once with ethyl acetate. The combined organic layers were dried over sodium sulfate and concentrated, and the residue was chromatographed on silica gel using 2:1 hexanes/ethyl acetate. The product fractions were combined, evaporated, and triturated with 1:1 hexanes/ethyl acetate to provide 240A (102 g) as a white solid.

B. Methyl 4-bromo-3-[(tetrahydro-2H-pyran-2-yl)oxymethyl]benzoate p-Toluenesulfonic acid hydrate (50 mg) was added to a solution of 240A (10 g, 41 mmol) and 3,4-dihydro-2H-pyran (10 g, 120 mmol) in dichloromethane (100 ml) at 0° C. After 1 h aqueous sodium bicarbonate solution was added, the layers were separated, and the organic layer was dried over sodium sulfate and concentrated to provide crude 240B (16 g) as a slightly yellow oil.

C. N-(3,4-Dimethyl-5-isoxazolyl)-4'-methoxycarbonyl-2'-[(tetrahydro-2H-pyran-2-yl)oxymethyl]-N-[(2-trimethylsilyl)ethoxymethyl][1,1'-biphenyl]-2-sulfonamide Crude 240B (10 g, aproximately 25 mmol) was subjected to Suzuki coupling according to General Method 1. Silica gel chromatography using 3:1 hexanes/ethyl acetate as eluant provided 240C (14 g) as a yellow oil.

D. N-(3,4-Dimethyl-5-isoxazolyl)-4'-hydroxymethyl-2'-[(tetrahydro-2H-pyran-2-yl)oxymethyl]-N-(2-trimethylsilyl)ethoxymethyl][1,1'-biphenyl]-2-sulfonamide A solution of 240C (10.5 g, 17 mmol) in THF (200 ml) was treated with DIBAL-H (23.4 ml of a 1.5 M solution in toluene, 35 mmol) at −78° C. The temperature was allowed to rise to −25° C. and the mixture was stirred for 2 h. Water (10 ml) and ether (100 ml) were added and the mixture was stirred at RT for 2 h. Ethyl acetate and hexanes were added, and the mixture was washed three times with aqueous sodium bicarbonate solution. The organic layer was dried over sodium sulfate and concentrated to provide crude 240D (9 g) as a deep maroon-colored oil.

E. N-(3,4-Dimethyl-5-isoxazolyl)-4'-(methanesulfonyloxy)methyl-2'-[(tetrahydro-2H-pyran-2-yl)oxymethyl]-N-[(2-trimethylsilyl)ethoxymethyl][1,1'-biphenyl]-2-sulfonamide 240D (4.5 g, 7.5 mmol) was converted to the corresponding methanesulfonate ester according to General Method 3. The entire crude product 240E was used in the next reaction step.

F. 4'-[(2-Butyl-4-oxo-1,3-diazaspiro[4.4]non-1-en-3-yl)methyl]-N-(3,4-dimethyl-5-isoxazolyl)-2'-[(tetrahydro-2H-pyran-2-yl)oxymethyl]-N-[(2-trimethylsilyl)ethoxymethyl][1,1'-biphenyl]-2-sulfonamide 240E was used to alkylate 2-butyl-1,3-diazaspiro[4.4]non-1-en-4-one according to General Method 4. The crude residue was chromatographed on silica gel using 3:2 hexanes/ethyl acetate as eluant to provide 240F (6.0 g) as a slightly yellow oil.

G. 4'-[(2-Butyl-4-oxo-1,3-diazaspiro[4.4]non-1-en-3-yl)methyl]-N-(3,4-dimethyl-5-isoxazolyl)-2'-hydroxymethyl-N-[(2-trimethylsilyl)ethoxymethyl][1,1'-biphenyl]-2-sulfonamide A solution of 240F (6.0 g, 7.7 mmol) and 2N hydrochloric acid (6 ml, 12 mmol) in methanol (150 ml) was stirred for 16 h at RT. The mixture was neutralized with aqueous sodium bicarbonate solution and the methanol was evaporated. Aqueous sodium bicarbonate solution was added and the mixture was extracted twice with ethyl acetate. The combined organic extracts were dried over sodium sulfate and concentrated to provide 240G (5.0 g) as a crude orange oil.

H. 2'-Bromomethyl-4'-[(2-butyl-4-oxo-1,3-diazaspiro[4.4]non-1-en-3-yl)methyl]-N-(3,4-dimethyl-5-isoxazolyl)-N-[(2-trimethylsilyl)ethoxymethyl][1,1'-biphenyl]-2-sulfonamide 240G (590 mg, 0.85 mmol) was converted to the corresponding bromide according to General Method 2, providing 240H (373 mg, 58%) as a yellow oil following silica gel chromatography using hexanes/ethyl acetate as eluant.

I. 4'-[(2-Butyl-4-oxo-1,3-diazaspiro[4.4]non-1-en-3-yl)methyl]-2'-(2.2-difluoroethoxymethyl)-N-(3,4-dimethyl-5-isoxazolyl)-N-[(2-trimethylsilyl)ethoxymethyl][1,1'-biphenyl]-2-sulfonamide 240H (370 mg, 0.49 mmol) was used to alkylate 2,2-difluoroethanol according to General Method 4. 240I (209 mg, 56%) was produced as a yellow oil following silica gel chromatography using hexanes/ethyl acetate as eluant.

J. 4'-[(2-Butyl-4-oxo-1,3-diazaspiro[4.4]non-1-en-3-yl)methyl]-2'-(2,2-difluoroethoxymethyl)-N-(3,4-dimethylisoxazol-5-yl)[1,1'-biphenyl]-2-sulfonamide 240I (205 mg, 0.27 mmol) was deprotected according to General Method 7. The crude product was purified by reverse-phase preparative HPLC to provide the title compound (104 mg, 60%) as a white solid: MS m/e 629 (ESI+ mode); HPLC retention time 17.18 min (Method E); HPLC purity >97%.

Example 241

4'-[(2-Butyl-4-oxo-1,3-diazaspiro[4.4]non-1-en-3-yl)methyl]-N-(3,4-dimethylisoxazol-5-yl)-2'-(2-fluoroethyl)[1,1'-biphenyl]-2-sulfonamide

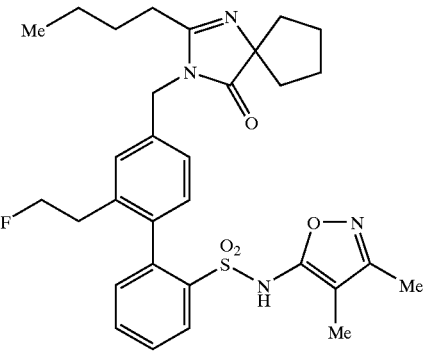

A. Methyl 3-(2-hydroxethyl)-4-(trifluoromethanesulfonyloxy)benzoate

An ozone/oxygen gas mixture was bubbled through a solution of 230A (8.3 g, 26 mmol) in methanol (100 ml) at −78° C. until a light blue color persisted. The solution was sparged with nitrogen to remove excess ozone, then triphenylphosphine (10 g, 38 mmol) was added in portions. The cooling bath was removed and the mixture was allowed to warm RT, then was concentrated. Ethanol (100 ml) was added to the residue and the resulting mixture was cooled to 0° C. Sodium borohydride (1.9 g, 51 mmol) was added. After 1 h, the mixture was allowed to warm to RT and the solvent was evaporated. The residue was taken up in 10% aqueous potassium dihydrogen phosphate solution and was extracted with ethyl acetate. The combined organic extracts were dried over sodium sulfate and concentrated, and the residue chromatographed on silica gel using 1:1 hexanes/ethyl acetate as eluant to yield 241A (4.5 g) as a colorless oil.

B. N-(3,4-Dimethyl-5-isoxazolyl)-2'-(2-hydroxethyl)-4'-(methoxycarbonyl)-N-[(2-trimethylsilyl)ethoxymethyl][1,1'-biphenyl]-2-sulfonamide Suzuki coupling of 241A (4.5 g, 14 mmol) according to the procedure of Example 229, step F, provided 241B (4.1 g) as a yellow solid following silica gel chromatography using 1:1 hexanes/ethyl acetate as eluant.

C. N-(3,4-Dimethyl-5-isoxazolyl)-2'-(2-fluoroethyl)-4'-(methoxycarbonyl)-N-[(2-trimethylsilyl)ethoxymethyl][1,1'-biphenyl]-2-sulfonamide A mixture of 241B (1.0 g, 1.8 mmol) and (diethylamino)sulfur trifluoride (0.71 ml, 5.4 mmol) was stirred at RT for 20 h. The mixture was poured onto ice. Aqueous sodium bicarbonate solution was added and the mixture was extracted with two portions of dichloromethane. The organic extracts were dried over sodium sulfate, concentrated, and the residue was chromatographed on silica gel using 1:1 hexanes/ethyl acetate as eluant to provide 241C (230 mg) as a yellow oil.

D. N-(3,4-Dimethyl-5-isoxazolyl)-2'-(2-fluoroethyl)-4'-(hydroxymethyl)-N-[(2-trimethylsilyl)ethoxymethyl][1,1'-biphenyl]-2-sulfonamide 241C (230 mg, 0.41 mmol) was treated with DIBAL-H according to the procedure of Example 230, step E, to provide crude 241D (320 mg) as a yellow oil

E. N-(3,4-Dimethyl-5-isoxazolyl)-2'-(2-fluoroethyl)-4'-(methanesulfonyloxy)methyl-N-[(2-trimethylsilyl)ethoxymethyl][1,1'-biphenyl]-2-sulfonamide 241D (320 mg) was converted to the corresponding methanesulfonate ester according to General Method 3. The entire crude product 241E was used directly in the next step.

F. 4'-[(2-Butyl-4-oxo-1,3-diazaspiro[4.4]non-1-en-3-yl)methyl]-N-(3,4-dimethyl-5-isoxazolyl)-2'-(2-fluoroethyl)-N-[(2-trimethylsilyl)ethoxymethyl][1,1'-biphenyl]-2-sulfonamide 241E was used to alkylate 2-butyl-1,3-diazaspiro[4.4]non-1-en-4-one according to General Method 4, to provide 241F (300 mg) as a yellow oil, which was used without further purification.

G. 4'-[(2-Butyl-4-oxo-1,3-diazaspiro[4.4]non-1-en-3-yl)methyl]-N-(3,4-dimethylisoxazol-5-yl)-2'-(2-fluoroethyl)[1,1'-biphenyl]-2-sulfonamide Crude 241F (300 mg) was deprotected according to General Method 8 (ethanol). The crude product was purified by silica gel chromatography using hexanes/ethyl acetate as eluant provided the title compound (16 mg) as a tan solid; LRMS m/z 581 (ESI+ mode); HPLC retention time 2.05 min (Method H); HPLC purity 97%.

Example 242

4'-[(2-Butyl-4-oxo-1,3-diazaspiro[4.4]non-1-en-3-yl)methyl]-N-(3,4-dimethylisoxazol-5-yl)-2'-(2-hydroxyethyl)[1,1'-biphenyl]-2-sulfonamide

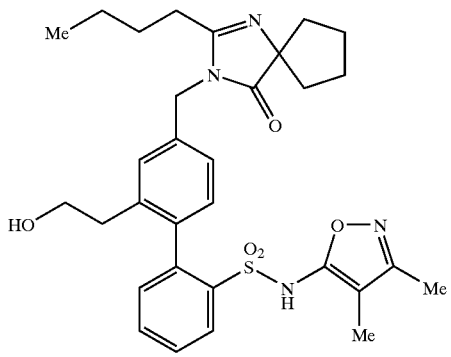

A. N-(3,4-Dimethyl-5-isoxazolyl)-4'-methoxycarbonyl-2'-[2-[(tetrahydro-2H-pyran-2-yl)oxy]ethyl]-N-[(2-trimethylsilyl)ethoxymethyl][1,1'-biphenyl]-2-sulfonamide Pyridinium p-toluenesulfonate (2 mg) was added to a solution of 241B (1.0 g, 1.8 mmol) and 3,4-dihydro-2H-pyran (0.48 ml, 5.4 mmol) in dichloromethane (4 ml) at 0° C. After 48 h aqueous sodium bicarbonate solution was added, the layers were separated, and the organic layer was dried over sodium sulfate and concentrated. The residue was chromatographed on silica gel using 2:1 hexanes/ethyl acetate to provide 242A (320 mg) as a slightly yellow oil.

B. N-(3,4-Dimethyl-5-isoxazolyl)-4'-(hydroxymethyl)-2'-[2-[(tetrahydro-2H-pyran-2-yl)oxy]ethyl]-N-[(2-trimethylsilyl)ethoxymethyl][1,1'-biphenyl]-2-sulfonamide 242A (320 mg, 0.50 mmol) was treated with DIBAL-H according to the procedure of Example 230, step E, to provide crude 242B (250 mg) as a yellow oil.

C. N-(3,4-Dimethyl-5-isoxazolyl)-4'-(methanesulfonyloxy)methyl-2'-[2-[(tetrahydro-2H-pyran-2-yl)oxy]ethyl]-N-[(2-trimethylsilyl)ethoxymethyl][1,1'-biphenyl]-2-sulfonamide 242B (250 mg) was converted to the corresponding methanesulfonate ester according to General Method 3. The entire crude product 242C was used in the next reaction step.

D. 4'-[(2-Butyl-4-oxo-1,3-diazaspiro[4.4]non-1-en-3-yl)methyl]-N-(3,4-dimethyl-5-isoxazolyl)-2'-[2-[(tetrahydro-2H-pyran-2-yl)oxy]ethyl]-N-[(2-trimethylsilyl)ethoxymethyl][1,1'-biphenyl]-2-sulfonamide 242C was used to alkylate 2-butyl-1,3-diazaspiro[4.4]non-1-en-4-one according to General Method 4. The crude 242D was used without further purification.

E. 4'-[(2-Butyl-4-oxo-1,3-diazaspiro[4.4]non-1-en-3-yl)methyl]-N-(3,4-dimethyl-5-isoxazolyl)-2'-(2-hydroxyethyl)[1,1'-biphenyl]-2-sulfonamide 242D was deprotected according to General Method 8 (ethanol). The crude product was purified by silica gel chromatography using 3% methanol in dichloromethane as eluant to provide the title compound (45 mg) as a white solid following lyophilization: MS m/e 579 (ESI+ mode); HPLC retention time 1.42 min (Method H); HPLC purity >98%.

Example 243

4'-[(2-Butyl-4-oxo-1,3-diazaspiro[4.4]non-1-en-3-yl)methyl]-N-(3,4-dimethylisoxazol-5-yl)-2'-(3-methylbutyl)[1,1'-biphenyl]-2-sulfonamide

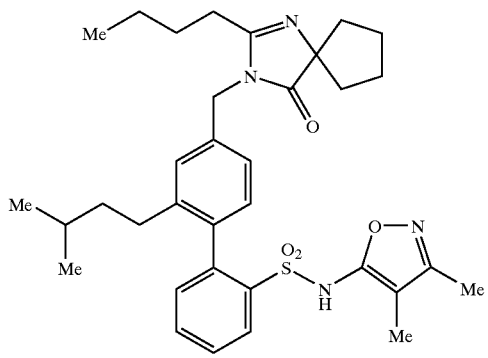

A. 4-Bromo-3-(3-methyl-1-butenyl)benzonitrile 2A (2.0 g, 9.5 mmol) was reacted with isobutyltriphenylphosphonium bromide following the procedure of Example 27, step A. The crude residue was chromatographed on silica gel using 9:1 hexanes/ethyl acetate to afford 243A (2.2 g, 91%) as an E/Z mixture.

B. 4-Bromo-3-(3-methylbutyl)benzonitrile

A mixture of 243A (2.2 g) and 220 mg of $PtO_2$ in 30 ml EtOH was hydrogenated at 35 PSI for 20 min. Filtration and concentration gave 1.9 g of 243B (86%).

C. 4-Bromo-3-(3-methylbutyl)benzaldehyde 243B (1.9 g) was treated with DIBAL-H according to General Method 14 to provide crude 243C (810 mg, 43%) as an oil.

D. N-(3,4-Dimethyl-5-isoxazolyl)-4'-formyl-2'-(3-methylbutyl)-N-[(2-methoxyethoxy)methyl][1,1'-biphenyl]-2-sulfonamide 243C (810 mg) was subjected to Suzuki coupling according to General Method 1 to provide 243D as a crude oil.

E. N-(3,4-Dimethyl-5-isoxazolyl)-4'-hydroxymethyl-2'-(3-methylbutyl)-N-[(2-methoxyethoxy)methyl][1,1'-biphenyl]-2-sulfonamide 243D (entire sample) was reduced with sodium borohydride in methanol according to General Method 11 to provide 243E (490 mg, 30% from 243C) as an oil following silica gel chromatography using hexanes/ethyl acetate as eluant.

F. 4'-Bromomethyl-N-(3,4-dimethyl-5-isoxazolyl)-2'-(3-methylbutyl)-N-[(2-methoxyethoxy)methyl][1,1'-biphenyl]-2-sulfonamide 243E (490 mg) was converted to the corresponding bromide according to General Method 2 to provide 243F (430 mg, 78%) as an oil following silica gel chromatography using hexanes/ethyl acetate as eluant.

G. 4'-[(2-Butyl-4-oxo-1,3-diazaspiro[4.4]non-1-en-3-yl)methyl]-2'-(3-methylbutyl)-N-[(2-methoxyethoxy)methyl]-N-(3,4-dimethyl-5-isoxazolyl)[1,1'-biphenyl]-2-sulfonamide 243F (430 mg) was used to alkylate 2-butyl-1,3-diazaspiro[4.4]non-1-en-4-one according to General Method 4. 243G (300 mg, 58%) was produced as an oil following silica gel chromatography using hexanes/ethyl acetate as eluant.

H. 4'-[(2-Butyl-4-oxo-1,3-diazaspiro[4.4]non-1-en-3-yl)methyl]-N-(3,4-dimethylisoxazol-5-yl)-2'-(3-methylbutyl)[1,1'-biphenyl]-2-sulfonamide 243G was deprotected according to General Method 7. The crude product was purified by reverse-phase preparative HPLC to provide the title compound (165 mg, 63%) as a white solid: mp 50–53° C.; MS m/e 605 (ESI+ mode); HPLC retention time 27.42 min (Method B); HPLC purity >97%.

Example 244

4'-[(2-Butyl-4-oxo-1,3-diazaspiro[4.4]non-1-en-3-yl)methyl]-N-(3,4-dimethylisoxazol-5-yl)-2'-(2-methypropyl)[1,1'-biphenyl]-2-sulfonamide

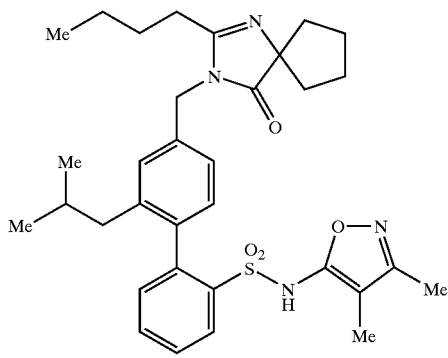

A. 4-[(2-Methyl-2-propenyl)oxy]benzonitrile

A mixture of 4-cyanophenol (9.0 g, 75 mmol), potassium carbonate (21 g, 150 mmol), and DMF (50 ml) was treated with methallyl bromide (7.8 ml, 77 mmol) at 0° C. The mixture was stirred at RT for 16 h, then was added to water and extracted with ethyl acetate (3×100 ml). The combined organic extracts were washed with water and dried and evaporated to give 244A (13 g, 99%) as an oil.

B. 4-Cyano-2-(2-methyl-2-propenyl)phenol

A solution of 244A (13 g, 75 mmol) and BHT (165 mg) in 1,2,4-trichlorobenzene (40 ml) was heated at 200° C. for 5 days. The mixture was cooled and diluted with ethyl acetate, then the organic layer was extracted with 10% NaOH solution (3×200 ml). The aqueous phase was made acidic with hydrochloric acid and extracted with ether (3×100 ml). The combined ether extracts were washed with water and dried and evaporated. The residue was chromatographed on silica gel using 9:1 hexanes/ethyl acetate to afford 244C (5.8 g, 45%) as a solid.

C. 4-Cyano-2-(2-methylpropyl)phenol

A mixture of 244B (1.1 g) and 110 mg of PtO₂ in 20 ml EtOH was hydrogenated at 35 PSI for 15 min. Filtration and concentration gave 0.73 g of 244C (66%).

D. 4-Hydroxy-3-(2-methylpropyl)benzaldehyde 244C (0.73 g) was treated with DIBAL-H according to General Method 14 to provide crude 244D (530 mg, 72%) as an oil.

E. 3-(2-Methylpropyl)-4-(trifluoromethanesulfonyloxy)benzaldehyde 244D (530 mg) was converted to the corresponding trifluoromethanesulfonate ester according to the procedure of Example 229, step E. The residue was chromatographed on silica gel using 4:1 hexanes/ethyl acetate to give 244E (295 mg, 33%) as an oil.

F. N-(3,4-Dimethyl-5-isoxazolyl)-4'-formyl-2'-(2-methylpropyl)-N-[(2-methoxyethoxy)methyl][1,1'-biphenyl]-2-sulfonamide Suzuki coupling of 244E (295 mg) according to the procedure of Example 229, step F, provided 244F (170 mg, 36%) as a yellow solid following silica gel chromatography using hexanes/ethyl acetate as eluant.

G. N-(3,4-Dimethyl-5-isoxazolyl)-4'-hydroxymethyl-2'-(2-methylpropyl)-N-[(2-methoxyethoxy)methyl][1,1'-biphenyl]-2-sulfonamide 244F (170 mg) was reduced with sodium borohydride in methanol according to General Method 11 to provide 244G (67 mg, 39%) as an oil.

H. 4'-Bromo-methyl-N-(3,4-dimethyl-5-isoxazolyl)-2'-(2-methylpropyl)-N-[(2-methoxyethoxy)methyl][1,1'-biphenyl]-2-sulfonamide 244G (67 mg) was converted to the corresponding bromide according to General Method 2 to provide 244H (42 mg, 56%) as an oil.

I. 4'-[(2-Butyl-4-oxo-1,3-diazaspiro[4.4]non-1-en-3-yl)methyl]-2'-(2-methylpropyl)-N-[(2-methoxyethoxy)methyl]-N-(3,4-dimethyl-5-isoxazolyl)[1,1'-biphenyl]-2-sulfonamide 244H (42 mg) was used to alkylate 2-butyl-1,3-diazaspiro[4.4]non-1-en-4-one according to General Method 4. 244I (36 mg, 45%) was produced as an oil following silica gel chromatography using hexanes/ethyl acetate as eluant.

J. 4'-[(2-Butyl-4-oxo-1,3-diazaspiro[4.4]non-1-en-3-yl)methyl]-2'-(2-methylpropyl)-N-(3,4-dimethyl-5-isoxazolyl)[1,1'-biphenyl]-2-sulfonamide 244I (36 mg) was deprotected according to General Method 7. The crude product was purified by reverse-phase preparative HPLC to provide the title compound (25 mg, 86%) as a white solid: mp 58–61° C.; MS m/e 591 (ESI+ mode); HPLC retention time 28.21 min (Method B); HPLC purity >98%.

Example 245

4'-[[2-(3,3-Difluorobutyl)-4-oxo-1,3-diazaspiro[4.4]non-1-en-3-yl]methyl]-N-(3,4-dimethylisoxazol-5-yl)-2'-(ethoxymethyl)[1,1'-biphenyl]-2-sulfonamide

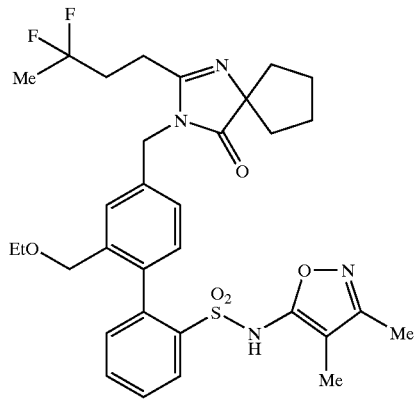

A. Methyl 1-[(3,3-difluorobutanoyl)amino]cyclopentane-1-carboxylate

A solution of 4,4-Difluoropentanoic acid (600 mg, 4.4 mmol, prepared according to Larsson, U.; Carlson, R.; Leroy, J. Acta Chem. Scand. 1993, 47, 380–90) in dichloromethane (10 ml) was treated at RT with oxalyl chloride (4.4 ml of a 2.0 M solution in dichloromethane, 8.8 mmol) and DMF (10 µl). After 20 min the mixture was evaporated and 10 ml fresh dichloromethane was added. The mixture was cooled to 0° C. and methyl 1-aminocyclopentane-1-carboxylate hydrochloride (1.6 g, 8.8 mmol) was added, followed by triethylamine (3.6 ml, 26 mmol) and DMAP (10 mg). The mixture was stirred at RT for 3 hours. Aqueous sodium bicarbonate solution was added and the mixture was extracted three times with dichloromethane. The combined organic extracts were dried over sodium sulfate and concentrated. The residue was chromatographed on silica gel using 1:2 hexanes/ethyl acetate as eluant to give 245A (520 mg, 46%) as an orange oil.

B. 2-(3,3-Difluorobutyl)-1,3-diazaspiro[4.4]non-1-en-4-one 245A (520 mg, 2.0 mmol) was treated according to the procedure of Example 22, step B. The crude residue was chromatographed on silica gel using 1:3 hexanes/ethyl acetate as eluant to yield 245B (150 mg, 33%) as a yellow oil.

C. 4'-[[2-(3,3-Difluorobutyl)-4-oxo-1,3-diazaspiro[4.4]non-1-en-3-yl]methyl]-N-(3,4-dimethylisoxazol-5-yl)-2'-(ethoxymethyl)-N-(2-methoxyethoxy)methyl[1,1'-biphenyl]-2-sulfonamide 245B (75 mg, 0.42 mmol) was alkylated with 4'-bromomethyl-N-(3,4-dimethyl-5-isoxazolyl)-2'-ethoxymethyl-N-(2-methoxyethoxy)methyl[1,1'-biphenyl]-2-sulfonamide (prepared as described in Example 226) according to General Method 4. Crude 245C (220 mg) was used without further purification.

D. 4'-[[2-(3,3-Difluorobutyl)-4-oxo-1,3-diazaspiro[4.4]non-1-en-3-yl]methyl]-N-(3,4-N-(3,4-dimethylisoxazol-5-yl)-2'-(ethoxymethyl)[1,1-biphenyl]-2-sulfonamide 245C (220 mg) was deprotected according to General Method 8 (EtOH). The crude product was purified by preparative thin-layer silica gel chromatography using 1:1 hexanes/acetone to proviode the title compound (57 mg) as a white lyophilized powder; MS m/e 629 (ESI+ mode); HPLC retention time 3.79 min (Method A); HPLC purity 96%.

Example 246

N-(3,4-Dimethyl-5-isoxazolyl)-4'-[[(3-methoxy-2,6-dimethyl-4-pyridinyl)oxy]methyl]-2'-(3,3,3-trifluoropropyl)[1,1'-biphenyl]-2-sulfonamide

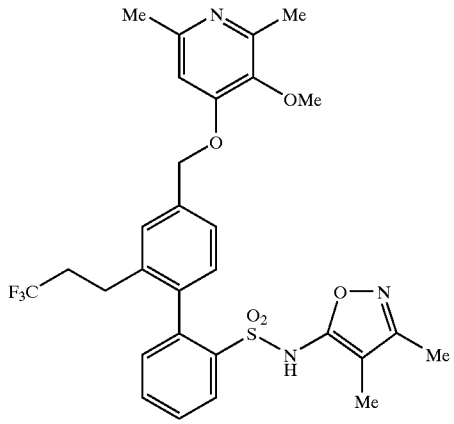

A. N-(3,4-Dimethyl-5-isoxazolyl)-4'-[[(3-methoxy-2,6-dimethyl-4-pyridinyl)oxy]methyl]-2'-(3,3,3-trifluoropropyl)-N-[(2-trimethylsilyl)ethoxymethyl][1,1'-biphenyl]-2-sulfonamide 229H (400 mg, 0.60 mmol) was used to alkylate 3-methoxy-2,6-dimethyl-4-(4H)-pyridinone according to General Method 22. The crude product was purified by silica gel chromatography using 1:2 hexanes/ethyl acetate as eluant to provide 246A (130 mg) as a slightly yellow oil.

B. N-(3,4-Dimethyl-5-isoxazolyl)-4'-[[(3-methoxy-2,6-dimethyl-4-pyridinyl)oxy]methyl]-2'-(3,3,3-trifluoropropyl)[1,1'-biphenyl]-2-sulfonamide 246A (130 mg, 0.18 mmol) was deprotected according to General Method 8 (EtOH). The crude product was purified by silica gel chromatography using 5% methanol in chloroform as eluant to provide the title compound (82 mg) as a pale orange powder after lyophilization; MS m/e 590 (ESI+ mode); HPLC retention time 3.35 min (Method A); HPLC purity 97%.

Example 247

4'-[(2-Butyl-4-oxo-1,3-diazaspiro[4.4]non-1-en-3-yl)methyl]-N-(3,4-dimethylisoxazol-5-yl)-2'-[(1,1-dimethylethoxy)methyl][1,1'-biphenyl]-2-sulfonamide

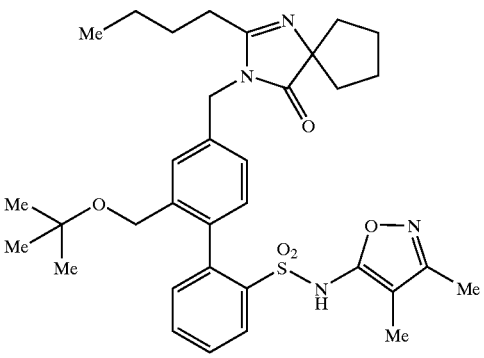

A. Methyl 4-bromo-3-[(1,1-dimethylethoxy)methyl]benzoate

To a solution of 240A (4.90 g, 20 mmol) in 40 ml cyclohexane and 20 ml dichloromethane was added t-butyl 2,2,2-trichloroacetimidate (4.81 g, 22 mmol) followed by 0.4 ml boron trifluoride diethyl etherate. The mixture was stirred at RT for 4 hours. 1 g solid sodium bicarbonate was added and the mixture was stirred for 10 min. The mixture was chromatographed directly on silica gel eluting with 20:1 hexanes/ethyl acetate to give compound 247A as an oil (5.33 g, 88%).

B. N-(3,4-Dimethyl-5-isoxazolyl)-2'-[(1,1-dimethylethoxy)methyl]-4'-methoxycarbonyl-N-[(2-trimethylsilyl)ethoxymethyl][1,1'-biphenyl]-2-sulfonamide 247A (5.3 g, 17.5 mmol) was subjected to Suzuki coupling according to General Method 1. Silica gel chromatography using hexanes/ethyl acetate as eluant provided 247B (6.4 g, 88%) as an oil.

C. N-(3,4-Dimethyl-5-isoxazolyl)-2'-[(1,1-dimethylethoxy)methyl]-4'-hydroxymethyl-N-(2-trimethylsilyl)ethoxymethyl][1,1'-biphenyl]-2-sulfonamide 247B (6.4 g, 10.7 mmol) was reduced with DIBAL-H according to the procedure of Example 230, step E, to provide crude 247C (5.5 g, 89%) as an orange oil.

D. 4'-Bromomethyl-N-(3,4-dimethyl-5-isoxazolyl)-2'-[(1,1-dimethylethoxy)methyl]-N-[(2-trimethylsilyl)ethoxymethyl][1,1'-biphenyl]-2-sulfonamide 247C (5.5 g, 9.6 mmol) was converted to the corresponding bromide according to General Method 2, providing 247D (5.6 g, 92%) as a yellow oil following silica gel chromatography using hexanes/ethyl acetate as eluant.

E. 4'-[(2-Butyl-4-oxo-1,3-diazaspiro[4.4]non-1-en-3-yl)methyl]-N-(3,4-dimethyl-5-isoxazolyl)-2'-[(1,1-dimethylethoxy)methyl]-N-[(2-trimethylsilyl)ethoxymethyl][1,1'-biphenyl]-2-sulfonamide 247D (380 mg, 0.60 mmol) was used to alkylate 2-butyl-1,3-diazaspiro[4.4]non-1-en-4-one according to General Method 4. The crude residue was chromatographed on silica gel using hexanes/ethyl acetate as eluant to provide 247E (410 mg, 92%) as a slightly yellow oil.

E. 4'-[(2-Butyl-4-oxo-1,3-diazaspiro[4.4]non-1-en-3-yl)methyl]-N-(3,4-dimethyl-5-isoxazolyl)-2'-[(1,1-dimethylethoxy)methyl][1,1'-biphenyl]-2-sulfonamide 247E (410 mg, 0.55 mmol) was deprotected with TBAF according to General Method 10. The crude product was purified by reverse-phase preparative HPLC to provide the title compound (230 mg, 66%) as a white solid: MS m/e 621 (ESI+ mode); HPLC retention time 20.97 min (Method E); HPLC purity 96%.

| EXAMPLE | STRUCTURE | NAME | STARTING MATERIAL | General Methods Applied (yield, %) | M/z (MH)+ | HPLC % Purity | HPLC ret time, min (method) |
|---|---|---|---|---|---|---|---|
| 248 | 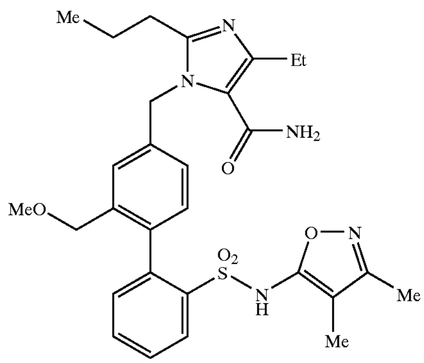 | 1-[[2'-[[(3,4-dimethyl-5-isoxazolyl)-amino]sulfonyl-2-methoxymethyl][1,1'-byphenyl]-4-yl]methyl]-4-ethyl-2-propyl-1H-imidazole-5-carboxamide | P2 | 22 (39); 8, EtOH, 15 (96); 12 (38) | 566 | 95 | 2.79 (C) |
| 249 | 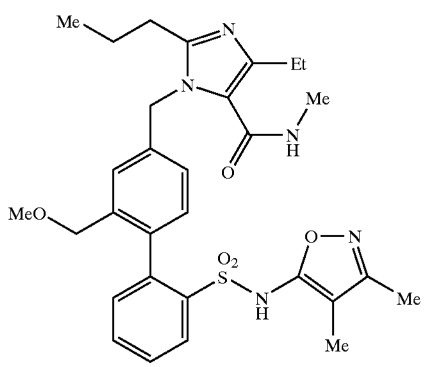 | 1-[[2'-[[(3,4-dimethyl-5-isoxazolyl)-amino]sulfonyl-2-methoxymethyl][1,1'-byphenyl]-4-yl]methyl]-4-ethyl-N-methyl-2-propyl-1H-imidazole-5-carboxamide | P2 | 22 (39); 8, EtOH, 15 (96); 12 (34) | 580 | 96 | 2.90 (C) |
| 250 | 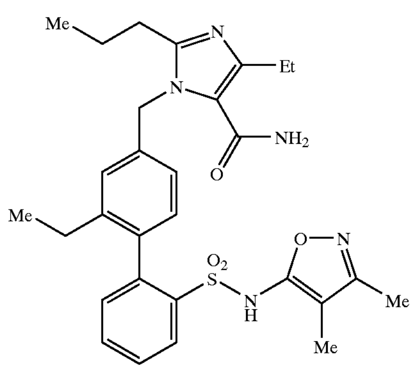 | 1-[[2'-[[(3,4-dimethyl-5-isoxazolyl)-amino]sulfonyl-2-methyl][1,1'-byphenyl]-4-yl]methyl]-4-ethyl-2-propyl-1H-imidazole-5-carboxamide | P13 | 22 (56); 8, EtOH, 15 (94); 12 (38) | 536 | 95 | 2.90 (C) |
| 251 | 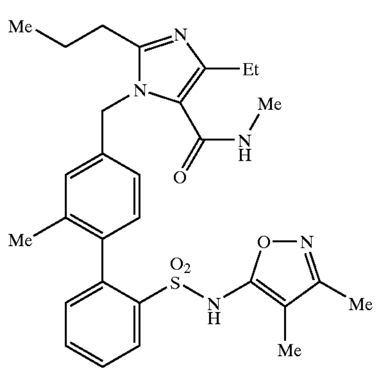 | 1-[[2'-[[(3,4-dimethyl-5-isoxazolyl)-amino]sulfonyl-2-methyl][1,1'-byphenyl]-4-yl]methyl]-4-ethyl-N-methyl-2-propyl-1H-imidazole-5-carboxamide | P13 | 22 (56); 8, EtOH, 15 (94); 12 (37) | 550 | 97 | 2.99 (C) |

Example 252

N-(4,5-Dimethyl-3-isoxazolyl)-2'-ethoxymethyl-4'-[[(3-methoxy-2,6-dimethyl-4-pyridinyl)oxy]methyl][1,1'-biphenyl]-2-sulfonamide

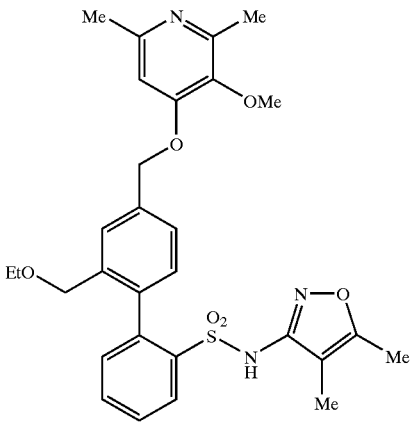

A. 4-Bromo-3-(ethoxymethyl)benzonitrile

P2A (8.7 g, 32 mmol) was treated with sodium hydride and ethanol according to General Method 4, producing crude 252A (5.8 g, 77%) as an oil.

B. 4-Bromo-3-(ethoxymethyl)benzaldehyde

Crude 252A (5.8 g, 24 mmol) was reduced with DIBAL-H according to General Method 14, yielding 252B (4.7 g, 80%) as an oil following silica gel chromatography with hexanes/ethyl acetate as eluant.

C. N-(4,5-Dimethyl-3-isoxazolyl)-2'-ethoxymethyl-4'-formyl-N-[(2-methoxyethoxy)methyl][1,1'-biphenyl]-2-sulfonamide 252B (800 mg, 3.3 mmol) was subjected to Suzuki coupling with [2-[[(4,5-dimethyl-3-isoxazolyl)[(2-methoxyethoxy)methyl]amino]-sulfonyl]phenyl]boronic acid according to General Method 1. 252C (1.2 g, 70%) was obtained as an orange oil following silica gel chromatography using hexanes/ethyl acetate as eluant.

D. N-(4,5-Dimethyl-3-isoxazolyl)-2'-ethoxymethyl-4'-hydroxymethyl-N-[(2-methoxyethoxy)methyl][1,1'-biphenyl]-2-sulfonamide 252C (1.2 g, 2.3 mmol) was reduced with sodium borohydride in methanol according to General Method 11 to provide crude 252D. This material was used without further purification.

E. 4'-Bromomethyl-N-(4,5-dimethyl-3-isoxazolyl)-2'-ethoxymethyl-N-[(2-methoxyethoxy)methyl][1,1'-biphenyl]-2-sulfonamide 252D (entire sample) was converted to the corresponding bromide according to General Method 2. 252E (1.1 g, 84% over two steps) was obtained as an oil following silica gel chromatography using hexanes/ethyl acetate as eluant.

F. N-(4,5-Dimethyl-3-isoxazolyl)-2'-ethoxymethyl-4'-[[(3-methoxy-2,6-dimethyl-4-pyridinyl)oxy]methyl]-N-[(2-methoxyethoxy)methyl][1,1'-biphenyl]-2-sulfonamide 252E (360 mg, 0.63 mmol) was used to alkylate 3-methoxy-2,6-dimethyl-4-(1H)-pyridinone according to General Method 22. 252F (310 mg, 76%) was produced as an oil following silica gel chromatography using hexanes/ethyl acetate as eluant.

G. N-(4,5-Dimethyl-3-isoxazolyl)-2'-ethoxymethyl-4'-[[(3-methoxy-2,6-dimethyl-4-pyridinyl)oxy]methyl][1,1'-biphenyl]-2-sulfonamide 252F (310 mg, 0.49 mmol) was deprotected according to General Method 7. The crude product was purified by silica gel column chromatography using methanol/dichloromethane as eluant to provide the title compound (240 mg, 91%) as a light yellow solid: mp 78–82° C.; MS m/e 552 (ESI+ mode); HPLC retention time 12.42 min (Method E); HPLC purity 97%.

Example 253

4'-[(2-Butyl-4-oxo-1,3-diazaspiro[4.4]non-1-en-3-yl)methyl]-N-(4,5-dimethyl-3-isoxazolyl)-2'-(2-fluoroethoxymethyl)[1,1'-biphenyl]-2-sulfonamide

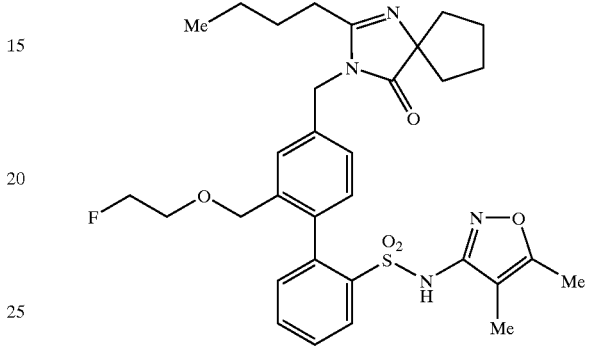

A. 4-Bromo-3-[(2-fluoroethoxy)methyl]benzonitrile

P2A (4.1 g, 15 mmol) was treated with sodium hydride and 2-fluoroethanol according to General Method 4. Water was added to the reaction mixture to precipitate 253A (2.9 g, 75%) as a brown solid.

B. 4-Bromo-3-[(2-fluoroethoxy)methyl]benzaldehyde 253A (2.9 g, 11 mmol) was reduced with DIBAL-H according to General Method 14, yielding 253B (2.5 g) as an oil, which was used without further purification.

C. N-(4,5-Dimethyl-3-isoxazolyl)-2'-[(2-fluoroethoxy)methyl]-4'-formyl-N-[(2-methoxyethoxy)methyl][1,1'-biphenyl]-2-sulfonamide 253B (2.5 g) was subjected to Suzuki coupling with [2-[[(4,5-dimethyl-3-isoxazolyl)[(2-methoxyethoxy)methyl]amino]-sulfonyl]phenyl]boronic acid according to General Method 1. 253C (1.4 g, 23% over two steps) was obtained as an oil following silica gel chromatography using hexanes/ethyl acetate as eluant.

D. N-(4,5-Dimethyl-3-isoxazolyl)-2'-[(2-fluoroethoxy)methyl]-4'-hydroxymethyl-N-[(2-methoxyethoxy)methyl][1,1'-biphenyl]-2-sulfonamide 253C (1.4 g, 2.6 mmol) was reduced with sodium borohydride in methanol according to General Method 11 to provide 253D as an oil. This material was used without further purification.

E. 4'-Bromomethyl-N-(4,5-dimethyl-3-isoxazolyl)-2'-[(2-fluoroethoxy)methyl]-N-[(2-methoxyethoxy)methyl][1,1'-biphenyl]-2-sulfonamide 253D (entire sample) was converted to the corresponding bromide according to General Method 2. 253E (1.3 g, 80% over two steps) was obtained as an oil following silica gel chromatography using hexanes/ethyl acetate as eluant.

F. 4'-[(2-Butyl-4-oxo-1,3-diazaspiro[4.4]non-1-en-3-yl) methyl]-N-(4,5-dimethyl-3-isoxazolyl)-2'-[(2-fluoroethoxy) methyl]-N-[(2-methoxyethoxy)methyl][1,1'-biphenyl]-2-sulfonamide 253E (430 mg) was used to alkylate 2-butyl-1,3-diazaspiro[4.4]non-1-en-4-one according to General Method 4. 253F (400 mg, 78%) was produced as an oil following silica gel chromatography using hexanes/ethyl acetate as eluant.

G. 4'-[(2-Butyl-4-oxo-1,3-diazaspiro[4.4]non-1-en-3-yl) methyl]-N-(4,5-dimethyl-3-isoxazolyl)-2'-[(2-fluoroethoxy) methyl][1,1'-biphenyl]-2-sulfonamide 253F (400 mg, 0.57 mmol) was deprotected according to General Method 7. The crude product was purified by silica gel column chromatography using methanol/ dichloromethane as eluant to provide the title compound (310 mg, 89%) as a white solid: mp 68–73° C.; MS m/e 611 (ESI+ mode); HPLC retention time 16.07 min (Method E); HPLC purity >97%.

Example 254

N-(4,5-Dimethyl-3-isoxazolyl)-2'-[(2-fluoroethoxy) methyl]-4'-[[(3-methoxy-2,6-dimethyl-4-pyridinyl)oxy] methyl][1,1'-biphenyl]-2-sulfonamide

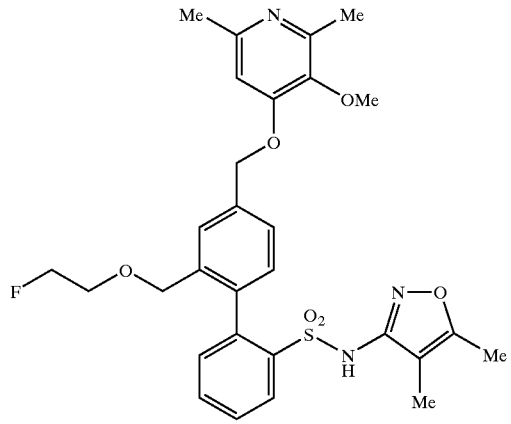

B. N-(4,5-Dimethyl-3-isoxazolyl)-2'-[(2-fluoroethoxy) methyl]-4'-[[(3-methoxy-2,6-dimethyl-4-pyridinyl)oxy] methyl]-N-[(2-methoxyethoxy)methyl][1,1'-biphenyl]-2-sulfonamide 253E (450 mg, 0.77 mmol) was used to alkylate 3-methoxy-2,6-dimethyl-4-(1H)-pyridinone according to General Method 22. The crude product was purified by silica gel chromatography using hexanes/ethyl acetate as eluant to provide 254A (380 mg, 76%) as a slightly yellow oil.

B. N-(4,5-Dimethyl-3-isoxazolyl)-2'-[(2-fluoroethoxy) methyl]-4'-[[(3-methoxy-2,6-dimethyl-4-pyridinyl)oxy] methyl][1,1'-biphenyl]-2-sulfonamide 254A (380 mg, 0.58 mmol) was deprotected according to General Method 7. The crude product was purified by silica gel chromatography using methanol/chloroform as eluant to provide the title compound (310 mg, 93%) as a light yellow solid; mp 81–86° C.; MS m/e 570 (ESI+ mode); HPLC retention time 10.54 min (Method E); HPLC purity >97%.

Example 255

N-(3,4-Dimethyl-5-isoxazolyl)-2'-[(2-fluoroethoxy) methyl]-4'-[[(3-methoxy-2,6-dimethyl-4-pyridinyl)oxy] methyl][1,1'-biphenyl]-2-sulfonamide

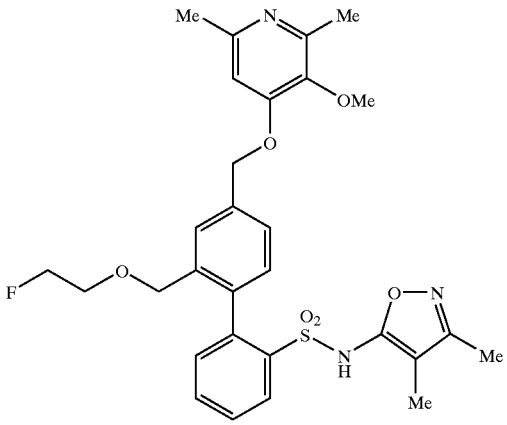

A. N-(3,4-Dimethyl-5-isoxazolyl)-2'-[(2-fluoroethoxy) methyl]-4'-formyl-N-[[(2-trimethylsilyl)ethoxy]methyl][1, 1'-biphenyl]-2-sulfonamide 253B (1.3 g, 4.9 mmol) was subjected to Suzuki coupling with [2-[[(3,4-dimethyl-5-isoxazolyl)[[(2-trimethylsilyl) ethoxy]methyl]amino]-sulfonyl]phenyl]boronic acid according to General Method 1. 255A (2.5 g, 90%) was obtained as an oil following silica gel chromatography using hexanes/ethyl acetate as eluant.

B. N-(3,4-Dimethyl-5-isoxazolyl)-2'-[(2-fluoroethoxy) methyl]-4'-hydroxymethyl-N-[[(2-trimethylsilyl)ethoxy] methyl][1,1'-biphenyl]-2-sulfonamide 255A (2.5 g, 4.4 mmol) was reduced with sodium borohydride in methanol according to General Method 11 to provide 255B as an oil. This material was used without further purification.

C. 4'-Bromomethyl-N-(3,4-dimethyl-5-isoxazolyl)-2'-[(2-fluoroethoxy)methyl]-N-[[(2-trimethylsilyl)ethoxy]methyl] [1,1'-biphenyl]-2-sulfonamide 255B (entire sample) was converted to the corresponding bromide according to General Method 2, furnishing 255C (2.1 g, 76% over two steps) as an oil following silica gel chromatography using hexanes/ethyl acetate as eluant.

D. N-(3,4-Dimethyl-5-isoxazolyl)-2'-[(2-fluoroethoxy) methyl]-4'-[[(3-methoxy-2,6-dimethyl-4-pyridinyl)oxy] methyl]-N-[[(2-trimethylsilyl)ethoxy]methyl][1,1'-biphenyl]-2-sulfonamide 255C (590 mg, 0.93 mmol) was used to alkylate 3-methoxy-2,6-dimethyl-4-(1H)-pyridinone according to General Method 22. 255D (290 mg, 44%) was produced as an oil following silica gel chromatography using hexanes/ ethyl acetate as eluant.

E. N-(3,4-Dimethyl-5-isoxazolyl)-2'-[(2-fluoroethoxy) methyl]-4'-[[(3-methoxy-2,6-dimethyl-4-pyridinyl)oxy] methyl][1,1'-biphenyl]-2-sulfonamide 255D was deprotected according to General Method 7. The crude product was purified by silica gel column chromatography using methanol/dichloromethane as eluant to provide the title compound (180 mg, 75%) as a white solid: mp 90–95° C.; MS m/e 570 (ESI+ mode); HPLC retention time 10.71 min (Method E); HPLC purity >97%.

Example 256

N-(3,4-Dimethyl-5-isoxazolyl)-2'-ethoxymethyl-4'-[[4-oxo-2-(3,3,3-trifluoropropyl)-1,3-diazaspiro[4.4]non-1-en-3-yl]methyl][1,1'-biphenyl]-2-sulfonamide

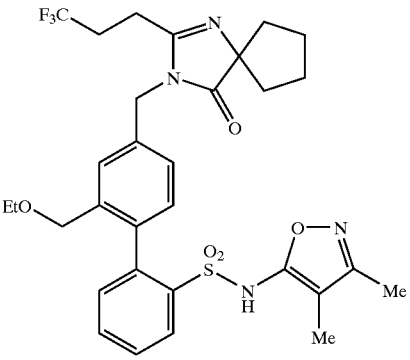

A. Methyl 1-[(4,4,4-trifluorobutanoyl)amino]cyclopentane-1-carboxylate

A solution of 4,4,4-trifluorobutanoic acid (5.0 g, 35 mmol) in dichloromethane (90 ml) was treated at 0° C. with oxalyl chloride (26 ml of a 2.0 M solution in dichloromethane, 52 mmol) and DMF (10 µl). After 20 min the mixture was concentrated to a volume of about 10 ml and 90 ml fresh dichloromethane was added. The mixture was cooled to 0° C. and methyl 1-aminocyclopentane-1-carboxylate hydrochloride (12.6 g, 70 mmol) was added, followed by triethylamine (30 ml, 210 mmol) and DMAP (10 mg). The mixture was stirred at RT for 60 hours. Aqueous sodium bicarbonate solution was added and the mixture was extracted three times with dichloromethane. The combined organic extracts were dried over sodium sulfate and concentrated. The residue was chromatographed on silica gel using 1:1 hexanes/ethyl acetate as eluant to give 256A (3.1 g, 33%) as an orange oil.

B. 2-(3,3,3-Trifluoropropyl)-1,3-diazaspiro[4.4]non-1-en-4-one

256A (3.1 g, 12 mmol) was treated according to the procedure of Example 22, step B. Evaporation of the crude extract provided 256B (2.0 g, 71%) as a white solid, which was used without further purification.

C. N-(3,4-Dimethyl-5-isoxazolyl)-2'-ethoxymethyl-4'-formyl-N-[[(2-trimethylsilyl)ethoxy]methyl][1,1'-biphenyl]-2-sulfonamide

252B (7.6 g, 31 mmol) was subjected to Suzuki coupling with [2-[[(3,4-dimethyl-5-isoxazolyl)[[(2-trimethylsilyl)ethoxy]methyl]amino]-sulfonyl]phenyl]boronic acid according to General Method 1. 256C (12.3 g, 72%) was obtained as an oil following silica gel chromatography using hexanes/ethyl acetate as eluant.

D. N-(3,4-Dimethyl-5-isoxazolyl)-2'-ethoxymethyl-4'-hydroxymethyl-N-[[(2-trimethylsilyl)ethoxy]methyl][1,1'-biphenyl]-2-sulfonamide

256C (1.0 g, 1.8 mmol) was reduced with sodium borohydride in ethanol according to General Method 11 to provide 256D (0.97 g, 95%) as a crude brown oil, which was used without further purification.

E. N-(3,4-Dimethyl-5-isoxazolyl)-2'-ethoxymethyl-4'-(methanesulfonyloxy)methyl-N-[[(2-trimethylsilyl)ethoxy]methyl][1,1'-biphenyl]-2-sulfonamide

256D (490 mg) was converted to the corresponding mesylate according to General Method 3 to provide 256E (560 mg) as crude orange oil.

F. N-(3,4-dimethyl-5-isoxazolyl)-2'-ethoxymethyl-4'-[[4-oxo-2-(3,3,3-trifluoropropyl)-1,3-diazaspiro[4.4]non-1-en-3-yl]methyl]-N-[[(2-trimethylsilyl)ethoxy]methyl][1,1'-biphenyl]-2-sulfonamide

256E (560 mg) was used to alkylate 256B (270 mg) according to General Method 4. 256F (570 mg) was produced as a crude brown oil, which was used without further purification.

G. N-(3,4-Dimethyl-5-isoxazolyl)-2'-ethoxymethyl-4'-[[4-oxo-2-(3,3,3-trifluoropropyl)-1,3-diazaspiro[4.4]non-1-en-3-yl]methyl][1,1'-biphenyl]-2-sulfonamide

256F (570 mg) was deprotected according to General Method 8 (EtOH). The crude product was purified by silica gel column chromatography using 2:1 hexanes/ethyl acetate as eluant to provide the title compound (92 mg, 8% from 256D) as a white solid: MS m/e 633 (ESI+ mode); HPLC retention time 3.96 min (Method C); HPLC purity 97%

Example 257

4'-[(2-Butyl-4-oxo-1,3-diazaspiro[4.4]non-1-en-3-yl)methyl]-N-(3,4-dimethyl-5-isoxazolyl)-2'-ethyl[1,1'-biphenyl]-2-sulfonamide

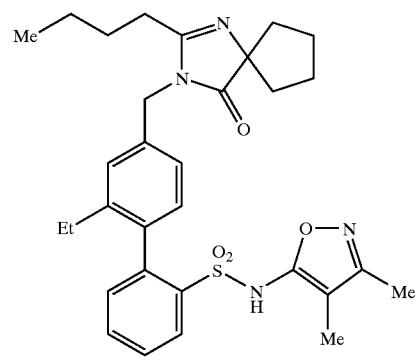

A. Methyl 4-bromo-3-ethylbenzoate

Methyllithium (57 ml of a 1.4 M solution in ether, 80 mmol) was added dropwise to a suspension of copper(I) iodide (76 g, 40 mmol) in ether (20 ml) at 0° C. The mixture was stirred for 20 min at 0° C. Solid 232A (12.3 g, 40 mmol) was added in portions over 45 min, after which THF (50 ml) was added. The heterogeneous mixture was stirred at 0° C. for 1 h, then aqueous ammonium chloride and aqueous ammonium hydroxide were added. The mixture was extracted with ethyl acetate, and the combined organic layers were concentrated. The residue was taken up in chloroform and partitioned against aqueous ammonium chloride. The chloroform layer was dried over sodium sulfate and concentrated, and the residue was chromatographed on silica gel, eluting with 9:1 hexanes/ethyl acetate, to provide 257A (3.2 g, 32%) as a yellow oil.

B. N-(3,4-Dimethyl-5-isoxazolyl)-2'-ethyl-4'-methoxycarbonyl-N-[[(2-trimethylsilyl)ethoxy]methyl][1,1'-biphenyl]-2-sulfonamide

257A (1.4 g, 5.6 mmol) was subjected to Suzuki coupling with [2-[[(3,4-dimethyl-5-isoxazolyl)[[(2-trimethylsilyl)ethoxy]methyl]amino]-sulfonyl]phenyl]boronic acid according to General Method 1. Silica gel chromatography provided 257B (3.2 g) as an oil, contaminated with byproducts deriving from the boronic acid.

C. N-(3,4-Dimethyl-5-isoxazolyl)-2'-ethyl-4'-hydroxymethyl-N-[[(2-trimethylsilyl)ethoxy]methyl][1,1'-biphenyl]-2-sulfonamide

257B (3.2 g) was treated with DIBAL-H according to the procedure of Example 230, step E, to provide 257C (4.0 g) as a crude oil.

D. N-(3,4-Dimethyl-5-isoxazolyl)-2'-ethyl-4'-(methanesulfonyloxy)methyl-N-[[(2-trimethylsilyl)ethoxy]methyl][1,1'-biphenyl]-2-sulfonamide 257C (4.0 g) was converted to the corresponding mesylate according to General Method 3 to provide 257D (3.7 g) as crude orange oil.

E. 4'-[[2-Butyl-4-oxo-1,3-diazaspiro[4.4]non-1-en-3-yl]methyl]-N-(3,4-dimethyl-5-isoxazolyl)-2'-ethyl-N-[[(2-trimethylsilyl)ethoxy]methyl][1,1'-biphenyl]-2-sulfonamide 257D (0.92 g) was used to alkylate 2-butyl-1,3-diazaspiro[4.4]non-1-en-4-one according to General Method 4. 257E (760 mg) was produced as a colorless oil following silica gel chromatography using 2:1 hexanes/ethyl acetate as eluant.

F. 4'-[(2-Butyl-4-oxo-1,3-diazaspiro[4.4]non-1-en-3-yl)methyl]-N-(3,4-dimethyl-5-isoxazolyl)-2'-ethyl[1,1'-biphenyl]-2-sulfonamide 257D (760 mg) was deprotected according to General Method 8 (EtOH). The crude product was purified by reverse-phase preparative HPLC to provide the title compound (200 mg) as a white solid following lyophilization: MS m/e 563 (ESI+ mode); HPLC retention time 3.69 min (Method C); HPLC purity >98%

Example 258

(+/−)-4'-[(2-Butyl-4-oxo-1,3-diazaspiro[4.4]non-1-en-3-yl)methyl]-N-(3,4-dimethyl-5-isoxazolyl)-2'-(1-hydroxyethyl)[1,1'-biphenyl]-2-sulfonamide

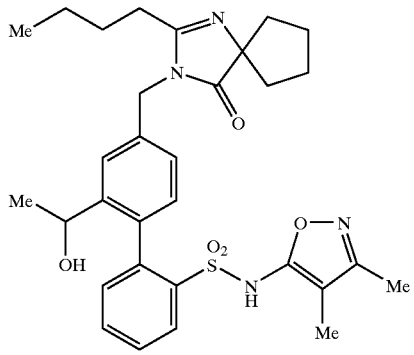

A. 4'-[(2-Butyl-4-oxo-1,3-diazaspiro[4.4]non-1-en-3-yl)methyl]-N-(3,4-dimethyl-5-isoxazolyl)-2'-formyl-N-[(2-trimethylsilyl)ethoxymethyl][1,1'-biphenyl]-2-sulfonamide 23A (600 mg, 1.0 mmol) was used to alkylate 2-butyl-1,3-diazaspiro[4.4]non-1-en-4-one according to General Method 4. 258A (510 mg, 74%) was produced as a yellow oil following silica gel chromatography using 1:1 hexanes/ethyl acetate as eluant.

B. (+/−)-4'-[(2-Butyl-4-oxo-1,3-diazaspiro[4.4]non-1-en-3-yl)methyl]-N-(3,4-dimethyl-5-isoxazolyl)-2'-(1-hydroxyethyl)-N-[(2-trimethylsilyl)ethoxymethyl][1,1'-biphenyl]-2-sulfonamide A solution of 258A (260 mg, 0.37 mmol) in dry ether (1 ml) was treated dropwise at −78° C. with methylmagnesium bromide (3.0 M solution in ether, 0.25 ml, 0.74 mmol). The mixture was allowed to warm to 0° C. and was then quenched with aqueous ammonium chloride. The mixture was extracted with ether. The combined organic extracts were dried over magnesium sulfate and concentrated to provide 258B (210 mg) as a colorless oil, which was used without further purification.

C. (+/−)-4'-[(2-Butyl-4-oxo-1,3-diazaspiro[4.4]non-1-en-3-yl)methyl]-N-(3,4-dimethyl-5-isoxazolyl)-2'-(1-hydroxyethyl)[1,1'-biphenyl]-2-sulfonamide 258B (210 mg) was deprotected according to General Method 8 (EtOH). The crude product was purified by preparative thin-layer silica gel chromatography using 9:1 chloroform/methanol as eluant to provide the title compound (6 mg, 3% from 258A) as a white solid: MS m/e 579 (ESI+ mode); HPLC retention time 3.07 and 3.40 min (Method A; product appears as two peaks); HPLC purity 92%.

Example 259

4'-[(2-Butyl-4-oxo-1,3-diazaspiro[4.4]non-1-en-3-yl)methyl]-N-(4,5-dimethyl-3-isoxazolyl)-2'-propyl[1,1'-biphenyl]-2-sulfonamide

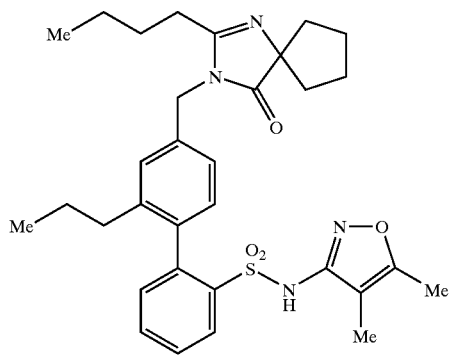

A. N-(4,5-Dimethyl-3-isoxazolyl)-4'-formyl-N-methoxymethyl-2'-propyl[1,1'-biphenyl]-2-sulfonamide 27C (570 mg, 2.5 mmol) was subjected to Suzuki coupling with [2-[[(4,5-dimethyl-3-isoxazolyl)(methoxymethyl)amino]-sulfonyl]phenyl]boronic acid according to General Method 1. 259A (1.1 g) was obtained as an impure yellow oil following silica gel chromatography using 4:1 hexanes/ethyl acetate.

B. N-(4,5-Dimethyl-3-isoxazolyl)-4'-hydroxymethyl-N-methoxymethyl-2'-propyl[1,1'-biphenyl]-2-sulfonamide 259A (1.1 g) was reduced with sodium borohydride in methanol according to General Method 11. 259B (520 mg, 47% over two steps) was obtained as an oil following silica gel chromatography with 1:1 hexanes/ethyl acetate as eluant.

C. 4'-Bromomethyl-N-(4,5-dimethyl-3-isoxazolyl)-N-methoxymethyl-2'-propyl[1,1'-biphenyl]-2-sulfonamide 259B (520 mg, 1.2 mmol) was converted to the corresponding bromide according to General Method 2, providing 259C (425 mg, 71%) as a yellow solid following silica gel chromatography using 9:1 hexanes/ethyl acetate as eluant.

D. 4'-[(2-Butyl-4-oxo-1,3-diazaspiro[4.4]non-1-en-3-yl)methyl]-N-(4,5-dimethyl-3-isoxazolyl)-N-methoxymethyl-2'-propyl[1,1'-biphenyl]-2-sulfonamide 259C (800 mg, 1.6 mmol) was used to alkylate 2-butyl-1,3-diazaspiro[4.4]non-1-en-4-one according to General Method 4. 259D (720 mg) was obtained as a crude oil, which was used without further purification.

E. 4'-[(2-Butyl-4-oxo-1,3-diazaspiro[4.4]non-1-en-3-yl)methyl]-N-(4,5-dimethyl-3-isoxazolyl)-2'-propyl[1,1'-biphenyl]-2-sulfonamide 259D (720 mg) was deprotected according to General Method 7. The crude product was purified by silica gel column chromatography using 1:1 hexanes/ethyl acetate as eluant to provide the title compound (390 mg, 42% over two steps) as a white solid: mp 64–66° C.; MS m/e 577 (ESI+ mode); HPLC retention time 30.78 min (Method B); HPLC purity >98%.

Example 260

N-(4,5-Dimethyl-3-isoxazolyl)-4'-[[(3-methoxy-2,6-dimethyl-4-pyridinyl)oxy]methyl]-2'-propyl[1,1'-biphenyl]-2-sulfonamide

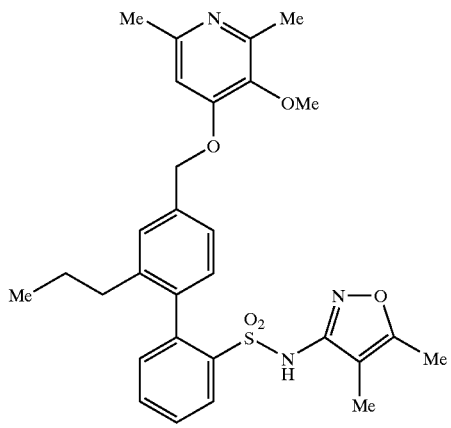

A. N-(4,5-Dimethyl-3-isoxazolyl)-4'-[[(3-methoxy-2,6-dimethyl-4-pyridinyl)oxy]methyl]-N-methoxymethyl-2'-propyl[1,1'-biphenyl]-2-sulfonamide 259C (1.9 g, 3.7 mmol) was used to alkylate 3-methoxy-2,6-dimethyl-4-(1H)-pyridinone according to General Method 22. The crude product was chromatographed on silica gel using 1:1 hexanes/ethyl acetate as eluant to provide 260A (1.3 g, 62%) as an oil.

B. N-(4,5-Dimethyl-3-isoxazolyl)-4'-[[(3-methoxy-2,6-dimethyl-4-pyridinyl)oxy]methyl]-2'-propyl[1,1'-biphenyl]-2-sulfonamide 260A (1.3 g, 2.2 mmol) was deprotected according to General Method 7. The crude product was purified by silica gel column chromatography using 3% methanol in dichloromethane as eluant, providing the title compound (540 mg, 45%) as a white solid: mp 56–59° C.; MS m/e 536 (ESI+ mode); HPLC retention time 26.73 min (Method B); HPLC purity 97%.

Example 261

1-[[2'-[[(3,4-Dimethyl-5-isoxazolyl)amino]sulfonyl-2-(ethoxymethyl)][1,1'-biphenyl]-4-yl]methyl]-4-ethyl-2-propyl-1H-imidazole-5-carboxamide

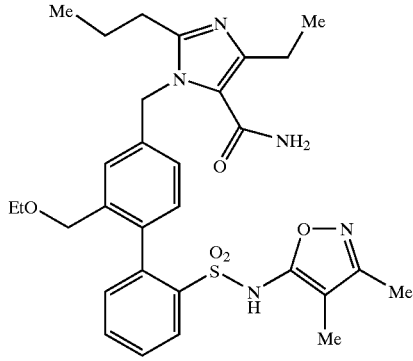

A. N-(3,4-Dimethyl-5-isoxazolyl)-4'-[(5-ethoxycarbonyl-4-ethyl-2-propylimidazol-1-yl)methyl]-2'-ethoxymethyl-N-[(2trimethylsilyl)ethoxymethyl][1,1'-biphenyl]-2-sulfonamide Ethyl 4-ethyl-2-propylimidazole-5-carboxylate (140 mg, 0.66 mmol) was alkylated with 256E according to General Method 22. Silica gel chromatography using 1:3 hexanes/ethyl acetate as eluant provided 261A (120 mg, 25%) as an orange oil.

B. 4'-[(5-Carboxy-4-ethyl-2-propylimidazol-1-yl)methyl]-N-(3,4-dimethyl-5-isoxazolyl)-2'-ethoxymethyl[1,1'-biphenyl]-2-sulfonamide 261A (120 mg, 0.16 mmol) was subjected to sulfonamide deprotection according to General Method 8 (EtOH). The crude residue was dissolved in methanol (2 ml) and was then treated with 45% aqueous potassium hydroxide (2 ml) and heated at 65° C. for 3 h. The mixture was cooled, adjusted to pH 4 by the addition of concentrated hydrochloric acid and aqueous sodium dihydrogen phosphate, and was then extracted with ethyl acetate. The combined organic extracts were dried over sodium sulfate and concentrated to provide 261B (64 mg) as a crude orange oil.

C. 1-[[2'-[[(3,4-Dimethyl-5-isoxazolyl)amino]sulfonyl-2-(ethoxymethyl)][1,1'-biphenyl]-4-yl]methyl]-4-ethyl-2-propyl-1H-imidazole-5-carboxamide 261B (20 mg) was subjected to amide formation according to General Method 12 using aqueous ammonia as the amine component. The crude material was purified by preparative thin-layer silica gel chromatography using 1:1 hexanes/acetone as eluant to provide the title compound (13 mg) as a white solid: MS m/e 580 (ESI+ mode); HPLC retention time 2.97 min (Method C); HPLC purity 98%.

Example 262

1-[[2'-[[(3,4-Dimethyl-5-isoxazolyl)amino]sulfonyl-2-(ethoxymethyl)][1,1'-biphenyl]-4-yl]methyl]-4-ethyl-N-methyl-2-propyl-1H-imidazole-5-carboxamide

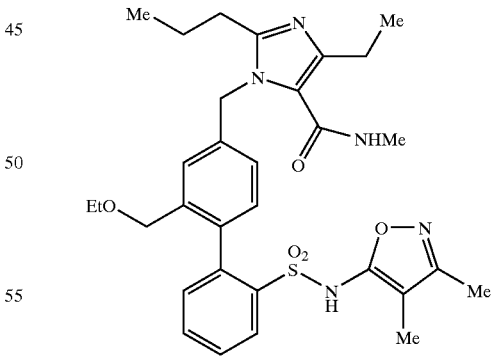

261B (44 mg) was subjected to amide formation according to General Method 12 using aqueous methylamine as the amine component. The crude material was purified by preparative thin-layer silica gel chromatography using 1:1 hexanes/acetone as eluant to provide the title compound (21 mg) as an off-white solid: MS m/e 594 (ESI+ mode); HPLC retention time 3.07 min (Method C); HPLC purity 97%.

Example 263

1-[[2'-[[(4,5-Dimethyl-3-isoxazolyl)amino]sulfonyl-2-methyl][1,1'-biphenyl]-4-yl]methyl]-4-ethyl-N-methyl-2-propyl-1H-imidazole-5-carboxamide

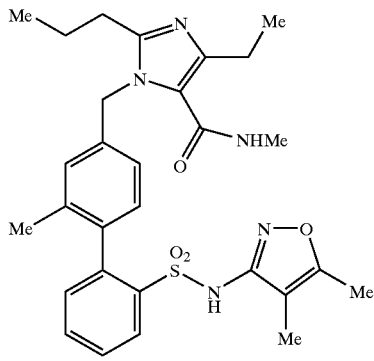

A. N-(4,5-Dimethyl-3-isoxazolyl)-4'-methoxycarbonyl-N-methoxymethyl-2'-methyl[1,1'-biphenyl]-2-sulfonamide Methyl 4-bromo-3-methylbenzoate (2.3 g, 10 mmol) was subjected to Suzuki coupling with [2-[[(4,5-dimethyl-3isoxazolyl)(methoxymethyl)amino]-sulfonyl]phenyl] boronic acid (3.2 g, 6.5 mmol) according to General Method 1. 263A (3.1 g) was obtained as an impure yellow oil following silica gel chromatography using 3:1 hexanes/ethyl acetate as eluant.

B. N-(4,5-Dimethyl-3-isoxazolyl)-4'-hydroxymethyl-N-methoxymethyl-2'-methyl[1,1'-biphenyl]-2-sulfonamide 263A (3.1 g) was treated with DIBAL-H according to the procedure of Example 230, step E, to provide 263B (2.7 g) as a crude yellow oil.

C. 4'-Bromomethyl-N-(4,5-dimethyl-3-isoxazolyl)-N-methoxymethyl-2'-methyl[1,1'-biphenyl]-2-sulfonamide 263B (2.7 g) was converted to the corresponding bromide according to General Method 2, providing 263C (1.7 g, 55% over 3 steps) as a colorless oil following silica gel choromatography using 5:1 hexanes/ethyl acetate as eluant.

D. N-(4,5-Dimethyl-3-isoxazolyl)-4'-[(5-ethoxycarbonyl-4-ethyl-2-propylimidazol-1-yl)methyl]-N-methoxymethyl-2'-methyl[1,1'-biphenyl]-2-sulfonamide 263C (1.7 g) was used to alkylate ethyl 4-ethyl-2-propylimidazole-5-carboxylate according to General Method 22. Silica gel chromatography using 3:1 hexanes/ethyl acetate as eluant provided 263D (880 mg, 41%) as an orange oil.

E. 4'-[(5-Carboxy-4-ethyl-2-propylimidazol-1-yl)methyl]-N-(4,5-dimethyl-3-isoxazolyl)-2'-methyl[1,1'-biphenyl]-2-sulfonamide 263D (880 mg) was subjected to the procedure of Example 261, step B, to provide 263E (870 mg) as a crude yellow solid.

F. 1-[[2'-[[(4,5-Dimethyl-3-isoxazolyl)amino]sulfonyl-2-methyl][1,1'-biphenyl]-4-yl]methyl]-4-ethyl-N-methyl-2-propyl-1H-imidazole-5-carboxamide 263E (830 mg) was subjected to amide formation according to General Method 12 using aqueous methylamine as the amine component. The crude material was purified by silica gel chromatography using 1:1 hexanes/acetone as eluant to provide the title compound (400 mg) as a white solid following lyophilization: MS m/e 550 (ESI+ mode); HPLC retention time 2.98 min (Method C); HPLC purity >98%.

Example 264

N,4-Diethyl-1-[[2'-[[(4,5-dimethyl-3-isoxazolyl)amino]sulfonyl-2-methyl][1,1'-biphenyl]-4-yl]methyl]-2-propyl-1H-imidazole-5-carboxamide

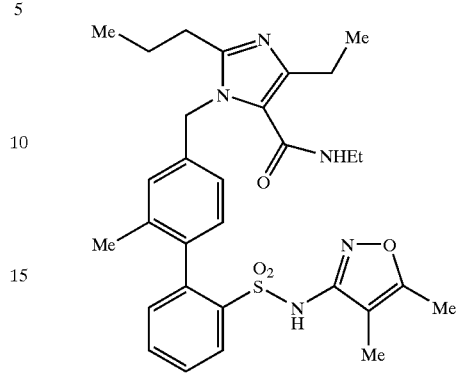

263E (20 mg) was subjected to amide formation according to General Method 12 using aqueous ethylamine as the amine component. The crude material was purified by preparative thin-layer silica gel chromatography using 9:1 methanol/chloroform as eluant to provide the title compound (10 mg) as a white solid following lyophilization: MS m/e 564 (ESI+ mode); HPLC retention time 3.10 min (Method C); HPLC purity 97%.

Example 265

1-[[2'-[[(3,4-Dimethyl-5-isoxazolyl)amino]sulfonyl-2-ethyl][1,1'-biphenyl]-4-yl]methyl]-4-ethyl-2-propyl-1H-imidazole-5-carboxamide

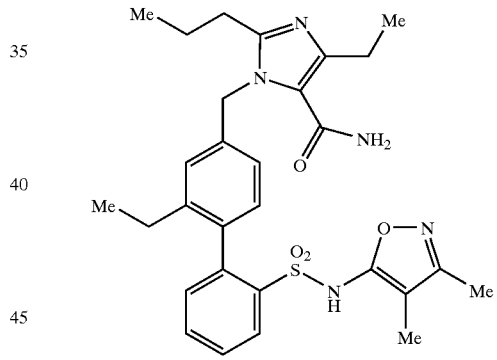

A. N-(3,4-Dimethyl-5-isoxazolyl)-4'-[(5-ethoxycarbonyl-4-ethyl-2-propyl-imidazol-1-yl)methyl]-2'-ethyl-N-[(2-trimethylsilyl)ethoxymethyl][1,1'-biphenyl]-2-sulfonamide Ethyl 4-ethyl-2-propylimidazole-5-carboxylate (600 mg, 2.9 mmol) was alkylated with 257D (1.76 g) according to General Method 22. Silica gel chromatography using 1:1 hexanes/ethyl acetate as eluant provided impure 265A (785 mg) as an orange oil.

B. 4'-[(5-Carboxy-4-ethyl-2-propylimidazol-1-yl)methyl]-N-(3,4-dimethyl-5-isoxazolyl)-2'-ethyl[1,1'-biphenyl]-2-sulfonamide 265A (785 mg) was subjected to the procedure of Example 261, step B. Purification of the crude material by preparative reverse-phase HPLC provided 265B (240 mg) as yellow oil.

C. 1-[[2'-[[(3,4-Dimethyl-5-isoxazolyl)amino]sulfonyl-2-ethyl][1,1'-biphenyl]-4-yl]methyl]-4-ethyl-2-propyl-1H-imidazole-5-carboxamide 265B (240 mg) was subjected to amide formation according to General Method 12 using aqueous ammonia as the amine component. The crude material was purified by silica gel chromatography using 1:2 hexanes/acetone as eluant to provide the title compound (110 mg) as a white solid following lyophilization: MS m/e 550 (ESI+ mode); HPLC retention time 3.05 min (Method C); HPLC purity >98%.

Example 266

1-[[2'-[[(4,5-Dimethyl-3-isoxazolyl)amino]sulfonyl-2-methyl][1,1'-biphenyl]-4-yl]methyl]-4-ethyl-N-(1-methylethyl)-2-propyl-1H-imidazole-5-carboxamide

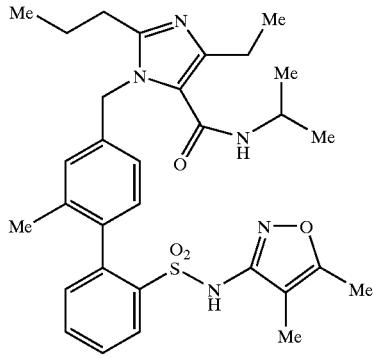

263E (150 mg) was subjected to amide formation according to General Method 12 using isopropylamine as the amine component. The crude material was chromatographed on silica gel using 1:1 hexanes/acetone as eluant to provide the title compound (27 mg) as a white solid: MS m/e 578 (ESI+ mode); HPLC retention time 3.21 min (Method C); HPLC purity 96%.

Example 267

1-[[2'-[[(3,4-Dimethyl-5-isoxazolyl)amino]sulfonyl-2-(2-fluoroethoxymethyl)][1,1'-biphenyl]-4-yl]methyl]-4-ethyl-2-propyl-1H-imidazole-5-carboxamide

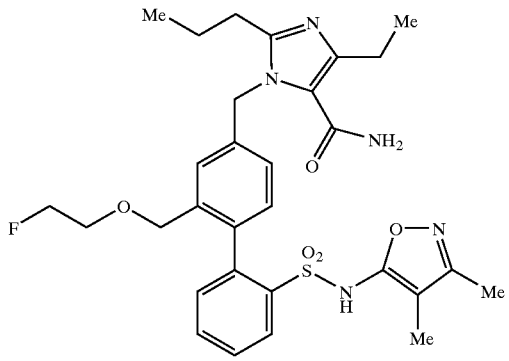

A. N-(3,4-Dimethyl-5-isoxazolyl)-4'-[(5-ethoxycarbonyl-4-ethyl-2-propyl-imidazol-1-yl)methyl]-2'-(2-fluoroethoxymethyl)-N-[(2-trimethylsilyl)ethoxymethyl][1,1'-biphenyl]-2-sulfonamide 255C (660 mg, 1.1 mmol) was used to alkylate ethyl 4-ethyl-2-propylimidazole-5-carboxylate according to General Method 22. Silica gel chromatography using 7:3 hexanes/ethyl acetate as eluant provided 267A (460 mg) as a yellow oil.

B. 4'-[(5-Carboxy-4-ethyl-2-propylimidazol-1-yl)methyl]-N-(3,4-dimethyl-5-isoxazolyl)-2'-(2-fluoroethoxymethyl)[1,1'-biphenyl]-2-sulfonamide 267A (460 mg) was subjected to the procedure of Example 261, step B. 267B (360 mg) was obtained as a crude yellow oil, which was used without further purification.

C. 1-[[2'-[[(3,4-Dimethyl-5-isoxazolyl)amino]sulfonyl-2-(2-fluoroethoxymethyl)][1,1'-biphenyl]-4-yl]methyl]-4-ethyl-2-propyl-1H-imidazole-5-carboxamide 267B (360 mg) was subjected to amide formation according to General Method 12 using aqueous ammonia as the amine component. The crude material was purified by silica gel chromatography using 1:2 hexanes/acetone as eluant to provide the title compound (180 mg) as a white solid following lyophilization: MS m/e 598 (ESI+ mode); HPLC retention time 2.83 min (Method C); HPLC purity >98%.

Example 268

N-(4,5-Dimethyl-3-isoxazolyl)-2'-ethoxymethyl-4'-[[(6-ethyl-3-methoxy-2-methyl-4-pyridinyl)oxy]methyl][1,1'-biphenyl]-2-sulfonamide

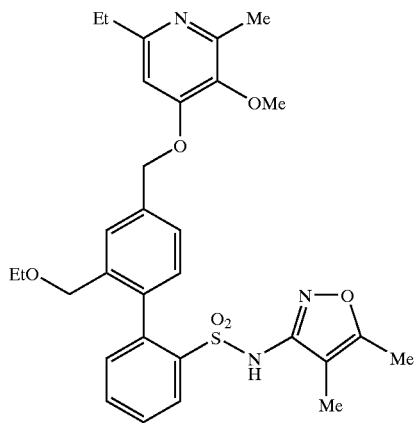

A. N-(4,5-Dimethyl-3-isoxazolyl)-2'-ethoxymethyl-4'-[[(6-ethyl-3-methoxy-2-methyl-4-pyridinyl)oxy]methyl]-N-[(2-methoxyethoxy)methyl][1,1'-biphenyl]-2-sulfonamide 252E (200 mg, 0.38 mmol) was used to alkylate 6-ethyl-3-methoxy-2-methyl-4-(1H)-pyridinone (prepared according to Katano, K.; et. al. *Meiji Seika Kenkyu Nenpo*, 1996, 35, 62–65) following General Method 22. 268A (155 mg, 70%) was produced as an oil following silica gel chromatography using 50:50:0.2 hexanes/ethyl acetate/triethylamine as eluant.

B. N-(4,5-Dimethyl-3-isoxazolyl)-2'-ethoxymethyl-4'-[[(6-ethyl-3-methoxy-2-methyl-4-pyridinyl)oxy]methyl][1,1'-biphenyl]-2-sulfonamide 268A was deprotected according to General Method 7. The crude product was purified by silica gel column chromatography using 1:30 methanol/dichloromethane as eluant, providing the title compound (108 mg, 74%) as a light yellow solid: mp 64–72° C.; MS m/e 566 (ESI+ mode); HPLC retention time 13.87 min (Method E); HPLC purity 95%.

Example 269

N2-[[2'-[[(4,5-Dimethyl-3-isoxazolyl)amino]sulfonyl][1,1'-biphenyl]-4-yl]methyl]-N-methyl-N2-(1-oxobutyl)-L-valinamide

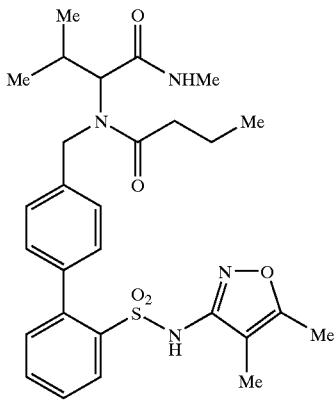

A. N-(4,5-Dimethyl-3-isoxazolyl)-N-[[(2-trimethylsilyl)ethoxy]methyl]-2-bromobenzenesulfonamide SEM-Cl (6.4 ml, 36 mmol) was added at 0° C. to a mixture of N-(4,5-dimethyl-3-isoxazolyl)-2-bromobenzenesulfonamide (11 g, 34 mmol), potassium carbonate (9.4 g, 68 mmol), and DMF (100 ml). The mixture was allowed to warm to rt and was stirred for 18 h. The solvent was evaporated, water (200 mL) was added, and the mixture was extracted with ethyl acetate. The crude extract was dried over sodium sulfate and concentrated, and the residue was chromatographed on silica gel using 4:1 hexanes/ethyl acetate as eluant to provide 269A (11 g, 70%) as an oil.

B. N-(4,5-Dimethyl-3-isoxazolyl)-4'-formyl-N-[[(2-trimethylsilyl)ethoxy]methyl][1,1'-biphenyl]-2-sulfonamide 269A (2.3 g, 5.0 mmol) was subjected to Suzuki coupling with 4-formylphenylboronic acid according to General Method 1. 269B (2.0 g, 83%) was obtained as yellow crystalline solid following silica gel chromatography using 4:1 hexanes/ethyl acetate as eluant.

C. N2-[[2'-[[N-(4,5-Dimethyl-3-isoxazolyl)-N-[[(2-trimethylsilyl)ethoxy]methyl]amino]sulfonyl][1,1'-biphenyl]-4-yl]methyl]-N-methyl-L-valinamide 269B (490 mg, 1.0 mmol) and L-valine N-methylamide were subjected to reductive amination according to General Method 5. Crude 269C (780 mg) was produced as an oil.

D. N2-[[2'-[[N-(4,5-Dimethyl-3-isoxazolyl)-N-[[(2-trimethylsilyl)ethoxy]methyl]amino]sulfonyl][1,1'-biphenyl]-4-yl]methyl]-N-methyl-N2-(1-oxobutyl)-L-valinamide 269C (750 mg) was acylated with butanoyl chloride according to General Method 6 to provide crude 269D (680 mg) as an oil.

E. N2-[[2'-[[(4,5-Dimethyl-3-isoxazolyl)amino]sulfonyl][1,1'-biphenyl]-4-yl]methyl]-N-methyl-N2-(1-oxobutyl)-L-valinamide 269D (680 mg) was deprotected according to General Method 10. Silica gel chromatography of the crude residue using dichloromethane/methanol as eluant provided the title compound (360 mg) as a white amorphous solid: MS m/e 541 (ESI+ mode); HPLC retention time 3.61 min (Method C); HPLC purity 95%.

Example 270

N2-[[2'-[[(4,5-Dimethyl-3-isoxazolyl)amino]sulfonyl][1,1'-biphenyl]-4-yl]methyl]-N,N-dimethyl-N2-(1-oxopentyl)-L-valinamide

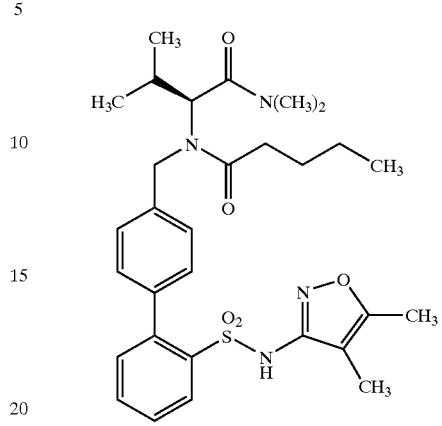

A. N2-[[2'-[[N-(4,5-Dimethyl-3-isoxazolyl)-N-[[(2-trimethylsilyl)ethoxy]methyl]amino]sulfonyl][1,1'-biphenyl]-4-yl]methyl]-N,N-dimethyl-L-valinamide 269B (490 mg, 1.0 mmol) and L-valine N,N-dimethylamide were subjected to reductive amination according to General Method 5. Crude 270A (780 mg) was produced as an oil.

B. N2-[[2'-[[N-(4,5-Dimethyl-3-isoxazolyl)-N-[[(2-trimethylsilyl)ethoxy]methyl]amino]sulfonyl][1,1'-biphenyl]-4-yl]methyl]-N,N-dimethyl-N2-(1-oxopentyl)-L-valinamide 270A (750 mg) was acylated with pentanoyl chloride according to General Method 6 to provide crude 270B (710 mg) as an oil.

C. N2-[[2'-[[(4,5-Dimethyl-3-isoxazolyl)amino]sulfonyl][1,1'-biphenyl]-4-yl]methyl]-N,N-dimethyl-N2-(1-oxopentyl)-L-valinamide 270B (710 mg) was deprotected according to General Method 10. Silica gel chromatography of the crude residue using dichloromethane/methanol as eluant provided the title compound (400 mg) as a white amorphous solid: MS m/e 569 (ESI+ mode); HPLC retention time 3.82 min (Method C); HPLC purity 95%.

Example 271

4'-[(2-Butyl-4-oxo-1,3-diazaspiro[4.4]non-1-en-3-yl)methyl]-N-(4,5-dimethyl-3-isoxazolyl)-2'-ethyl[1,1'-biphenyl]-2-sulfonamide

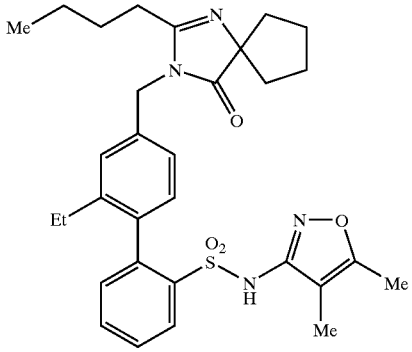

A. N-(4,5-Dimethyl-3-isoxazolyl)-2'-ethyl-4'-methoxycarbonyl-N-(methoxymethyl)[1,1'-biphenyl]-2-sulfonamide 257A (5.9 g, 24 mmol) was subjected to Suzuki coupling with 2-[[N-(4,5-dimethyl-3-isoxazolyl)-N-(methoxymethyl) amino]sulfonyl]phenylboronic acid according to General Method 1. Silica gel chromatography provided 271A (6.0 g) as an oil, contaminated with byproducts deriving from the boronic acid. 257A (4.5 g) was also recovered. A single recycling of the recovered 257A yielded 6.6 g of the 271A product mix (12.6 g total combined yield).

B. N-(4,5-Dimethyl-3-isoxazolyl)-2'-ethyl-4'-hydroxymethyl-N-(methoxymethyl)[1,1'-biphenyl]-2-sulfonamide 271A (11.1 g) was treated with DIBAL-H according to the procedure of Example 230, step E, to provide 271B (6.5 g) as a crude oil.

C. 4'-Bromomethyl-N-(4,5-dimethyl-3-isoxazolyl)-2'-ethyl-N-(methoxymethyl)[1,1'-biphenyl]-2-sulfonamide 271B (6.5 g) was converted to the corresponding bromide according to General Method 2 to provide 271C (4.2 g) as an orange oil following silica gel chromatography using 3:1 hexanes/ethyl acetate as eluant.

D. 4'-[[2-Butyl-4-oxo-1,3-diazaspiro[4.4]non-1-en-3-yl]methyl]-N-(4,5-dimethyl-3-isoxazolyl)-2'-ethyl-N-(methoxymethyl)[1,1'-biphenyl]-2-sulfonamide 271C (2.0 g) was used to alkylate 2-butyl-1,3-diazaspiro[4.4]non-1en-4-one according to General Method 4. 271D (1.6 g) was produced as a colorless oil following silica gel chromatography using 1:1 hexanes/ethyl acetate as eluant.

E. 4'-[(2-Butyl-4-oxo-1,3-diazaspiro[4.4]non-1-en-3-yl)methyl]-N-(4,5-dimethyl-3-isoxazolyl)-2'-ethyl[1,1'-biphenyl]-2-sulfonamide 271D (1.6 g) was deprotected according to General Method 8 (EtOH). The crude product was purified by silica gel chromatography using 1:1 hexanes/ethyl acetate as eluant to provide the title compound (815 mg) as a white amorphous solid: MS m/e 563 (ESI+ mode); HPLC retention time 2.18 min (Method H); HPLC purity >98%.

Example 272

4'-[(5-Acetyl-4-ethyl-2-propylimidazol-1-yl)methyl]-N-(4,5-dimethyl-3-isoxazolyl)-2'-methyl[1,1'-biphenyl]-2-sulfonamide

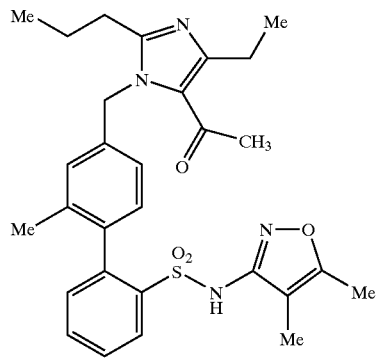

A. 5-Acetyl-4-ethyl-2-propylimidazole

4-Ethyl-5-formyl-2-propylimidazole (4 g, 24 mmol) was subjected to the procedure of Example 38, steps A and B. Silica gel chromatography using 1:3 hexanes/ethyl acetate as eluant provided 272A (2.4 g, 55% over two steps) as a brown oil.

B. 4'-[(5-Acetyl-4-ethyl-2-propylimidazol-1-yl)methyl]-N-(4,5-dimethyl-3-isoxazolyl)-N-methoxymethyl-2'-methyl[1,1'-biphenyl]-2-sulfonamide 272A (800 mg, 4.4 mmol) was alkylated with 263C according to General Method 22. Silica gel chromatography using 1:3 hexanes/ethyl acetate as eluant provided 272B (990 mg, 38%) as an orange oil.

C. 4'-[(5-Acetyl-4-ethyl-2-propylimidazol-1-yl)methyl]-N-(4,5-dimethyl-3-isoxazolyl)-2'-methyl[1,1'-biphenyl]-2-sulfonamide 272B (940 mg, 1.6 mmol) was subjected to sulfonamide deprotection according to General Method 8 (water). The crude material was purified by reverse-phase preparative HPLC followed by preparative thin-layer silica gel chromatography (chloroform/methanol eluant) to provide the title compound (9 mg) as a white solid following lyophilization: MS m/e 535 (ESI+ mode); HPLC retention time 1.98 min (Method H); HPLC purity 98%.

Example 273

N-(4,5-Dimethyl-3-isoxazolyl)-2'-ethyl-4'-[[(3-methoxy-2,6-dimethyl-4-pyridinyl)oxy]methyl][1,1'-biphenyl]-2-sulfonamide

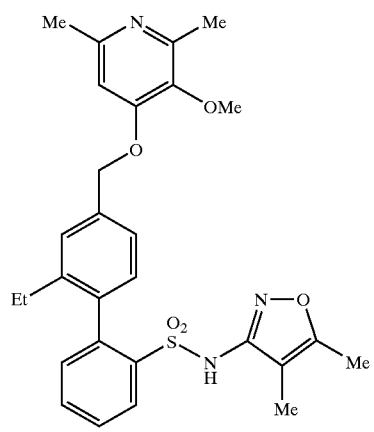

A. N-(4,5-Dimethyl-3-isoxazolyl)-2'-ethyl-4'-[[(3-methoxy-2,6-dimethyl-4-pyridinyl)oxy]methyl]-N-(methoxymethyl)[1,1'-biphenyl]-2-sulfonamide 271C (2.0 g, 4.0 mmol) was used to alkylate 3-methoxy-2,6-dimethyl-4-(1H)-pyridinone according to General Method 22. The crude product was purified by silica gel chromatography using 1:1 hexanes/ethyl acetate as eluant to provide 273A (1.2 g, 52%) as an orange oil.

B. N-(4,5-Dimethyl-3-isoxazolyl)-2'-ethyl-4'-[[(3-methoxy-2,6-dimethyl-4-pyridinyl)oxy]methyl][1,1'-biphenyl]-2-sulfonamide 273A (1.2 g, 2.2 mmol) was deprotected according to General Method 8 (EtOH). The crude product was crystallized from methanol/dichloromethane to provide the title compound (172 mg) as a white solid: MS m/e 522 (ESI+ mode); HPLC retention time 1.53 min (Method H); HPLC purity 95%.

Example 274

N-(4,5-Dimethyl-3-isoxazolyl)-4'-[[(6-ethyl-3-methoxy-2-methyl-4pyridinyl)oxy]methyl]-2'-propyl[1,1'-biphenyl]-2-sulfonamide

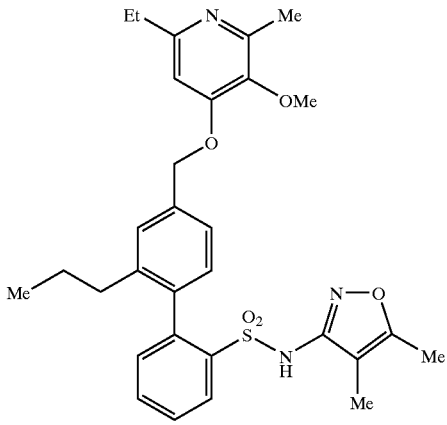

A. N-(4,5-Dimethyl-3-isoxazolyl)-4'-[[(6-ethyl-3-methoxy-2-methyl-4-pyridinyl)oxy]methyl]-N-methoxymethyl-2'-propyl[1,1'-biphenyl]-2-sulfonamide 259C (1.97 g) was used to alkylate 6-ethyl-3-methoxy-2-methyl-4-(1H)-pyridinone (500 mg, prepared according to Katano, K.; et. al. *Meiji Seika Kenkyu Nenpo*, 1996, 35, 62–65) following General Method 22. 274A (1.23 g, 76%) was produced as an oil following silica gel chromatography using hexanes/ethyl acetate/triethylamine as eluant.

B. N-(4,5-Dimethyl-3-isoxazolyl)-4'-[[(6-ethyl-3-methoxy-2-methyl-4-pyridinyl)oxy]methyl]-2'-propyl[1,1'-biphenyl]-2-sulfonamide 274A (1.23 g) was deprotected according to General Method 7. The crude product was purified by silica gel column chromatography using methanol/dichloromethane as eluant, providing the title compound (820 mg, 72%) as a white solid: mp 63–65° C.; MS m/e 550 (ESI+ mode); HPLC retention time 3.04 min (Method A); HPLC purity >98%.

Example 275

4'-[(2-Butyl-4-oxo-1,3-diazaspiro[4.4]non-1-en-3-yl)methyl]-N-(4,5-dimethyl-3-isoxazolyl)-2'-(ethoxymethyl)[1,1'-biphenyl]-2-sulfonamide[crystalline]

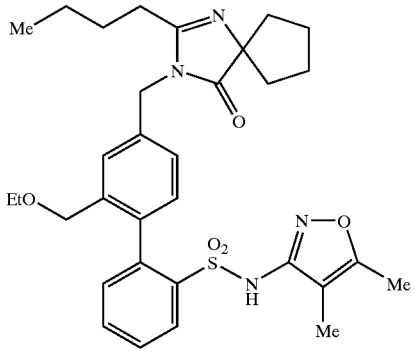

(Alternative Synthesis of Example 227)

A. Ethyl 4-bromo-3-(bromomethyl)benzoate

Ethyl 4-bromo-3-methylbenzoate (110 g, 450 mmol) was treated with NBS according to the procedure of P2A. Silica gel chromatography with hexanes/ethyl acetate as eluant provided 275A (91 g, 62%) as a white solid.

B. Ethyl 4-bromo-3-(ethoxymethyl)benzoate

A solution of 275A (89 g, 280 mmol) in a mixture of ethanol (300 ml) and DMF (50 ml) was treated at 0° C. with sodium ethoxide (135 ml of a 21% solution in ethanol). The mixture was allowed to warm to rt and was stirred for 16 h. The ethanol was evaporated under reduced pressure. Ethyl acetate was added to the residue and the mixture was washed with water and brine. The organic layer was dried over sodium sulfate and concentrated, and the residue was chromatographed on silica gel using hexanes/ethyl acetate as eluant to provide 275B (67 g, 84%) as a slightly yellow oil.

C. N-(4,5-Dimethyl-3-isoxazolyl)-4'-(ethoxycarbonyl)-2'-(ethoxymethyl)-N-(methoxymethyl)[1,1'-biphenyl]-2-sulfonamide 275B (32 g, 100 mmol) was subjected to Suzuki coupling with 2-[[N-(4,5-dimethyl-3-isoxazolyl)-N-(methoxymethyl)amino]sulfonyl]-phenylboronic acid according to General Method 1. Silica gel chromatography using hexanes/ethyl acetate as eluant provided 275C (52 g) as a yellow oil, contaminated with byproducts deriving from the boronic acid.

D. N-(4,5-Dimethyl-3-isoxazolyl)-2'-(ethoxymethyl)-4'-(hydroxymethyl)-N-(methoxymethyl)[1,1'-biphenyl]-2-sulfonamide 275C (entire sample) was treated with DIBAL-H according to the procedure of Example 230, step E, with the following difference: Workup was by addition of saturated aqueous ammonium chloride to the cooled reaction mixture, followed by extraction with ethyl acetate. The combined organic layers were dried over sodium sulfate and concentrated to provide 275D as a crude yellow oil.

E. 4'-(Bromomethyl)-N-(4,5-dimethyl-3-isoxazolyl)-2'-(ethoxymethyl)-N-(methoxymethyl)[1,1'-biphenyl]-2-sulfonamide 275D (entire sample) was converted to the corresponding bromide according to General Method 2. Silica gel chromatography using hexanes/ethyl acetate as eluant provided 275E (38 g, purity estimated to be 83% by $^1$H NMR) as a light yellow oil.

F. 4'-[(2-Butyl-4-oxo-1,3-diazaspiro[4.4]non-1-en-3-yl)methyl]-N-(4,5-dimethyl-3-isoxazolyl)-2'-(ethoxymethyl)-N-(methoxymethyl)[1,1'-biphenyl]-2-sulfonamide 275E (entire sample) was used to alkylate 2-butyl-1,3-diazaspiro[4.4]non-1-en-4-one according to General Method 4. The crude residue was chromatographed on silica gel using hexanes/ethyl acetate/triethylamine as eluant to provide 275F (32 g, 53% from 275B) as a slightly yellow oil.

G. 4'-[(2-Butyl-4-oxo-1,3-diazaspiro[4.4]non-1-en-3-yl)methyl]-N-(4,5-dimethyl-3-isoxazolyl)-2'-(ethoxymethyl)[1,1'-biphenyl]-2-sulfonamide 275F (32 g, 53 mmol) was deprotected according to General Method 7. The crude product was purified by silica gel chromatography using hexanes/ethyl acetate/acetic acid as eluant to provide the title compound (26 g, 88%) as an amorphous foam: MS m/e 593 (ESI+ mode); HPLC retention time 18.75 min (Method E); HPLC purity >96%.

H. 4'-[(2-Butyl-4-oxo-1,3-diazaspiro[4.4]non-1-en-3-yl)methyl]-N-(4,5-dimethyl-3-isoxazolyl)-2'-(ethoxymethyl)[1,1'-biphenyl]-2-sulfonamide
(Crystallization)

The amorphous 275F (1 g) was dissolved in 5 mL of isopropanol and 5 mL of water was added to the mixture dropwise and the mixture was warmed up to 40° C. to provide a clear solution. The solution was let stand at room temperature and the white crystals thus obtained was filtered and washed with a small amount of 2:1 mixture of isopropanol/water and dried to give 0.87 g of a white crystalline solid. mp. 148° C.

Example 276
4'-[(2-Butyl-4-oxo-1,3-diazaspiro[4.4]non-1-en-3-yl)methyl]-3'-chloro-N-(4,5-dimethyl-3-isoxazolyl)-5-methoxy[1,1'-biphenyl]-2-sulfonamide

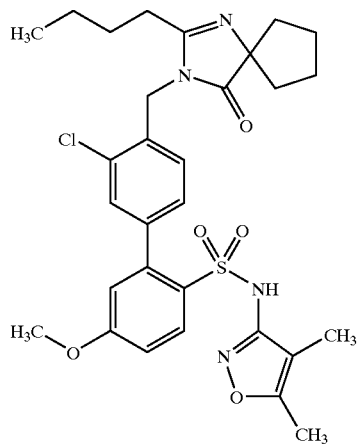

A. (2-Butyl-4-oxo-1,3-diazaspiro[4.4]non-1-en-3-yl)methyl-2-chloro-4-bromobenzene α-Bromomethyl-4-bromo-2-chlorobenzene (1.6 gm) was used to alkylate 2-butyl-1,3-diazaspiro[4.4]non-1-en-4-one (1.2 gm) according to General Method 4 to yield 276A (2.2 gm, 98%) as a solid. MS m/e 399.13.

B. 4'-[(2-Butyl-4-oxo-1,3-diazaspiro[4.4]non-1-en-3-yl)methyl]-3'-chloro-N-[(2-methoxyethoxy)methyl]-N-(4,5-dimethyl-3-isoxazolyl)[1,1'-biphenyl]-2-sulfonamide.

276A (218 mg) was subjected to Suzuki coupling with {2-[[4,5-dimethyl-3-isoxazolyl){2-methoxyethoxy)methyl]amino]-sulfonyl]-5-methoxyphenyl]boronic acid (270 mg)according to General Method 1 to provide 276B (280 mg, 67%) as an oil.

C. Title Compound 276B (280 mg) was deprotected according to General Method 8 to provide the title compound (178 mg, 98%) as a white amorphous solid: MS m/e 583.

Examples 277–297

The compounds of Examples 277–297 were prepared in a manner similar to that described in Example 276. The reported HPLC retention times were contained under the following conditions.

Column: YMC S5 ODS 4.6×50 mm (4 min); Wavelength: 220 nm;
Solvent: Gradient elution 10% MeOH—90% MeOH in water (0.2% H3PO4).

| EXAMPLE | STRUCTURE | NAME | M/z (MH)+ | HPLC ret time, min |
|---|---|---|---|---|
| 277 | 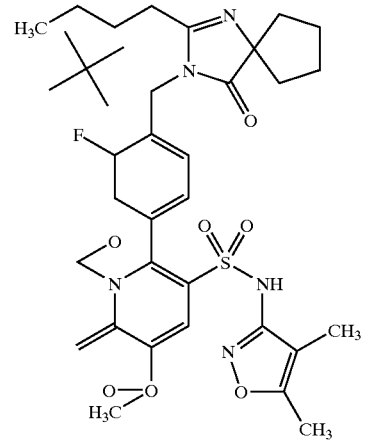 | 4'-[(2-Butyl-4-oxo-1,3-diazaspiro[4.4]non-1-en-3-yl)methyl]-N-(4,5-dimethyl-3-isoxazolyl)-3'-fluoro-4-methoxy[1,1'-biphenyl]-2-sulfonamide | 583.3 | 3.2 min |

-continued

| EXAMPLE | STRUCTURE | NAME | M/z (MH)+ | HPLC ret time, min |
|---|---|---|---|---|
| 278 | 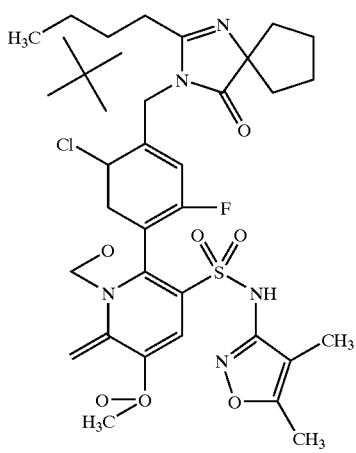 | 4'-[(2-Butyl-4-oxo-1,3-diazaspiro[4.4]non-1-en-3-yl)methyl]-5'-chloro-N-(4,5-dimethyl-3-isoxazolyl)-2'-fluoro-4-methoxy[1,1'-biphenyl]-2-sulfonamide | 617.3 | 3.3 min |
| 279 | 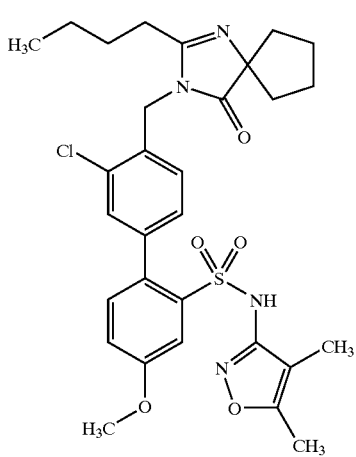 | 4'-[(2-Butyl-4-oxo-1,3-diazaspiro[4.4]non-1-en-3-yl)methyl]-3'-chloro-N-(4,5-dimethyl-3-isoxazolyl)-4-methoxy[1,1'-biphenyl]-2-sulfonamide | 599.2 | 3.4 min |
| 280 | 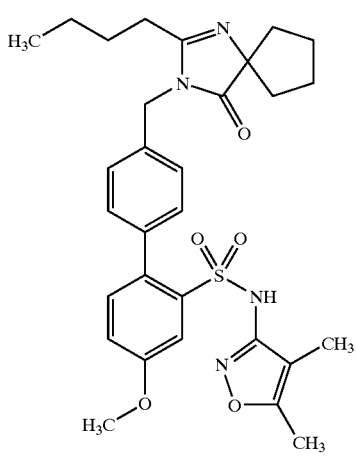 | 4'-[(2-Butyl-4-oxo-1,3-diazaspiro[4.4]non-1-en-3-yl)methyl]-N-(4,5-dimethyl-3-isoxazolyl)-4-methoxy[1,1'-biphenyl]-2-sulfonamide | 565.3 | 3.0 min |

-continued

| EXAMPLE | STRUCTURE | NAME | M/z (MH)+ | HPLC ret time, min |
|---|---|---|---|---|
| 281 | 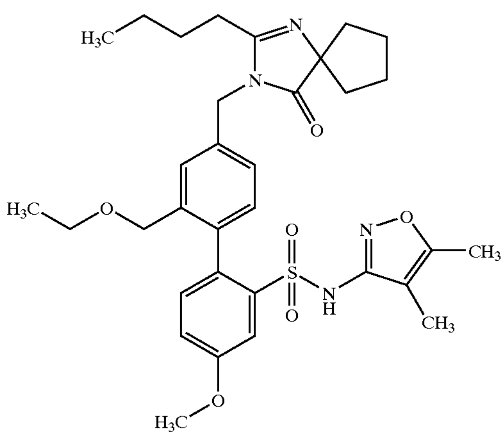 | 4'-[(2-Butyl-4-oxo-1,3-diazaspiro[4.4]non-1-en-3-yl)methyl]-N-(4,5-dimethyl-3-isoxazolyl)-2'-(ethoxymethyl)-4-methoxy[1,1'-biphenyl]-2-sulfonamide | 623.51 | 3.11 min |
| 282 | 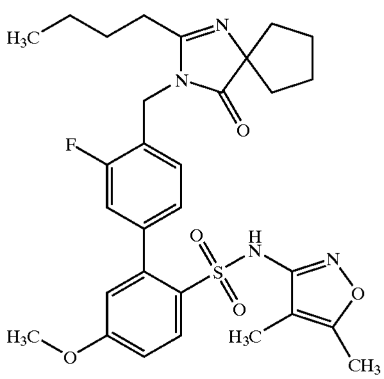 | 4'-[(2-Butyl-4-oxo-1,3-diazaspiro[4.4]non-1-en-3-yl)methyl]-N-(4,5-dimethyl-3-isoxazolyl)-3'-fluoro-5-methoxy[1,1'-biphenyl]-2-sulfonamide | 583 | 3.1 min |
| 283 | 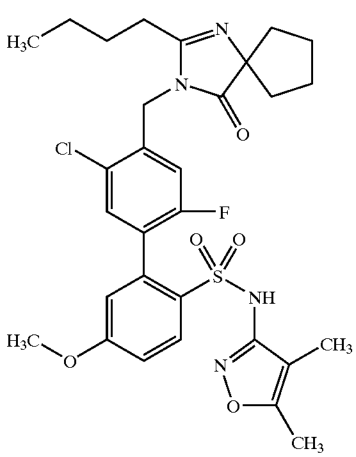 | 4'-[(2-Butyl-4-oxo-1,3-diazaspiro[4.4]non-1-en-3-yl)methyl]-5'-chloro-N-(4,5-dimethyl-3-isoxazolyl)-2'-fluoro-5-methoxy[1,1'-biphenyl]-2-sulfonamide | 617.5 | 3.3 min |

| EXAMPLE | STRUCTURE | NAME | M/z (MH)+ | HPLC ret time, min |
|---|---|---|---|---|
| 284 | 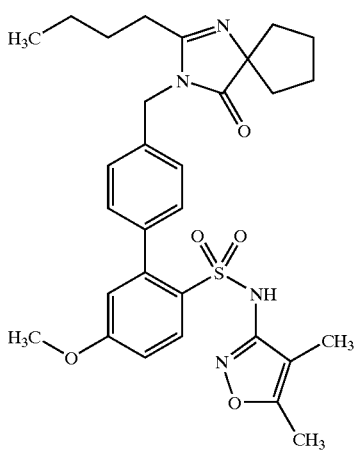 | 4'-[(2-Butyl-4-oxo-1,3-diazaspiro[4.4]non-1-en-3-yl)methyl]-N-(4,5-dimethyl-3-isoxazolyl)-5-methoxy[1,1'-biphenyl]-2-sulfonamide | 565.3 | 3.0 min |
| 285 | 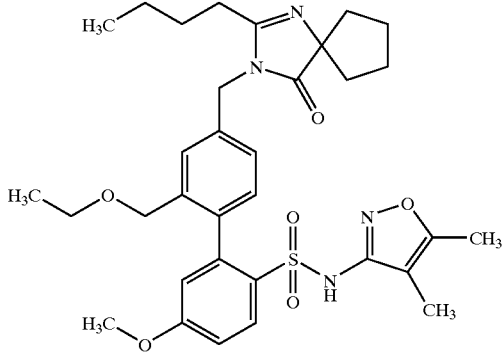 | 4'-[(2-Butyl-4-oxo-1,3-diazaspiro[4.4]non-1-en-3-yl)methyl]-N-(4,5-dimethyl-3-isoxazolyl)-2'-(ethoxymethyl)-5-methoxy[1,1'-biphenyl]-2-sulfonamide | 623.6 | 3.03 min |
| 286 | 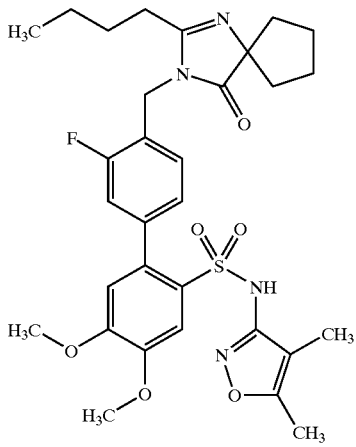 | 4'-[(2-Butyl-4-oxo-1,3-diazaspiro[4.4]non-1-en-3-yl)methyl]-N-(4,5-dimethyl-3-isoxazolyl)-3'-fluoro-4,5-dimethoxy[1,1'-biphenyl]-2-sulfonamide | 613.4 | 3.04 min |

| EXAMPLE | STRUCTURE | NAME | M/z (MH)+ | HPLC ret time, min |
|---------|-----------|------|-----------|---------------------|
| 287 | 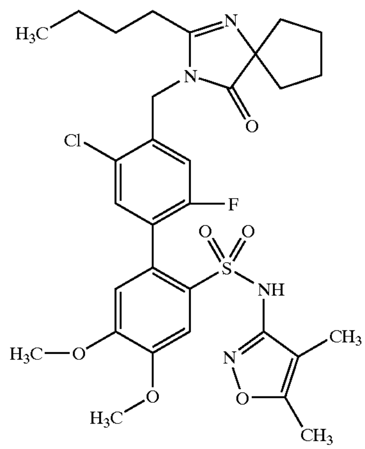 | 4'-[(2-Butyl-4-oxo-1,3-diazaspiro[4.4]non-1-en-3-yl)methyl]-5'-chloro-N-(4,5-dimethyl-3-isoxazolyl)-2'-fluoro-4,5-dimethoxy[1,1'-biphenyl]-2-sulfonamide | 647.2 | 3.2 min |
| 288 | 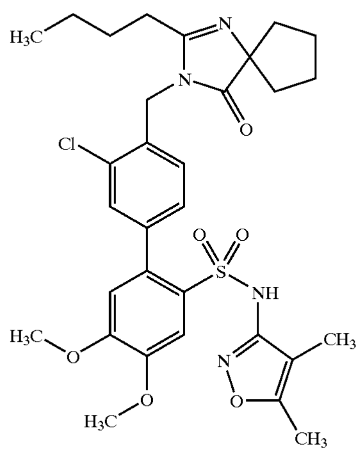 | 4'-[(2-Butyl-4-oxo-1,3-diazaspiro[4.4]non-1-en-3-yl)methyl]-3'-chloro-N-(4,5-dimethyl-3-isoxazolyl)-4,5-dimethoxy[1,1'-biphenyl]-2-sulfonamide | 629.2 | 3.2 min |
| 289 | 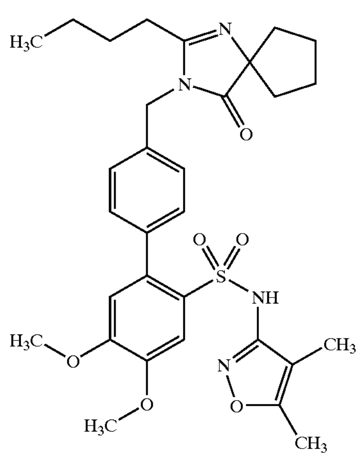 | 4'-[(2-Butyl-4-oxo-1,3-diazaspiro[4.4]non-1-en-3-yl)methyl]-N-(4,5-dimethyl-3-isoxazolyl)-4,5-dimethoxy[1,1'-biphenyl]-2-sulfonamide | 595.3 | 2.8 min |

-continued

| EXAMPLE | STRUCTURE | NAME | M/z (MH)+ | HPLC ret time, min |
|---|---|---|---|---|
| 290 | 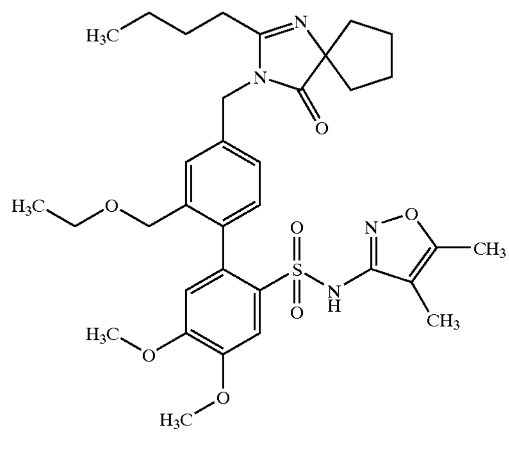 | 4'-[(2-Butyl-4-oxo-1,3-diazaspiro[4.4]non-1-en-3-yl)methyl]-N-(4,5-dimethyl-3-isoxazolyl)-2'-(ethoxymethyl)-4,5-dimethoxy[1,1'-biphenyl]-2-sulfonamide | 653.48 | 2.89 min |
| 291 | 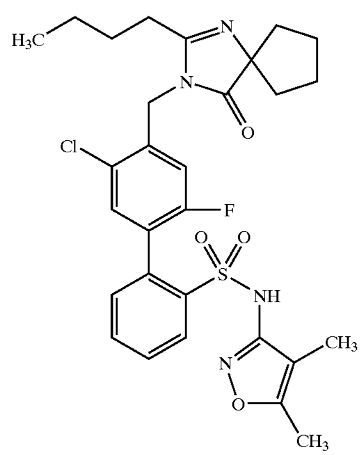 | 4'-[(2-Butyl-4-oxo-1,3-diazaspiro[4.4]non-1-en-3-yl)methyl]-5'-chloro-N-(4,5-dimethyl-3-isoxazolyl)-2'-fluoro[1,1'-biphenyl]-2-sulfonamide | 587.2 | 3.3 min |
| 292 | 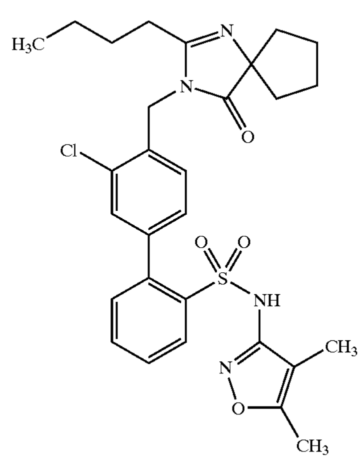 | 4'-[(2-Butyl-4-oxo-1,3-diazaspiro[4.4]non-1-en-3-yl)methyl]-3'-chloro-N-(4,5-dimethyl-3-isoxazolyl)[1,1'-biphenyl]-2-sulfonamide | 569.2 | 3.2 min |

| EXAMPLE | STRUCTURE | NAME | M/z (MH)+ | HPLC ret time, min |
|---|---|---|---|---|
| 293 | 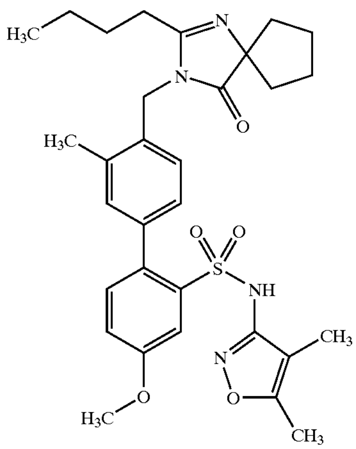 | 4'-[(2-Butyl-4-oxo-1,3-diazaspiro[4.4]non-1-en-3-yl)methyl]-N-(4,5-dimethyl-3-isoxazolyl)-4-methoxy-3'-methyl[1,1'-biphenyl]-2-sulfonamide | 579.4 | 3.2 min |
| 294 | 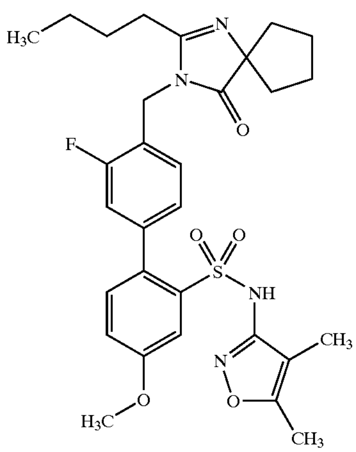 | 4'-[(2-Butyl-4-oxo-1,3-diazaspiro[4.4]non-1-en-3-yl)methyl]-N-(4,5-dimethyl-3-isoxazolyl)-3'-fluoro-4-methoxy[1,1'-biphenyl]-2-sulfonamide | 553.1 | 3.0 min |
| 295 | 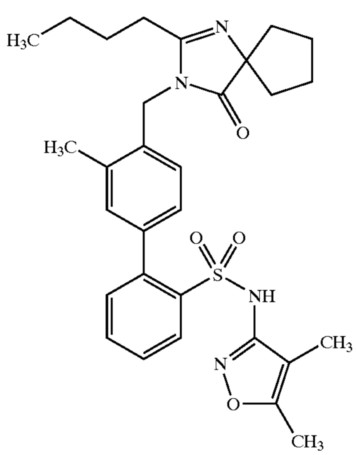 | 4'-[(2-Butyl-4-oxo-1,3-diazaspiro[4.4]non-1-en-3-yl)methyl]-N-(4,5-dimethyl-3-isoxazolyl)-3'-methyl[1,1'-biphenyl]-2-sulfonamide | 549.2 | 3.01 min |

-continued

| EXAMPLE | STRUCTURE | NAME | M/z (MH)+ | HPLC ret time, min |
|---|---|---|---|---|
| 296 | 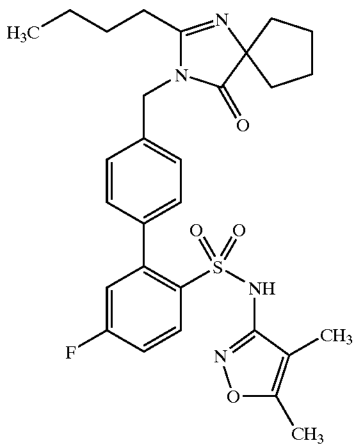 | 4'-[(2-Butyl-4-oxo-1,3-diazaspiro[4.4]non-1-en-3-yl)methyl]-N-(4,5-dimethyl-3-isoxazolyl)-5-fluoro[1,1'-biphenyl]-2-sulfonamide | 553.23 | 2.90 min |

Examples 297–309

The compounds of Examples 297–309 were prepared in a manner similar to that described in Example 269. The reported HPLC retention times were obtained under the following conditions.

Column: YMC S5 ODS 4.6×50 mm (4 min); Wavelength: 220 nm;

Solvent: Gradient elution 10% MeOH—90% MeOH in water (0.2% H3PO4).

| EXAMPLE | STRUCTURE | NAME | M/z (MH)+ | HPLC ret time, min |
|---|---|---|---|---|
| 297 | 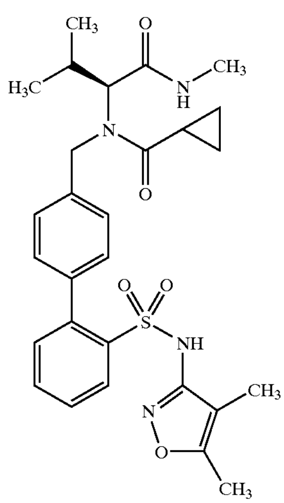 | $N^2$-(Cyclopropylcarbonyl)-$N^2$-[[2'-[[(4,5-dimethyl-3-isoxazolyl)amino]sulfonyl][1,1'-biphenyl]-4-yl]methyl]-N-methyl-L-valinamide | 539.17 | 3.08 min |

-continued

| EXAMPLE | STRUCTURE | NAME | M/z (MH)+ | HPLC ret time, min |
|---|---|---|---|---|
| 298 | 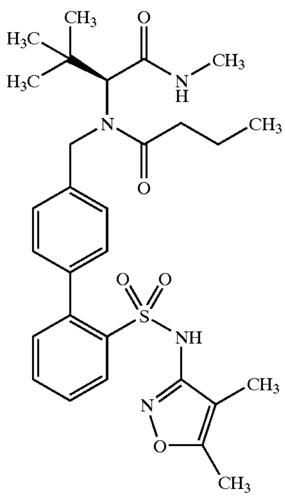 | N²-[[2'-[[(4,5-Dimethyl-3-isoxazolyl)amino]sulfonyl][1,1'-biphenyl]-4-yl]methyl]-N,3-dimethyl-N²-(1-oxobutyl)-L-valinamide | 555.24 | 3.40 min |
| 299 | 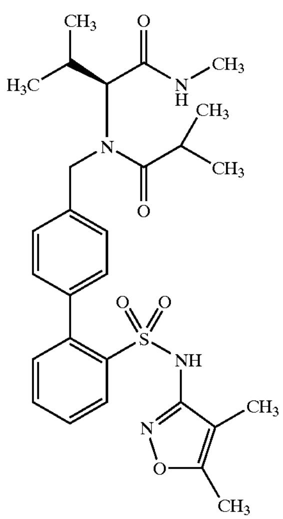 | N²-[[2'-[[(4,5-Dimethyl-3-isoxazolyl)amino]sulfonyl][1,1'-biphenyl]-4-yl]methyl]-N-methyl-N²-(2-methyl-1-oxopropyl)-L-valinamide | 541.29 | 3.17 min |
| 300 | 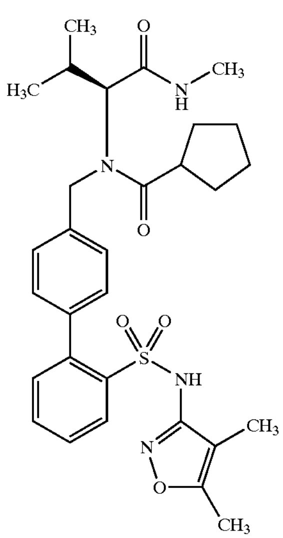 | N²-(Cyclopentylcarbonyl)-N²-[[2'-[[(4,5-dimethyl-3-isoxazolyl)amino]sulfonyl][1,1'-biphenyl]-4-yl]methyl]-N-methyl-L-valinamide | 567.28 | 3.40 min |

-continued

| EXAMPLE | STRUCTURE | NAME | M/z (MH)+ | HPLC ret time, min |
|---|---|---|---|---|
| 301 | 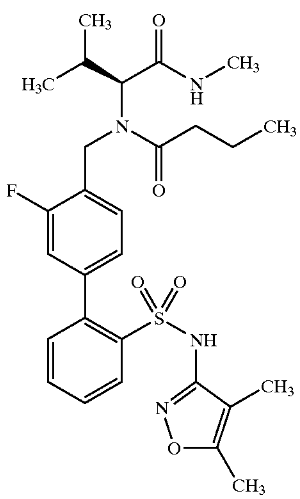 | N²-[[2'-[[(4,5-Dimethyl-3-isoxazolyl)amino]sulfonyl]-3-fluoro[1,1'-biphenyl]-4-yl]methyl]-N-methyl-N²-(1-oxobutyl)-L-valinamide | 559.2 | 3.40 min |
| 302 | 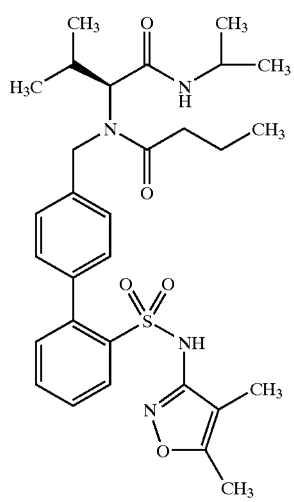 | N²-[[2'-[[(4,5-Dimethyl-3-isoxazolyl)amino]sulfonyl][1,1'-biphenyl]-4-yl]methyl]-N-(1-methylethyl)-N²-(1-oxobutyl)-L-valinamide | 569.3 | 3.40 min |
| 303 | 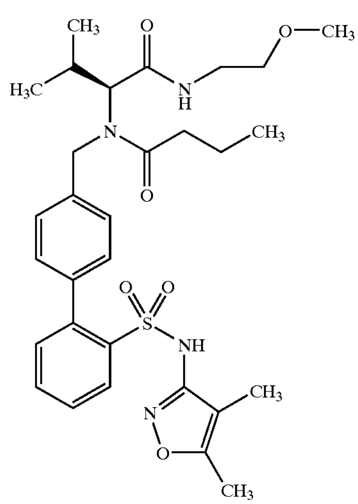 | N²-[[2'-[[(4,5-Dimethyl-3-isoxazolyl)amino]sulfonyl][1,1'-biphenyl]-4-yl]methyl]-N-(2-methoxyethyl)-N²-(1-oxobutyl)-L-valinamide | 585.3 | 3.27 min |

-continued

| EXAMPLE | STRUCTURE | NAME | M/z (MH)+ | HPLC ret time, min |
|---|---|---|---|---|
| 304 | 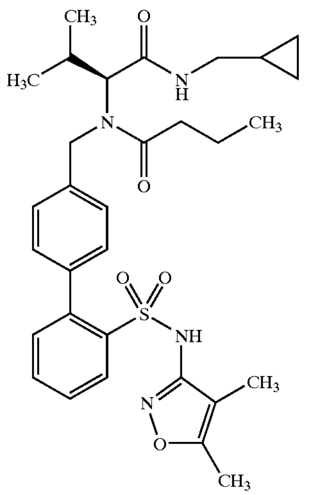 | N-(Cyclopropylmethyl)-N²-[[2'-[[(4,5-dimethyl-3-isoxazolyl)amino]sulfonyl][1,1'-biphenyl]-4-yl]methyl]-N²-(1-oxobutyl)-L-valinamide | 581.3 | 3.44 min |
| 305 | 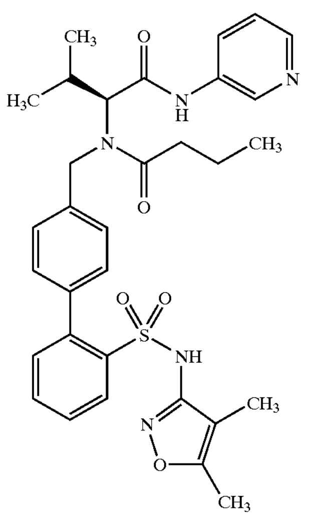 | N²-[[2'-[[(4,5-Dimethyl-3-isoxazolyl)amino]sulfonyl][1,1'-biphenyl]-4-yl]methyl]-N²-(1-oxobutyl)-N-(3-pyridinyl)-L-valinamide | 604.3 | 2.87 min |
| 306 | 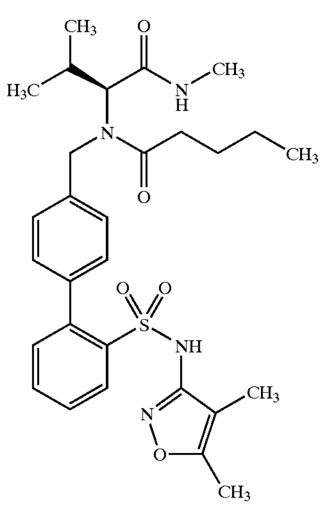 | N²-[[2'-[[(4,5-Dimethyl-3-isoxazolyl)amino]sulfonyl][1,1'-biphenyl]-4-yl]methyl]-N-methyl-N²-(1-oxopentyl)-L-valinamide | 555.17 | 3.36 min |

-continued

| EXAMPLE | STRUCTURE | NAME | M/z (MH)+ | HPLC ret time, min |
|---|---|---|---|---|
| 307 | 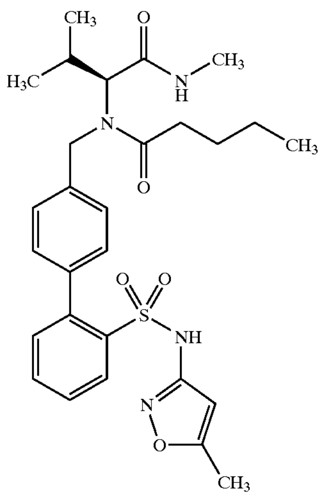 | N-Methyl-N²-[[2'-[[(5-methyl-3-isoxazolyl)amino]sulfonyl][1,1'-biphenyl]-4-yl]methyl]-N²-(1-oxopentyl)-L-valinamide | 541.2 | 3.40 min |
| 308 | 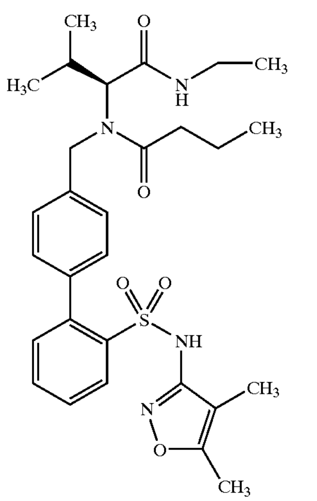 | N²-[[2'-[[(4,5-Dimethyl-3-isoxazolyl)amino]sulfonyl][1,1'-biphenyl]-4-yl]methyl]-N-ethyl-N²-(1-oxobutyl)-L-valinamide | 555.3 | 3.17 min |
| 309 | 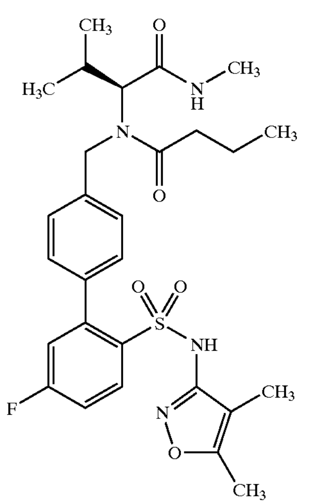 | N²-[[2'-[[(4,5-Dimethyl-3-isoxazolyl)amino]sulfonyl]-5'-fluoro[1,1'-biphenyl]-4-yl]methyl]-N-methyl-N²-(1-oxobutyl)-L-valinamide | 558.76 | 3.28 min |

Examples 310–311

The compounds of Examples 310–311 were prepared in a manner similar to that described in Example 252. The reported HPLC retention times were obtained under the following conditions.

Column: YMC S5 ODS 4.6×50 mm (4 min); Wavelength: 220 nm;
Solvent: Gradient elution 10% MeOH—90% MeOH in water (0.2% H3PO4).

| EXAMPLE | STRUCTURE | NAME | M/z (MH)+ | HPLC ret time, min |
|---|---|---|---|---|
| 310 | 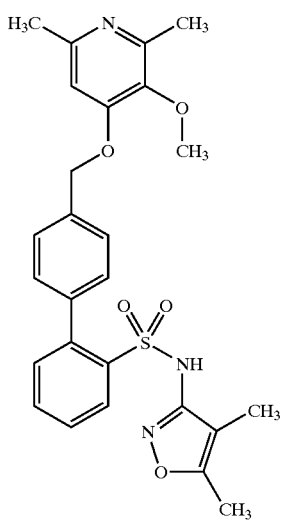 | N-(4,5-Dimethyl-3-isoxazolyl)-4'-[[(2,6-dimethyl-3-methoxy-4-pyridinyl)oxy]methyl][1,1'-biphenyl]-2-sulfonamide | 494 | 2.28 min |
| 311 | 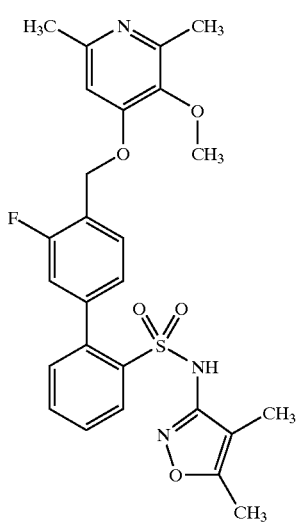 | N-(4,5-Dimethyl-3-isoxazolyl)-4'-[[(2,6-dimethyl-3-methoxy-4-pyridinyl)oxy]methyl]-3'-fluoro[1,1'-biphenyl]-2-sulfonamide | 512 | 2.41 min |

Examples 312–314

The compounds of Examples 312–314 were prepared in a manner similar to that described in Example 228. The reported HPLC retention times were obtained under the following conditions.

Column: YMC S5 ODS 4.6×50 mm (4 min); Wavelength: 220 nm;
Solvent: Gradient elution 10% MeOH—90% MeOH in water (0.2% H3PO4).

| EXAMPLE | STRUCTURE | NAME | M/z (MH)+ | HPLC ret time, min |
|---------|-----------|------|-----------|--------------------|
| 312 | 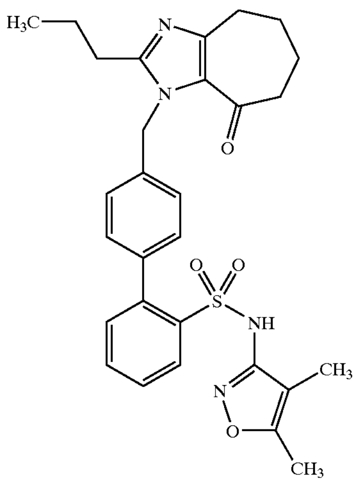 | N-(4,5-Dimethyl-3-isoxazolyl)-4'-[(1,4,5,6,7,8-hexahydro-8-oxo-2-propyl-1-cycloheptimidazolyl)methyl][1,1'-biphenyl]-2-sulfonamide | 533.3 | 2.35 min |
| 313 | 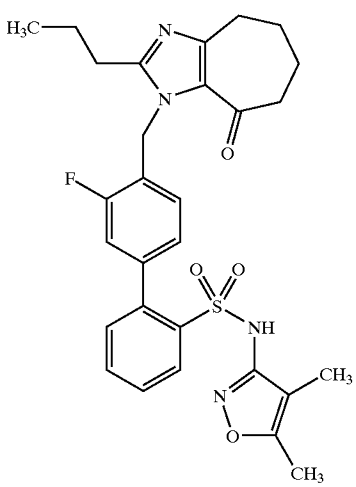 | N-(4,5-Dimethyl-3-isoxazolyl)-3'-fluoro-4'-[(1,4,5,6,7,8-hexahydro-8-oxo-2-propyl-1-cycloheptimidazolyl)methyl][1,1'-biphenyl]-2-sulfonamide | 551.3 | 2.35 min |

-continued

| EXAMPLE | STRUCTURE | NAME | M/z (MH)+ | HPLC ret time, min |
|---|---|---|---|---|
| 314 | 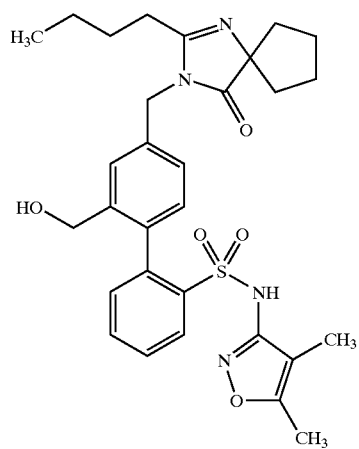 | N-(4,5-Dimethyl-3-isoxazolyl)-5-fluoro-4'-[(1,4,5,6,7,8-hexahydro-8-oxo-2-propyl-1-cycloheptimidazolyl)methyl][1,1'-biphenyl]-2-sulfonamide | 551.17 | 2.32 min |

Example 315

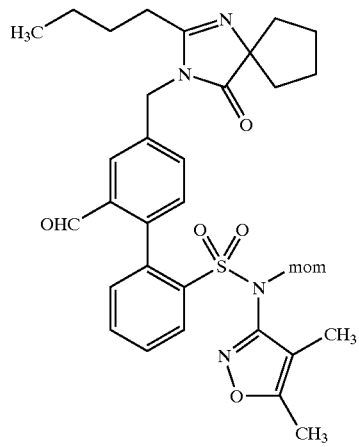

4'-[(2-Butyl-4-oxo-1,3-diazaspiro[4.4]non-1-en-3-yl)methyl]-N-(4,5-dimethyl-3-isoxazolyl)-2'-(hydroxymethyl)[1,1'-biphenyl]-2-sulfonamide

A.

5E (4.49 g, 11.48 mmol) was subjected to Suzuki coupling with [2-[[(4,5-dimethyl-3-isoxazolyl)-N-methoxymethyl]amino]-sulfonyl]phenylboronic acid according to General Method 1. 316A (5.0 g, 72%) was obtained as an orange oil following silica gel chromatography using hexanes/ethyl acetate as eluant.

B.

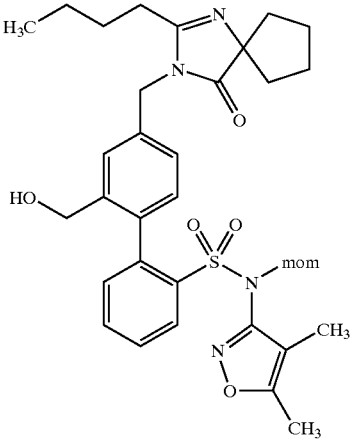

315A (0.7 g) was dissolved in 10 mL of methylene chloride and 2 mL of triethylsilane and 2 mL of trifluoroacetic acid were added to the mixture. The solution was stirred at room tempertaure for 1 h and concentrated. 315B (0.6 g, 85%) was obtained as an orange oil following silica gel chromatography using hexanes/ethyl acetate as eluant.

C.

315B (0.6 g) was deprotected according to General Method 8 (EtOH). The crude product was purified by silica gel chromatography using 1:1 hexanes/ethyl acetate as eluant to provide the title compound (0.44 g, 79%) as a white amorphous solid. mp. 90–98° C. M+H: 565.2

Example 316

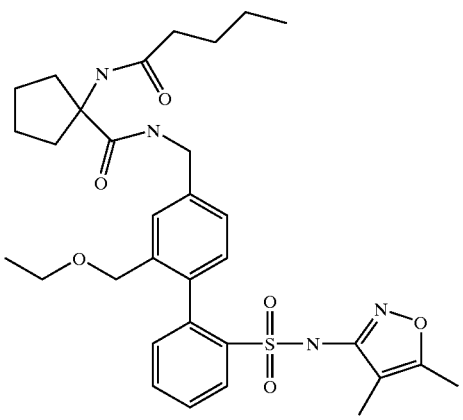

N-[[2'-[[(4,5-Dimethyl-3-isoxazolyl)amino]sulfonyl]-2-(ethoxymethyl)[1,1'-biphenyl]-4-yl]methyl]-1-[(1-oxopentyl)amino]cyclopentanamide (A Metabolite of Example 227)

227 (30 mg) was dissolved in 1 mL DMF and 0.6 mL of 20% aqueous NaOH was added and the mixture was stirred at 60° C. for 24 h. The mixture was purified by HPLC to provide the target compound as a white solid. HPLC RT: 3.21 min. M+H: 611.3

Example 317

(+)-4'-[(2-Butyl-4-oxo-1,3-diazaspiro[4.4]non-1-en-3-yl)methyl]-N-(4,5-dimethyl-3-isoxazolyl)-2'-(ethoxymethyl)[1,1'-biphenyl]-2-sulfonamide and (−)-4'-[(2-Butyl-4-oxo-1,3-diazaspiro[4.4]non-1-en-3-yl)methyl]-N-(4,5-dimethyl-3-isoxazolyl)-2'-(ethoxymethyl)[1,1'-biphenyl]-2-sulfonamide 10 μl of a solution of 275F (2 mg/mL) in isopropanol was injected onto an HPLC column (Chiral AD, 250×4.6 (10μ)) eluting with a mobil phase of 80% hexane, 20% IPA, 0.1% TFA, 0.1% TEA at 0.75 mL/min. The HPLC column temperature was maintained at 15° C. Detection was carried out at 210 nm using a UV detector. The enantiomers of 275 were resolved into two peaks, with one enantiomer eluting at 11.6 min and the other at 15.1 min. yielding the two title compounds as pure enantiomers.

What is claimed is:

1. A compound of the following formula I, enantiomers, diastereomers, salts and solvates thereof:

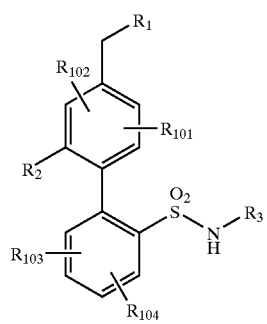

wherein:

$R_1$ is

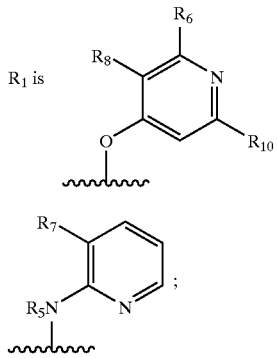 or

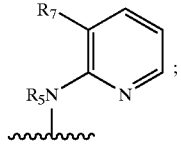

$R_2$ is hydrogen, halogen, —CHO, alkyl, haloalkyl, (cycloalkyl)alkyl, alkenyl, alkynyl, alkoxyalkyl, haloalkoxyalkyl, alkoxy, aryloxy alkoxyalkoxy, cyano, hydroxy, hydroxyalkyl, nitro, —CH($OR_{13}$)($OR_{14}$), or —$(CH_2)_wY$;

$R_3$ is heteroaryl;

$R_5$ is alkyl, hydroxyalkyl, cycloalkyl, hydroxy substituted cycloalkyl, alkoxyalkyl, or hydroxy substituted alkoxyalkyl;

$R_6$ is alkyl, hydroxyalkyl, haloalkyl, hydroxy substituted haloalkyl, cycloalkyl, hydroxy substituted cycloalkyl, (cycloalkyl)alkyl, hydroxy substituted (cycloalkyl)alkyl, aralkyl, alkoxy, hydroxy substituted alkoxy, alkoxyalkyl, hydroxy substituted alkoxyalkyl, or —$NR_{16}R_{17}$;

$R_7$ is —$(CH_2)_w$—$CO_2R_{15}$, —$(CH_2)_w$—(C=O)$NR_{16}R_{17}$, —$(CH_2)_w$—$NR_{15}$(C=O)$NR_{16}R_{17}$, —$(CH_2)_wCH_2OH$, —$(CH_2)_w$—(C=O)$R_{15}$, tetrazolyl, oxadiazolyl or triazolyl wherein said tetrazolyl, oxadiazolyl or triazolyl may optionally be substituted with hydrogen, alkyl, hydroxy or halogen; and $R_{10}$ and $R_{12}$ are each independently hydrogen, halogen, alkyl, hydroxyalkyl, cycloalkyl, (cycloalkyl)alkyl, aryl, heteroaryl, arylalkyl, alkylthioalkyl, alkoxy or alkoxyalkyl;

$R_{13}$ and $R_{14}$ are alkyl or together form a five to six-membered ring;

$R_{15}$, $R_{16}$ and $R_{17}$ are independently hydrogen, alkyl, hydroxyalkyl, cycloalkyl, (cycloalkyl)alkyl, alkoxyalkyl, aralkyl, heterocycloalkyl, aryl, heteroaryl or —$(CH_2)_wQ$, or $R_{16}$ and $R_{17}$ may together form a four to six-membered heterocyclic ring;

w is 0, 1, or 2;

Y is heteroaryl, —COOH, —$COOR_{18}$, —$CONR_{19}R_{20}$, —$NR_{19}R_{20}$, —$NR_{19}$—$OR_{20}$, —$NR_{21}$(C=O)$R_{22}$, —$NR_{21}$,(C=O)$NR_{19}R_{20}$, —N($R_{19}$)-(alk)-$NR_{21}$(C=O)$R_{22}$, —$NR_{21}$(C=O)$OR_{18}$, —$NR_{21}SO_2R_{22}$, —$SO_2R_{22}$, Q, R or S;

Q is 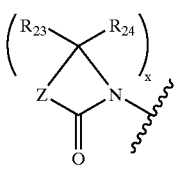 ;

-continued

R is 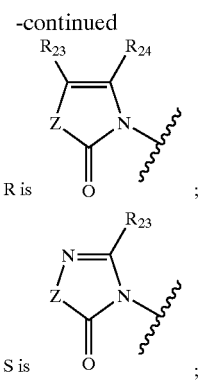;

S is $R_{18}$, $R_{19}$, $R_{20}$, $R_{21}$ and $R_{22}$ are each independently hydrogen, alkyl, haloalkyl, alkoxyalkyl, cycloalkyl, alkenyl, alkynyl, aryl, aralkyl, heteroaryl, or $R_{19}$ and $R_{20}$ may together form a four to seven-membered heterocyclic ring;

$R_{23}$ and $R_{24}$ are each independently hydrogen, alkyl or cycloalkyl, or may together form a three to seven membered cycloalkyl ring;

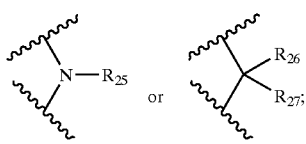

Z is oxygen, x is 2, 3 or 4;

$R_{25}$, $R_{26}$ and $R_{27}$ are each independently hydrogen, alkyl or cycloalkyl, or $R_{26}$ and $R_{27}$ may together form a three to seven-membered cycloalkyl ring;

$R_{101}$, $R_{102}$, $R_{103}$, and $R_{104}$ are each independently hydrogen, halogen, —CHO, alkyl, haloalkyl, (cycloalkyl)alkyl, alkenyl, alkynyl, alkoxyalkyl, haloalkoxyalkyl, alkoxy, alkoxyalkoxy, cyano, hydroxy, hydroxyalkyl, nitro, —CH(OR$_{13}$)(OR$_{14}$), or —(CH$_2$)$_w$Y;

wherein said rings; aryl alone or as part of another group; or heteroaryl alone or as part of another group may each optionally be substituted by one or more hydrogen, halogen, cyano, alkyl, hydroxyalkyl, alkoxy, nitro or trifluoromethyl groups.

2. A compound of claim 1, wherein

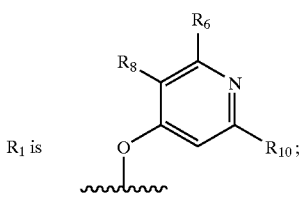

$R_2$ is alkyl, haloalkyl, (cycloalkyl)alkyl, alkoxyalkyl, haloalkoxyalkyl, alkoxy, alkoxyalkoxy, hydroxyalkyl, or —(CH$_2$)$_w$Y;

$R_3$ is isoxazolyl pyridizinyl, pyrazinyl or pyrimidinyl, each optionally independently substituted with one to three substituents selected from hydrogen, halogen, cyano, alkyl, alkoxy, trifluoromethyl or nitro;

$R_6$ is alkyl, haloalkyl, cycloalkyl or alkoxy; and $R_{10}$ are each independently hydrogen, halogen, alkyl, cycloalkyl, alkoxy or alkoxyalkyl;

$R_{15}$, $R_{16}$ and $R_{17}$ are independently hydrogen, alkyl or cycloalkyl or $R_{16}$ and $R_{17}$ may together form a four to six-membered heterocyclic ring;

w is 0, 1, or 2;

Y is —COOR$_{18}$, —NR$_{21}$(C=O)R$_{22}$, —NR$_{21}$(C=O)NR$_{19}$R$_{20}$, —NR$_{21}$(C=O)OR$_{18}$, —NR$_{21}$SO$_2$R$_{22}$, —SO$_2$R$_{22}$ or Q;

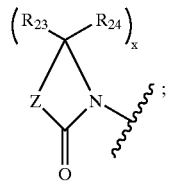

Q is $R_{18}$, $R_{19}$, $R_{20}$, $R_{21}$ and $R_{22}$ are each independently hydrogen, alkyl, cycloalkyl, or $R_{19}$ and $R_{20}$ may together form a four to seven-membered heterocyclic ring;

$R_{23}$ and $R_{24}$ are each independently hydrogen, alkyl or cycloalkyl, or may together form a three to seven membered cycloalkyl ring;

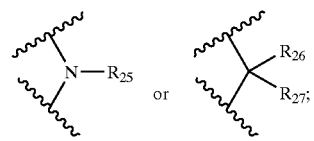

Z is oxygen, x is 2, 3 or 4;

$R_{25}$, $R_{26}$ and $R_{27}$ are each independently hydrogen, alkyl or cycloalkyl, or $R_{26}$ and $R_{27}$ may together form a three to seven-membered cycloalkyl ring;

$R_{101}$, $R_{102}$, $R_{103}$, and $R_{104}$ are each independently hydrogen, halogen, alkoxy or alkyl.

3. A compound of claim 1, wherein

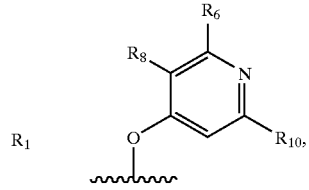

$R_2$ is alkyl, haloalkyl, (cycloalkyl)alkyl, alkoxyalkyl, haloalkoxyalkyl, alkoxy, hydroxyalkyl, or —(CH$_2$)$_w$Y, or when $R_1$ is D, $R_2$ is hydrogen, alkyl, haloalkyl, (cycloalkyl)alkyl, alkoxyalkyl, haloalkoxyalkyl, alkoxy, alkoxyalkoxy, hydroxyalkyl, or —(CH$_2$)$_w$Y;

$R_3$ is isoxazolyl, optionally independently substituted with one or two substituents selected from hydrogen, halogen, cyano, alkyl, alkoxy, trifluoromethyl or nitro;

$R_6$ is alkyl, haloalkyl, cycloalkyl or alkoxy; and $R_{10}$ are each independently hydrogen, halogen, alkyl, cycloalkyl, alkoxy or alkoxyalkyl;

$R_{15}$, $R_{16}$ and $R_{17}$ are independently hydrogen, alkyl, or cycloalkyl or $R_{16}$ and $R_{17}$ may together form a four to six-membered heterocyclic ring;

w is 0, 1, or 2;

Y is —$NR_{21}(C=O)R_{22}$, —$NR_{21}(C=O)NR_{19}R_{20}$, —$NR_{21}(C=O)OR_{18}$, —$NR_{21}SO_2R_{22}$, —$SO_2R_{22}$ or Q;

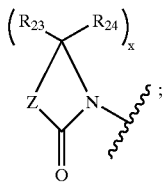

Q is $R_{18}$, $R_{19}$, $R_{20}$, $R_{21}$, and $R_{22}$ are each independently hydrogen, alkyl, cycloalkyl, or $R_{19}$ and $R_{20}$ may together form a four to seven-membered heterocyclic ring;

$R_{23}$ and $R_{24}$ are each independently hydrogen, alkyl or cycloalkyl, or may together form a three to seven membered cycloalkyl ring;

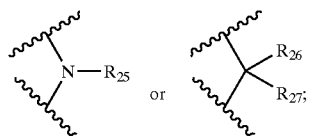

Z is oxygen, x is 2, 3 or 4;

$R_{25}$, $R_{26}$ and $R_{27}$ are each independently hydrogen, alkyl or cycloalkyl, or $R_{26}$ and $R_{27}$ may together form a three to seven-membered cycloalkyl ring;

$R_{101}$, $R_{102}$, $R_{103}$, and $R_{104}$ are each independently hydrogen, halogen, or alkyl.

4. A compound of claim 1, wherein

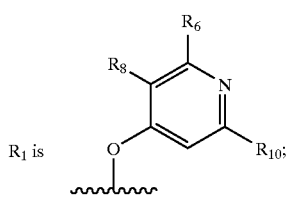

$R_2$ is alkyl, haloalkyl, (cycloalkyl)alkyl, alkoxyalkyl, haloalkoxyalkyl, alkoxy, alkoxyalkoxy, hydroxyalkyl, or —$(CH_2)_wY$;

$R_3$ is isoxazol-5-yl or isoxazol-3-yl independently substituted with two substituents selected from alkyl or halogen;

$R_6$ is alkyl, haloalkyl, cycloalkyl or alkoxy; and $R_{10}$ are independently H, alkyl, cycloalkyl, alkoxy or alkoxyalkyl;

w is 0, 1, or 2;

Y is —$NR_{21}(C=O)R_{22}$, —$NR_{21}(C=O)NR_{19}R_{20}$, —$NR_{21}(C=O)OR_{18}$, —$NR_{21}SO_2R_{22}$ or Q;

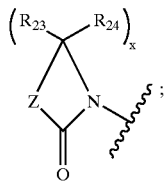

Q is $R_{18}$, $R_{19}$, $R_{20}$, $R_{21}$, and $R_{22}$ are each independently hydrogen, alkyl, cycloalkyl, or $R_{19}$ and $R_{20}$ may together form a four-, five-, six- or to seven-membered heterocyclic ring;

$R_{23}$ and $R_{24}$ are each independently hydrogen, alkyl or cycloalkyl, or may together form a three to seven membered cycloalkyl ring;

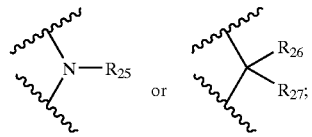

Z is x is 2;

$R_{25}$, $R_{26}$ and $R_{27}$ are each independently hydrogen, alkyl or cycloalkyl, or $R_{26}$ and $R_{27}$ may together form a three-, four-, five, six- or seven-membered cycloalkyl ring;

$R_{101}$, $R_{102}$, $R_{103}$, and $R_{104}$ are each independently hydrogen, halogen, or alkyl.

5. A compound of claim 1, wherein $R_3$ is isoxazol-5-yl or isoxazol-3-yl independently substituted with two substituents selected from alkyl or halogen.

6. A compound of claim 5, wherein $R_1$ is

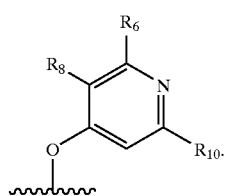

7. A compound of claim 6, wherein $R_2$ is alkyl, haloalkyl, alkoxyalkyl or haloalkoxyalkyl and $R_{101}$, $R_{102}$, $R_{103}$, $R_{104}$ are each independently hydrogen, halogen, or alkyl.

8. A compound of claim 6, wherein $R_2$ is —$CH_2Y$.

9. A compound of claim 8, wherein Y is Q.

10. A compound of claim 1, wherein $R_2$ is alkoxyalkyl, haloalkyl or haloalkoxyalkyl.

11. A compound of claim 10, wherein $R_3$ is isoxazol-5-yl or isoxazol-3-yl independently substituted with two substituents selected from alkyl or halogen.

12. A compound of claim 1, wherein $R_2$ is —$CH_2Y$.

13. A compound of claim 12, wherein $R_3$ is isoxazol-5-yl or isoxazol-3-yl independently substituted with two substituents selected from alkyl or halogen.

14. A compound of claim 12, wherein Y is Q.

15. A compound of claim 14, wherein $R_3$ is isoxazol-5-yl or isoxazol-3-yl independently substituted with two substituents selected from alkyl or halogen.

16. A compound of the formula

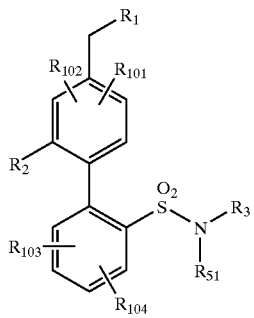

LVI wherein $R_1$, $R_2$, $R_3$, $R_{101}$, $R_{102}$, $R_{103}$, and $R_{104}$ are as defined in claim 1; and $R_{51}$ is a suitable nitrogen protecting group.

17. The compound of claim 16, wherein $R_{51}$ is —CH$_2$OCH$_2$CH$_2$OCH$_3$, —CH$_2$OCH$_2$CH$_2$Si(CH$_3$)$_3$, —CH$_2$OCH$_3$, or —CH$_2$OCH$_2$-aryl.

18. N-(4,5-Dimethyl-3-isoxazolyl)-2'-ethoxymethyl-4'-[[(3-methoxy-2,6-dimethyl-4-pyridinyl)oxy]methyl][1,1'-biphenyl]-2-sulfonamide or a salt, enantiomer or diastereiomer thereof.

19. N-(4,5-Dimethyl-3-isoxazolyl)-2'-[(2-fluoroethoxy)methyl)]-4'-[[(3-methoxy-2,6-dimethyl-4-pyridinyl)oxy]methyl][1,1-biphenyl]-2-sulfonamide or a salt, enantiomer or diasteriomer thereof.

20. N-(4,5-Dimethyl-3-isoxazolyl)-4'-[[(3-methoxy-2,6-dimethyl-4-pyridinyl)oxy]methyl]-2'-propyl[1,1'-biphenyl]-2-sulfonamide or a salt, enantiomer or diasteriomer thereof.

21. A pharmaceutical composition for the treatment of an endothelin-dependent or angiotensin II-dependent disorder, comprising a pharmaceutically acceptable vehicle or diluent and at least one compound of claim 1 in an amount effective therefor.

22. The pharmaceutical composition of claim 21 further comprising at least one ACE inhibitor.

23. The pharmaceutical composition of claim 22 wherein said ACE inhibitor is selected from captopril, zofenopril, fosinopril, ceranapril, alacepril, enalapril, delapril, pentopril, quinapril, ramipril, or lisinopril.

24. The pharmaceutical composition of claim 21 further comprising at least one vasopepsidase inhibitor.

25. The pharmaceutical composition of claim 24 wherein said vasopepsidase inhibitor is selected from omapatrilat or gemopatrilat.

26. The pharmaceutical composition of claim 21 further comprising at least one HMG CoA reductase inhibitor.

27. The pharmaceutical composition of claim 26 wherein said HMG CoA reductase inhibitor is selected from pravastatin, lovastatin, atorvastatin, simvastatin, NK-104 or ZD-4522.

28. The pharmaceutical composition of claim 21 further comprising at least one anti-platelet agent.

29. The pharmaceutical composition of claim 28 wherein said anti-platelet agent is selected from clopidigrel, ticlopidine, CS-747 or aspirin.

30. The pharmaceutical composition of claim 21 further comprising at least one anti-diabetic agent.

31. The pharmaceutical composition of claim 30 wherein said anti-diabetic agent is selected from biguanides or biguanide/glyburide combinations.

32. The pharmaceutical composition of claim 21 further comprising at least one beta-adrenergic agent.

33. The pharmaceutical composition of claim 32 wherein said beta-adrenergic agent is selected from carvedilol or metoprolol.

34. The pharmaceutical composition of claim 21 further comprising at least one mineralocorticoid receptor antagonist.

35. The pharmaceutical composition of claim 34 wherein said mineralocorticoid receptor antagonist is selected from spironolactone or eplerenone.

* * * * *